(12) United States Patent
Wright et al.

(10) Patent No.: US 6,720,479 B1
(45) Date of Patent: Apr. 13, 2004

(54) PLANT RETROELEMENTS AND METHODS RELATED THERETO

(75) Inventors: David A. Wright, Boone, IA (US); Daniel F. Voytas, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 35 days.

(21) Appl. No.: 09/586,106

(22) Filed: Jun. 2, 2000

Related U.S. Application Data

(63) Continuation-in-part of application No. 09/322,478, filed on May 28, 1999, now Pat. No. 6,331,662
(60) Provisional application No. 60/087,125, filed on May 29, 1998.

(51) Int. Cl.$^7$ .............................. C12N 5/04; A01H 1/00; A01H 3/00; A01H 4/00; C07H 21/04
(52) U.S. Cl. .................... 800/298; 435/320.1; 435/410; 435/419; 800/305; 800/306; 800/307; 800/309; 800/310; 800/312; 800/313; 800/314; 800/315; 800/316; 800/317; 800/317.1; 800/317.2; 800/317.3; 800/317.4; 800/318; 800/319; 800/320; 800/320.1; 800/320.2; 800/320.3; 800/322; 800/373.3; 536/23.1; 536/23.72; 536/24.1
(58) Field of Search .............................. 435/320.1, 410, 435/419; 800/298, 305, 306, 307, 309, 310, 312, 313, 314, 315, 316, 317, 317.1, 317.2, 317.3, 317.4, 318, 319, 320, 320.1, 320.2, 320.3, 322, 373.3; 536/23.1, 23.72, 24.1

(56) References Cited

PUBLICATIONS

Doolittle, et al., 64 *Quart. Rev. Biol.* 1–30 (1989).
Xiong and Eickbush, 9 *EMBO J* 3353–3362 (1990).
Boeke and Sandmeyer, Yeast Transposable Elements. In Molecular and Cellular Biology of the Yeast Saccharomyces, edited by J. Broach, E. Jones and J. Pringle, pp. 193–261. Cold Spring Harbor Laboratory, Cold Spring Harbor, N.Y. (1991).
Boeke, et al., Pseudoviridae. In Virus Taxonomy: ICTV VIIth Report, edited by F.A. Murphy, Springer–Verlag, New York 1–14 (1998).
Boeke, et al., Metaviridae. In Virus Taxonomy: ICTV VIIth Report, edited by F.A. Murphy, Springer–Verlag, New York pp. 1–11 (1998).
Kim, et al., 91 *Proc. Natl. Acad. Sci. USA* 1285–1289 (1994).
Song, et al., 8 *Genes and Dev.* 2046–2057 (1994).
Bennetzen, 4 *Trends Microbiol.* 347–353 (1996).
Voytas 142, *Genetics* 569–578 (1996).
Grandbastien, et al., 337 *Nature* 376–380 (1989).
Hirochika, et al., 93 *Proc. Natl. Acad. Sci. USA* 7783–7788 (1996).
Purugganan and Wessler, 91 *Proc. Natl. Acad. Sci. USA* 11674–11678 (1994).
White, et al., 91 *Proc Natl. Acad. Sci USA* 11792–11796 (1994).
Maestre, et al., 14 *EMBO J*. 6333–6338 (1995).
Bureau, et al., 77 *Cell* 479–480 (1994).
Jin and Bennetzen, 6 *Plant Cell* 1177–1186 (1994).
Konieczny, et al., 127 *Genetics* 801–809 (1991).
Voytas and Ausubel, 336 *Nature* 242–244 (1988).
Voytas, et al., 126 *Genetics* 713–721 (1990).
Chavanne, et al., 37 *Plant Molecular Biol.* 363–375 (1998).
Malik, et al., Poised for contagion: evolutionary origins of the infectious abilities of invertebrate retroviruses. *Genome Research (in press)*, pp. 1–7 (1999).
RNA Tumor Viruses. In Molecular Biology of Tumor Viruses, edited by R. Weiss, N. Teich and J. Coffin, pp. 25–207. Cold Spring Harbor Laboratory, Cold Spring Harbor, N.Y. (1982).
Retroviruses. In Mobile DNA, edited by D. Berg and M. Howe, pp. 53–108. American Society for Microbiology, Washington, D.C. (1989).

*Primary Examiner*—David Guzo
(74) *Attorney, Agent, or Firm*—Fish & Richardson P.C., P.A.

(57) ABSTRACT

The present invention provides plant retroelements useful as molecular tools. In one embodiment, the present invention provides nucleic acids encoding gag, pol and/or env genes of plant retroelements. The elements can be used, among other uses, as building blocks of other constructs, tools to find other nucleic acid sequences and tools to transfer nucleic acid into cells.

15 Claims, No Drawings

PLANT RETROELEMENTS AND METHODS RELATED THERETO

This application is a continuation in part to U.S. patent application Ser. No. 09/322,478, now U.S. Pat. No. 6,331, 662, which application was filed May 28, 1999, which application claimed priority to U.S. Provisional Patent Application Ser. No. 60/087125, filed May 29, 1998.

The present invention was funded, in part, by the United States Department of Agriculture, Contract Number IOW03120; the United States Government may have certain rights in the invention.

FIELD OF THE INVENTION

The present invention provides plant retroelements and methods related to plant retroelements. The invention involves techniques from the fields of: molecular biology, virology, genetics, bioinformatics, and, to a lesser extent, other related fields.

BACKGROUND OF THE INVENTION

The eukaryotic retrotransposons are divided into two distinct classes of elements based on their structure: the long terminal repeat (LTR) retrotransposons and the LINE-like or non LTR elements. Doolittle et al. (1989) Quart. Rev. Biol. 64: 1–30; xiong and Eickbush (1990) EMBO J 9: 3353–3362. These element classes are related by the fact that each must undergo reverse transcription of an RNA intermediate to replicate, and each generally encodes its own reverse transcriptase. The LTR retrotransposons replicate by a mechanism which resembles that of the retroviruses. Boeke and Sandmeyer, (1991) Yeast transposable elements. In The Molecular and Cellular Biology of the Yeast Saccharomyces, edited by J. Broach, E. Jones and J. Pringle, pp. 193–261. Cold Spring Harbor Laboratory, Cold Spring Harbor, N.Y. They typically use a specific tRNA to prime reverse transcription, and a linear cDNA is synthesized through a series of template transfers that require redundant LTR sequences at each end of the element mRNA. This all occurs within a virus-like particle formed from proteins encoded by the retrotransposon mRNA. After reverse transcription, an integration complex is organized that directs the resulting cDNA to a new site in the genome of the host cell.

Phylogenetic analyses based on reverse transcriptase amino acid sequences resolve the LTR retrotransposons into two families: the Ty3/gypsy retrotransposons (Metaviridae), and the Ty1/copia elements (Pseudoviridae). Boeke et al., (1998) Metaviridae. In Virus Taxonomy: ICTV VIIth Report, edited by F. A. Murphy. Springer-Verlag, N.Y.; Boeke et al. (1998) Pseudoviridae. In Virus Taxonomy: ICTV VIIth Report, edited by F. A. Murphy. Springer Verlag, N.Y.; Xiong and Eickbush (1990) EMBO J. 9: 3353–3362. Although distinct, Ty3/gypsy elements are more closely related to the retroviruses than to the Ty1/copia elements. They also share a similar genetic organization with the retroviruses, principally in the order of integrase and reverse transcriptase in their pol genes. For the Ty3/gypsy elements, reverse transcriptase precedes integrase, and this order is reversed for the Ty1/copia elements. In addition, some Ty3/gypsy elements have an extra open reading frame (ORF) similar to retroviral envelope (env) proteins, which is required for viral infectivity. The Drosophila melanogaster gypsy retrotransposons encode an env-like ORF and can be transmitted between cells. Kim et al. (1994) Proc. Natl. Acad. Sci. USA 91: 1285–1289; Song et al. (1994) Genes & Dev. 8: 2046–2057. Thus there are two distinct lineages of infectious LTR retroelements, the retroviruses and those Ty3/gypsy retrotransposons that encode envelope-like proteins. The Ty3/gypsy elements have been divided into two genera, the metaviruses and the errantiviruses, the latter of which include all elements with env-like genes. Boeke et al., (1998) Metaviridae. In Virus Taxonomy: ICTV VIIth Report, edited by F. A. Murphy. Springer-Verlag, N.Y.

In plants, retrotransposons have been extremely successful. Bennetzen (1996) Trends Microbiol. 4: 347–353; Voytas (1996) Genetics 142: 569–578. The enormous size of many plant genomes demonstrates a great tolerance for repetitive DNA, a substantial proportion of which appears to be composed of retrotransposons. Because of their abundance, retrotransposons have undoubtedly influenced plant gene evolution. They can cause mutations in coding sequences (Grandbastien et al. (1989) Nature 337: 376–380; Hirochika et al. (1996) Proc. Natl. Acad. Sci. USA 93: 7783–7788; Purugganan and Wessler (1994) Proc. Natl. Acad. Sci. USA 91: 11674–11678), and the promoter regions of some plant genes contain relics of retrotransposon insertions that contribute transcriptional regulatory sequences. White et al. (1994) Proc. Natl. Acad. Sci. USA 91: 11792–11796. Retrotransposons also generate gene duplications: Repetitive retrotransposon sequences provide substrates for unequal crossing over, and such an event is thought to have caused a zein gene duplication in maize. White et al. (1994) Proc. Natl. Acad. Sci. USA 91: 11792–11796. Occasionally, cellular mRNAs are reverse transcribed and the resultant cDNA recombines into the genome giving rise to new genes, or more frequently, cDNA pseudogenes. Maestre et al. (1995) EMBO J. 14: 6333–6338. The transduction of gene sequences during reverse transcription, which produced the oncogenic retroviruses, has also been documented to occur for a plant retrotransposon (Bureau et al. (1994) Cell 77: 479–480; Jin and Bennetzen (1994) Plant Cell 6: 1177 1186); a maize Bsl insertion in Adhl carries part of an ATPase gene and is the only known example of a retrotransposon-mediated gene transduction event.

Plant genomes encode representatives of the two major lineages of LTR retrotransposons that have been identified in other eukaryotes. Among these are numerous examples of Ty 1/copia elements (e.g. Konieczny et al. (1991) Genetics 127: 801–809; Voytas and Ausubel (1988) Nature 336: 242–244; Voytas et al. (1990) Genetics 126: 713–721) Also prevalent are Ty3/gypsy elements, which are members of the genus Metaviridae (Smyth et al. 1989; Purugganan and Wessler 1994 Proc. Natl. Acad. Sci. USA 91: 11674–11678; Su and Brown 1997). As stated above, the metaviruses do not encode an envelope protein characteristic of the retroviruses. It has been suggested that some plant retrovirus-like elements may have lost, or not yet gained, genes such as the envelope gene required for cell-to-cell transmission (Bennetzen (1996) Trends Microbiol. 4: 347–353). As one group of researchers described the uncertainty, "[s]ince genes encoding ENV [envelope] functions are very heterogeneous at the sequence level and difficult to identify by homology even between retroviruses, the possibility cannot be completely excluded at the present time that the 3' ORF of Cyclops [the retrotransposon described in the paper] is, in fact, an env gene and, hence, Cyclops is a retrovirus or a descendant of one." Chavanne et al. (1998) Plant Molecular Biol 37: 363–375.

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

In general, the present invention provides materials, such as nucleic acids, vectors, cells, and plants (including plant parts, seeds, embryos, etc.), and methods to manipulate the materials. In particular, molecular tools are provided in the form of retroelements and retroelement-containing vectors, cells and plants. The particular methods include methods to introduce the retroelements into cells, especially wherein the retroelements carries at least one agronomically-significant characteristic. The best mode of the present invention is a particular method to transfer agronomically-significant characteristics to plants wherein a helper cell line which expresses gag, pol and env sequences is used to enable transfer of a secondary construct which carries an agronomically-significant characteristic and has retroelement sequences that allow for replication and integration.

In one embodiment, there are provided isolated nucleic acid molecules, wherein said nucleic acid molecules encode at least a portion of a plant retroelement and comprises a nucleic acid sequence selected from the group consisting of:

(a) a nucleic acid sequence which is a plant retroelement primer binding site and which has more than 95% identity to SEQ ID NO 2, wherein said identity can be determined using the DNAsis computer program and default parameters;

(b) a nucleic acid sequence which is at least a portion of a plant retroelement envelope sequence and which has more than 50% identity to SEQ ID NO 5, wherein said identity can be determined using the DNAsis computer program and default parameters;

(c) a nucleic acid sequence which is at least a portion of a plant retroelement gag sequence and which has more than 50% identity to SEQ ID NO 7, wherein said identity can be determined using the DNAsis computer program and default parameters;

(d) a nucleic acid sequence which is at least a portion of a plant retroelement integrase sequence and which has more than 70% identity to SEQ ID NO 9, wherein said identity can be determined using the DNAsis computer program and default parameters;

(e) a nucleic acid sequence which is at least a portion of a plant retroelement reverse transcriptase sequence and which has more than 70% identity to SEQ ID NO 11, wherein said identity can be determined using the DNAsis computer program and default parameters;

(f) a nucleic acid sequence which is at least a portion of a plant retroelement protease sequence and which has more than 50% identity to SEQ ID NO 13, wherein said identity can be determined using the DNAsis computer program and default parameters;

(g) a nucleic acid sequence which is at least a portion of a plant retroelement RNAseH sequence and which has more than 70% identity to SEQ ID NO 15, wherein said identity can be determined using the DNAsis computer program and default parameters;

(h) a nucleic acid sequence which is at least a portion of a plant retroelement sequence and which has more than 50% identity to SEQ ID NO 17, wherein said identity can be determined using the DNAsis computer program and default parameters;

(i) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17.

(j) a nucleic acid sequence which encodes an amino acid sequence which is at least a portion of a plant retroelement envelope sequence and has more than 30% identity to SEQ ID NO 6, wherein said identity can be determined using the DNAsis computer program and default parameters;

(k) a nucleic acid sequence which encodes an amino acid sequence which is at least a portion of a plant retroelement gag sequence and has more than 30% identity to SEQ ID NO 8, wherein said identity can be determined using the DNAsis computer program and default parameters;

(l) a nucleic acid sequence which encodes an amino acid sequence which is at least a portion of a plant retroelement integrase sequence and has more than 75% identity to SEQ ID NO 10, wherein said identity can be determined using the DNAsis computer program and default parameters;

(m) a nucleic acid sequence which encodes an amino acid sequence which is at least a portion of a plant retroelement reverse transcriptase sequence and has more than 79% identity to SEQ ID NO 12, wherein said identity can be determined using the DNAsis computer program and default parameters;

(n) a nucleic acid sequence which encodes an amino acid sequence which is at least a portion of a plant retroelement protease sequence and has more than 55% identity to SEQ ID NO 14, wherein said identity can be determined using the DNAsis computer program and default parameters;

(o) a nucleic acid sequence which encodes an amino acid sequence which is at least a portion of a plant retroelement RNAseH sequence and has more than 90% identity to SEQ ID NO 16, wherein said identity can be determined using the DNAsis computer program and default parameters;

(p) a nucleic acid sequence which encodes an amino acid sequence which is at least a portion of a plant retroelement sequence and has more than 40% identity to SEQ ID NO 18, wherein said identity can be determined using the DNAsis computer program;

(q) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;

(r) a nucleic acid sequence which encodes an allelic variant of an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18; and (s) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); a nucleic acid sequence of (e); a nucleic acid sequence of (f); a nucleic acid sequence of (g); a nucleic acid sequence of (h); a nucleic acid sequence of (i); a nucleic acid sequence of (j); a nucleic acid sequence of (k); a nucleic acid sequence of (l); a nucleic acid sequence of (m); a nucleic acid sequence of (n); a nucleic acid sequence of (o); a nucleic acid sequence of (p); a nucleic acid sequence of (q); and a nucleic acid sequence of (r).

Seeds and plants comprising a nucleic acid as above are particularly provided. Nucleic acid molecules as above which comprise gag, pol and env genes and which comprise adenine-thymidine-guanidine as the gag gene start codon are also particularly provided. Those which comprise gag, pol and env genes, the adenine-thymidine-guanidine as the gag gene start codon, and which further comprises SEQ ID NO 4 are also provided.

Plant envelope sequences and constructs which comprise the sequences are provided, as are cells, seeds, embryos and plants comprising them. Preferred are isolated nucleic acid molecules, wherein said nucleic acid molecules encode at least a portion of a plant envelope sequence and comprises a nucleic acid sequence selected from the group consisting of:

(a) a nucleic acid sequence which has more than 90% identity to SEQ ID NO 5, wherein said identity can be determined using the DNAsis computer program and default parameters;

(b) a nucleic acid sequence which encodes SEQ ID NO 5;

(c) a nucleic acid sequence which encodes an amino acid sequence which has greater than 85% identity to SEQ ID NO 6, wherein said identity can be determined using the DNAsis computer program and default parameters;

(d) a nucleic acid sequence which encodes amino acid sequence SEQ ID NO 6;

(e) a nucleic acid sequence which encodes an allelic variant of SEQ ID NO 6; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant envelope proteins comprising an amino acid sequence encoded by the above. Methods to impart agronomically-significant characteristics to at least one plant cell are also provided, comprising: contacting a plant envelope protein as described to at least one plant cell under conditions sufficient to allow a nucleic acid molecule to enter said cell, wherein said nucleic acid molecule encodes an agronomically-significant characteristic.

Plant integrase sequences and constructs which comprise the sequences are provided, as are cells, seeds, embryos and plants comprising them. Preferred are isolated nucleic acid molecules, wherein said nucleic acid molecules encode at least a portion of a plant integrase sequence and comprises a nucleic acid sequence selected from the group consisting of:

(a) a nucleic acid sequence which has more than 90% identity to SEQ ID NO 9, wherein said identity can be determined using the DNAsis computer program and default parameters;

(b) a nucleic acid sequence which encodes SEQ ID NO 9;

(c) a nucleic acid sequence which encodes an amino acid sequence which has greater than 85% identity to SEQ ID NO 10, wherein said identity can be determined using the DNAsis computer program and default parameters;

(d) a nucleic acid sequence which encodes amino acid sequence SEQ ID NO 10;

(e) a nucleic acid sequence which encodes an allelic variant of SEQ ID NO 10; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant integrase proteins comprising an amino acid sequence encoded by the above. Methods to impart agronomically-significant characteristics to at least one plant cell are also provided, comprising: contacting a plant integrase protein as described to at least one plant cell under conditions sufficient to allow a nucleic acid molecule to enter said cell, wherein said nucleic acid molecule encodes an agronomically-significant characteristic.

Plant reverse transcriptase sequences and constructs which comprise the sequences are provided, as are cells, seeds, embryos and plants comprising them. Preferred are isolated nucleic acid molecules, wherein said nucleic acid molecules encode at least a portion of a plant reverse transcriptase sequence and comprises a nucleic acid sequence selected from the group consisting of:

(a) a nucleic acid sequence which has more than 90% identity to SEQ ID NO 11, wherein said identity can be determined using the DNAsis computer program and default parameters;

(b) a nucleic acid sequence which encodes SEQ ID NO 11;

(c) a nucleic acid sequence which encodes an amino acid sequence which has greater than 85% identity to SEQ ID NO 12, wherein said identity can be determined using the DNAsis computer program and default parameters;

(d) a nucleic acid sequence which encodes amino acid sequence SEQ ID NO 12;

(e) a nucleic acid sequence which encodes an allelic variant of SEQ ID NO 12; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant reverse transcriptase proteins comprising an amino acid sequence encoded by the above. Methods to impart agronomically-significant characteristics to at least one plant cell are also provided, comprising; contacting a plant reverse transcriptase protein as described to at least one plant cell under conditions sufficient to allow a nucleic acid molecule to enter said cell, wherein said nucleic acid molecule encodes an agronomically-significant characteristic.

Plant RNAseH sequences and constructs which comprise the sequences are provided, as are cells, seeds, embryos and plants comprising them. Preferred are isolated nucleic acid molecules, wherein said nucleic acid molecules encode at least a portion of a plant RNAseH sequence and comprises a nucleic acid sequence selected from the group consisting of:

(a) a nucleic acid sequence which has more than 90% identity to SEQ ID NO 15, wherein said identity can be determined using the DNAsis computer program and default parameters;

(b) a nucleic acid sequence which encodes SEQ ID NO 15;

(c) a nucleic acid sequence which encodes an amino acid sequence which has greater than 95% identity to SEQ ID NO 16, wherein said identity can be determined using the DNAsis computer program and default parameters;

(d) a nucleic acid sequence which encodes amino acid sequence SEQ ID NO 16;

(e) a nucleic acid sequence which encodes an allelic variant of SEQ ID NO 16; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant RNAseH proteins comprising an amino acid sequence encoded by the above. Methods to impart agronomically-significant characteristics to at least one plant cell are also provided, comprising: contacting a plant RNAseH protein as described to at least one plant cell under conditions sufficient to allow a nucleic acid molecule to enter said cell, wherein said nucleic acid molecule encodes an agronomically-significant characteristic.

Plant retroelement sequences and constructs which comprise the sequences are provided, as are cells, seeds, embryos and plants comprising them. Preferred are isolated nucleic acid molecules, wherein said nucleic acid molecules encode at least a portion of a plant retroelement sequence and comprises a nucleic acid sequence selected from the group consisting of:

(a) a nucleic acid sequence which has more than 95% identity to a nucleic acid sequence selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17, wherein said identity can be determined using the DNAsis computer program and default parameters;

(b) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17;

(c) a nucleic acid sequence which encodes an amino acid sequence which has more than 90% identity to an amino acid sequence selected from the group consisting of SEQ ID NO 4; SEQ ID NO 6; SEQ ID NO 8; SEQ ID NO 10; SEQ ID NO 12; SEQ ID NO 14; SEQ ID NO 16; SEQ ID NO 18, wherein said identity can be determined using the DNAsis computer program and default parameters;

(d) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;

(e) a nucleic acid sequence which encodes an allelic variant of an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Nucleic acid molecule as above, which further comprises at least one nucleic acid sequence which encodes at least one agronomically-significant characteristic are preferred. More preferred are those nucleic acid molecules as described wherein the agronomically-significant characteristic is selected from the group consisting of: male sterility; self-incompatibility; foreign organism resistance; improved biosynthetic pathways; environmental tolerance; photosynthetic pathways; and nutrient content and those wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Seeds and plants comprising a nucleic acid molecule as described are also preferred. More preferred are plants as described, wherein the plant is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower, brussel sprouts; onion; garlic; leek; squash; pumpkin; celery; pea; bean (including various legumes); strawberries; grapes; apples; pears; peaches; banana; palm; cocoa; cucumber, pineapple; apricot; plum; sugar beet; lawn grasses; maple; triticale; safflower, peanut; and olive. Most preferred are plants as described which are soybean plants. Plant retroelements comprising an amino acid sequence encoded by a nucleic acid sequence described are also provided. Plant cells comprising a nucleic acid molecule described herein, as well as plant retroviral proteins encoded by nucleic acid molecules described herein are provided.

Moreover, methods to transfer nucleic acid into a plant cell, comprising contacting a nucleic acid molecule of the present invention with at least one plant cell under conditions sufficient to allow said nucleic acid molecule to enter at least one cell of said plant are provided. In particular there is provided, methods to impart agronomically-significant characteristics to at least one plant cell, comprising: contacting a plant retroelement of the present invention to at least one plant cell under conditions sufficient to allow a nucleic acid molecule to enter said cell, wherein said nucleic acid molecule encodes an agronomically-significant characteristic. Methods as described, wherein the agronomically-significant characteristic is selected from the group consisting of: male sterility; self-incompatibility; foreign organism resistance; improved biosynthetic pathways; environmental tolerance; photosynthetic pathways; and nutrient content and those wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Plant retroelement sequences comprising specialized signals, and constructs which comprise the sequences are provided, as are cells, seeds, embryos and plants comprising them. Preferred are isolated nucleic acid molecules, comprising a nucleic acid sequence selected from the group consisting of:

(a) a nucleic acid sequence which has more than 95% identity to SEQ ID NO 2; wherein said identity can be determined using the DNAsis computer program and default parameters;

(b) a nucleic acid sequence which is SEQ ID NO 2;

(c) a nucleic acid sequence which encodes amino acid sequence SEQ ID NO 4; and (d) a nucleic acid sequence fully complementary to a nucleic acid sequence selected from the group consisting of: a nucleic acid sequence of (a); a nucleic acid sequence of (b); and a nucleic acid sequence of (c).

Plant retroelements as described above, which further comprise at least one nucleic acid sequence which encodes at least one agronomically-significant characteristic are preferred. More preferred are those methods wherein the agronomically-significant characteristic is selected from the group consisting of: male sterility; self-incompatibility; foreign organism resistance; improved biosynthetic pathways; environmental tolerance; photosynthetic pathways; and nutrient content and those wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content. Preferred are plant retroviral particles comprising an isolated retroelement as described, and seeds and plants comprising the retroelements as described. More preferred plants include soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber, pineapple; apricot; plum; sugar beet; lawn grasses; maple; triticale; safflower; peanut; and olive. Soybean is most preferred.

Also provided are methods to transfer nucleic acid into a plant cell, comprising contacting a plant retroelement as described with at least one plant cell under conditions sufficient to allow said plant retroelement to enter said cell. Methods to impart agronomically-significant characteristics to a plant, comprising contacting a plant retroelement as described with at least one plant cell under conditions sufficient to allow said plant retroelement to enter said cell are also preferred. Those methods wherein the plant retroelement is contacted with said cell via a plant retroviral particle described herein are preferred.

Plant retroviruses are also provided. In particular, plant retroviral particles comprising a plant-derived retrovirus envelope protein are provided. Plant retroviral particles comprising a plant-derived retrovirus envelope protein and which further comprise a plant retroviral protein selected from the group consisting of: plant-derived integrase; plant derived reverse transcriptase; plant-derived gag; and plant-derived RNAseH are preferred.

Plant retroviral particles comprising specialized retroviral proteins, and cells, seeds, embryos and plants which comprise the retroviral particles are provided. Preferred are isolated retroviral particles comprising a plant retroviral protein encoded by a nucleic acid sequence selected from the group consisting of:

(a) a nucleic acid sequence comprising (i) a nucleic acid sequence which encodes at least one plant retroviral envelope protein, and (ii) a nucleic acid sequence which has more than 60% identity to a nucleic acid sequence selected from the group consisting of: SEQ ID NO 9; SEQ ID NO 11; SEQ ID NO 15; SEQ ID NO 26; SEQ ID NO 27; SEQ ID NO 28; SEQ ID NO 29; SEQ D NO 30; and SEQ ID NO 31, wherein said identity can be determined using the DNAsis computer program and default parameters;

(b) a nucleic acid sequence which encodes an amino acid sequence encoded by a nucleic acid sequence (a);

(c) a nucleic acid sequence which encodes an allelic variant of an amino acid sequence encoded by a nucleic acid sequence of (a); and (d) a nucleic acid sequence fully complementary to a nucleic acid sequence selected from the group consisting of: a nucleic acid sequence of (a); a nucleic acid sequence of (b); and a nucleic acid sequence of (c).

In particular, there are provided plant retroviral particles, wherein said nucleic acid sequence as described in (a) comprises a plant envelope nucleic acid specifically mentioned in claim 6 is preferred. Those particles which further comprise at least one nucleic acid sequence which encodes at least one agronomically-significant characteristic are preferred.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

More preferred are isolated retroviral particles comprising a plant retroviral protein encoded by a nucleic acid sequence selected from the group consisting of:

(a) a nucleic acid sequence which has more than 80% identity to a nucleic acid sequence selected from the group consisting of: SEQ ID NO 9; SEQ ID NO 11; and SEQ ID NO 15, wherein said identity can be determined using the DNAsis computer program and default parameters;

(b) a nucleic acid sequence which encodes a nucleic acid selected from the group consisting of: SEQ ID NO 9; SEQ ID NO 11; and SEQ ID NO 15;

(c) a nucleic acid sequence which encodes an amino acid sequence encoded by a nucleic acid sequence selected from the group consisting of: a nucleic acid sequence of (a); and a nucleic acid sequence of (b);

(d) a nucleic acid sequence which encodes an allelic variant of an amino acid sequence encoded by a nucleic acid selected from the group consisting of: a nucleic acid sequence of (a); and a nucleic acid sequence of (b); and (e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Nucleic acids as above, which further comprises at least one nucleic acid sequence which encodes at least one agronomically-significant characteristic are preferred. More preferred are those nucleic acids wherein the agronomically-significant characteristic is selected from the group consisting of: male sterility; self-incompatibility; foreign organism resistance; improved biosynthetic pathways; environmental tolerance; photosynthetic pathways; and nutrient content. Also more preferred are those isolated nucleic acid molecule as described, wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

Also preferred are isolated retroviral particles comprising a plant retroviral protein encoded by a nucleic acid sequence selected from the group consisting of:

(a) a nucleic acid sequence which has more than 60% identity to a nucleic acid sequence selected from the group consisting of SEQ ID NO 9; SEQ ID NO 11; SEQ ID NO 15; SEQ ID NO 26; SEQ ID NO 27; SEQ ID NO 28; SEQ ID NO 29; SEQ ID NO 30; and SEQ ID NO 31, wherein said identity can be determined using the DNAsis computer program and default parameters;

(b) a nucleic acid sequence which encodes a nucleic acid selected from the group consisting of: SEQ ID NO 9; SEQ ID NO 11; SEQ ID NO 15; SEQ ID NO 26; SEQ ID NO 27; SEQ ID NO28; SEQ ID NO 29; SEQ ID NO 30; and SEQ ID NO 31;

(c) a nucleic acid sequence which encodes an amino acid sequence encoded by a nucleic acid sequence selected from the group consisting of: a nucleic acid sequence of (a); and a nucleic acid sequence of (b);

(d) a nucleic acid sequence which encodes an allelic variant of an amino acid sequence encoded by a nucleic acid selected from the group consisting of: a nucleic acid sequence of (a); and a nucleic acid sequence of (b); and (e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Plant retroviral particles as described above, which further comprises an envelope-encoding nucleic acid sequence specifically described herein are preferred. Preferred are those retroviral particles which further comprise at least one nucleic acid sequence which encodes at least one agronomically-significant characteristic.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

Also provided by the present invention are isolated nucleic acid molecules, wherein said nucleic acid molecule encodes at least a portion of a plant retroelement reverse transcriptase and comprises a nucleic acid sequence selected from the group consisting of:

(a) a nucleic acid sequence having more than 85% identity to a nucleic acid sequence selected from the group consisting of even-numbered SEQ ID NOs inclusive from SEQ ID NO 42 to SEQ ID NO 164, wherein said identity can be determined using the DNAsis computer program and default parameters;

(b) a nucleic acid sequence which encodes an amino acid sequence having more than 85% identity to an amino acid sequence selected from the group consisting of odd-numbered SEQ ID NOs inclusive from SEQ ID NO 43 through SEQ ID NO 165, wherein said identity can be determined using the DNAsis computer program and default parameters;

(c) a nucleic acid sequence which encodes an allelic variant of a nucleic acid sequence selected from the group consisting of: a nucleic acid sequence of (a); a nucleic acid sequence of (b).

(d) a nucleic acid sequence fully complementary to a nucleic acid sequence selected from the group consisting of: a nucleic acid sequence of (a); a nucleic acid sequence of (b).

Seeds and plants comprising the nucleic acid molecules are also provided, as are nucleic acids as described which comprise gag, pol and env genes and which comprises adenine-thymidine-guanidine as the gag gene start codon. Moreover, those nucleic acids which further comprises SEQ ID NO 5 are also provided. Also provided by the present invention are isolated nucleic acid molecules described, wherein said nucleic acid molecule encodes at least a portion of a plant envelope sequence and comprises a nucleic acid sequence selected from the group consisting of:

(a) a nucleic acid sequence which has more than 90% identity to SEQ ID NO 5, wherein said identity can be determined using the DNAsis computer program and default parameters;

(b) a nucleic acid sequence which encodes an amino acid sequence which has greater than 85% identity to SEQ ID NO 6, wherein said identity can be determined using the DNAsis computer program and default pararmeters;

(c) a nucleic acid sequence which encodes an allelic variant of SEQ ID NO 5; and (d) a nucleic acid sequence fully complementary to a nucleic acid sequence selected from the group consisting of: a nucleic acid sequence of (a); a nucleic acid sequence of (b); and a nucleic acid sequence of c).

Plant cells comprising this embodiment are also provided. Methods to impart agronomically-significant characteristics to at least one plant cell, comprising:

contacting a nucleic acid molecule described to at least one plant cell under conditions sufficient to allow at least one agronomically-significant nucleic acid molecule to enter said cell.

Also part of the present invention are isolated nucleic acid molecules, wherein said nucleic acid molecule encodes at least a portion of a plant retroelement reverse transcriptase and comprises a nucleic acid sequence selected from the group consisting of:

(a) a nucleic acid sequence having more than 95% identity to a nucleic acid sequence selected from the group consisting of even-numbered SEQ ID NOs inclusive from SEQ ID NO 42 to SEQ ID NO 164, wherein said identity can be determined using the DNAsis computer program and default parameters;

(b) a nucleic acid sequence which encodes an amino acid sequence having more than 95% identity to an amino acid sequence selected from the group consisting of odd-numbered SEQ ID NOs inclusive from SEQ ID NO 43 through SEQ ID NO 165, wherein said identity can be determined using the DNAsis computer program and default parameters;

(c) a nucleic acid sequence which encodes an allelic variant of a nucleic acid sequence selected from the group consisting of: a nucleic acid sequence of (a); a nucleic acid sequence of (b).

(d) a nucleic acid sequence fully complementary to a nucleic acid sequence selected from the group consisting of: a nucleic acid sequence of (a); a nucleic acid sequence of (b).

Seeds and plants comprising the nucleic acid molecules are also provided, as are nucleic acids as described which comprise gag, pol and env genes and which comprises adenine-thymidine-guanidine as the gag gene start codon. Moreover, those nucleic acids which further comprises SEQ ID NO 5 are also provided. Methods to impart agronomically-significant characteristics to at least one plant cell, comprising:

contacting a nucleic acid molecule described to at least one plant cell under conditions sufficient to allow at least one agronomically-significant nucleic acid molecule to enter said cell.

Also provided are isolated nucleic acid molecule, wherein said nucleic acid molecule encodes at least a portion of a plant retroelement reverse transcriptase and comprises a nucleic acid sequence selected from the group consisting of:

(a) a nucleic acid sequence selected from the group consisting of even-numbered SEQ ID NOs inclusive from SEQ ID NO 42 to SEQ ID NO 164, wherein said identity can be determined using the DNAsis computer program and default parameters;

(b) a nucleic acid sequence which encodes an amino acid sequence selected from the group consisting of odd-numbered SEQ ID NOs inclusive from SEQ ID NO 43 through SEQ ID NO 165, wherein said identity can be determined using the DNAsis computer program and default parameters;

(c) a nucleic acid sequence which encodes an allelic variant of a nucleic acid sequence selected from the group consisting of: a nucleic acid sequence of (a); a nucleic acid sequence of (b).

(d) a nucleic acid sequence fully complementary to a nucleic acid sequence selected from the group consisting of: a nucleic acid sequence of (a); a nucleic acid sequence of (b).

Seeds and plants comprising the nucleic acid molecules are also provided, as are nucleic acids as described which comprise gag, pol and env genes and which comprises adenine-thymidine-guanidine as the gag gene start codon. Moreover, those nucleic acids which further comprises SEQ ID NO 5 are also provided. Methods to impart agronomically-significant characteristics to at least one plant cell, comprising:

contacting a nucleic acid molecule described to at least one plant cell under conditions sufficient to allow at least one agronomically-significant nucleic acid molecule to enter said cell.

Nucleic acid molecules of the present invention which further comprise at least one nucleic acid sequence which encodes at least one agronomically-significant characteristic are also provided. Those nucleic acid molecules wherein the agronomically-significant characteristic is selected from the group consisting of: male sterility; self-incompatibility; foreign organism resistance; improved biosynthetic pathways; environmental tolerance; photosynthetic pathways; and nutrient content are preferred. Also preferred are those nucleic acid molecules wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Also provided are isolated plant retroviral particles comprising a nucleic acid molecule of the present invention.

Preferred plants are selected from the group consisting of: soybean; maize; sugar cane; beet; tobacco; wheat; barley; poppy; rape; sunflower, alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber, pineapple; apricot; plum; sugar beet; lawn grasses; maple; triticale; safflower, peanut; and olive.

In the present invention, it is preferred that the nucleic acid sequences are transmissible to either all plants, or to a limited set of plants, such as a species. For instance, plant viruses in general only infect a narrow host range or maybe infect a single species, and the present compounds may be genetically engineered to be similar. However, if a broad host range is desirable, those features which cause specificity can be removed or overridden by the feature of broad transmissibility. The present invention is drawn to both these embodiments, as well as other variations.

"Allelic variant" is meant to refer to a full length gene or partial sequence of a full length gene that occurs at essentially the same locus (or loci) as the referent sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

By "agronomically-significant" it is meant any trait of a plant which is recognized by members of the agricultural industry as desirable.

"Fragment" is meant to refer to any subset of the referent nucleic acid molecule.

By "plant" it is meant one or more plant seed, plant embryo, plant part or whole plant. The plant may be an angiosperm (monocot or dicot), gymnosperm, man-made or naturally-occurring.

By "proteins" it is meant any compounds which comprise amino acids, including peptides, polypeptides, fusion proteins, etc.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis. Lastly, "more than" and "greater than" are interchangeable, and when used to modify a percent identity, ie. "more than 90% identity", mean any increment to 100%, so long as the increment were greater than the percentage specifically named. In the example of "more than 90% identity", the term would include, among all other possibilities, 90.00001, 93.7, 98.04 and 99. 0827 and 100%.

The following is a summary of the sequence listing, as a convenient reference.

| SEQ ID NO | Description |
| --- | --- |
| 1 | specialized primer binding site version 1 |
| 2 | specialized primer binding site version 2 |
| 3 | specialized polypurine tract |
| 4 | targeting sequence |
| 5 | NA generic envelope |
| 6 | AA of 5 |
| 7 | NA of generic gag |
| 8 | AA of 7 |
| 9 | NA of generic integrase |
| 10 | AA of 9 |
| 11 | NA of generic reverse transcriptase |
| 12 | AA of 11 |
| 13 | generic protease |
| 14 | AA of 13 |
| 15 | generic RNAseH |
| 16 | AA of 15 |
| 17 | generic retroelement |
| 18 | AA of 17 |
| 19 | NA of calypso 1-1 |
| 20 | NA of calypso 1-2 |
| 21 | NA of calypso 1-3 |
| 22 | NA of calypso 2-1 |
| 23 | NA of calypso 2-2 |
| 24 | NA athila env |
| 25 | NA cyclops env |
| 26 | NA athila integrase |
| 27 | NA athila reverse transcriptase |
| 28 | NA athila RNAseH |
| 29 | NA cyclops reverse transcriptase |
| 30 | NA cyclops RNAseH |
| 31 | NA cyclops integrase |
| 32 | NA calypso envelope |
| 33 | NA calypso RNAseH |
| 34 | NA calypso reverse transcriptase |
| 35 | NA calypso integrase |
| 36 | Primer binding site A |
| 37 | Primer binding site B |
| 38 | Primer binding site minimum |
| 39 | Primer binding site extended |
| 40 | polypurine tract A |
| 41 | polypurine tract B |
| 42 | Tobacco1 DNA |
| 43 | Tobacco1 AA |
| 44 | Tobacco2-2 DNA |
| 45 | Tobacco2-2 AA |
| 46 | Tobacco4-1 DNA |
| 47 | Tobacco4-1 AA |
| 48 | Tobacco5-3 DNA |
| 49 | Tobacco5-3 AA |
| 50 | Rice1 DNA |
| 51 | Rice1 AA |
| 52 | Rice2-10 DNA |

-continued

| SEQ ID NO | Description |
| --- | --- |
| 53 | Rice2-10 AA |
| 54 | Rice2-17 DNA |
| 55 | Rice2-17 AA |
| 56 | Rice5-2 DNA |
| 57 | Rice5-2 AA |
| 58 | Barley2-4 DNA |
| 59 | Barley2-4 AA |
| 60 | Barley2-12 DNA |
| 61 | Barley2-12 AA |
| 62 | Barley2-19 DNA |
| 63 | Barley2-19 AA |
| 64 | Barley7 DNA |
| 65 | Barley7 AA |
| 66 | Oat6-1 DNA |
| 67 | Oat6-1 AA |
| 68 | Oat6-7 DNA |
| 69 | Oat6-7 AA |
| 70 | Oat6-8 DNA |
| 71 | Oat6-8 AA |
| 72 | Rye5-2 DNA |
| 73 | Rye5-2 AA |
| 74 | Rye3-4 DNA |
| 75 | Rye3-4 AA |
| 76 | Rye4-4 DNA |
| 77 | Rye4-4 AA |
| 78 | Rye5-4 DNA |
| 79 | Rye5-4 AA |
| 80 | Wheat3-1 DNA |
| 81 | Wheat3-1 AA |
| 82 | Wheat5-3 DNA |
| 83 | Wheat5-3 AA |
| 84 | Wheat8-2 DNA |
| 85 | Wheat8-2 AA |
| 86 | Wheat8-5 DNA |
| 87 | Wheat8-5 AA |
| 88 | Wheat8-11 DNA |
| 89 | Wheat8-11 AA |
| 90 | Cotton5-3 DNA |
| 91 | Cotton5-3 AA |
| 92 | Cotton8-6 DNA |
| 93 | Cotton8-6 AA |
| 94 | Cotton8-7 DNA |
| 95 | Cotton8-7 AA |
| 96 | Tomato4-4 DNA |
| 97 | Tomato4-4 AA |
| 98 | Tomato4-10 DNA |
| 99 | Tomato4-10 AA |
| 100 | Tomato10-4 DNA |
| 101 | Tomato10-4 AA |
| 102 | Tomato10-16 DNA |
| 103 | Tomato10-16 AA |
| 104 | Potato5-1 DNA |
| 105 | Potato5-1 AA |
| 106 | Potato8-3 DNA |
| 107 | Potato8-3 AA |
| 108 | Potato8-4 DNA |
| 109 | Potato8-4 AA |
| 110 | Potato8-5 DNA |
| 111 | Potato8-5 AA |
| 112 | Potato8-8 DNA |
| 113 | Potato8-8 AA |
| 114 | Potato8-10 DNA |
| 115 | Potato8-10 AA |
| 116 | Sycamore2-3 DNA |
| 117 | Sycamore2-3 AA |
| 118 | Sycamore4-2 DNA |
| 119 | Sycamore4-2 AA |
| 120 | Sycamore4-3 DNA |
| 121 | Sycamore4-3 AA |
| 122 | Sycamore4-7 DNA |
| 123 | Sycamore4-7 AA |
| 124 | Sorghum4-3 DNA |
| 125 | Sorghum4-3 AA |
| 126 | Sorghum5-2 DNA |
| 127 | Sorghum5-2 AA |
| 128 | Sorghum5-4 DNA |
| 129 | Sorghum5-4 AA |

-continued

| SEQ ID NO | Description |
|---|---|
| 130 | Sorghum5-5 DNA |
| 131 | Sorghum5-5 AA |
| 132 | Sorghum5-6 DNA |
| 133 | Sorghum5-6 AA |
| 134 | Sorghum5-8 DNA |
| 135 | Sorghum5-8 AA |
| 136 | L85 Soybean8-2 DNA |
| 137 | L85 Soybean8-2 AA |
| 138 | L85 Soybean2 DNA |
| 139 | L85 Soybean2 AA |
| 140 | L85 Soybean9-2 DNA |
| 141 | L85 Soybean9-2 AA |
| 142 | L85 Soybean9-3 DNA |
| 143 | L85 Soybean9-3 AA |
| 144 | L85 Soybean9-6 DNA |
| 145 | L85 Soybean9-6 AA |
| 146 | Williams Soybean8-2 DNA |
| 147 | Williams Soybean8-2 AA |
| 148 | Williams Soybean8-3 DNA |
| 149 | Williams Soybean8-3 AA |
| 150 | Williams Soybean2 DNA |
| 151 | Williams Soybean2 AA |
| 152 | Williams Soybean3 DNA |
| 153 | Williams Soybean3 AA |
| 154 | Hark Soybean2 DNA |
| 155 | Hark Soybean2 AA |
| 156 | Hark Soybean5-1 DNA |
| 157 | Hark Soybean5-1 AA |
| 158 | Hark Soybean5 DNA |
| 159 | Hark Soybean5 AA |
| 160 | Pea1 DNA |
| 161 | Pea1 AA |
| 162 | Pea8-1 DNA |
| 163 | Pea8-1 AA |
| 164 | Pea9-1 DNA |
| 165 | Pea9-1 AA |

DETAILED DESCRIPTION OF THE INVENTION

In one embodiment, there are provided isolated nucleic acid molecules, wherein said nucleic acid molecules encode at least a portion of a plant retroelement and comprises a nucleic acid sequence selected from the group consisting of:

(a) a nucleic acid sequence which is a plant retroelement primer binding site and which has more than 95% identity to SEQ ID NO 2, wherein said identity can be determined using the DNAsis computer program and default parameters;

(b) a nucleic acid sequence which is at least a portion of a plant retroelement envelope sequence and which has more than 50% identity to SEQ ID NO 5, wherein said identity can be determined using the DNAsis computer program and default parameters;

(c) a nucleic acid sequence which is at least a portion of a plant retroelement gag sequence and which has more than 50% identity to SEQ ID NO 7, wherein said identity can be determined using the DNAsis computer program and default parameters;

(d) a nucleic acid sequence which is at least a portion of a plant retroelement integrase sequence and which has more than 70% identity to SEQ ID NO 9, wherein said identity can be determined using the DNAsis computer program and default parameters;

(e) a nucleic acid sequence which is at least a portion of a plant retroelement reverse transcriptase sequence and which has more than 70% identity to SEQ ID NO 11, wherein said identity can be determined using the DNAsis computer program and default parameters;

(f) a nucleic acid sequence which is at least a portion of a plant retroelement protease sequence and which has more than 50% identity to SEQ ID NO 13, wherein said identity can be determined using the DNAsis computer program and default parameters;

(g) a nucleic acid sequence which is at least a portion of a plant retroelement RNAseH sequence and which has more than 70% identity to SEQ ID NO 15, wherein said identity can be determined using the DNAsis computer program and default parameters;

(h) a nucleic acid sequence which is at least a portion of a plant retroelement sequence and which has more than 50% identity to SEQ ID NO 17, wherein said identity can be determined using the DNAsis computer program and default parameters;

(i) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17.

(j) a nucleic acid sequence which encodes an amino acid sequence which is at least a portion of a plant retroelement envelope sequence and has more than 30% identity to SEQ ID NO 6, wherein said identity can be determined using the DNAsis computer program and default parameters;

(k) a nucleic acid sequence which encodes an amino acid sequence which is at least a portion of a plant retroelement gag sequence and has more than 30% identity to SEQ ID NO 8, wherein said identity can be determined using the DNAsis computer program and default parameters;

(l) a nucleic acid sequence which encodes an amino acid sequence which is at least a portion of a plant retroelement integrase sequence and has more than 75% identity to SEQ ID NO 10, wherein said identity can be determined using the DNAsis computer program and default parameters;

(m) a nucleic acid sequence which encodes an amino acid sequence which is at least a portion of a plant retroelement reverse transcriptase sequence and has more than 79% identity to SEQ ID NO 12, wherein said identity can be determined using the DNAsis computer program and default parameters;

(n) a nucleic acid sequence which encodes an amino acid sequence which is at least a portion of a plant retroelement protease sequence and has more than 55% identity to SEQ ID NO 14, wherein said identity can be determined using the DNAsis computer program and default parameters;

(o) a nucleic acid sequence which encodes an amino acid sequence which is at least a portion of a plant retroelement RNAseH sequence and has more than 90% identity to SEQ ID NO 16, wherein said identity can be determined using the DNAsis computer program and default parameters;

(p) a nucleic acid sequence which is at least a portion of a plant retroelement sequence and has more than 40% identity to SEQ ID NO 18, wherein said identity can be determined using the DNAsis computer program;

(q) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;

(r) a nucleic acid sequence which encodes an allelic variant of an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18; and (s) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); a nucleic acid sequence of (e); a nucleic acid sequence of (f); a nucleic acid sequence of (g); a nucleic acid sequence of (h); a nucleic acid sequence of (i); a nucleic acid sequence of (j); a nucleic acid sequence of (k); a nucleic acid sequence of (l); a nucleic acid sequence of (m); a nucleic acid sequence of (n); a nucleic acid sequence of (o); a nucleic acid sequence of (p); a nucleic acid sequence of (q); and a nucleic acid sequence of (r).

Seeds and plants comprising a nucleic acid as above are particularly provided. Nucleic acid molecules as above which comprise gag, pol and env genes and which comprise adenine-thymidine-guanidine as the gag gene start codon are also particularly provided. Those which comprise gag, pol and env genes, the adenine-thymidine-guanidine as the gag gene start codon, and which further comprises SEQ ID NO 4 are also provided.

Included within the scope of the present invention, with particular regard to the nucleic acids above, are allelic variants, degenerate sequences and homologues. The present invention also includes variants due to laboratory manipulation, such as, but not limited to, variants produced during polymerase chain reaction amplification or site directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide. Lastly, a nucleic acid sequence homologous to the exemplified nucleic acid molecules (or allelic variants or degenerates thereof) will have at least 85%, preferably 90%, and most preferably 95% sequence identity with a nucleic acid molecule in the sequence listing.

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVecto™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

Knowing the nucleic acid sequences of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain similar nucleic acid molecules from other species. Such nucleic acid molecules can be obtained in a variety of ways including screening appropriate expression libraries with antibodies of the present invention; traditional cloning techniques using oligonucleotide probes of the present invention to screen appropriate libraries of DNA; and PCR amplification of appropriate libraries or DNA using oligonucleotide primers of the present invention. Preferred libraries to screen or from which to amplify nucleic acid molecules include canine cDNA libraries as well as genomic DNA libraries. Similarly, preferred DNA sources to screen or from which to amplify nucleic acid molecules include adult cDNA and genomic DNA. Techniques to clone and amplify genes are disclosed, for example, in Sambrook et al., ibid.

Recombination constructs can be made using the starting materials above or with additional materials, using methods well-known in the art. In general, the sequences can be manipulated to have ligase-compatible ends, and incubated with ligase to generate full constructs. For example, restriction enzymes can be chosen on the basis of their ability to cut at an acceptable site in both sequence to be ligated, or a linker may be added to convert the sequence end(s) to ones that are compatible. The methods for conducting these types of molecular manipulations are well-known in the art, and are described in detail in Sambrook et al., Molecular Cloning. A Laboratory Manual (Cold Spring Harbor Laboratory Press, 1989) and Ausubel et al., Current Protocols in Molecular Biology (Greene Publishing Associates, Inc., 1993). The methods described herein according to Tinland et al., 91 Proc. Natl. Acad. Sci. USA 8000 (1994) can also be used.

The present invention also includes nucleic acid molecules that are oligonucleotides capable of hybridizing, under stringent hybridization conditions, with complementary regions of other, preferably longer, nucleic acid molecules of the present invention. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents. Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, Molecular Cloning: A Laboratory Manual, Cold Spring Harbor Labs Press, and Meinkoth, et al., 1984, Anal. Biochem. 138, 267–284.

Recombinant molecules of the present invention may also (a) contain secretory signals (i.e., signal segment nucleic acid sequences) to enable an expressed protein of the present invention to be secreted from the cell that produces the protein and/or (b) contain fusion sequences which lead to the expression of nucleic acid molecules of the present invention as fusion proteins. Recombinant molecules may also include intervening and/or untranslated sequences surrounding and/or within the nucleic acid sequences of nucleic acid molecules of the present invention.

One embodiment of the present invention includes recombinant vectors, which include at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequences that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda pL and lambda pR and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, Heliothis zea insect virus, vaccinia virus, herpesvirus, raccoon poxvirus, other poxvirus, adenovirus, cytomegalovirus (such as intermediate early promoters), simian virus 40, retrovirus, actin, retrovirl long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with plants. The present invention also comprises expression vectors comprising a nucleic acid molecule described herein.

For instance, the following promoters would be useful in early expression of the present sequences: Ogs4B (Tsuchiya et al., 36 Plant Cell Physiology 487 (1994); TA29 (Koltunow et al., 2 Plant Cell 1201 (1990); A3 & A9 (Paul et al., 19 Plant Molecular Biology 611 (1992). In order to then constitutively express the sequences described above, the construct optionally contains, for example, a 35S promoter.

Vectors which comprise the above sequences are within the scope of the present invention, as are plants transformed with the above sequences. Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.). Preferred vectors are those which are capable of transferring the sequences disclosed herein into plant cells or plant parts.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Nucleic acids of the present invention may be transferred to cells according to the methods of the present invention, as well as using any of the following well-known means: infective, vector-containing bacterial strains (such as Agrobacterium rhizogenes and Agrobacterium tumefaciens) according to ie. Zambryski, 43 Ann. Rev. Pl. Physiol. Pl. Mol. Biol. 465 (1992); pollen-tube transformation [Zhonxun et al., 6 Plant Molec. Bio. 165 (1988)]; direct transformation of germinating seeds [Toepfer et al., 1 Plant Cell 133 (1989)]; polyethylene glycol or electroporation transformation [Christou et al., 84 Proc. Nat. Acad. Sci. 3662 (1987)]; and biolistic processes [Yang & Cristou, Particle Bombardment Technology for Gene Transfer (1994)].

The transformed cells may be induced to form transformed plants via organogenesis or embryogenesis, according to the procedures of Dixon Plant Cell Culture: A Practical Approach (IRL Press, Oxford 1987).

Any seed, embryo, plant or plant part is amenable to the present techniques. Of course, the agronomically-significant seeds, embryos, plants or plant parts are preferred. Soybean; maize; sugar cane; beet; tobacco; wheat; barley; poppy; rape; sunflower, alfalfa; sorghum; rose; carnation; gerbera; carrot; tomato; lettuce; chicory; pepper, melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legunes); strawberries; grapes; apples; pears; peaches; banana; palm; cocoa; cucumber, pineapple; apricot; plum; sugar beet; lawn grasses; maple; triticale; safflower, peanut; and olive are among the preferred seeds, embryos, plants or plant parts. Particularly preferred are: soybean, tobacco and maize seeds, embryos, plants or plant parts. However, Arabidopsis seeds, embryos, plants or plant parts are also preferred, since it is an excellent system for study of plant genetics.

Preferred are those genes or sequences which are agronomically significant. For example, genes encoding male sterility, foreign organism resistance (viruses or bacteria), including genes which produce bacterial endotoxins, such as bacillus thurigiensis endotoxin, genes involved in specific biosynthetic pathways (eg. in fruit ripening, oil or pigment biosynthesis, seed formation, or carbohydrate metabolism), genes involved in environmental tolerance (eg. salt tolerance, lodging tolerance, cold/frost tolerance, drought tolerance, or tolerance to anaerobic conditions), or genes involved in nutrient content (eg. protein content, carbohydrate content, amino acid content, fatty acid content), genes involved in photosynthetic pathways, or genes involved in self-incompatibility. The choice of gene or sequence induced to recombine in the present invention is not limited. Examples of genes and how to obtain them are available through reference articles, books and supply catalogs, such as The Sourcebook (1-800-551-5291). Sambrook et al., Molecular Cloning. A Laboratory Manual (Cold Spring Harbor Laboratory Press, 1989) and Weising et al., 22 Ann Rev. Gen. 421 (1988) contain a synthesis of the information that is well-known in this art.

Plant envelope sequences and constructs which comprise the sequences are provided, as are cells, seeds, embryos and plants comprising them. Preferred are isolated nucleic acid molecules, wherein said nucleic acid molecules encode at least a portion of a plant envelope sequence and comprises a nucleic acid sequence selected from the group consisting of:

(a) a nucleic acid sequence which has more than 90% identity to SEQ ID NO 5, wherein said identity can be determined using the DNAsis computer program and default parameters;

(b) a nucleic acid sequence which encodes SEQ ID NO 5;

(c) a nucleic acid sequence which encodes an amino acid sequence which has greater than 85% identity to SEQ ID NO 6, wherein said identity can be determined using the DNAsis computer program and default parameters;

(d) a nucleic acid sequence which encodes amino acid sequence SEQ ID NO 6;

(e) a nucleic acid sequence which encodes an allelic variant of SEQ ID NO 6; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant envelope proteins comprising an amino acid sequence encoded by the above. Methods to impart agronomically-significant characteristics to at least one plant cell are also provided, comprising: contacting a plant envelope protein as described to at least one plant cell under conditions sufficient to allow a nucleic acid molecule to enter said cell, wherein said nucleic acid molecule encodes an agronomically-significant characteristic.

Plant integrase sequences and constructs which comprise the sequences are provided, as are cells, seeds, embryos and plants comprising them. Preferred are isolated nucleic acid molecules, wherein said nucleic acid molecules encode at least a portion of a plant integrase sequence and comprises a nucleic acid sequence selected from the group consisting of:

(a) a nucleic acid sequence which has more than 90% identity to SEQ ID NO 9, wherein said identity can be determined using the DNAsis computer program and default parameters;

(b) a nucleic acid sequence which encodes SEQ ID NO 9;

(c) a nucleic acid sequence which encodes an amino acid sequence which has greater than 85% identity to SEQ ID NO 10, wherein said identity can be determined using the DNAsis computer program and default parameters;

(d) a nucleic acid sequence which encodes amino acid sequence SEQ ID NO 10;

(e) a nucleic acid sequence which encodes an allelic variant of SEQ ID NO 10; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant integrase proteins comprising an amino acid sequence encoded by the above. Methods to impart agronomically-significant characteristics to at least one plant cell are also provided, comprising: contacting a plant integrase protein as described to at least one plant cell under conditions sufficient to allow a nucleic acid molecule to enter said cell, wherein said nucleic acid molecule encodes an agronomically-significant characteristic.

Plant reverse transcriptase sequences and constructs which comprise the sequences are provided, as are cells, seeds, embryos and plants comprising them. Preferred are isolated nucleic acid molecules, wherein said nucleic acid molecules encode at least a portion of a plant reverse transcriptase sequence and comprises a nucleic acid sequence selected from the group consisting of:

(a) a nucleic acid sequence which has more than 90% identity to SEQ ID NO 11, wherein said identity can be determined using the DNAsis computer program and default parameters;

(b) a nucleic acid sequence which encodes SEQ ID NO 11;

(c) a nucleic acid sequence which encodes an amino acid sequence which has greater than 85% identity to SEQ ID NO 12, wherein said identity can be determined using the DNAsis computer program and default parameters;

(d) a nucleic acid sequence which encodes amino acid sequence SEQ ID NO 12;

(e) a nucleic acid sequence which encodes an allelic variant of SEQ ID NO 12; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant reverse transcriptase proteins comprising an amino acid sequence encoded by the above. Methods to impart agronomically-significant characteristics to at least one plant cell are also provided, comprising: contacting a plant reverse transcriptase protein as described to at least one plant cell under conditions sufficient to allow a nucleic acid molecule to enter said cell, wherein said nucleic acid molecule encodes an agronomically-significant characteristic.

Plant RNAseH sequences and constructs which comprise the sequences are provided, as are cells, seeds, embryos and plants comprising them. Preferred are isolated nucleic acid molecules, wherein said nucleic acid molecules encode at least a portion of a plant RNAseH sequence and comprises a nucleic acid sequence selected from the group consisting of:

(a) a nucleic acid sequence which has more than 90% identity to SEQ ID NO 15, wherein said identity can be determined using the DNAsis computer program and default parameters;

(b) a nucleic acid sequence which encodes SEQ ID NO 15;

(c) a nucleic acid sequence which encodes an amino acid sequence which has greater than 95% identity to SEQ ID NO 16, wherein said identity can be determined using the DNAsis computer program and default parameters;

(d) a nucleic acid sequence which encodes amino acid sequence SEQ ID NO 16;

(e) a nucleic acid sequence which encodes an allelic variant of SEQ ID NO 16; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Plant cells comprising an isolated nucleic acid molecule above are particularly preferred. Also preferred are plant RNAseH proteins comprising an amino acid sequence encoded by the above. Methods to impart agronomically-significant characteristics to at least one plant cell are also provided, comprising: contacting a plant RNAseH protein as described to at least one plant cell under conditions sufficient to allow a nucleic acid molecule to enter said cell, wherein said nucleic acid molecule encodes an agronomically-significant characteristic.

Plant retroelement sequences and constructs which comprise the sequences are provided, as are cells, seeds, embryos and plants comprising them. Preferred are isolated nucleic acid molecules, wherein said nucleic acid molecules encode at least a portion of a plant retroelement sequence and comprises a nucleic acid sequence selected from the group consisting of:

(a) a nucleic acid sequence which has more than 95% identity to a nucleic acid sequence selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17, wherein said identity can be determined using the DNAsis computer program and default parameters;

(b) a nucleic acid sequence which is selected from the group consisting of: SEQ ID NO 2; SEQ ID NO 5; SEQ ID NO 7; SEQ ID NO 9; SEQ ID NO 11; SEQ ID NO 13; SEQ ID NO 15; and SEQ ID NO 17;

(c) a nucleic acid sequence which encodes an amino acid sequence which has more than 90% identity to an amino acid sequence selected from the group consisting of SEQ ID NO 4; SEQ ID NO 6; SEQ ID NO8; SEQ ID NO 10; SEQ ID NO 12; SEQ ID NO 14; SEQ ID NO 16; SEQ ID NO 18, wherein said identity can be determined using the DNAsis computer program and default parameters;

(d) a nucleic acid sequence which encodes an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO 18;

(e) a nucleic acid sequence which encodes an allelic variant of an amino acid sequence selected from the group consisting of: SEQ ID NO 4; SEQ ID NO 6; SEQ ID NO 8; SEQ ID NO 10; SEQ ID NO 12; SEQ ID NO 14; SEQ ID NO 16; and SEQ ID NO18; and (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (d); and a nucleic acid sequence of (e).

Nucleic acid molecule as above, which further comprises at least one nucleic acid sequence which encodes at least one agronomically-significant characteristic are preferred. More preferred are those nucleic acid molecules as described wherein the agronomically-significant characteristic is selected from the group consisting of: male sterility; self-incompatibility; foreign organism resistance; improved biosynthetic pathways; environmental tolerance; photosynthetic pathways; and nutrient content. Also more preferred are those isolated nucleic acid molecule as described, wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Seeds and plants comprising a nucleic acid molecule as described are also preferred. More preferred are plants as described, wherein the plant is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower, brussel sprouts; onion; garlic; leek; squash; pumpkin; celery; pea; bean (including various legumes); strawberries; grapes; apples; pears; peaches; banana; palm;

cocoa; cucumber; pineapple; apricot; plum; sugar beet; lawn grasses; maple; triticale; safflower, peanut; and olive. Most preferred are plants as described which is a soybean plant. Plant retroelements comprising an amino acid sequence encoded by a nucleic acid sequence described are also provided. Plant cells comprising a nucleic acid molecule described herein, as well as plant retroviral proteins encoded by nucleic acid molecules described herein are provided.

Moreover, methods to transfer nucleic acid into a plant cell, comprising contacting a nucleic acid molecule of the present invention with at least one plant cell under conditions sufficient to allow said nucleic acid molecule to enter at least one cell of said plant are provided. In particular there is provided, methods to impart agronomically-significant characteristics to at least one plant cell, comprising: contacting a plant retroelement of the present invention to at least one plant cell under conditions sufficient to allow a nucleic acid molecule to enter said cell, wherein said nucleic acid molecule encodes an agronomically-significant characteristic. Methods as described, wherein the agronomically-significant characteristic is selected from the group consisting of: male sterility; self-incompatibility; foreign organism resistance; improved biosynthetic pathways; environmental tolerance; photosynthetic pathways; and nutrient content are preferred, as are methods wherein the agronomically-significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Plant retroelement sequences comprising specialized signals, and constructs which comprise the sequences are provided, as are cells, seeds, embryos and plants comprising them. Preferred are isolated nucleic acid molecules, comprising a nucleic acid sequence selected from the group consisting of:

(a) a nucleic acid sequence which has more than 95% identity to SEQ ID NO 2; wherein said identity can be determined using the DNAsis computer program and default parameters;

(b) a nucleic acid sequence which is SEQ ID NO 2;

(c) a nucleic acid sequence which encodes amino acid sequence SEQ ID NO 4; and (d) a nucleic acid sequence fully complementary to a nucleic acid sequence selected from the group consisting of: a nucleic acid sequence of (a); a nucleic acid sequence of (b); and a nucleic acid sequence of (c).

Plant retroelements as described above, which further comprise at least one nucleic acid sequence which encodes at least one agronomically-significant characteristic are preferred. More preferred are those methods wherein the agronomically-significant characteristic is selected from the group consisting of: male sterility; self-incompatibility; foreign organism resistance; improved biosynthetic pathways; environmental tolerance; photosynthetic pathways; and nutrient content or those wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Preferred are plant retroviral particles comprising an isolated retroelement as described, and seeds and plants comprising the retroelements as described. More preferred plants include soybean; maize; sugar cane; beet; tobacco; wheat; barley; poppy; rape; sunflower; alfalfa; sorghum; rose; carnation; gerbera; carrot; tomato; lettuce; chicory; pepper, melon; cabbage; oat; rye; cotton; flax; potato; pine; walnut; citrus (including oranges, grapefruit etc.); hemp; oak; rice; petunia; orchids; Arabidopsis; broccoli; cauliflower; brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive. Soybean is most preferred.

Also provided are methods to transfer nucleic acid into a plant cell, comprising contacting a plant retroelement as described with at least one plant cell under conditions sufficient to allow said plant retroelement to enter said cell. Methods to impart agronomically-significant characteristics to a plant, comprising contacting a plant retroelement as described with at least one plant cell under conditions sufficient to allow said plant retroelement to enter said cell are also preferred. Those methods wherein the plant retroelement is contacted with said cell via a plant retroviral particle described herein are preferred.

Plant retroviruses are also provided. In particular, plant retroviral particles comprising a plant-derived retrovirus envelope protein are provided. Plant retroviral particles comprising a plant-derived retrovirus envelope protein and which further comprise a plant retroviral protein selected from the group consisting of: plant-derived integrase; plant derived reverse transcriptase; plant-derived gag; and plant-derived RNAseH are preferred.

Plant retroviral particles comprising specialized retroviral proteins, and cells, seeds, embryos and plants which comprise the retroviral particles are provided. Preferred are isolated retroviral particles comprising a plant retroviral protein encoded by a nucleic acid sequence selected from the group consisting of:

(a) a nucleic acid sequence comprising (i) a nucleic acid sequence which encodes at least one plant retroviral envelope protein, and (ii) a nucleic acid sequence which has more than 60% identity to a nucleic acid sequence selected from the group consisting of: SEQ ID NO 9; SEQ ID NO 11; SEQ ID NO 15; SEQ ID NO 26; SEQ ID NO 27; SEQ ID NO 28; SEQ ID NO 29; SEQ ID NO 30; and SEQ ID NO 31, wherein said identity can be determined using the DNAsis computer program and default parameters;

(b) a nucleic acid sequence which encodes an amino acid sequence encoded by a nucleic acid sequence (a);

(c) a nucleic acid sequence which encodes an allelic variant of an amino acid sequence encoded by a nucleic acid sequence of (a); and (d) a nucleic acid sequence fully complementary to a nucleic acid sequence selected from the group consisting of: a nucleic acid sequence of (a); a nucleic acid sequence of (b); and a nucleic acid sequence of (c).

In particular, there are provided plant retroviral particles, wherein said nucleic acid sequence as described in (a) comprises a plant envelope nucleic acid specifically mentioned in claim 6 is preferred. Those particles which further comprise at least one nucleic acid sequence which encodes at least one agronomically-significant characteristic are preferred.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

More preferred are isolated retroviral particles comprising a plant retroviral protein encoded by a nucleic acid sequence selected from the group consisting of:
- (a) a nucleic acid sequence which has more than 80% identity to a nucleic acid sequence selected from the group consisting of: SEQ ID NO 9; SEQ ID NO 11; and SEQ ID NO 15, wherein said identity can be determined using the DNAsis computer program and default parameters;
- (b) a nucleic acid sequence which encodes a nucleic acid selected from the group consisting of: SEQ ID NO 9; SEQ ID NO 11; and SEQ ID NO 15;
- (c) a nucleic acid sequence which encodes an amino acid sequence encoded by a nucleic acid sequence selected from the group consisting of: a nucleic acid sequence of (a); and a nucleic acid sequence of (b);
- (d) a nucleic acid sequence which encodes an allelic variant of an amino acid sequence encoded by a nucleic acid selected from the group consisting of: a nucleic acid sequence of (a); and a nucleic acid sequence of (b); and
- (e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Nucleic acids as above, which further comprises at least one nucleic acid sequence which encodes at least one agronomically-significant characteristic are preferred. More preferred are those nucleic acids wherein the agronomically-significant characteristic is selected from the group consisting of: male sterility; self-incompatibility; foreign organism resistance; improved biosynthetic pathways; environmental tolerance; photosynthetic pathways; and nutrient content, or wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

Also preferred are isolated retroviral particles comprising a plant retroviral protein encoded by a nucleic acid sequence selected from the group consisting of:
- (a) a nucleic acid sequence which has more than 60% identity to a nucleic acid sequence selected from the group consisting of SEQ ID NO 9; SEQ ID NO 11; SEQ ID NO 15; SEQ ID NO 26; SEQ ID NO 27; SEQ ID NO 28; SEQ ID NO 29; SEQ ID NO 30; and SEQ ID NO 31, wherein said identity can be determined using the DNAsis computer program and default parameters;
- (b) a nucleic acid sequence which encodes a nucleic acid selected from the group consisting of: SEQ ID NO 9; SEQ ID NO 11; SEQ ID NO 15; SEQ ID NO 26; SEQ ID N027; SEQ ID NO 28; SEQ ID NO 29; SEQ ID NO 30; and SEQ ID NO 31;
- (c) a nucleic acid sequence which encodes an amino acid sequence encoded by a nucleic acid sequence selected from the group consisting of: a nucleic acid sequence of (a); and a nucleic acid sequence of (b);
- (d) a nucleic acid sequence which encodes an allelic variant of an amino acid sequence encoded by a nucleic acid selected from the group consisting of: a nucleic acid sequence of (a); and a nucleic acid sequence of (b); and
- (e) a nucleic acid sequence fully complementary to a nucleic acid sequence selected from the group consisting of: a nucleic acid sequence of (a); a nucleic acid sequence of (b); a nucleic acid sequence of (c); and a nucleic acid sequence of (d).

Also preferred are isolated retroviral particles comprising a plant retroviral sequence encoded by a nucleic acid sequence selected from the group consisting of:
- (a) a nucleic acid sequence which has more than 80% identity to a nucleic acid sequence selected from the group consisting of SEQ ID NO 1; SEQ ID NO 2; SEQ ID NO 3, wherein said identity can be determined using the DNAsis computer program and default parameters;
- (b) a nucleic acid sequence which encodes a nucleic acid selected from the group consisting of: SEQ ID NO 1; SEQ ID NO 2; and SEQ ID NO 3;
- (c) a nucleic acid sequence which encodes SEQ ID NO 4;
- (d) a nucleic acid sequence which encodes an amino acid sequence encoded by a nucleic acid sequence selected from the group consisting of: a nucleic acid sequence of (a); a nucleic acid sequence of (b); and a nucleic acid sequence of (c);
- (e) a nucleic acid sequence which encodes an allelic variant of an amino acid sequence encoded by a nucleic acid selected from the group consisting of: a nucleic acid sequence of (a); a nucleic acid sequence of (b); and a nucleic acid sequence of (c) and
- (f) a nucleic acid sequence fully complementary to a nucleic acid sequence selected from the group consisting of: a nucleic acid sequence of (a); a nucleic acid sequence of (b); a nucleic acid sequence of (c); a nucleic acid sequence of (e); and a nucleic acid sequence of (f).

Plant retroviral particles as described above, which further comprises an envelope-encoding nucleic acid sequence specifically described herein are preferred. Preferred are those retroviral particles which further comprise at least one nucleic acid sequence which encodes at least one agronomically-significant characteristic.

Also provided are methods to transfer nucleic acid into a plant cell, comprising contacting a plant retroviral particle as described above to at least one plant cell under conditions sufficient to allow said nucleic acid to enter said cell. More preferred are methods to impart agronomically-significant characteristics to a plant, comprising contacting a plant retroviral particle as described to at least one plant cell under conditions sufficient to allow said nucleic acid to enter said cell.

Also provided, as part of the present invention, are isolated nucleic acid having at least 20 contiguous nucleotides of the sequence shown in SEQ ID NO 17. "At least" means that this is the lower limit and the number can be any whole number increment up to the total number of bases in SEQ ID NO 17. For example, isolated nucleic acid sequences which are 25, 30, 35, 40, 45, 50, 55, 60, 65 and 70 are within the scope of the present invention.

The following paragraph is designed to elaborate on the best mode and is not indicative of the sole means for making and carrying out the present invention. This paragraph is not intended to be limiting. The best way to make the present nucleic acids is to clone the nucleic acids from the respective organisms or amplified from genomic cDNA by the polymerase chain reaction using appropriate primers. The best way to make the present retroelements is to assemble the nucleic acids using standard cloning procedures. Transcriptional controls can be manipulated by inserting enhancers in or near the 5' LTR. Marker genes or genes of interest can be inserted within the retroelement. The best way to make the present retroviral particles is to express the retroelement, preferably at high levels, in plant cells and the particles harvested by sucrose gradient fractionation. The best way to use the present nucleic acids is by allowing retroviral particles to come into contact with plant cells. Expression of marker genes carried by the retroelement can be used as one measure of infection and integration.

Also provided by the present invention are isolated nucleic acid molecules, wherein said nucleic acid molecule encodes at least a portion of a plant retroelement reverse transcriptase and comprises a nucleic acid sequence selected from the group consisting of:
  (a) a nucleic acid sequence having more than 85% identity to a nucleic acid sequence selected from the group consisting of even-numbered SEQ ID NOs inclusive from SEQ ID NO 42 to SEQ ID NO 164, wherein said identity can be determined using the DNAsis computer program and default parameters;
  (b) a nucleic acid sequence which encodes an amino acid sequence having more than 85% identity to an amino acid sequence selected from the group consisting of odd-numbered SEQ ID NOs inclusive from SEQ ID NO 43 through SEQ ID NO 165, wherein said identity can be determined using the DNAsis computer program and default parameters;
  (c) a nucleic acid sequence which encodes an allelic variant of a nucleic acid sequence selected from the group consisting of: a nucleic acid sequence of (a); a nucleic acid sequence of (b).
  (d) a nucleic acid sequence fully complementary to a nucleic acid sequence selected from the group consisting of: a nucleic acid sequence of (a); a nucleic acid sequence of (b).

Seeds and plants comprising the nucleic acid molecules are also provided, as are nucleic acids as described which comprise gag, pol and env genes and which comprises adenine-thymidine-guanidine as the gag gene start codon. Moreover, those nucleic acids which further comprises SEQ ID NO 5 are also provided. Also provided by the present invention are isolated nucleic acid molecules described, wherein said nucleic acid molecule encodes at least a portion of a plant envelope sequence and comprises a nucleic acid sequence selected from the group consisting of:
  (a) a nucleic acid sequence which has more than 90% identity to SEQ ID NO 5, wherein said identity can be determined using the DNAsis computer program and default parameters;
  (b) a nucleic acid sequence which encodes an amino acid sequence which has greater than 85% identity to SEQ ID NO 6, wherein said identity can be determined using the DNAsis computer program and default parameters;
  (c) a nucleic acid sequence which encodes an allelic variant of SEQ ID NO 5; and
  (d) a nucleic acid sequence fully complementary to a nucleic acid sequence selected from the group consisting of: a nucleic acid sequence of (a); a nucleic acid sequence of (b); and a nucleic acid sequence of c).

Plant cells comprising this embodiment are also provided. Methods to impart agronomically-significant characteristics to at least one plant cell, comprising:
  contacting a nucleic acid molecule described to at least one plant cell under conditions sufficient to allow at least one agronomically-significant nucleic acid molecule to enter said cell.

Also part of the present invention are isolated nucleic acid molecules, wherein said nucleic acid molecule encodes at least a portion of a plant retroelement reverse transcriptase and comprises a nucleic acid sequence selected from the group consisting of:
  (a) a nucleic acid sequence having more than 95% identity to a nucleic acid sequence selected from the group consisting of even-numbered SEQ ID NOs inclusive from SEQ ID NO 42 to SEQ ID NO 164, wherein said identity can be determined using the DNAsis computer program and default parameters;
  (b) a nucleic acid sequence which encodes an amino acid sequence having more than 95% identity to an amino acid sequence selected from the group consisting of odd-numbered SEQ ID NOs inclusive from SEQ ID NO 43 through SEQ ID NO 165, wherein said identity can be determined using the DNAsis computer program and default parameters;
  (c) a nucleic acid sequence which encodes an allelic variant of a nucleic acid sequence selected from the group consisting of: a nucleic acid sequence of (a); a nucleic acid sequence of (b).
  (d) a nucleic acid sequence fully complementary to a nucleic acid sequence selected from the group consisting of: a nucleic acid sequence of (a); a nucleic acid sequence of (b).

Seeds and plants comprising the nucleic acid molecules are also provided, as are nucleic acids as described which comprise gag, pol and env genes and which comprises adenine-thymidine-guanidine as the gag gene start codon. Moreover, those nucleic acids which further comprises SEQ ID NO 5 are also provided. Methods to impart agronomically-significant characteristics to at least one plant cell, comprising:
  contacting a nucleic acid molecule described to at least one plant cell under conditions sufficient to allow at least one agronomically-significant nucleic acid molecule to enter said cell.

Also provided are isolated nucleic acid molecule, wherein said nucleic acid molecule encodes at least a portion of a plant retroelement reverse transcriptase and comprises a nucleic acid sequence selected from the group consisting of:
  (a) a nucleic acid sequence selected from the group consisting of even-numbered SEQ ID NOs inclusive from SEQ ID NO 42 to SEQ ID NO 164, wherein said identity can be determined using the DNAsis computer program and default parameters;
  (b) a nucleic acid sequence which encodes an amino acid sequence selected from the group consisting of odd-numbered SEQ ID NOs inclusive from SEQ ID NO 43 through SEQ ID NO 165, wherein said identity can be determined using the DNAsis computer program and default parameters;
  (c) a nucleic acid sequence which encodes an allelic variant of a nucleic acid sequence selected from the group consisting of: a nucleic acid sequence of (a); a nucleic acid sequence of (b).

(d) a nucleic acid sequence fully complementary to a nucleic acid sequence selected from the group consisting of: a nucleic acid sequence of (a); a nucleic acid sequence of (b).

Seeds and plants comprising the nucleic acid molecules are also provided, as are nucleic acids as described which comprise gag, pol and env genes and which comprises adenine-thymidine-guanidine as the gag gene start codon. Moreover, those nucleic acids which further comprises SEQ ID NO 5 are also provided. Methods to impart agronomically-significant characteristics to at least one plant cell, comprising:

contacting a nucleic acid molecule described to at least one plant cell under conditions sufficient to allow at least one agronomically-significant nucleic acid molecule to enter said cell.

Nucleic acid molecules of the present invention which further comprise at least one nucleic acid sequence which encodes at least one agronomically-significant characteristic are also provided. Those nucleic acid molecules wherein the agronomically-significant characteristic is selected from the group consisting of: male sterility; self-incompatibility; foreign organism resistance; improved biosynthetic pathways; environmental tolerance; photosynthetic pathways; and nutrient content are preferred. Also preferred are those nucleic acid molecules wherein the agronomically significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

Also provided are isolated plant retroviral particles comprising a nucleic acid molecule of the present invention.

Preferred plants are selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus (including oranges, grapefruit etc.); hemp; oak; rice; petunia; orchids; Arabidopsis; broccoli; cauliflower, brussel sprouts; onion; garlic; leek; squash; pumpkin; celery; pea; bean (including various legumes); strawberries; grapes; apples; pears; peaches; banana; palm; cocoa; cucumber; pineapple; apricot; plum; sugar beet; lawn grasses; maple; triticale; safflower; peanut; and olive.

In these new aspects of the invention, it is understood that the materials and methods described previously are useful in obtaining the present materials. Moreover, the discussion as to scope and usefulness of the invention, including the percent identities, retroviral uses and constructs, plants transfected, methods for improving crops, etc. are applicable for the present new aspects as well. For instance, combination of the previously disclosed materials with the present materials are certainly within the scope of the present disclosure.

The following examples are not intended to limit the scope of the present invention as described and claimed. They are simply for the purpose of illustration.

EXAMPLES

Example 1

Characterizing the Arabidopsis Retroelements ("Tat" and "Athila" Elements)

Plant material and Southern hybridizations: The Arabidopsis Information Service supplied the following seed stocks (Kranz and Kirchheim (1987) Arabidopsis Inform. Serv. 24): Col-0, La-0, Kas-1, Co-4, Sei-0, Mv-0, Ll-0, Cvi-0, Fi-3, Ba-1, Hau-0, Aa-0, Ms0, Ag-0, Ge-0, No-0 and Mh-0. Genomic DNA was extracted using Qiagen genomic tips and protocols supplied by Qiagen. For Southern hybridizations, the resulting DNA was digested with EcoRI, electrophoresed on 0.8% agarose and transferred to Gene Screen Plus membranes using the manufacturer's alkaline transfer protocol (New England Nuclear). All hybridizations were performed as described. Church and Gilbert (1984) Proc. Natl. Acad. Sci. USA 81: 1991–1995.

Library screening, probe preparation and PCR: Tat1 clones were obtained by screening a Landsberg erecta (La-0) 1 phage library (Voytas et al. (1990) Genetics 126: 713–721), using a probe derived by PCR amplification of La-0 DNA. The primers for probe amplification were based on the three published Tat1 sequences (DVO 158, 5'-GGGATCCGCAATTAGAATCT-3' (SEQ ID NO:170); DVO0159, 5'-CGAATTCGGTCCACTTCGGA-3' (SEQ ID NO:171)). See, Peleman et al. (1991) Proc. Natl. Acad. Sci. USA 88:3618–3622. Subsequent probes were restriction fragments of cloned Tat1 elements, and all probes were radiolabeled by random priming (Promega). Long PCR was performed using the Expand Long Template PCR System (Boehringer Mannheim) with LTR-specific primers (DVO354, 5'-CCACAAGATTCTAATTGCGGATTC-3', SEQ ID NO:172; DVO355, 5'-CCGAAATGGACCGAACCCGACATC-3', SEQ ID NO:173). The protocol used was for PCR amplification of DNA up to 15 kb. The following PCR primers were used to confirm the structure of Tat1-3: DVO405 (5'-TTTCCAGGCTCTTGACGAGATTTG-3'; SEQ ID NO:174) for the 3' non-coding region, DVO385 (5'-CGACTCGAGCTCCATAGCGATG-3'; SEQ ID NO:175) for the second ORF of Tat1-3 (note that the seventh base was changed from an A to a G to make an XhoI and a SalI restriction site) and DVO371 (5'-CGGATTGGGCCGAAATGGACCGAA-3'; SEQ ID NO:176) for the 3' LTR.

DNA sequencing: Clones were sequenced either by the DNA sequencing facility at Iowa State University or with the finol sequencing kit (Promega). DNA from the I phage clones was initially subcloned into the vector pBluescript II KS- and transformed into the E. coli host strain XL1 Blue (Stratagene). AUSUBEL et al. (1987) Current Protocols in Molecular Biology. Greene/Wiley Interscience, New York. Subclones in the vector pMOB were used for transposon mutagenesis with the TN 1000 sequencing kit (Gold Biotechnologies). Transposon-specific primers were used for DNA sequencing reactions.

Sequence analysis: Sequence analysis was performed using the GCG software package (Devereux et al. (1984) Nucl. Acids Res. 12: 387–395), DNA Strider 1.2 (Marck (1991) DNA Strider 1.2, Gif-sur-Yvette, France), the BLAST search tool (Altschul et al. (1990) J. Mol. Biol. 215: 403–410) and the tRNAscan-SE 1.1 program (Lowe and Eddy (1997) Nucl. Acids Res. 25: 955–964). Phylogenetic relationships were determined by the neighbor-joining distance algorithm using Phylip (Felsenstein (1993) PHYLIP (Phylogeny Inference Package). Department of Genetics, University of Washington, Seattle; SAITOU and NEI (1987) Mol. Biol. Evol. 4: 406–425) and were based on reverse transcriptase amino acid sequences that had been aligned with ClustalW1.7. THOMPSON, et al. (1994) Nucl. Acids Res. 22: 4673–4680. Transmembrane helices were identified using the PHDhtm program. ROST et al. (1995) Prot. Science 4: 521–533. All DNA sequences have been submitted to the DDBS/EMBL/GenBank databases under the accession numbers X12345, X23456, X34567 and X45678.

RESULTS

Tat1 is a retrotransposon: Tat1 insertions share features with retrotransposon solo LTRs. We reasoned that if Tat1 is a retrotransposon, then there should be full-length elements in the genome consisting of two Tat1 sequences flanking an internal retrotransposon coding region. To test this hypothesis, additional Tat1 elements were isolated by screening a Landsberg (La-0) genomic DNA library with a Tat1 probe. Twenty-one I phage clones were isolated and Southern analysis revealed two clones (pDW42 and pDW99) each with two copies of Tat1 (data not shown). The two Tat1 elements in each clone were sequenced, along with the intervening DNA. All Tat1 sequences shared >89% nucleotide identity to the previously characterized Tat1a–Tat1c elements. Peleman et al. (1991) Proc. Natl. Acad. Sci. USA 88: 3618–3622. In clone pDW99, the 5' and 3' Tat1 sequences were 433 bases in length and only differed at two base positions. These Tat1 sequences also had conserved features of LTRs, including the dinucleotide end-sequences (5' TG-CA 3') that were part of 12 base inverted terminal repeats. If the two Tat1 elements in clone pDW99 were retrotransposon LTRs, then both, along with the intervening DNA, should be flanked by a target site duplication. A putative five base target site duplication (TATGT) was present immediately adjacent to the 5' and 3' Tat1 elements, supporting the hypothesis that they and the intervening DNA inserted as a single unit. In clone pDW42, the 5' Tat1 was 432 bases in length and shared 98% nucleotide sequence identity to the 3' Tat1. The last ~74 bases of the 3' Tat1 was truncated during library construction and lies adjacent to one phage arm. A target site duplication, therefore, could not be identified in this clone.

DNA sequences were analyzed for potential coding information between the 5' and 3' Tat1 elements. Nearly identical ORFs of 424 and 405 amino acids were found encoded between the Tat1 sequences in pDW42 and pDW99, respectively. The derived amino acid sequences of these ORFs were used to search the DNA sequence database with the BLAST search tool, and significant similarity was found to the Zea mays retrotransposable element Zeon-1 (p=4.4e-08). HU et al. (1995) Mol. Gen. Genet. 248: 471480. The ORFs have ~44% similarity across their entirety to the 628 amino acid ORF encoded by Zeon-1 (see below). The Zeon-1 ORF includes a zinc finger motif characteristic of retrotransposon gag protein RNA binding domains. Hu et al. (1995) Mol. Gen. Genet. 248: 471–480. Although the Tat1 ORFs do not include the zinc finger motif, the degree of similarity suggests that they are part of a related gag protein.

If the Tat1 sequences in pDW42 and pDW99 defined retrotransposon insertions, a PBS would be predicted to lie adjacent to the 5' Tat1 elements in both clones. The putative Tat1 PBS shares similarity with PBSs of Zeon-1 and another maize retrotransposon called Cinful (see below), but it is not complementary to an initiator methionine tRNA as is the case for most plant retrotransposons. Additionally, a possible polypurine tract (PPT), the primer for second strand cDNA synthesis, was observed one base upstream of the 3' Tat1 sequence in both phage clones (5'-GAGGACTTGGGGGGCAAA-3'; SEQ ID NO:177). We concluded from the available evidence that Tat1 is a retrotransposon, and we have designated the 3960 base insertion in pDW42 as Tat1-1 and the 3879 base insertion in pDW99 as Tat1-2. It is apparent that both Tat1-1 and Tat1-2 are non-functional. Their ORFs are truncated with respect to the coding information found in transposition-competent retrotransposons, and they lack obvious pol motifs.

In light of our findings, the previously reported Tat1 sequences can be reinterpreted. Tat1a and Tat1b, which are flanked by putative target site duplications, are solo LTRs. Tat1c, the only element without a target site duplication, is actually the 5' LTR and part of the coding sequence for a larger Tat1 element.

Copy number of Tat1 among A. thaliana ecotypes: To estimate Tat1 copy number, the 5' LTR, gag and the 3' non-coding region were used as separate probes in Southern hybridizations. The Southern filters contained genomic DNA from 17 ecotypes representing wild populations of A. thaliana from around the world. This collection of ecotypes had previously been used to evaluate retrotransposon population dynanics. Konieczny et al. (1991) Genetics 127: 801–809; Voytas et al. (1990) Genetics 126: 713–721; Wright et al. (1996) Genetics 142: 569–578. Based on the hybridization with the gag probe, element copy number ranges from two to approximately ten copies per ecotype. The copy number of the LTRs is higher, likely due to the presence of two LTRs flanking full-length elements or solo LTRs scattered throughout the genome. The Tat1 copy number contrasts with the copy numbers (typically less than three per ecotype) observed for 28 other A. thaliana retrotransposon families. Konieczny et al. (1991) Genetics 127: 801–809; Voytas et al. (1990) Genetics 126: 713–721; Wright et al. (1996) Genetics 142: 569–578. In addition, the Tat1-hybridizing restriction fragments are highly polymorphic among strains. This degree of polymorphism, coupled with the high copy number, suggested that Tat1 has been active in transposition since the separation of the ecotypes.

The Tat1 3' non-coding region contains DNA sequences from elsewhere in the genome: In an attempt to identify a complete and functional Tat1 element, LTR-specific primers were used in PCR reactions optimized for amplification of large DNA fragments. Most full-length retrotransposable elements are between five and six kb in length. DNAs from all 17 ecotypes were used as templates, and each gave amplification products of ~3.2 kb, the size predicted for Tat1-1 and Tat1-2 (data not shown). In La-0, however, a 3.8 kb PCR product was also recovered. This PCR product was cloned, sequenced and called Tat1-3. This insertion is expected to be about 4.6 kb in total length if the LTR sequences are included.

Tat1-3 differed from Tat1-1 and Tat1-2 in that it had two ORFs separated by stop codons and a 477 base insertion in the 3' non-coding region. The first ORF (365 amino acids) was similar to but shorter than the ORFs of the other Tat1 elements. The sequences constituting the second ORF (188 amino acids) were not present in the other Tat1 insertions and were not related to other sequences in the DNA databases. Database searches with the 477 base insertion in the 3' non-coding region, however, revealed three regions of similarity to other genomic sequences. A region of 113 bases matched a region of 26 bp repeats in the 5' untranslated sequence of the AT-P5C1 mRNA, which encodes pyrroline-5-carboxylate reductase (p=2.1e-19). Verbruggen et al. (1993) Plant Physiol. 103: 771–781. In addition, 50 bases appear to be a remnant of another retrotransposon related to Tat1. These 50 bases are 71% identical to the 3' end of the Tat1-3 LTR and the putative primer binding site. The putative primer binding site, however, is more closely related to those of other plant retrotransposons such as Huck-2 (Sanmiguel et al. (1996) Science 274: 765–768). Finally, sequences in the remainder of the insertion showed significant similarity to a region on chromosome 5. To confirm that Tat1-3 was not a PCR artifact, two additional primer pairs were used in separate amplifications. Both amplifications gave PCR products of the predicted sizes, which were cloned and confirmed to be Tat1-3 by DNA sequencing.

PCR amplifications with the additional primer pairs also yielded a product 0.8 kb longer than that expected for Tat1-3. This product was cloned, sequenced and found to be another Tat1 element, designated Tat1-4. This element has sequences similar to a Tat1 LTR, polypurine tract and the second ORF of Tat1-3. In Tat1-4, 1182 bases of DNA are found in the 3' non-coding region at the position corresponding to the 477 base insertion in Tat1-3. This region does not match any sequences in the DNA databases.

Other Tat1-like elements in *A. thaliana*: A BLAST search of DNA sequences generated by the *A. thaliana* genome project identified two more solo LTRs similar to Tat1. All share similarities throughout but most strikingly, they are very well conserved at the 5' and 3' ends where it is expected integrase would bind. Braiterman and Boeke (1994) Mol. Cell. Biol. 14: 5731–5740. These conserved end-sequences suggest that the integrases encoded by full-length elements are also related, and that the LTRs have evolved under functional constraints; that is, they are not simply degenerate Tat1 LTRs. The two new LTRs are designated as Tat2-1 and Tat3-1. Tat2-1 is 418 bases long, is flanked by a five base target site duplication (CTATT) and is ~63% identical to the Tat1-2 5' LTR. Tat3–1 is 463 bases long and is also flanked by a target site duplication (ATATT). Tat3-1 is ~53% identical to the Tat1 -2 5' LTR.

Tat1 and Athila are related to Ty3/gypsy retrotransposons: Further analysis of data from the *A. thaliana* genome project revealed two slightly degenerate retrotransposons with similarity to the Tat1 ORF. These elements were identified within the sequence of the P1 phage clones MXA21 (Accession AB005247; bases 54,977–66,874) and MX110 (Accession AB005248; bases 24,125–35,848). Each has two LTRs, a putative PBS, and long ORFs between their LTRs. The genetic organization of these elements is depicted in FIGS. 5A and 6A. Amino acid sequence analysis indicated the presence of an RNA binding domain that defines gag in both elements. This region is followed by conserved reverse transcriptase, RNaseH, and integrase amino acid sequence domains characteristic of pol (data not shown). Classification of eukaryotic retrotransposons into the Ty1/copia elements (Pseudoviridae) and Ty3/gypsy elements (Metaviridae) is based on pol gene structure. Boeke et al. (1998) Metaviridae. In Virus Taxonomy: ICTV VIIth Report, edited by F. A. Murphy. Springer-Verlag, N.Y.; Boeke et al. (1998b) Pseudoviridae. In Virus Taxonomy: ICTV VIIth Report, edited by F. A. Murphy. Springer Verlag, N.Y. The domain order of the pol genes (reverse transcriptase precedes integrase) and similarities among their encoded reverse transcriptase (see below) identifies these elements as the first full-length *A. thaliana* Ty3gypsy elements.

Because the characterized Tat1 insertions do not encode pol genes, this element family could not be classified. However, the amino acid sequence of the Tat1-2 ORF is 51% similar to the gag region of the MXA21 retrotransposon. Since plant retrotransposons within the Tylicopia or Ty3/gypsy families, even those with highly similar pol genes, share little amino acid sequence similarity in their gag regions, Tati is likely a Ty3/gypsy element. This conclusion is further supported by the report that the Tat-like Zeon-1 retrotransposon is very similar to a *Z. mays* Ty3/gypsy element called cinful (Bennetzen (1996) Trends Microbiol. 4: 347–353); however, only the 5' LTR and putative primer binding site (PBS) sequences are available in the sequence database for analysis (Accession U68402). Because of the extent of similarity to Tat1, we have named the MXA21 insertion Tat4- 1.

The gag region of the MX110 element is 62% similar (p=1.1e-193) to the first ORF of Athila, which has previously been unclassified (Pelissier et al. (1995) Plant Mol. Biol. 29: 441 452). This implies that Athila is also a Ty3/gypsy element, and we have designated the MX110 insertion as Athila1-1. Our classification of Athila as a Ty3/gypsy element is further supported by the observation that the Athila gag amino acid sequences shares significant similarity to the gag protein encoded by the cyclops-2 Ty3/gypsy retrotransposon of pea (Accession AJ000640; p=1.1e-46; data not shown). Further analysis of the available *A. thaliana* genome sequences identified three additional Athila homologs. They include an additional Athila1element, designated Athila 1-2, and two more distantly related Athila-like elements, designated Athila2-1 and Athila3-1.

In addition to similarities among their gag amino acid sequences, the Tat elements have short LTRs (<550 bp) and long 3' non-coding regions (>2 kb). In contrast, the Athila-like elements have long LTRs (>1.2 kb) and are very large retrotransposons (>11 kb). One additional feature to note about both the Athila-like and Tat-like elements is the high degree of sequence degeneracy of their internal coding regions. This contrasts with the near sequence identity of their 5' and 3' LTRs, which is typically greater than 95%. Because a single template is used in the synthesis of both LTRs, LTR sequences are usually identical at the time of integration. The degree of sequence similarity between the LTRs suggests that most elements integrated relatively recently. The polymorphisms observed in the internal domains of these insertions, therefore, may have been present in their progenitors, and these elements may have been replicated in trans.

A novel, conserved coding region in Athila elements: A surprising feature of Athila1-1 is the presence of an additional ORF after integrase. Like gag, this ORF shares significant similarity across its entirety (p=3.8e-08) to the second ORF of Athila. This ORF is also encoded by the Athila2-1 and Athila3-1 elements, although it is somewhat more degenerate. The presence of this coding sequence among these divergent retrotransposons suggests that it plays a functional role in the element replication cycle. However, the ORF shows no similarity to retrotransposon gag or pol genes. The retroviruses and some Ty3/gypsy retrotransposons encode an env gene after integrase. Although not well-conserved in primary sequence, both viral and retrotransposon envelope proteins share some structural similarities. They are typically translated from spliced mRNAs and the primary translation product encodes a signal peptide and a transmembrane domain near the C-terminus. All four families of Athila elements encode a domain near the center of the ORF that is strongly predicted to be a transmembrane region (70% –90% confidence, depending on the element analyzed) (ROST et al. (1995) Prot. Science 4: 521–533). Two retrotransposons, Athila and Athila2-1, also have a hydrophobic transmembrane domain near the 5' end of their env-like ORFs, which may serve as a secretory signal sequence. Von Heijne (1986) Nucl. Acids Res. 14: 4683–4690.

Two lineages of plant Ty3/gypsy retrotransposons: Relationships among Ty3/gypsy retrotransposons from *A. thaliana* and other organisms were assessed by constructing a neighbor-joining tree of their reverse transcriptase amino acid sequences. Included in the analysis were reverse transcriptases from two additional families of *A. thaliana* Ty3/gypsy elements that we identified from the unannotated genome sequence data (designated Tma elements; Tma1-1 and Tma3-1); two other Tma element families were identified in the genome sequence that did not encode complete reverse transcriptases (Tma2-1 and Tma4-1; Table 1). Also included in the phylogenetic analyses were reverse transcriptases from a faba bean retrotransposon and the cyclops-2 element from pea. The plant Ty3/gypsy group retrotransposons resolved into two lineages: One was made up of dell from lily, the IFG7 retrotransposon from pine, reina from Z. mays, and Tma1-1 and Tma3-1. This group of elements formed a single branch closely related to numerous fungal retrotransposons (branch 1). The second branch (branch 2) was well-separated from all other known Ty3/gypsy group elements, and was further resolved into two lineages: Athila1-1, cyclops-2 and the faba bean reverse transcriptase formed one lineage (the Athila branch), and Tat4-1 and Grande1-4 from Zea diploperennis formed a separate, distinct branch (the Tat branch).

Primer binding sites: Most plant Ty1/copia retrotransposons as well as the branch 1 Ty3/gypsy elements have PBSs complementary to the 3'-end of an initiator methionine tRNA. This is not the case for any of the branch 2 Ty3/gypsy elements. We compared the putative PBSs of Tat-branch and Athila-branch elements to known plant TRNA genes as well as to the 11 tRNA genes that had been identified to date in sequences generated by the *A. thaliana* genome project. In addition, we searched the unannotated *A. thaliana* genome sequences and identified 30 more *A. thaliana* TRNA genes using the program tRNAscan-SE (Lowe and Eddy (1997) Nucl. Acids Res. 25: 955–964). The PBS of Tat1 is complementary to 10 bases at the 3' end of the asparagine tRNA for the AAC codon; these 10 bases are followed by a two base mismatch and six additional bases of perfect complementarity. The Tat4-1 PBS is complementary to 20 bases at the 3' end of the arginine tRNA for the AGG codon with one mismatch 10 bases from the 3' end; Huck-2, Grande-zm1, Grande1-4, and the retrotransposon-like insertion in the 3' non-coding region of Tat1-3 all have 20-base perfect complementarity to this tRNA. The PBS of Athila1-1 is perfectly complementary to 15 bases at the 3' end of the aspartic acid TRNA for the GAC codon, and Athila and Athila2-1 have 13 bases of complementarity to this tRNA. At this time there is no known plant tRNA complementary to the PBS of Zeon-1, which has the same PBS as the maize retrotransposon cinful. As more tRNA sequences become available, a candidate primer may be identified for these elements. Example 2

Characterizing the Pisum Sativum Retroelement ("Cyclops" Element) Env Gene

After identifying the retrovirus-like elements in *A. thaliana*, the element called Cyclops2 from Pisum sativum (Chavanne et al. (1998) Plant Mol. Biol. 37:363–375) was examined. Comparison of this element to the Athila-like elements both in size and amino acid and nucleotide sequence composition was made. Cyclops2 also encodes an open reading frame (ORF) in the position corresponding to the env-like gene of the Athila elements. This Cyclops2 ORF was examined using the same methods used to characterize the Athila group env-like genes (see Example 1). The Cyclops2 ORF was found to have a potential splice site at its N-terminus and transmembrane domains at the N-terminus, the central region and the C-terminus. Based on the presence of these features, it was concluded that Cyclops2 is a retrovirus-like retroelement that encodes on env-like gene.

Example 3

Obtaining the Soybean Retroelements ("Calypso" Elements)

Materials and Methods

Library Screening and Southern Hybridization. A soybean genomic lambda phage library (line L85–3044) was initially screened with a reverse transcriptase probe under low stringency conditions (50 degrees Celsius with a 1% SDS wash) (Church and Gilbert (1984) Proc. Natl. Acad. Sci. USA 81:1991–1995). The library was previously described (Chen et al. (1998) Soybean Genetics Newsletter 25:132–134). The probe was obtained by PCR amplification of genornic *P. sativum* DNA using primers based on the reverse transcriptase of Cyclops2 ( DVO701 and DVO702). All probes were radio-labeled using random primers and protocols supplied by Promega (Madison, Wis.). For Southern hybridizations, DNA was digested, electrophoresed on 0.8% agarose gels, and transferred to Gene Screen Plus membranes using the manufactureris alkaline transfer protocol (New England Nuclear, Boston, Mass.). All high stringency hybridizations were as described (Church and Gilbert (1984) Proc. Natl. Acad. Sci. USA 81:1991–1995).

DNA sequencing. Lambda phage clones were subcloned into the vector pBluescript KSII - and transformed into the *E.coli* host strain XL1 Blue (Stratagene, La Jolla, Calif.) (Ausubel et al., Current Protocols in Molecular Biology (Greene Publishing Associates, Inc., 1993). Subclones were sequenced by primer walking at the Iowa State University DNA sequencing facility.

Sequence Analysis. DNA Sequence analysis was performed using the GCG software package (Devereux et al. (1984) Nucleic Acids Res. 12:387–395), DNA Strider 1.2 (Marck (1991) DNA Strider 1.2, Gif-sur-Yvette, France) and the BLAST search tool (Altschul et al. (1990) J. Mol. Biol. 215: 403410). Phylogenetic relationships were determined by the neighbor-joining distance algorithm (Saitou and Nei (1987) Mol. Biol. Evol. 4: 406425) using PAUP v4.0 beta 1 (Swofford (1993) Illinois Natural History Survey, Champaign, IL) and were based on reverse transcriptase amino acid sequences that had been aligned with ClustaIX v1.63b (Thompson et al. (1994) Nucl. Acids Res. 22: 4673–4680). Transmembrane helices were identified using the PHDhtrn program and TMPred (Rost et al. (1995) Prot. Science 4: 521–533; Hofmann and Stoffel (1993) Biol. Chem. 374:166).

Results

Retrovirus-like elements in Glycine max. Soybean retrovirus-like elements were identified by a low stringency (50 degrees C.) screen of a soybean lambda library using a reverse transcriptase probe. The probe was based on a sequence from Cyclops2 (Chavanne et al. (1998) Plant Mol. Biol. 37:363–375). The screen produced 63 lambda clones that appeared to contain a retrovirus-like reverse transcriptase based on hybridization to the probe. Thirty-five of these putative elements were sequenced to varying degrees and 24 encoded readily identifiable retrovirus-like sequences. Most of the elements were distantly related and had premature stop codons, frame shifts, deletions or insertions. A related group of three elements and another related pair were completely sequenced and analyzed. The three elements in the first group are referred to as Calypso1-1, Calypso1-2, and Calypso1-3. The elements in the second pair are referred to as Calypso2-1 and Calypso2-2. The remaining soybean retrovirus-like elements will be given the Calypso name and a sequential designator number based on their family grouping.

The Calypso retrovirus-like elements have the same overall structure and sequence homology as the previously described Athila and Cyclops elements. The elements are ~12 kb in length; they have a 5' LTR, a PBS (Primer Binding Site), a gag protein, a pol protein, a spacer, an env-like protein, another spacer region, a PPT (Polypurine Tract) and a 3' LTR. The LTRs vary from ~1.3 to ~1.5 kb in length and characteristically begin with TG and end with CA. The PBS is similar to that used by the Athila and Cyclops elements; it is 4 to 6 bases past the 5' LTR and matches the 3' end of a soybean aspartic acid tRNA for 18 to 19 bases with 1 mismatch. The fact that the sequences of the Calypso primer binding sites are shared with the *A. thaliana* and *P. sativum* retrovirus-like elements, indicates that this sequence is a unique marker for envelope-encoding retroelements. The gag protein extends ~850 amino acids and encodes a zinc finger domain (characterized by the amino acid motif Cxx-CxxxHxxxxC; SEQ ID NO:178) and a protease domain (characterized by the amino acid motif LIDLGA (SEQ ID NO:179)). These domains are located at approximately the same positions within gag as in other retroelements. The ~600 amino acid reverse transcriptase region follows gag and has the conserved plant retrovirus-like motifs which approximate the following amino acids: KTAF (SEQ ID NO:180), MP/SFGLCNA (SEQ ID NO:181), V/I/MEVFMDDFS/WV/I (SEQ ID NO:182), FELMCDASDYAI/VGAVLGQR (SEQ ID NO:183), and YATT/EKEL/MLAIVF/YAL/FEKFR/KSYLI/VGSR/KV (SEQ ID NO:184), respectively. The ~450 amino acid integrase domain has the plant retrovirus-like integrase motifs that approximate HCHxSxxGGH30xCDxCQR (SEQ ID NO:185) for the Zn finger as well as two other motifs that approximate WGIDFI/V/MGP (SEQ ID NO:186), and PYHPQTxGQA/VE (SEQ ID NO:187). After integrase, there is a ~0.7kb spacer then a ~450 amino acid env-like protein coding region. The env-like protein of the Calypso elements is well conserved through most of the ORF but conservation decreases toward the C-terminus. The conservation includes 2 or 3 presumed transmembrane domains and a putative RNA splice site acceptor. The coding sequence for the env-like protein is followed by a ~2 kb spacer and then a polypurine tract with the approximate sequence ATTTGGGGG/AANNT (SEQ ID NO:188). The 3' LTR starts immediately after the final T of the PPT.

Calypso elements are abundant and heterogeneous. The Calypso elements appear to be abundant in the soybean genome. High stringency Southern blots of soybean DNA probed with reverse transcriptase, gag or env-like sequences produced smeared hybridization patterns, suggesting that the elements are abundant and heterogeneous. Their heterogeneity was also supported by DNA sequence analysis, which revealed a maximum of 93% nucleotide identity among elements, and most elements averaged ~88% nucleotide identify. This identity can be region-specific or dispersed over the element's entirety. For example, reverse transcriptase, integrase and envelope-like coding regions may be well conserved, whereas the LTR, gag and spacer regions may have very little sequence conservation.

Phylogenetic analysis of Calypso reverse transcriptase. The reverse transcriptase of retroelements is the preferred protein for assessment of phylogenetic relationships (Xiong and Eickbush (1990) EMBO J. 9:3353–3362). This is due to the high degree of amino acid sequence conservation found in reverse transcriptase proteins from many sources. The Calypso retrovirus-like elements were compared to previously described Ty3/gypsy and retrovirus-like elements from plants, fungi and invertebrate animals. The Calypso elements formed a distinct group with other plant retrovirus-like elements from *A. thaliana* and *P. sativum* and *Faba bean*. This group did not include plant Ty3/gypsy elements that are members of the metavirus genus. This indicates that the plant retrovirus-like elements from these four plant species are closely related and form a new element group that may be present in all or most plant species.

The Calypso reverse transcriptase and integrase are well-conserved. Frame shifts in the retrovirus-like elements were repaired through sequence comparison between the retrovirus-like elements from *A. thaliana, P. sativum* and *G. max*. Restoration typically involved an insertion or deletion of a single nucleotide or a single nucleotide substitution. When the edited ORFs of seven plant retrovirus-like elements from three species were compared, it was found that the gag domain had very little conservation. The amino acid sequence around the protease domain was reasonably conserved (~50%) but the reverse transcriptase and integrase domains were highly conserved (~70%).

The env-like ORF of Calypso is well-conserved. Animal retrovirus env proteins share little in common. They are however cleaved into two functional units that consist of the surface (SU) and transmembrane (TM) peptides. The SU peptide contains a transmembrane secretory signal at the N-terminus. The TM peptide has two transmembrane domains, one at the N-terminus, which functions in membrane fusion, and another near the C-terminus, which acts as an anchor site. The retrovirus env protein is expressed from an RNA that is spliced near the beginning of the env ORF. There are currently nine Athila group elements from *A. thaliana* that have an identifiable env-like ORF. Alignment of the env-like amino acid sequence shows that there are five subgroups of env-like proteins in the Athila family. Three are distinct, four are closely related and another pair is closely related. As a whole, these env-like sequences share limited homology over the entire length of the ORF, but within subgroups, they share high homology (data not shown). Some of the Athila env-like proteins have an apparent secretory peptide and a central transmembrane domain, suggesting that they may have an env-like function.

Among the Calypso elements, seven have been characterized that encode env-like ORFs. These env-like ORFs form four families that have a high degree of overall sequence similarity beginning at the first methionine and continuing for three quarters of the ORF; sequence similarity falls off dramatically near the C-terminus. The amino acid sequence at the first methionine has the consensus sequence QMASR/KKRR/KA (SEQ ID NO:189), which appears to be a nuclear targeting signal, however, the program PSORT only predicts a 0.300 confidence level for this targeting role (Nakai and Horton (1999) Trends Biochem. Sci. 24:34–36). A similar sequence (ASKKRK; SEQ ID NO:190) is found at the same position in the env-like ORF of Cyclops2, suggesting that it serves a similar purpose. No other potential targeting peptide stands out from the sequence that has been analyzed so far. There is a conserved region that is predicted to be a transmembrane domain near the center of the Calypso env-like protein and a second transmembrane domain located at variable positions near the C-terminus. These may be the fusion and anchor functions of a TM peptide. It should also be noted that five of the seven ORFs are predicted to have a transmembrane domain that is just before and includes the first methionine. This N-terminal transmembrane domain may be a secretory signal of an SU peptide. The program TMpred estimates these transmembrane domains to be significant based on a score >500 (Hofmann and Stoffel (1993) Biol. Chem. 374:166). These three transmembrane domains are found in the Cyclops2 env-like protein at similar locations but at a reduced significance score. Another feature of the Calypso env-like ORF is the conserved splice site that is predicted to be at the first methionine by the program NetGene2 v. 2.4 with a confidence level of 1.00 (Hebsgaard et al. (1996) Nucleic Acids Res. 24:3439–3452); Brunak et al. (1991) J. Mol. Biol. 220:49–65). There are other less preferred putative splice sites in the region, but only the splice site near the methionine is optimally placed and conserved in all seven env-like ORFs.

Example 4

Obtaining the Generic Plant Retroelements ("Generic" Elements)

ClustalX v1.63b (Thompson et al. (1994) Nucl. Acids Res. 22: 4673–4680) was used to align nucleotide sequences of Calypso1-1, Calypso1-2 and Calypso1-3. A consensus sequence was generated from the ClustalX output. The consensus sequence file was then translated and compared using ClustalX to amino acid sequences of retrovirus-like elements from soybean, pea (Cyclops2) and *A. thaliana* (Athila-like elements) using the GCG computer software package (Devereux et al. (1984) Nucleic Acids Res. 12:387–395). For coding regions encompassing protease, reverse transcriptase and integrase, a new consensus sequence was generated that best matched the coding information in all elements. This second consensus sequence forms the protease, reverse transcriptase and integase genes of the generic element The gag gene of the generic element is a consensus sequence generated by editing alignments between Calypso1-1 and Calypso2-2. The env gene is a consensus sequence based on env gene sequence alignments of all Calypso elements. All non-coding regions for the generic element were obtained>from Calypso1-2, with the exception of the LTRs, which were taken from Calypso1-1. A generic retrovirus will be constructed by first generating a DNA sequence that approximates the sequence of the generic element. An element that closely matches the consensus—for example, Calypso1-1-1—will be modified by PCR-based site-directed mutagenesis (Ausubel et al., Current Protocols in Molecular Biology (Greene Publishing Associates, Inc., 1993). Modifications will be sequentially introduced into the starting element until it conforms to the sequence of the generic element.

The generic element will be modified so that it will be expressed at high levels in plant cells. This will be accomplished by inserting an enhancer —such as the cauliflower mosaic virus 35S enhancer—into the 5' LTR. To monitor replication, a marker gene will be inserted into the virus between the end of the coding region for the env gene and the polypurine tract. The marker gene may encode resistance to an herbicide or antibiotic. The modified generic element will then be introduced into plant cells by standard means of plant transformation. Because the modified generic element will be expressed at high levels, retroviral particles will be produced by the host plant cell. These will be harvested and purified by passing cell lysates over sucrose density gradients.

The plant retroviral particles will be incubated in the presence of non-transformed plant cells. The virus will associate with the plant cell and fuse with the plant cell membrane. The mRNA carried by the virus will be reverse transcribed and the resultant cDNA will be integrated into the genome of the plant. The integration of the viral DNA and the expression of the marker gene it carries will confer antibiotic resistance to the plant cell. Cells that carry integrated viruses can be identified through genetic selection.

Example 5

Obtaining a Library of Reverse Transcriptase Sequences

The degenerate oligos DVOI 197 (5' GTG-CGN-AAR-GAR-GTN-NTN-AAR-YT 3' (SEQ ID NO:166) for the N terminal amino acid sequence VRKEVLKL (SEQ ID NO:167)) and DVO 1198 (5' AAC-YTT-NGW-RAA-RTC-YTT-DAT-RAA 3' (SEQ ID NO:168) for the C terminal amino acid sequence VKSFDKIF (SEQ ID NO:169)) were used to amplify the Xiong/Eickbush plant retrovirus reverse transcriptase domain from genomic DNA of the following plants: New sequences were obtained from *Nicotiana tabacum* (Tobacco), *Platanus occidentalis* (Sycamore), *Gossypium hirsutum* (Cotton), *Lycopersicon esculentum* (Tomato) *Solanum tuberosum* (Potato), *Oryza satvia* (Rice), *Triticum aestivun* (Wheat), *Hordeum vulgare* (Barley), *Sorghum bicolor* (Sorghum), *Avena sativa* (Oat), *Secale cereale* (Rye). No sequence was obtained fro *Pinus coulteri* (Bigcone pine), *Zea mays* (Corn), *Zea mays* subspecies *parviglumis* (Teosinte), and a Tripsacum species. A positive control for PCR was used to obtain previously known sequences from: *Arabidopsis thaliana, Pisum sativum* (pea) and three varieties (Hark 89, L85 and Williams) of *Glycine max* (soybean).

The conditions for PCR were as follows: 50 microliter reactions were set up with 5 microliters of Promega Taq enzyme buffer, 1 microliter of Taq enzyme, 5 microliters of Promega 25 millimolar magnesium chloride, 100 nanograms genomic DNA, 5 microliters of 2.5 millimolar Promega dNTP (deoxynucleotide mixture) and 7.5 microliters of each oligo from a 20 picomole/microliter solution. The reaction volume was brought to 50 microliters with deionized water. PCR was done with a 92 degrees Celsius melting temperature for 2 minutes for the first cycle and 20 seconds for each cycle thereafter, 50 degrees Celsius annealing temperature for 30 seconds and 72 degrees Celsius extension for 1 minute 30 seconds. There was a total of thirty cycles. Based on known sequence data, a 762 base pair band was expected for each PCR reaction.

The PCR reactions were run out on a 0.8% agarose gel, the approximately sized 762 based pair band was excised for each species and ligated to a T-vector pBLUESCRIPT II KS-. The ligations were transformed into the *E.coli* strain XLI BLUE, selected and sequenced. The results are in the Sequence Listing, at SEQ ID Nos 42 through 165, with the even numbered sequences in that range being the DNA sequences identified, and the odd-numbered sequences being the amino acid sequences deduced from the DNA sequences.

Although the present invention has been fully described herein, it is to be noted that various changes and modifications are apparent to those skilled in the art. Such changes and modifications are to be understood as included within the scope of the present invention as defined by the appended claims.

What is claimed is:

1. An isolated nucleic acid molecule comprising a nucleotide sequence selected from the group consisting of:
   (a) the sequence set forth in SEQ ID NO:62;
   (b) a sequence encoding a polypeptide having the amino acid sequence set forth in SEQ ID NO:63; and
   (c) a sequence fully complementary to (a) or (b).

2. A transformed seed containing a recombinant construct comprising the nucleic acid of claim 1.

3. A transformed plant containing a recombinant construct comprising the nucleic acid of claim 1.

4. The nucleic acid molecule of claim 1, which further comprises at least one nucleic acid sequence which encodes at least one agronomically-significant characteristic.

5. The nucleic acid molecule of claim 1, wherein said nucleic acid molecule encodes a polypeptide having the amino acid sequence set forth in SEQ ID NO:63.

6. The nucleic acid molecule of claim 1, wherein a pol coding sequence comprises said nucleic acid.

7. The nucleic acid molecule of claim 1, wherein said nucleotide sequence is the sequence set forth in SEQ ID NO:62.

8. The nucleic acid molecule of claim 6, said nucleic acid further comprising a gag coding sequence and an env coding sequence, wherein adenine-thymidine-guanidine is the gag coding sequence start codon.

9. The plant of claim 3, which plant is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; cabbage; oat; rye; cotton; flax; potato; pine; walnut; citrus; hemp; oak; nice; penmia; orchids; Arabidopsis; broccoli; cauliflower; brussel sprouts; onion; garlic; leek; squash; pumpkin; celery; pea; bean; strawberries; grapes; apples; pears; peaches; banana; palm; cocoa; cucumber; pineapple; apricot; plum; sugar beet; lawn grasses; maple; triticale; safflower; peanut; and olive.

10. The nucleic acid molecule of claim 4, wherein the agronomically-significant characteristic is selected from the group consisting of: male sterility; self-incompatibility; foreign organism resistance; improved biosynthetic pathways; environmental tolerance; photosynthetic pathways; and nutrient content.

11. The nucleic acid molecule of claim 4, wherein the agronomically-significant characteristic is selected from the group consisting of: fruit ripening; oil biosynthesis; pigment biosynthesis; seed formation; starch metabolism; salt tolerance; cold/frost tolerance; drought tolerance; tolerance to anaerobic conditions; protein content; carbohydrate content (including sugars and starches); amino acid content; and fatty acid content.

12. A transformed seed containing a recombinant construct comprising the nucleic acid of claim 5.

13. A transformed plant containing a recombinant construct comprising the nucleic acid of claim 5.

14. The nucleic acid molecule of claim 5, wherein a pol coding sequence comprises said nucleic acid.

15. The nucleic acid molecule of claim 14, said nucleic acid further comprising a gag coding sequence and an env coding sequence, wherein adenine-thymidine-guanidine is the gag coding sequence start codon.

* * * * *

UNITED STATES PATENT AND TRADEMARK OFFICE
CERTIFICATE OF CORRECTION

PATENT NO.   : 6,720,479 B1
DATED        : April 13, 2004
INVENTOR(S)  : David A. Wright and Daniel F. Voytas It is certified that error appears in the above-identified patent and that said Letters Patent is hereby corrected as shown below:

Column 286,
Line 1, please delete "penmia" and insert -- petunia -- therefor.

Signed and Sealed this

Eighth Day of February, 2005

JON W. DUDAS
*Director of the United States Patent and Trademark Office*

SEQUENCE LISTING

<160> NUMBER OF SEQ ID NOS: 190

<210> SEQ ID NO 1
<211> LENGTH: 18
<212> TYPE: DNA
<213> ORGANISM: Glycine max

<400> SEQUENCE: 1
tggcgccgtt gccaattg                                                       18

<210> SEQ ID NO 2
<211> LENGTH: 18
<212> TYPE: DNA
<213> ORGANISM: Glycine max

<400> SEQUENCE: 2
tggcgccgtt gtcgggga                                                       18

<210> SEQ ID NO 3
<211> LENGTH: 6
<212> TYPE: DNA
<213> ORGANISM: Glycine max

<400> SEQUENCE: 3 ttgggg                                                                     6

<210> SEQ ID NO 4
<211> LENGTH: 7
<212> TYPE: PRT
<213> ORGANISM: Artificial Sequence
<220> FEATURE:
<223> OTHER INFORMATION: plant retroelement sequence

<400> SEQUENCE: 4

Met Ala Ser Arg Lys Arg Lys
 1               5

<210> SEQ ID NO 5
<211> LENGTH: 1263
<212> TYPE: DNA
<213> ORGANISM: Artificial Sequence
<220> FEATURE:
<223> OTHER INFORMATION: plant retroelement sequence

<400> SEQUENCE: 5
atggcctccc gtaaacgcaa agctgtgccc acacccgggg aagcgtccaa ctgggactct          60
tcacgtttca ctttcgagat tgcttggcac agataccagg atagcattca gctccggaac        120
atccttccag agaggaatgt agagcttgga ccagggatgt ttgatgagtt cctgcaggaa        180
ctccagaggc tcagatggga ccaggttctg acccgacttc agagaagtg gattgatgtt        240 gctctggtga aggagtttta ctccaaccta tatgatccag aggaccacag tccgaagttt        300
tggagtgttc gaggacaggt tgtgagattt gatgctgaga cgattaatga tttcctcgac        360
accccggtca tcttggcaga gggagaggat tatccagcct actctcagta cctcagcact        420
cctccagacc atgatgccat cctttccgct ctgtgtactc caggggacg atttgttctg        480 aatgttgata gtgccccctg gaagctgctg cggaaggatc tgatgacgct cgcgcagaca        540
tggagtgtgc tctcttattt taaccttgca ctgacttttc acacttctga tattaatgtt        600
gacagggccc gactcaatta tggcttggtg atgaagatgg acctggacgt gggcagcctc        660

-continued

```
atttctcttc agatcagtca gatcgcccag tccatcactt ccaggcttgg gttcccagcg    720
ttgatcacaa cactgtgtga gattcagggg gttgtctctg atacccctgat ttttgagtca   780 ctcagtcctg tgatcaacct tgcctacatt aagaagaact gctggaaccc tgccgatcca   840
tctatcacat tcaggggac cgccgcacg cgcaccagag cttcggcgtc ggcatctgag    900
gctcctcttc catcccagca tccttctcag ccttttttccc agagaccacg gcctccactt   960
ctatccacct cagcacctcc atacatgcat ggacagatgc tcaggtcctt gtaccagggt  1020
cagcagatca tcattcagaa cctgtatcga ttgtccctac atttgcagat ggatctgcca  1080
ctcatgactc cggaggccta tcgtcagcag gtcgccaagc taggagacca gccctccact  1140
gacagggggg aagagccttc tggagccgct gctactgagg atcctgccgt tgatgaagac  1200
ctcatagctg acttggctgg cgctgattgg agcccatggg cagacttggg cagaggcagc  1260
tga                                                                1263
```

<210> SEQ ID NO 6
<211> LENGTH: 421
<212> TYPE: PRT
<213> ORGANISM: Artificial Sequence
<220> FEATURE:
<223> OTHER INFORMATION: plant retroelement sequence

<400> SEQUENCE: 6

```
Met Ala Ser Arg Lys Arg Lys Ala Val Pro Thr Pro Gly Glu Ala Ser
 1               5                  10                  15

Asn Trp Asp Ser Ser Arg Phe Thr Phe Glu Ile Ala Trp His Arg Tyr
             20                  25                  30

Gln Asp Ser Ile Gln Leu Arg Asn Ile Leu Pro Glu Arg Asn Val Glu
         35                  40                  45

Leu Gly Pro Gly Met Phe Asp Glu Phe Leu Gln Glu Leu Gln Arg Leu
     50                  55                  60

Arg Trp Asp Gln Val Leu Thr Arg Leu Pro Glu Lys Trp Ile Asp Val
 65                  70                  75                  80

Ala Leu Val Lys Glu Phe Tyr Ser Asn Leu Tyr Asp Pro Glu Asp His
                 85                  90                  95

Ser Pro Lys Phe Trp Ser Val Arg Gly Gln Val Val Arg Phe Asp Ala
            100                 105                 110

Glu Thr Ile Asn Asp Phe Leu Asp Thr Pro Val Ile Leu Ala Glu Gly
        115                 120                 125

Glu Asp Tyr Pro Ala Tyr Ser Gln Tyr Leu Ser Thr Pro Pro Asp His
    130                 135                 140

Asp Ala Ile Leu Ser Ala Leu Cys Thr Pro Gly Gly Arg Phe Val Leu
145                 150                 155                 160

Asn Val Asp Ser Ala Pro Trp Lys Leu Leu Arg Lys Asp Leu Met Thr
                165                 170                 175

Leu Ala Gln Thr Trp Ser Val Leu Ser Tyr Phe Asn Leu Ala Leu Thr
            180                 185                 190

Phe His Thr Ser Asp Ile Asn Val Asp Arg Ala Arg Leu Asn Tyr Gly
        195                 200                 205

Leu Val Met Lys Met Asp Leu Asp Val Gly Ser Leu Ile Ser Leu Gln
    210                 215                 220

Ile Ser Gln Ile Ala Gln Ser Ile Thr Ser Arg Leu Gly Phe Pro Ala
225                 230                 235                 240

Leu Ile Thr Thr Leu Cys Glu Ile Gln Gly Val Val Ser Asp Thr Leu
                245                 250                 255
```

```
Ile Phe Glu Ser Leu Ser Pro Val Ile Asn Leu Ala Tyr Ile Lys Lys
            260                 265                 270

Asn Cys Trp Asn Pro Ala Asp Pro Ser Ile Thr Phe Gln Gly Thr Arg
        275                 280                 285

Arg Thr Arg Thr Arg Ala Ser Ala Ser Ala Ser Glu Ala Pro Leu Pro
    290                 295                 300

Ser Gln His Pro Ser Gln Pro Phe Ser Gln Arg Pro Arg Pro Pro Leu
305                 310                 315                 320

Leu Ser Thr Ser Ala Pro Pro Tyr Met His Gly Gln Met Leu Arg Ser
            325                 330                 335

Leu Tyr Gln Gly Gln Gln Ile Ile Ile Gln Asn Leu Tyr Arg Leu Ser
            340                 345                 350

Leu His Leu Gln Met Asp Leu Pro Leu Met Thr Pro Glu Ala Tyr Arg
        355                 360                 365

Gln Gln Val Ala Lys Leu Gly Asp Gln Pro Ser Thr Asp Arg Gly Glu
    370                 375                 380

Glu Pro Ser Gly Ala Ala Ala Thr Glu Asp Pro Ala Val Asp Glu Asp
385                 390                 395                 400

Leu Ile Ala Asp Leu Ala Gly Ala Asp Trp Ser Pro Trp Ala Asp Leu
            405                 410                 415

Gly Arg Gly Ser Glx
            420

<210> SEQ ID NO 7
<211> LENGTH: 1596
<212> TYPE: DNA
<213> ORGANISM: Artificial Sequence
<220> FEATURE:
<223> OTHER INFORMATION: plant retroelement sequence

<400> SEQUENCE: 7
atgcgaggta gaactgcatc tggagacgtt gttcctatta acttagaaat tgaagctacg      60
tgtcggcgta caacgctgc aagaagaaga agggagcaag acatagaagg aagtagttac     120
acctcacctc ctccttctcc aaattatgct cagatggacg gggaaccggc acaaagagtc     180
acactagagg acttctctaa taccaccact cctcagttct ttacaagtat cacaaggccg     240
gaagtccaag cagatctcct tactcaaggg aacctcttcc atggtcttcc aaatgaagat     300
ccatatgcgc atctagcctc atacatagag atatgcagca ccgttaaaat cgccggagtt     360
ccaaaagatg cgatactcct taacctcttt tccttttccc tagcaggaga ggcaaaaaga     420
tggttgcact cctttaaagg caatagctta agaacatggg aagaagtagt ggaaaaattc     480
ttaaagaagt atttcccaga gtcaaagacc gtcgaacgaa agatggagat tcttatttc     540 catcaatttc tggatgaatc ccttagcgaa gcactagacc atttccacgg attgctaaga     600
aaaacaccaa cacacagata cagcgagcca gtacaactaa acatattcat cgatgacttg     660
caactcttaa tcgaaacagc tactagaggg aagatcaagc tgaagactcc cgaagaagcg     720
atggagctcg tcgagaacat ggcggctagc gatcaagcaa tccttcatga tcacacttat     780
gttcccacaa aaagaagcct cttggagctt agcacgcagg acgcaacttt ggtacaaaac     840
aagctgttga cgaggcagat agaagccctc atcgaaaccc tcagcaagct gcctcaacaa     900
ttacaagcga taagttcttc ccactcttct gttttgcagg tagaagaatg ccccacatgc     960
agagggacac atgagcctgg acaatgtgca agccaacaag acccctctcg tgaagtaaat    1020
tatataggca tactaaatcg ttacggattt cagggctaca accagggaaa tccatctgga    1080
```

-continued

```
ttcaatcaag gggcaacaag atttaatcac gagccaccgg ggtttaatca aggaagaaac    1140
ttcatgcaag gctcaagttg gacgaataaa ggaaatcaat ataaggagca aaggaaccaa    1200
ccaccatacc agccaccata ccagcaccct agccaaggtc cgaatcagca agaaaagccc    1260
accaaaatag aggaactgct gctgcaattc atcaaggaga caagatcaca tcaaaagagc    1320
acggatgcag ccattcggaa tctagaagtt caaatgggcc aactggcgca tgacaaagcc    1380
gaacggccca ctagaacttt cggtgctaac atggagagaa gaaccccaag gaaggataaa    1440
gcagtactga ctagagggca gagaagagcg caggaggagg gtaaggttga aggagaagac    1500
tggccagaag aaggaaggac agagaagaca gaagaagaag agaaggtggc agaagaacct    1560
aagcgtacca agagccagag agcaagggaa gccaag                              1596
```

<210> SEQ ID NO 8
<211> LENGTH: 532
<212> TYPE: PRT
<213> ORGANISM: Artificial Sequence
<220> FEATURE:
<223> OTHER INFORMATION: plant retroelement sequence

<400> SEQUENCE: 8

```
Met Arg Gly Arg Thr Ala Ser Gly Asp Val Val Pro Ile Asn Leu Glu
 1               5                  10                  15

Ile Glu Ala Thr Cys Arg Arg Asn Asn Ala Ala Arg Arg Arg Arg Glu
                20                  25                  30

Gln Asp Ile Glu Gly Ser Ser Tyr Thr Ser Pro Pro Ser Pro Asn
            35                  40                  45

Tyr Ala Gln Met Asp Gly Glu Pro Ala Gln Arg Val Thr Leu Glu Asp
        50                  55                  60

Phe Ser Asn Thr Thr Thr Pro Gln Phe Phe Thr Ser Ile Thr Arg Pro
 65                  70                  75                  80

Glu Val Gln Ala Asp Leu Leu Thr Gln Gly Asn Leu Phe His Gly Leu
                85                  90                  95

Pro Asn Glu Asp Pro Tyr Ala His Leu Ala Ser Tyr Ile Glu Ile Cys
            100                 105                 110

Ser Thr Val Lys Ile Ala Gly Val Pro Lys Asp Ala Ile Leu Leu Asn
        115                 120                 125

Leu Phe Ser Phe Ser Leu Ala Gly Glu Ala Lys Arg Trp Leu His Ser
130                 135                 140

Phe Lys Gly Asn Ser Leu Arg Thr Trp Glu Glu Val Val Glu Lys Phe
145                 150                 155                 160

Leu Lys Lys Tyr Phe Pro Glu Ser Lys Thr Val Glu Arg Lys Met Glu
                165                 170                 175

Ile Ser Tyr Phe His Gln Phe Leu Asp Glu Ser Leu Ser Glu Ala Leu
            180                 185                 190

Asp His Phe His Gly Leu Leu Arg Lys Thr Pro Thr His Arg Tyr Ser
        195                 200                 205

Glu Pro Val Gln Leu Asn Ile Phe Ile Asp Asp Leu Gln Leu Leu Ile
    210                 215                 220

Glu Thr Ala Thr Arg Gly Lys Ile Lys Leu Lys Thr Pro Glu Glu Ala
225                 230                 235                 240

Met Glu Leu Val Glu Asn Met Ala Ala Ser Asp Gln Ala Ile Leu His
                245                 250                 255

Asp His Thr Tyr Val Pro Thr Lys Arg Ser Leu Leu Glu Leu Ser Thr
            260                 265                 270
```

-continued

```
Gln Asp Ala Thr Leu Val Gln Asn Lys Leu Leu Thr Arg Gln Ile Glu
            275                 280                 285
Ala Leu Ile Glu Thr Leu Ser Lys Leu Pro Gln Gln Leu Gln Ala Ile
            290                 295                 300
Ser Ser Ser His Ser Ser Val Leu Gln Val Glu Glu Cys Pro Thr Cys
305                 310                 315                 320
Arg Gly Thr His Glu Pro Gly Gln Cys Ala Ser Gln Gln Asp Pro Ser
                325                 330                 335
Arg Glu Val Asn Tyr Ile Gly Ile Leu Asn Arg Tyr Gly Phe Gln Gly
                340                 345                 350
Tyr Asn Gln Gly Asn Pro Ser Gly Phe Asn Gln Gly Ala Thr Arg Phe
                355                 360                 365
Asn His Glu Pro Pro Gly Phe Asn Gln Gly Arg Asn Phe Met Gln Gly
                370                 375                 380
Ser Ser Trp Thr Asn Lys Gly Asn Gln Tyr Lys Glu Gln Arg Asn Gln
385                 390                 395                 400
Pro Pro Tyr Gln Pro Pro Tyr Gln His Pro Ser Gln Gly Pro Asn Gln
                405                 410                 415
Gln Glu Lys Pro Thr Lys Ile Glu Glu Leu Leu Leu Gln Phe Ile Lys
                420                 425                 430
Glu Thr Arg Ser His Gln Lys Ser Thr Asp Ala Ala Ile Arg Asn Leu
            435                 440                 445
Glu Val Gln Met Gly Gln Leu Ala His Asp Lys Ala Glu Arg Pro Thr
            450                 455                 460
Arg Thr Phe Gly Ala Asn Met Glu Arg Arg Thr Pro Arg Lys Asp Lys
465                 470                 475                 480
Ala Val Leu Thr Arg Gly Gln Arg Arg Ala Gln Glu Glu Gly Lys Val
                485                 490                 495
Glu Gly Glu Asp Trp Pro Glu Glu Gly Arg Thr Glu Lys Thr Glu Glu
                500                 505                 510
Glu Glu Lys Val Ala Glu Glu Pro Lys Arg Thr Lys Ser Gln Arg Ala
            515                 520                 525
Arg Glu Ala Lys
            530

<210> SEQ ID NO 9
<211> LENGTH: 603
<212> TYPE: DNA
<213> ORGANISM: Artificial Sequence
<220> FEATURE:
<223> OTHER INFORMATION: plant retroelement sequence

<400> SEQUENCE: 9
tgtgataaat gccagagaac agggggata tctcgaagaa atgagatgcc tttgcagaat     60
atcatggaag tagagatctt tgactgttgg ggcatagact tcatgggcc ttttccttcg    120 tcatacggga atgtctacat cttggtagct gtggattacg tctccaaatg ggtggaagcc   180
atagccacgc caaaggacga tgccagggta gtgatcaaat ttctgaagaa gaacattttt   240
tcccgttttg gagtcccacg agccttgatt agtgataggg gaacgcactt ctgcaacaat   300
cagttgaaga aagtcctgga gcactataat gtccgacata aggtggccac acctatcac   360 cctcagacaa atggccaagc agaaatttct aacagggagc tcaagcgaat cctggaaaag   420
acagttgcat caacaagaaa ggattggtcc ttgaagctcg atgatgctct ctgggcctat   480
```

| | |
|---|---|
| aggacagcgt tcaagactcc catcggctta tcaccatttc agctagtgta tgggaaggca | 540 |
| tgtcattac cagtggagct ggagtacaaa gcatattggg ctctcaagtt gctcaactt | 600 |
| gac | 603 |

<210> SEQ ID NO 10
<211> LENGTH: 201
<212> TYPE: PRT
<213> ORGANISM: Artificial Sequence
<220> FEATURE:
<223> OTHER INFORMATION: plant retroelement sequence

<400> SEQUENCE: 10

```
Cys Asp Lys Cys Gln Arg Thr Gly Gly Ile Ser Arg Arg Asn Glu Met
 1               5                  10                  15

Pro Leu Gln Asn Ile Met Glu Val Glu Ile Phe Asp Cys Trp Gly Ile
            20                  25                  30

Asp Phe Met Gly Pro Phe Pro Ser Ser Tyr Gly Asn Val Tyr Ile Leu
        35                  40                  45

Val Ala Val Asp Tyr Val Ser Lys Trp Val Glu Ala Ile Ala Thr Pro
    50                  55                  60

Lys Asp Asp Ala Arg Val Val Ile Lys Phe Leu Lys Lys Asn Ile Phe
65                  70                  75                  80

Ser Arg Phe Gly Val Pro Arg Ala Leu Ile Ser Asp Arg Gly Thr His
                85                  90                  95

Phe Cys Asn Asn Gln Leu Lys Lys Val Leu Glu His Tyr Asn Val Arg
            100                 105                 110

His Lys Val Ala Thr Pro Tyr His Pro Gln Thr Asn Gly Gln Ala Glu
        115                 120                 125

Ile Ser Asn Arg Glu Leu Lys Arg Ile Leu Glu Lys Thr Val Ala Ser
    130                 135                 140

Thr Arg Lys Asp Trp Ser Leu Lys Leu Asp Asp Ala Leu Trp Ala Tyr
145                 150                 155                 160

Arg Thr Ala Phe Lys Thr Pro Ile Gly Leu Ser Pro Phe Gln Leu Val
                165                 170                 175

Tyr Gly Lys Ala Cys His Leu Pro Val Glu Leu Glu Tyr Lys Ala Tyr
            180                 185                 190

Trp Ala Leu Lys Leu Leu Asn Phe Asp
        195                 200
```

<210> SEQ ID NO 11
<211> LENGTH: 600
<212> TYPE: DNA
<213> ORGANISM: Artificial Sequence
<220> FEATURE:
<223> OTHER INFORMATION: plant retroelement sequence

<400> SEQUENCE: 11

| | |
|---|---|
| ttggaggctg ggctcatata ccccatctct gacagcgctt gggtaagccc agtacaggtg | 60 |
| gttcccaaga aagtggaat gacagtggta cgagatgaga ggaatgactt gataccaaca | 120 |
| cgaactgtca ctggttggcg aatgtgtatc gactatcgca agctgaatga agccacacgg | 180 |
| aaggaccatt tcccttacc tttcatggat cagatgctgg agagacttgc agggcaggca | 240 |
| tactactgtt tcttggatgg atactcggga tacaaccaga tcgcggtaga ccccagagat | 300 |
| caggagaaga cggcctttac atgccccttt ggcgtctttg cttacagaag gatgccattc | 360 |
| gggttatgta atgcaccagc cacatttcag aggtgcatgc tggccatttt ttcagacatg | 420 |

-continued

```
gtggagaaaa gcatcgaggt atttatggac gacttctcgg tttttggacc ctcatttgac      480
agctgtttga ggaacctaga gagggtactt cagaggtgcg aagagactaa cttggtactg      540
aattgggaaa agtgtcattt catggttcga gagggcatag tcctaggcca caagatctca      600
```

<210> SEQ ID NO 12
<211> LENGTH: 200
<212> TYPE: PRT
<213> ORGANISM: Artificial Sequence
<220> FEATURE:
<223> OTHER INFORMATION: plant retroelement sequence

<400> SEQUENCE: 12

```
Leu Glu Ala Gly Leu Ile Tyr Pro Ile Ser Asp Ser Ala Trp Val Ser
 1               5                  10                  15

Pro Val Gln Val Val Pro Lys Lys Gly Gly Met Thr Val Val Arg Asp
            20                  25                  30

Glu Arg Asn Asp Leu Ile Pro Thr Arg Thr Val Thr Gly Trp Arg Met
        35                  40                  45

Cys Ile Asp Tyr Arg Lys Leu Asn Glu Ala Thr Arg Lys Asp His Phe
    50                  55                  60

Pro Leu Pro Phe Met Asp Gln Met Leu Glu Arg Leu Ala Gly Gln Ala
65                  70                  75                  80

Tyr Tyr Cys Phe Leu Asp Gly Tyr Ser Gly Tyr Asn Gln Ile Ala Val
                85                  90                  95

Asp Pro Arg Asp Gln Glu Lys Thr Ala Phe Thr Cys Pro Phe Gly Val
            100                 105                 110

Phe Ala Tyr Arg Arg Met Pro Phe Gly Leu Cys Asn Ala Pro Ala Thr
        115                 120                 125

Phe Gln Arg Cys Met Leu Ala Ile Phe Ser Asp Met Val Glu Lys Ser
    130                 135                 140

Ile Glu Val Phe Met Asp Asp Phe Ser Val Phe Gly Pro Ser Phe Asp
145                 150                 155                 160

Ser Cys Leu Arg Asn Leu Glu Arg Val Leu Gln Arg Cys Glu Glu Thr
                165                 170                 175

Asn Leu Val Leu Asn Trp Glu Lys Cys His Phe Met Val Arg Glu Gly
            180                 185                 190

Ile Val Leu Gly His Lys Ile Ser
        195                 200
```

<210> SEQ ID NO 13
<211> LENGTH: 858
<212> TYPE: DNA
<213> ORGANISM: Artificial Sequence
<220> FEATURE:
<223> OTHER INFORMATION: plant retroelement sequence

<400> SEQUENCE: 13

```
aaggaagaac cactagccct tccacaggat ctcccatatc ctatggcacc caccaagaag       60
aacaaggagc gttactttgc acgtttcttg gaaatattca aagggttaga aatcactatg      120
ccattcgggg aagccttaca gcagatgccc tctactcca aatttatgaa agacatcctc       180
accaagaagg ggaagtatat tgacaacgag atattgtgg taggaggcaa ttgcagtgcg       240
ataatacaaa ggattctacc caagaagttt aaagaccccg gaagtgttac catcccgtgc      300
accattggga aggaagccgt aaacaaggcc ctcattgatc taggagcaag tatcaatctg      360
atgcccttgt caatgtgcaa aagaattggg aatttgaaga tagatcccac caagatgacg      420
```

```
cttcaactgg cagaccgctc aatcacaagg ccatatgggg tggtagaaga tgtcctggtc    480
aaggtacgcc acttcacttt tccggtggac tttgttatca tggatatcga agaagacact    540
gagattcccc ttatcttagg cagacccttc atgctgactg ccaactgtgt ggtggatatg    600
gggaaaggga acttagagtt gactattgat aatcagaaga tcacctttga ccttatcaag    660
gcaatgaagt acccacagga gggttggaag tgcttcagaa tagaggagat tgatgaggaa    720
gatgtcagtt ttctcgagac accaaagact tcgctagaaa aagcaatggt aaatcattta    780
gactgtctaa ccagtgaaga ggaagaagat ctgaaggctt gcttggaaaa cttggatcaa    840
gaagacagta ttcctgag                                                 858
```

<210> SEQ ID NO 14
<211> LENGTH: 286
<212> TYPE: PRT
<213> ORGANISM: Artificial Sequence
<220> FEATURE:
<223> OTHER INFORMATION: plant retroelement sequence

<400> SEQUENCE: 14

```
Lys Glu Glu Pro Leu Ala Leu Pro Gln Asp Leu Pro Tyr Pro Met Ala
 1               5                  10                  15

Pro Thr Lys Lys Asn Lys Glu Arg Tyr Phe Ala Arg Phe Leu Glu Ile
            20                  25                  30

Phe Lys Gly Leu Glu Ile Thr Met Pro Phe Gly Glu Ala Leu Gln Gln
        35                  40                  45

Met Pro Leu Tyr Ser Lys Phe Met Lys Asp Ile Leu Thr Lys Lys Gly
    50                  55                  60

Lys Tyr Ile Asp Asn Glu Asn Ile Val Val Gly Asn Cys Ser Ala
65                  70                  75                  80

Ile Ile Gln Arg Ile Leu Pro Lys Lys Phe Lys Asp Pro Gly Ser Val
                85                  90                  95

Thr Ile Pro Cys Thr Ile Gly Lys Glu Ala Val Asn Lys Ala Leu Ile
            100                 105                 110

Asp Leu Gly Ala Ser Ile Asn Leu Met Pro Leu Ser Met Cys Lys Arg
        115                 120                 125

Ile Gly Asn Leu Lys Ile Asp Pro Thr Lys Met Thr Leu Gln Leu Ala
    130                 135                 140

Asp Arg Ser Ile Thr Arg Pro Tyr Gly Val Val Glu Asp Val Leu Val
145                 150                 155                 160

Lys Val Arg His Phe Thr Phe Pro Val Asp Phe Val Ile Met Asp Ile
                165                 170                 175

Glu Glu Asp Thr Glu Ile Pro Leu Ile Leu Gly Arg Pro Phe Met Leu
            180                 185                 190

Thr Ala Asn Cys Val Val Asp Met Gly Lys Gly Asn Leu Glu Leu Thr
        195                 200                 205

Ile Asp Asn Gln Lys Ile Thr Phe Asp Leu Ile Lys Ala Met Lys Tyr
    210                 215                 220

Pro Gln Glu Gly Trp Lys Cys Phe Arg Ile Glu Glu Ile Asp Glu Glu
225                 230                 235                 240

Asp Val Ser Phe Leu Glu Thr Pro Lys Thr Ser Leu Glu Lys Ala Met
                245                 250                 255

Val Asn His Leu Asp Cys Leu Thr Ser Glu Glu Glu Asp Leu Lys
            260                 265                 270

Ala Cys Leu Glu Asn Leu Asp Gln Glu Asp Ser Ile Pro Glu
```

```
                275                 280                 285

<210> SEQ ID NO 15
<211> LENGTH: 192
<212> TYPE: DNA
<213> ORGANISM: Artificial Sequence
<220> FEATURE:
<223> OTHER INFORMATION: plant retroelement sequence

<400> SEQUENCE: 15
tttgaactaa tgtgtgatgc cagtgattat gcagtaggag cagttttggg acagaggaaa      60
gacaaggtat tcacgccat ctattatgct agcaaggtcc tgaatgaagc acagttgaat     120
tatgcaacca cagaaaagga gatgctagcc attgtctttg ccttggagaa gttcaggtca     180
tacttgatag gg                                                         192

<210> SEQ ID NO 16
<211> LENGTH: 64
<212> TYPE: PRT
<213> ORGANISM: Artificial Sequence
<220> FEATURE:
<223> OTHER INFORMATION: plant retroelement sequence

<400> SEQUENCE: 16

Phe Glu Leu Met Cys Asp Ala Ser Asp Tyr Ala Val Gly Ala Val Leu
 1               5                  10                  15

Gly Gln Arg Lys Asp Lys Val Phe His Ala Ile Tyr Tyr Ala Ser Lys
            20                  25                  30

Val Leu Asn Glu Ala Gln Leu Asn Tyr Ala Thr Thr Glu Lys Glu Met
        35                  40                  45

Leu Ala Ile Val Phe Ala Leu Glu Lys Phe Arg Ser Tyr Leu Ile Gly
    50                  55                  60

<210> SEQ ID NO 17
<211> LENGTH: 12286
<212> TYPE: DNA
<213> ORGANISM: Artificial Sequence
<220> FEATURE:
<223> OTHER INFORMATION: plant retroelement sequence

<400> SEQUENCE: 17
tgataactgc taaataattg tgaattaata gtagaaaatt agtcaaattt tggcttaaaa      60
ttaattattt agcagttatt tgtgattaaa agttagaaaa gcaattaagt tgaattttg      120 gccatagata tgaaaactga aggtacaaca agcaaaaggc agcagaaagt gaagaaaaag    180
aataaaatct gaagcagacc cagcccaaca cgcgccctta gcgcgcgtca cgcgctaagc    240
ttgcaaggca gcacaggcac taagcgaggc gttaagcacg aagatgcagg attcgttacg    300
tgcgctaagc gcgaggcaca cgctaagcgc gcgatccaac agaagcacac gctaagcctg    360
cagcatgcgc taagcgcgcc tacgaaggcc caaagcccat tctacacct ataaatagag     420 atccaagcca agggagaatg tacaccttgc ctcagagcac ttctctcagc attccaagct    480
tgagctctcc cttttctctc tatattcttt gcttttatta tccattcttt ctttcacccc    540
agttgtaaag cccctcaatg gccatgagtg gttaatcccc tagctacggc ctggtaggcc    600
taaaaagcca atgatgtatg gtgtacttca agagttatca atgcaaagag gattcattcc    660
aggttttatg ttctaattct ttccttttta tcttgcattt atgtcttaaa tttctgttgg    720 gtttattcg ctcgggagag ggtatttcct aataaggggtt taagaagtaa tgcatgcatc    780
agttttaggg gttatacgct tggtaaaggg taacacctaa tagaacaaat taagaaaagg    840
```

```
atcgtcgggc tagcattgct aggcatagaa tgatggccca atgcccatgc atttagcaac      900
atctagaatt taaccttaat gcattttaat tattgaatct tcacaaaggc atttgggaga      960
taggtagtta aaataggctt gtcatcgtga ggcatcaagg gcaagtaaaa ttaatagatg     1020
tgggtagaac taattcaact gcattggtaa tgaacatcat aaattcattc atcgtaggcc     1080
aattaggttt gtccggtctt ggcattttca tcaattgtct tcctaaatta tttgatctaa     1140
tagcaacaat ttattcttat gcctattcct gtttttacta tttactttta cttacaaatt     1200
gaagagtatt caataaagtg caataaaatc cctatggaaa cgatactcgg acttccgaga     1260
attactactt agaacgattt ggtacacttg tcaaacacct caacaagttt ttggcgccgt     1320
tgtcggggat tttgttctcg cacttaattg ccatactata ttagtttgta agcttaattc     1380
ttcttttctt ggctcattct tttattattc tttactttac ttttttcttct atcctttctt     1440
tcttctccca taaattgcac gggtagtgcc ttttgtttt tatgcgaggt agaactgcat     1500
ctggagacgt tgttcctatt aacttagaaa ttgaagctac gtgtcggcgt aacaacgctg     1560
caagaagaag aagggagcaa gacatagaag gaagtagtta ccctcacct cctccttctc     1620
caaattatgc tcagatggac ggggaaccgg cacaaagagt cacactagag gacttctcta     1680
ataccaccac tcctcagttc tttacaagta tcacaaggcc ggaagtccaa gcagatctcc     1740
ttactcaagg gaacctcttc catggtcttc caaatgaaga tccatatgcg catctagcct     1800
catacataga gatatgcagc accgttaaaa tcgccggagt tccaaaagat gcgatactcc     1860
ttaacctctt ttccttttcc ctagcaggag aggcaaaaag atggttgcac tcctttaaag     1920
gcaatagctt aagaacatgg gaagaagtag tggaaaaatt cttaaagaag tatttcccag     1980
agtcaaagac cgtcgaacga aagatggaga tttcttattt ccatcaattt ctggatgaat     2040
cccttagcga agcactagac catttccacg gattgctaag aaaaacacca acacacagat     2100
acagcgagcc agtacaacta acatattca tcgatgactt gcaactctta atcgaaacag     2160
ctactagagg gaagatcaag ctgaagactc ccgaagaagc gatggagctc gtcgagaaca     2220
tggcggctag cgatcaagca atccttcatg atcacactta tgttcccaca aaaagaagcc     2280
tcttggagct tagcacgcag gacgcaactt tggtacaaaa caagctgttg acgaggcaga     2340
tagaagccct catcgaaacc ctcagcaagc tgcctcaaca attacaagcg ataagttctt     2400
cccactcttc tgttttgcag gtagaagaat gccccacatg cagagggaca catgagcctg     2460
gacaatgtgc aagccaacaa gacccctctc gtgaagtaaa ttatataggc atactaaatc     2520
gttacggatt tcagggctac aaccaggaa atccatctgg attcaatcaa ggggcaacaa     2580
gatttaatca cgagccaccg gggtttaatc aaggaagaaa cttcatgcaa ggctcaagtt     2640
ggacgaataa aggaaatcaa tataaggagc aaaggaacca accaccatac cagccaccat     2700
accagcaccc tagccaaggt ccgaatcagc aagaaaagcc caccaaaata gaggaactgc     2760
tgctgcaatt catcaaggag acaagatcac atcaaaagag cacggatgca gccattcgga     2820
atctagaagt tcaaatgggc caactggcgc atgacaaagc cgaacggccc actagaactt     2880
tcggtgctaa catggagaga agaaccccaa ggaaggataa agcagtactg actagagggc     2940
agagaagagc gcaggaggag ggtaaggttg aaggagaaga ctggccagaa gaaggaagga     3000
cagagaagac agaagaagaa gagaaggtgg cagaagaacc taagcgtacc aagagccaga     3060
gagcaaggga agccaagaag gaagaaccac tagcccttcc acaggatctc ccatatccta     3120
tggcacccac caagaagaac aaggagcgtt actttgcacg tttcttggaa atattcaaag     3180
```

-continued

```
ggttagaaat cactatgcca ttcggggaag ccttacagca gatgccctc tactccaaat    3240
ttatgaaaga catcctcacc aagaagggga agtatattga caacgagaat attgtggtag    3300
gaggcaattg cagtgcgata atacaaagga ttctacccaa gaagtttaaa gaccccggaa    3360
gtgttaccat cccgtgcacc attgggaagg aagccgtaaa caaggccctc attgatctag    3420
gagcaagtat caatctgatg cccttgtcaa tgtgcaaaag aattgggaat ttgaagatag    3480
atcccaccaa gatgacgctt caactggcag accgctcaat cacaaggcca tgggggtgg    3540
tagaagatgt cctggtcaag gtacgccact tcacttttcc ggtggacttt gttatcatgg    3600
atatcgaaga agacactgag attccccctta tcttaggcag acccttcatg ctgactgcca    3660
actgtgtggt ggatatgggg aaagggaact tagagttgac tattgataat cagaagatca    3720
cctttgacct tatcaaggca atgaagtacc cacaggaggg ttggaagtgc ttcagaatag    3780
aggagattga tgaggaagat gtcagttttc tcgagacacc aaagacttcg ctagaaaaag    3840
caatggtaaa tcatttagac tgtctaacca gtgaagagga agaagatctg aaggcttgct    3900
tggaaaactt ggatcaagaa gacagtattc ctgagggaga agccaatttc gaggagctag    3960
agaaggaagt tccgtctgag aagccgaaga tagagttgaa gatattgcct gatcatctga    4020
agtatgtgtt cttggaggaa gataaaccta tagtgatcag taacgcactc acaacagagg    4080
aggaaaatag gttggtagat gtcctcaaga aacacaggga agcaattgga tggcacatat    4140
cggatctcaa ggaaattagc cctgcttact gcatgcacag gataatgatg gaagaggact    4200
acaagccagt ccgacaaccc cagaggcggc tgaatccaac aatgaaggaa gaggtaagaa    4260
aggaggtact caagctcttg gaggctgggc tcatataccc catctctgac agcgcttggg    4320
taagcccagt acaggtggtt cccaagaaag gtggaatgac agtggtacga gatgagagga    4380
atgacttgat accaacacga actgtcactg gttggcgaat gtgtatcgac tatcgcaagc    4440
tgaatgaagc cacacggaag gaccatttcc ccttaccttt catggatcag atgctggaga    4500
gacttgcagg gcaggcatac tactgttttct tggatggata ctcgggatac aaccagatcg    4560
cggtagaccc cagagatcag gagaagacgg ccttttacatg cccctttggc gtctttgctt    4620
acagaaggat gccattcggg ttatgtaatg caccagccac atttcagagg tgcatgctgg    4680
ccattttttc agacatggtg gagaaaagca tcgaggtatt tatggacgac ttctcggttt    4740
ttggaccctc atttgacagc tgtttgagga acctagagag ggtacttcag aggtgcgaag    4800
agactaactt ggtactgaat tgggaaaagt gtcatttcat ggttcgagag ggcatagtcc    4860
taggccacaa gatctcagcc agagggattg aggttgatcg ggcaaagata gacgtcatcg    4920
agaagctgcc accaccactg aatgttaaag gggttagaaa tttcttaggg catgcaggtt    4980
tctacaggag gtttatcaag gacttctcga agattgccag gcccttaagc aatctgttga    5040
ataaagacgt ggcttttgtg tttgatgaag aatgtttagc agcatttcaa tcactgaaga    5100
ataagctcgt cactgcaccc gtaatgattg cacccgactg gaataaagat tttgaactaa    5160
tgtgtgatgc cagtgattat gcagtaggag cagttttggg acagaggaaa gacaaggtat    5220
ttcacgccat ctattatgct agcaaggtcc tgaatgaagc acagttgaat tatgcaacca    5280
cagaaaagga gatgctagcc attgtctttg ccttggagaa gttcaggtca tacttgatag    5340
ggtcgagggt catcatttac acagatcatg ctgccatcaa gcacctgctc gccaaaacag    5400
actcaaagcc gaggttgatt agatgggtcc tgctgttaca agaatttgac atcatcatca    5460
aggacaagaa aggatccgag aatgtggtag ccaatcatct atctcgatta aagaatgaag    5520
aagtcaccaa ggaagaacca gaggtaaaag gtgaatttcc tgatgagttt cttttgcagg    5580
```

```
ttaccgaaag accttggttt gcagacatgg ctaactacaa agccacggga gtcattccag    5640
aggagtttaa ttggagtcag aggaagaaat tcttgcacga tgcacgcttc tatgtgtggg    5700
atgatcctca tttgttcaag gcaggagcag ataatttatt aaggagatgc gtcacaaagg    5760
aggaagcacg gagcattctt tggcactgcc acagttcacc ctatggcgga caccacagtg    5820
gggacagaac agcagcaaaa gtgctacaat caggtttttt ctggccctct attttttaaag   5880 atgctcacga gtttgtgcgt tgttgtgata aatgccagag aacaggggggg atatctcgaa   5940 gaaatgagat gcctttgcag aatatcatgg aagtagagat ctttgactgt tggggcatag    6000
acttcatggg gccttttcct tcgtcatacg ggaatgtcta catcttggta gctgtggatt    6060
acgtctccaa atgggtggaa gccatagcca cgccaaagga cgatgccagg gtagtgatca    6120
aatttctgaa gaagaacatt ttttcccgtt ttggagtccc acgagccttg attagtgata    6180
ggggaacgca cttctgcaac aatcagttga agaaagtcct ggagcactat aatgtccgac    6240
ataaggtggc cacaccttat caccctcaga caaatggcca agcagaaatt ctaacaggg    6300 agctcaagcg aatcctggaa aagacagttg catcaacaag aaaggattgg tccttgaagc    6360
tcgatgatgc tctctgggcc tataggacag cgttcaagac tcccatcggc ttatcaccat    6420
ttcagctagt gtatgggaag gcatgtcatt taccagtgga gctggagtac aaagcatatt    6480
gggctctcaa gttgctcaac tttgacaaca acgcatgcgg ggaaaagagg aagctacagc    6540
tgctggaatt agaagagatg agactgaatg cctacgagtc atccaaaatt tacaaggaaa    6600
agatgaaggc atatcatgac aagaagctac tgaggaaaga attccagcca gggcagcagg    6660
tattactctt taactcaagg ctaaggctat tcccaggtaa gctgaagtcc aagtggtcag    6720
ggccattcat aatcaaagaa gtcagacctt acggagcagt agaattggtg gaccctagag    6780
aagaggactt tgagaagaaa tggatcgtca atggacagcg cttgaagcct tataacggag    6840
gacaactaga gcgattgacg accatcatct acttaaatga ccccttgagaa ggcctactgt    6900 ctagctaaag acaataaact aagcgctggt tgggaggcaa cccaacatat tttgtaaaaa    6960
tgtagttatc tttattctat gtaaaaaaaa aaaaaagcc caataggtgc aaataggaaa    7020
caggaggtgc aaaaagcaaa ggcccaacag gtgaagacaa caataggagg ggtgccaata    7080
gcaaaactga agtgggctgc acgaagccac gcgcccaatt cttggtcttt tcacacaaaa    7140
caatcactaa cgaaggtaaa gaattgcttt gtatggatgt tgttatgaat gcacaggtaa    7200
cagcacgcta agccctgctc gacgcttagc caatgaagac ggattgaagg ccataacgac    7260
gagctcgtta agcgtgacga agcacgctaa gcaggcgcct gacaggacga gaaagcaaag    7320
cgcgcgctta gccggcactt ccgcgctaag cgcgctcatg aacatcactg aacgcgctaa    7380
acgtgtgcca gaggcgctaa acgcgtgcca gaggcgctaa acgcgtgcat tagtcacagc    7440
aggatggtgc taagcgcggg gttgggcctc agggcccatc aaccctcgca ccttacttgt    7500
tgcaccccta tttctactat tcccactccc ttctaatttc ttttttgcacc cccttctttt   7560 actgactgca cctctatttt gattactttt tgcaccccccc ctgattgcta acttcagact   7620
atctttcttg ttttttttgttt ttttggttttt ttggtcagat ggcctcccgt aaacgcaaag  7680
ctgtgcccac acccggggaa gcgtccaact gggactcttc acgtttcact ttcgagattg    7740
cttggcacag ataccaggat agcattcagc tccggaacat ccttccagag aggaatgtag    7800
agcttggacc agggatgttt gatgagttcc tgcaggaact ccagaggctc agatgggacc    7860
aggttctgac ccgacttcca gagaagtgga ttgatgttgc tctggtgaag gagtttttact   7920
```

-continued

| | | | | | |
|---|---|---|---|---|---|
| ccaacctata | tgatccagag | gaccacagtc | cgaagttttg | gagtgttcga | ggacaggttg | 7980 |
| tgagatttga | tgctgagacg | attaatgatt | tcctcgacac | cccggtcatc | ttggcagagg | 8040 |
| gagaggatta | tccagcctac | tctcagtacc | tcagcactcc | tccagaccat | gatgccatcc | 8100 |
| tttccgctct | gtgtactcca | gggggacgat | ttgttctgaa | tgttgatagt | gccccctgga | 8160 |
| agctgctgcg | gaaggatctg | atgacgctcg | cgcagacatg | gagtgtgctc | tcttatttta | 8220 |
| accttgcact | gacttttcac | acttctgata | ttaatgttga | cagggcccga | ctcaattatg | 8280 |
| gcttggtgat | gaagatggac | ctggacgtgg | gcagcctcat | ttctcttcag | atcagtcaga | 8340 |
| tcgcccagtc | catcacttcc | aggcttgggt | tcccagcgtt | gatcacaaca | ctgtgtgaga | 8400 |
| ttcaggggt | tgtctctgat | accctgattt | ttgagtcact | cagtcctgtg | atcaaccttg | 8460 |
| cctacattaa | gaagaactgc | tggaaccctg | ccgatccatc | tatcacattt | caggggaccc | 8520 |
| gccgcacgcg | caccagagct | tcggcgtcgg | catctgaggc | tcctcttcca | tcccagcatc | 8580 |
| cttctcagcc | ttttttcccag | agaccacggc | ctccacttct | atccacctca | gcacctccat | 8640 |
| acatgcatgg | acagatgctc | aggtccttgt | accagggtca | gcagatcatc | attcagaacc | 8700 |
| tgtatcgatt | gtccctacat | ttgcagatgg | atctgccact | catgactccg | gaggcctatc | 8760 |
| gtcagcaggt | cgccaagcta | ggagaccagc | cctccactga | caggggggaa | gagccttctg | 8820 |
| gagccgctgc | tactgaggat | cctgccgttg | atgaagacct | catagctgac | ttggctggcg | 8880 |
| ctgattggag | cccatgggca | gacttgggca | gaggcagctg | atcttatgct | ttaatgtttt | 8940 |
| cttttatatt | atgtttgtgt | tctcttttat | gttttatgtt | atgtttttat | gtagtctgtt | 9000 |
| tggtaattaa | aaagaggtag | tagtaaaaat | attagtattt | cagtatgtgt | tttctgagta | 9060 |
| ataagtgcat | gataactcaa | gcaatcataa | ttctttagct | tgttcagaaa | ggttcaacac | 9120 |
| ttgagatgcc | actgatcctt | ggagaaacac | tggttctgga | agcaaaagtc | aggtcaagaa | 9180 |
| atggaacatg | aatagcacag | agtggaaagg | ttagcttgat | ggaacaaggt | cataactggt | 9240 |
| acgccgaata | cttgtttaag | tccctgtgag | catggttgtc | aaactctaga | gtcaactcat | 9300 |
| agactctcat | gagtttaaga | gtttacttca | gtcccgcgag | ttgactcgga | agcaaactcg | 9360 |
| cttttgagca | aactcgtgga | ctcggagtga | actcatgtaa | actcgtaaga | gtctacgagt | 9420 |
| tgactctaga | gtttgacaac | catgcataag | tgttcaaaat | taaagcattt | aaataattaa | 9480 |
| aaaaagcaca | aatgtcttca | agaagcatg | ttcaatcctc | taataggatc | atcttcatga | 9540 |
| atatcatcac | tttcatcatc | atctccatct | ccatcatcat | catcaaggtc | ttcctcagat | 9600 |
| tgtgcatcat | cattaggttc | cacaaagatt | aaattatcta | gatcaaaagc | ttaaaataga | 9660 |
| tatcaaatat | gctatattag | aaatagttaa | aacttaaaat | aatacacaag | caaattttaa | 9720 |
| atatgagaaa | gttcagaaat | tatacctttt | cttggtgtta | ttaaagtttc | attttatctt | 9780 |
| ctcttttgca | ttttccatct | cctcacatat | gaaaagcata | attctattga | atttcagtaa | 9840 |
| caagtttgat | ccaactccaa | cattgtaagg | tcagttgttg | tgttttgtaa | tagactaata | 9900 |
| tgaagtatga | agtatgaact | atgaacttat | tgtcatctgt | ttgcaaattg | gtgcattttg | 9960 |
| aatatattta | cttattatcc | atttttttt | ttttacgaag | tagactctca | cgagtctgcg | 10020 |
| tagactctcg | atatcgataa | ccttgccgat | gagagtgtga | acttaattgt | gagagaaaat | 10080 |
| gcctattttt | aagttcctgg | ttttgcatca | ttcttagacg | gttagaatag | ttacttaagg | 10140 |
| tggatatgat | caaggccatg | tttgtttgtt | tacctactta | gccaaaaagc | caacctaaca | 10200 |
| tagttttacc | ccttgcaccc | atgattgagc | caactgatta | ttttgaatta | accttgagcc | 10260 |
| aattaaacaa | aatcctgacc | ttttaggatt | ttaagagagt | aaaaatgggt | tataaaggtc | 10320 |

```
ttaatttggg ggattttggg aaataggtag ccaagacaat aagtacagca cacaaagtag    10380
gacaccttt  acaaacagta ggcccaattt cgaaaaaaaa atgaaaagaa tttaataaag    10440
ggcagaaaca aaagagcaag agaggtgtca aagaaaagt  gttgtgggga aataaaaggg    10500
ctaagtaaaa aggcctaggc agaattggaa attttgttc  tcttttaatc ctaactttga    10560
atttccaaga aaaccatga  tttttgtaa  gccaggcccc gatacaagcc aataaagtcc    10620
ttagtgatcc accaaaggta actagagata actgtaactg agatgaaatg caaaattttg    10680
aagtgttact tgcaggttgt tatcaaattg caaacactaa actaggcact tgtgagcaga    10740
gggaaacacc agccttgtga ggaaagtaag gcaagccaaa tttgattgag ttccagatga    10800
ctaactgatt caattcttct gttgtaatgc tttcatttta agatgttgac agatgcagaa    10860
aggaccagtg aaagaaggag gaactgagcc attgatagtg ttggaatatt aagaacttg     10920
cttgagaatt tacttgtttt tggttttctt ggggacaagc aaagtttcat ttggggaatt    10980
ttgataactg ctaaataatt gtgaattaat agtagaaaat tagtcaaatt ttggcttaaa    11040
attaattatt tagcagttat ttgtgattaa agttagaaa  agcaattaag ttgaattttt    11100
ggccatagat atgaaaactg aaggtacaac aagcaaaagg cagcagaaag tgaagaaaaa    11160
gaataaaatc tgaagcagac ccagcccaac acgcgccctt agcgcgcgtc acgcgctaag    11220
cttgcaaggc agcacaggca ctaagcgagg cgttaagcac gaagatgcag gattcgttac    11280
gtgcgctaag cgcgaggcac acgctaagcg cgcgatccaa cagaagcaca cgctaagcct    11340
gcagcatgcg ctaagcgcgc ctacgaaggc ccaaagccca tttctacacc tataaataga    11400
gatccaagcc aagggagaat gtacaccttg cctcagagca cttctctcag cattccaagc    11460
ttgagctctc cctttctct  ctatattctt tgcttttatt atccattctt tctttcaccc    11520
cagttgtaaa gccctcaat  ggccatgagt ggttaatccc ctagctacgg cctggtaggc    11580
ctaaaaagcc aatgatgtat ggtgtacttc aagagttatc aatgcaaaga ggattcattc    11640
caggttttat gttctaattc tttccttttt atcttgcatt tatgtcttaa atttctgttg    11700
ggttttattc gctcgggaga gggtatttcc taataagggt ttaagaagta atgcatgcat    11760
cagttttagg ggttatacgc ttggtaaagg gtaacaccta atagaacaaa ttaagaaaag    11820
gatcgtcggg ctagcattgc taggcataga atgatggccc aatgcccatg catttagcaa    11880
catctagaat ttaaccttaa tgcatttaa  ttattgaatc ttcacaaagg catttgggag    11940
ataggtagtt aaaataggct tgtcatcgtg aggcatcaag ggcaagtaaa attaatagat    12000
gtgggtagaa ctaattcaac tgcattggta atgaacatca taaattcatt catcgtaggc    12060
caattaggtt tgtccggtct tggcattttc atcaattgtc ttcctaaatt atttgatcta    12120
atagcaacaa tttattctta tgcctattcc tgtttttact atttacttt  acttacaaat    12180
tgaagagtat tcaataaagt gcaataaaat ccctatggaa acgatactcg gacttccgag    12240
aattactact tagaacgatt tggtacactt gtcaaacacc tcaaca                  12286
```

<210> SEQ ID NO 18
<211> LENGTH: 1802
<212> TYPE: PRT
<213> ORGANISM: Artificial Sequence
<220> FEATURE:
<223> OTHER INFORMATION: plant retroelement sequence

<400> SEQUENCE: 18

```
Met Arg Gly Arg Thr Ala Ser Gly Asp Val Val Pro Ile Asn Leu Glu
 1               5                  10                  15
```

-continued

```
Ile Glu Ala Thr Cys Arg Arg Asn Asn Ala Ala Arg Arg Arg Glu
             20                  25                  30
Gln Asp Ile Glu Gly Ser Ser Tyr Thr Ser Pro Pro Ser Pro Asn
             35                  40                  45
Tyr Ala Gln Met Asp Gly Pro Ala Gln Arg Val Thr Leu Glu Asp
             50                  55                  60
Phe Ser Asn Thr Thr Thr Pro Gln Phe Phe Thr Ser Ile Thr Arg Pro
 65                  70                  75                  80
Glu Val Gln Ala Asp Leu Leu Thr Gln Gly Asn Leu Phe His Gly Leu
                 85                  90                  95
Pro Asn Glu Asp Pro Tyr Ala His Leu Ala Ser Tyr Ile Glu Ile Cys
                100                 105                 110
Ser Thr Val Lys Ile Ala Gly Val Pro Lys Asp Ala Ile Leu Leu Asn
                115                 120                 125
Leu Phe Ser Phe Ser Leu Ala Gly Glu Ala Lys Arg Trp Leu His Ser
    130                 135                 140
Phe Lys Gly Asn Ser Leu Arg Thr Trp Glu Glu Val Val Glu Lys Phe
145                 150                 155                 160
Leu Lys Lys Tyr Phe Pro Glu Ser Lys Thr Val Glu Arg Lys Met Glu
                165                 170                 175
Ile Ser Tyr Phe His Gln Phe Leu Asp Glu Ser Leu Ser Glu Ala Leu
                180                 185                 190
Asp His Phe His Gly Leu Leu Arg Lys Thr Pro Thr His Arg Tyr Ser
    195                 200                 205
Glu Pro Val Gln Leu Asn Ile Phe Ile Asp Asp Leu Gln Leu Leu Ile
210                 215                 220
Glu Thr Ala Thr Arg Gly Lys Ile Lys Leu Lys Thr Pro Glu Glu Ala
225                 230                 235                 240
Met Glu Leu Val Glu Asn Met Ala Ala Ser Asp Gln Ala Ile Leu His
                245                 250                 255
Asp His Thr Tyr Val Pro Thr Lys Arg Ser Leu Leu Glu Leu Ser Thr
                260                 265                 270
Gln Asp Ala Thr Leu Val Gln Asn Lys Leu Leu Thr Arg Gln Ile Glu
    275                 280                 285
Ala Leu Ile Glu Thr Leu Ser Lys Leu Pro Gln Gln Leu Gln Ala Ile
    290                 295                 300
Ser Ser Ser His Ser Ser Val Leu Gln Val Glu Cys Pro Thr Cys
305                 310                 315                 320
Arg Gly Thr His Glu Pro Gly Gln Cys Ala Ser Gln Asp Pro Ser
                325                 330                 335
Arg Glu Val Asn Tyr Ile Gly Ile Leu Asn Arg Tyr Gly Phe Gln Gly
                340                 345                 350
Tyr Asn Gln Gly Asn Pro Ser Gly Phe Asn Gln Gly Ala Thr Arg Phe
    355                 360                 365
Asn His Glu Pro Pro Gly Phe Asn Gln Gly Arg Asn Phe Met Gln Gly
    370                 375                 380
Ser Ser Trp Thr Asn Lys Gly Asn Gln Tyr Lys Glu Gln Arg Asn Gln
385                 390                 395                 400
Pro Pro Tyr Gln Pro Pro Tyr Gln His Pro Ser Gln Gly Pro Asn Gln
                405                 410                 415
Gln Glu Lys Pro Thr Lys Ile Glu Glu Leu Leu Leu Gln Phe Ile Lys
                420                 425                 430
```

-continued

```
Glu Thr Arg Ser His Gln Lys Ser Thr Asp Ala Ala Ile Arg Asn Leu
        435                 440                 445

Glu Val Gln Met Gly Gln Leu Ala His Asp Lys Ala Glu Arg Pro Thr
        450                 455                 460

Arg Thr Phe Gly Ala Asn Met Glu Arg Arg Thr Pro Arg Lys Asp Lys
465                 470                 475                 480

Ala Val Leu Thr Arg Gly Gln Arg Arg Ala Gln Glu Glu Gly Lys Val
                485                 490                 495

Glu Gly Glu Asp Trp Pro Glu Gly Arg Thr Glu Lys Thr Glu Glu
            500                 505                 510

Glu Glu Lys Val Ala Glu Pro Lys Arg Thr Lys Ser Gln Arg Ala
        515                 520                 525

Arg Glu Ala Lys Lys Glu Glu Pro Leu Ala Leu Pro Gln Asp Leu Pro
        530                 535                 540

Tyr Pro Met Ala Pro Thr Lys Lys Asn Lys Glu Arg Tyr Phe Ala Arg
545                 550                 555                 560

Phe Leu Glu Ile Phe Lys Gly Leu Glu Ile Thr Met Pro Phe Gly Glu
                565                 570                 575

Ala Leu Gln Gln Met Pro Leu Tyr Ser Lys Phe Met Lys Asp Ile Leu
                580                 585                 590

Thr Lys Lys Gly Lys Tyr Ile Asp Asn Glu Asn Ile Val Val Gly Gly
        595                 600                 605

Asn Cys Ser Ala Ile Ile Gln Arg Ile Leu Pro Lys Lys Phe Lys Asp
610                 615                 620

Pro Gly Ser Val Thr Ile Pro Cys Thr Ile Gly Lys Glu Ala Val Asn
625                 630                 635                 640

Lys Ala Leu Ile Asp Leu Gly Ala Ser Ile Asn Leu Met Pro Leu Ser
                645                 650                 655

Met Cys Lys Arg Ile Gly Asn Leu Lys Ile Asp Pro Thr Lys Met Thr
                660                 665                 670

Leu Gln Leu Ala Asp Arg Ser Ile Thr Arg Pro Tyr Gly Val Val Glu
        675                 680                 685

Asp Val Leu Val Lys Val Arg His Phe Thr Phe Pro Val Asp Phe Val
        690                 695                 700

Ile Met Asp Ile Glu Glu Asp Thr Glu Ile Pro Leu Ile Leu Gly Arg
705                 710                 715                 720

Pro Phe Met Leu Thr Ala Asn Cys Val Val Asp Met Gly Lys Gly Asn
                725                 730                 735

Leu Glu Leu Thr Ile Asp Asn Gln Lys Ile Thr Phe Asp Leu Ile Lys
                740                 745                 750

Ala Met Lys Tyr Pro Gln Glu Gly Trp Lys Cys Phe Arg Ile Glu Glu
        755                 760                 765

Ile Asp Glu Glu Asp Val Ser Phe Leu Glu Thr Pro Lys Thr Ser Leu
        770                 775                 780

Glu Lys Ala Met Val Asn His Leu Asp Cys Leu Thr Ser Glu Glu
785                 790                 795                 800

Glu Asp Leu Lys Ala Cys Leu Glu Asn Leu Asp Gln Glu Asp Ser Ile
                805                 810                 815

Pro Glu Gly Glu Ala Asn Phe Glu Leu Glu Lys Val Pro Ser
                820                 825                 830

Glu Lys Pro Lys Ile Glu Leu Lys Ile Leu Pro Asp His Leu Lys Tyr
        835                 840                 845

Val Phe Leu Glu Glu Asp Lys Pro Ile Val Ile Ser Asn Ala Leu Thr
```

-continued

```
            850                 855                 860
Thr Glu Glu Asn Arg Leu Val Asp Val Leu Lys Lys His Arg Glu
865                 870                 875                 880

Ala Ile Gly Trp His Ile Ser Asp Leu Lys Glu Ile Ser Pro Ala Tyr
                    885                 890                 895

Cys Met His Arg Ile Met Met Glu Glu Asp Tyr Lys Pro Val Arg Gln
                900                 905                 910

Pro Gln Arg Arg Leu Asn Pro Thr Met Lys Glu Glu Val Arg Lys Glu
            915                 920                 925

Val Leu Lys Leu Leu Glu Ala Gly Leu Ile Tyr Pro Ile Ser Asp Ser
            930                 935                 940

Ala Trp Val Ser Pro Val Gln Val Val Pro Lys Lys Gly Gly Met Thr
945                 950                 955                 960

Val Val Arg Asp Glu Arg Asn Asp Leu Ile Pro Thr Arg Thr Val Thr
                965                 970                 975

Gly Trp Arg Met Cys Ile Asp Tyr Arg Lys Leu Asn Glu Ala Thr Arg
                980                 985                 990

Lys Asp His Phe Pro Leu Pro Phe Met Asp Gln Met Leu Glu Arg Leu
            995                 1000                1005

Ala Gly Gln Ala Tyr Tyr Cys Phe Leu Asp Gly Tyr Ser Gly Tyr Asn
            1010                1015                1020

Gln Ile Ala Val Asp Pro Arg Asp Gln Glu Lys Thr Ala Phe Thr Cys
1025                1030                1035                1040

Pro Phe Gly Val Phe Ala Tyr Arg Arg Met Pro Phe Gly Leu Cys Asn
                1045                1050                1055

Ala Pro Ala Thr Phe Gln Arg Cys Met Leu Ala Ile Phe Ser Asp Met
                1060                1065                1070

Val Glu Lys Ser Ile Glu Val Phe Met Asp Asp Phe Ser Val Phe Gly
                1075                1080                1085

Pro Ser Phe Asp Ser Cys Leu Arg Asn Leu Glu Arg Val Leu Gln Arg
                1090                1095                1100

Cys Glu Glu Thr Asn Leu Val Leu Asn Trp Glu Lys Cys His Phe Met
1105                1110                1115                1120

Val Arg Glu Gly Ile Val Leu Gly His Lys Ile Ser Ala Arg Gly Ile
                1125                1130                1135

Glu Val Asp Arg Ala Lys Ile Asp Val Ile Glu Lys Leu Pro Pro Pro
                1140                1145                1150

Leu Asn Val Lys Gly Val Arg Ser Phe Leu Gly His Ala Gly Phe Tyr
                1155                1160                1165

Arg Arg Phe Ile Lys Asp Phe Ser Lys Ile Ala Arg Pro Leu Ser Asn
            1170                1175                1180

Leu Leu Asn Lys Asp Val Ala Phe Val Phe Asp Glu Glu Cys Leu Ala
1185                1190                1195                1200

Ala Phe Gln Ser Leu Lys Asn Lys Leu Val Thr Ala Pro Val Met Ile
                1205                1210                1215

Ala Pro Asp Trp Asn Lys Asp Phe Glu Leu Met Cys Asp Ala Ser Asp
                1220                1225                1230

Tyr Ala Val Gly Ala Val Leu Gly Gln Arg Lys Asp Lys Val Phe His
                1235                1240                1245

Ala Ile Tyr Tyr Ala Ser Lys Val Leu Asn Glu Ala Gln Leu Asn Tyr
            1250                1255                1260

Ala Thr Thr Glu Lys Glu Met Leu Ala Ile Val Phe Ala Leu Glu Lys
1265                1270                1275                1280
```

-continued

```
Phe Arg Ser Tyr Leu Ile Gly Ser Arg Val Ile Ile Tyr Thr Asp His
            1285                1290                1295
Ala Ala Ile Lys His Leu Leu Ala Lys Thr Asp Ser Lys Pro Arg Leu
        1300                1305                1310
Ile Arg Trp Val Leu Leu Gln Glu Phe Asp Ile Ile Lys Asp
        1315                1320                1325
Lys Lys Gly Ser Glu Asn Val Val Ala Asn His Leu Ser Arg Leu Lys
        1330                1335            1340
Asn Glu Glu Val Thr Lys Glu Pro Glu Val Lys Gly Glu Phe Pro
1345                1350                1355                1360
Asp Glu Phe Leu Leu Gln Val Thr Glu Arg Pro Trp Phe Ala Asp Met
            1365                1370                1375
Ala Asn Tyr Lys Ala Thr Gly Val Ile Pro Glu Glu Phe Asn Trp Ser
            1380                1385                1390
Gln Arg Lys Lys Phe Leu His Asp Ala Arg Phe Tyr Val Trp Asp Asp
            1395                1400                1405
Pro His Leu Phe Lys Ala Gly Ala Asp Asn Leu Leu Arg Arg Cys Val
        1410                1415                1420
Thr Lys Glu Glu Ala Arg Ser Ile Leu Trp His Cys His Ser Ser Pro
1425                1430                1435                1440
Tyr Gly Gly His His Ser Gly Asp Arg Thr Ala Ala Lys Val Leu Gln
            1445                1450                1455
Ser Gly Phe Phe Trp Pro Ser Ile Phe Lys Asp Ala His Glu Phe Val
            1460                1465                1470
Arg Cys Cys Asp Lys Cys Gln Arg Thr Gly Gly Ile Ser Arg Arg Asn
            1475                1480                1485
Glu Met Pro Leu Gln Asn Ile Met Glu Val Glu Ile Phe Asp Cys Trp
        1490                1495                1500
Gly Ile Asp Phe Met Gly Pro Phe Pro Ser Ser Tyr Gly Asn Val Tyr
1505                1510                1515                1520
Ile Leu Val Ala Val Asp Tyr Val Ser Lys Trp Val Glu Ala Ile Ala
            1525                1530                1535
Thr Pro Lys Asp Asp Ala Arg Val Val Ile Lys Phe Leu Lys Lys Asn
        1540                1545                1550
Ile Phe Ser Arg Phe Gly Val Pro Arg Ala Leu Ile Ser Asp Arg Gly
        1555                1560                1565
Thr His Phe Cys Asn Asn Gln Leu Lys Lys Val Leu Glu His Tyr Asn
        1570                1575                1580
Val Arg His Lys Val Ala Thr Pro Tyr His Pro Gln Thr Asn Gly Gln
1585                1590                1595                1600
Ala Glu Ile Ser Asn Arg Glu Leu Lys Arg Ile Leu Glu Lys Thr Val
            1605                1610                1615
Ala Ser Thr Arg Lys Asp Trp Ser Leu Lys Leu Asp Asp Ala Leu Trp
            1620                1625                1630
Ala Tyr Arg Thr Ala Phe Lys Thr Pro Ile Gly Leu Ser Pro Phe Gln
            1635                1640                1645
Leu Val Tyr Gly Lys Ala Cys His Leu Pro Val Glu Leu Glu Tyr Lys
        1650                1655                1660
Ala Tyr Trp Ala Leu Lys Leu Leu Asn Phe Asp Asn Asn Ala Cys Gly
1665                1670                1675                1680
Glu Lys Arg Lys Leu Gln Leu Leu Glu Leu Glu Glu Met Arg Leu Asn
            1685                1690                1695
```

```
Ala Tyr Glu Ser Ser Lys Ile Tyr Lys Glu Lys Met Lys Ala Tyr His
            1700                1705                1710
Asp Lys Lys Leu Leu Arg Lys Glu Phe Gln Pro Gly Gln Gln Val Leu
        1715                1720                1725
Leu Phe Asn Ser Arg Leu Arg Leu Phe Pro Gly Lys Leu Lys Ser Lys
    1730                1735                1740
Trp Ser Gly Pro Phe Ile Ile Lys Glu Val Arg Pro Tyr Gly Ala Val
1745                1750                1755                1760
Glu Leu Val Asp Pro Arg Glu Asp Phe Glu Lys Lys Trp Ile Val
                1765                1770                1775
Asn Gly Gln Arg Leu Lys Pro Tyr Asn Gly Gly Gln Leu Glu Arg Leu
            1780                1785                1790
Thr Thr Ile Ile Tyr Leu Asn Asp Pro Glx
        1795                1800
```

<210> SEQ ID NO 19
<211> LENGTH: 9829
<212> TYPE: DNA
<213> ORGANISM: Glycine max

<400> SEQUENCE: 19

```
tgataactgc taaataattg tgaattaata gtagaaaatt agtcaaattt tggcttaaaa    60
ttaattattt agcagttatt tgtgattaaa agttagaaaa gcaattaagt tgaattttttg   120
gccatagata tgaaaactga aggtacaaca agcaaaaggc agcagaaagt gaagaaaaag   180
aataaaatct gaagcagacc cagcccaaca cgcgccctta gcgcgcgtca cgcgctaagc   240
ttgcaaggca gcacaggcac taagcgaggc gttaagcacg aagatgcagg attcgttacg   300
tgcgctaagc gcgaggcaca cgctaagcgc gcgatccaac agaagcacac gctaagcctg   360
cagcatgcgc taagcgcgcc tacgaaggcc caaagcccat ttctacacct ataaatagag   420
atccaagcca agggagaatg tacaccttgc ctcagagcac ttctctcagc attccaagct   480
tgagctctcc cttttctctc tatattcttt gctttttatta tccattcttt ctttcacccc   540
agttgtaaag cccctcaatg gccatgagtg ttaatcccc tagctacggc ctggtaggcc    600
taaaagccaa atgatgtatg gtgtacttca agagttatca atgcaaagag gattcattcc    660
aggttttatg ttctaattct ttccttttta tcttgcattt atgtcttaaa tttctgttgg    720
gtttttattcg ctcgggagag ggtatttcct aataagggtt taagaagtaa tgcatgcatc    780
agttttaggg gttatacgct tggtaaaggg taacacctaa tagaacaaat taagaaaagg    840
atcgtcgggc tagcattgct aggcatagaa tgatggccca atgcccatgc atttagcaac    900
atctagaatt taaccttaat gcattttaat tattgaatct tcacaaaggc atttgggaga    960
taggtagtta aaataggctt gtcatcgtga ggcatcaagg gcaagtaaaa ttaatagatg   1020
tgggtagaac taattcaact gcattggtaa tgaacatcat aaattcattc atcgtaggcc   1080
aattaggttt gtccggtctt ggcattttca tcaattgtct tcctaaatta tttgatctaa   1140
tagcaacaat ttattcttat gcctattcct gtttttacta tttactttta cttacaaatt   1200
gaagagtatt caataaagtg caataaaatc cctatggaaa cgatactcgg acttccgaga   1260
attactactt agaacgattt ggtacacttg tcaaacacct caacaagttt ttggcgccgt   1320
tgtcggggat tttgttctcg cacttaattg ccatactata ttagtttgta agcttaattc   1380
ttcttttctt ggctcattct tttattattc tttactttac ttttttcttct atccttttctt   1440
tcttctccca taaattgcac gggtagtgcc tttttgtttt tatacgaggt agaactgcat   1500
```

-continued

```
ctggagacgt tgttcctatt aacttagaaa ttgaagctac gtgtcggcgt aacaacgctg      1560
caagaagaag aagggagcaa gacatagaag gaagtagtta caccctcacct cctccttctc      1620 caaattatgc tcagatggac ggggaaccgg cacaaagagt cacactagag gacttctcta      1680
ataccaccac tcctcagttc tttacaagta tcacaaggcc ggaagtccaa gcagatctcc      1740
tactcaaggg aacctcttcc atggtcttcc aaatgaagat ccatatgcgc atctagcctc      1800
atacatagag atatgcagca ccgttaaaat cgccggagtt ccaaaagatg cgatactcct      1860
taacctcttt tccttttccc tagcaggaga ggcaaaaaga tggttgcact cctttaaagg      1920
caatagctta agaacatggg aagaagtagt ggaaaaattc ttaaagaagt atttcccaga      1980
gtcaaagacc gtcgaacgaa agatggagat ttcttatttc catcaatttc tggatgaatc      2040
ccttagcgaa gcactagacc atttccacgg attgctaaga aaaacaccaa cacacagata      2100
cagcgagcca gtacaactaa acatattcat cgatgacttg caaccttaat cgaaacagct      2160
actagaggga agatcaagct gaagactccc gaagaagcga tggagctcgt cgagaacatg      2220
gcggctagcg atcaagcaat ccttcatgat cacacttatg ttcccacaaa agaagcctc       2280 ttggagctta gcacgcagga cgcaactttg gtacaaaaca agctgttgac gaggcagata      2340
gaagccctca tcgaaaccct cagcaagctg cctcaacaat tacaagcgat aagttcttcc      2400
cactcttctg ttttgcaggt agaagaatgc cccacatgca gagggacaca tgagcctgga      2460
caatgtgcaa gccaacaaga cccctctcgt gaagtaaatt atataggcat actaaatcgt      2520
tacggatttc agggctacaa ccagggaaat ccatctggat tcaatcaagg ggcaacaaga      2580
tttaatcacg agccaccggg gtttaatcaa ggaagaaact tcatgcaagg ctcaagttgg      2640
acgaataaag gaaatcaata taaggagcaa aggaaccaac caccatacca gccaccatac      2700
cagcacccta gccaaggtcc gaatcagcaa gaaaagccca ccaaaataga ggaactgctg      2760
ctgcaattca tcaaggagac aagatcacat caaaagagca cggatgcagc cattcggaat      2820
ctagaagttc aaatgggcca actggcgcat gacaaagccg aacggcccac tagaactttc      2880
ggtgctaaca tggagaagaa ccccaaggaa gaatgaaaag cagtactgac ttgagggcag      2940
agaagagcgc aggaggaggg taaggttgaa ggagaagact ggccagaaga aggaaggaca      3000
gagaagacag aagaagaaga aaggtggca tcaccaccta agaccaagag ccagagagca      3060
agggaagcca agaaggaaga accactagcc cttccacagg atctcccata tcttatggca      3120
cccaccaaga agaacaagga gcgttacttt agacgtttct tggaaatatt caagggtta       3180 gaaatcacta tgccattcgg ggaagcctta cagcagatgc ccctctactc caaatttatg      3240
aaagacatcc tcaccaagaa ggggaagtat attgacaacg agaatattgt ggtaggaggc      3300
aattgcagtg cgataataca aaggaagcta cccaagaagt ttaaagaccc cggaagtgtt      3360
accatcccgt gcaccattgg gaaggaagcc gtaaacaagg ccctcattga tctaagagca      3420
agtatcaatc tgatgccctt gtcaatgtgc aaaagaattg ggaatttgaa gatagatccc      3480
accaagatga cgcttcaact ggcagaccgc tcaatcacaa ggccatatgg ggtgtagaa       3540 gatgtcctgg tcaaggtacg ccacttcact tttccggtgg acttttttat catggatatc      3600
gaagaagaca ctgagattcc ccttatctta ggcagaccct tcatgctgac tgccaactgt      3660
gtggtggata tgggaatgg gaacttagag ttgactattg ataatcagaa gatcaccttt       3720
gaccttatca aggcaatgaa gtacccacag gagggttgga agtgcttcag aatagaggag      3780
attgatgagg aagatgtcag ttttctcgag acaccataga cttcgctaga aaaagcaatg      3840
gtaaatgctt tagactgtct aaccagtgaa gaggaagaag atctgaaggc ttgcttggaa      3900
```

```
aacttggatc aagaagacag tattcctgag ggagaagcca atttcgagac gctagagaag    3960
gaagttccgt ctgagaagaa gaagatagag ttgaagatat tgcctaatca tttgaagtat    4020
gtgttcttgg aggaagataa gcctatagtg atcagtaatg cactcacaac agaggaagaa    4080
aataggttgg tagacgtcct aaagaaacac agggaagcaa ttggatggca catatcggat    4140
ctcaggaatt agccctgcct actgcatgca catgataatg atggaagagg actacaagcc    4200
agtccgacaa ccctagaggc ggctgaatcc aacaatgaag gaagaggtaa gaaaggaggt    4260
gctcaagctt ttggaggctg ggttcatata ccccatctct gatagcgctt gggtaagtcc    4320
agtacaggtg gttcctaaga aaggcggaat gacagtggta cgaaatgaga ggaatgactt    4380
gataccaaca cgaactgcca ctggttggtg gatgtgtatc gactatcgca agttgaatga    4440
agccacacag aaggaccatt tccccttacc tttcatggat tagatgctgg aaaggcttgc    4500
agggcaggca tactactgct tttgatggat attcaggat acaaccagat cgcggtagac    4560
cccagagatc aggagaagac ggcctttaca tgccccttcg gcgtctttgc ttacagaagg    4620
atgtcattcg ggttatgtaa cgcactagcc atatttcaga ggtgcatgct agccattttt    4680
tcagacatgg tggagaagag catcgaggta tttatggacg acttctggat ttttggaccc    4740
tcatttgaca actatttgag gaacctagag atggtactac agaggtgcgt atagactaac    4800
ttggtactaa attgggaaaa gtgtcatttc atggttcgag agggcatagt cctgagccac    4860
aagatctcag ccagagggat tgaggttgat cagacaaaga tagacgtcat tgagaagttg    4920
ccgccaccaa tgaatgttaa aggtgtcaga agtttcttag ggcatgcagg tttctacagg    4980
aggtccatca aggacttctc gaagattgcc aggcccttaa gcaatctgtt gaataaggat    5040
gtggctttta agtttgatga agaatgttca gcagcatttt tagacactaa agaataagct    5100
caccactgca ccagtaatga ttgcaccaga ctggaataaa gattttgaac taatgtgtga    5160
tgccagtgat tatgcagtag gagcagtttt gggacagagg cacgacaagg tatttcacgc    5220
catctattat gctagtaagg tccttaataa agcataacta aattatgcga ccacagaaaa    5280
gcagatgcta gccattgtct tttccttgga gaagttcagg tcgtacttga tagggtcgag    5340
ggtcaccatt ttcacaaatc atgctgccat caagcacttg ctcgccaaaa cagactcaaa    5400
gctgaggttg attagatggg tcctgctgat acaagaattt gacatcatca tcaaggacaa    5460
taaaggatcc aagaatgtgg tagccaatca tttatcctga ttaaagaatg aagaagtcac    5520
caaggaagaa ccagaggtaa aaggagaatt tcctgatgaa tttcttttgt aggttaccac    5580
cagaccttgg tttgcagaga tggctaacta caaagccaca ggagtcattc cagaggagtt    5640
taattggagt cagaggaaga aattcttgca tgatgcacgc ttctatgtgt gggataatcc    5700
tcatttgttt agggcaggag ctgataatct attaaggaga tgcgtcacaa aggaggaagc    5760
acagagcatt ctttggcact gccacagttc accctatggc ggacaccaca gtggggacag    5820
aacagcagca aaagtgctac aatcaggttt tttctggcct tctattttta agatgcttaa    5880
cgagtttgtg cgttgttgtg ataaatgcca gagaacaggg gggatatctc gaaggatgga    5940
gatgcctttg cagaatatca tggaagtaga gatctttgac tgttggggca tagacttcat    6000
ggggcctctt ccttcttcat acgagaatgt ttacatcctg gtagctgtgg attacgtctc    6060
caaatgggtg gaggccatag ccattccaaa agacgatgcc aggtagtgaa taaaatttct    6120
gaagaagaac atcttttccc attttggagt cccatgagcc ttgattagtg atggggaacg    6180
cacttctgca ataatcagtt gaagaaagtc ctggagcact ataatgtaag acataaggtg    6240
```

```
                                    -continued
gccacacctt atcaccctca gacaaatggc caagtagaaa tttctaacaa agagctcaag    6300
cgaatcctgg agaagacagt tgcatcatca agaaagaatt gggccttgaa gctcgatgat    6360
actctttggg cctacagggc agcattcaaa actcccatcg gcttatcacc gtttcagcta    6420
gtgtatggga aggcatgtca tttaccagtg gagctggagc acaaagcata ttaggctctc    6480
gagttactca actttgataa caacgcatgc ggagaaaaga ggaagctaca gttgctggaa    6540
ttagaagaga tgagactgaa tgcctacgag tcatccaaaa tttacaacca aagatgaag     6600 gcatatcatg acaagaagct acagaggaaa gaattccaac catggcagca ggtattactc    6660
tttaaatcaa ggctaaggct attcccaggt aagctgaagt ccaagtggtt agggccgttc    6720
ataatcaatg aagtcagacc tcacggagca gtagaattgg gggaccctag agaagagaac    6780
tttgagaaga aatggatcgt caatggacaa cgcttaaagc tttataacga aggacaacta    6840
gagcgattga cgaccatcat ctacttgaat gacccttgag gaggcctagt gtctagctaa    6900
agacaataaa ctaagcgctg gttgggaggc aacccaacat attttgtaaa aatgtagtca    6960
tttttctgta ttccttcaaa aaaaagggga aaagcccaat aggtgcaaat agaaaacagc    7020
aggtgcagaa agtaaagacc cagtaggtga agtcagcaat aggaggggtg ccaatagaag    7080
aagcgaagtg ggctgcacga agccacgcgc atctaggcgc taagcgccta ggtatatttt    7140 caattttta attttaaaaa ttctgaggga aaccaaggga cgcttccctt ggtatgctta    7200
gcgaccagat gcgcgctaag cgcgcgaacc ataaattgct ggacagtttt caaaactgtc    7260
ccacccctca gctgcccttt tgtattttaa atttcaacca cctcattttt ttttctcttc    7320
tgcgcactcc cactccctat accctttttc tctacatttc ctctaaactt actcgcctcc    7380
ctgtgcctct tcacgtagtt tttacgaaaa taggtgagat tgggaatctg gactgttgct    7440
gtaatacttt gcaggtacca tcacgctaag ccctacacaa aggcttagcg agaaaaagaa    7500
acatagaaag gaagaaagaa gcatgcgcta agcctgcgcc agacaggaca agaaaacaca    7560
gcatgcgttt agccggcacc tcgtgctaag cgcgctcatg agactcagtg aacgcgctaa    7620
gcatggggct gggccttagg gcccatcagc cctcgtgcct tactttctgc accctctttt    7680
tcactaacta cactcccttc tgaatttctt tttgcaccct cctctattac taaccacaat    7740 ctattttttcc gtctttgttt ctttgttttt tcagatggcc tcccgcaaac gccgagctgt    7800
gcccacacct ggggaagcat caagctggga ctcttcccgc ttcacctcgg agatcatttg    7860
gcatagatac caggataaca ttcagctccg gaacattctt ctggagagga atgtcgagct    7920
cacacccagg atgtttgatg agttcctcca ggagctccag aggtgcagat gggaccaggt    7980
gttaacccga cttccagaga agaggattga tgtcgctctg gtgaaggagt tttactccaa    8040
cttatatgat ccagaggacc atagtccaaa gttttgtagg gttcaaggac aggtcatgtg    8100
gtttgatgca gagacgatta acgacttcct tgacacccca gtcatcctgg cagatgtaga    8160
ggagtaccca gcctactctc agtacctccg cactcctccc gatcatgatg ccatcctctc    8220
cactttgtgt actccagggg gacggtttgt tctgaatgtt gatggtgccc cctagaagtt    8280
gctgcggaag gatctgacga cactcgctca gacatagagt gtccttcctt atttttaaccct   8340 tgttcttact tctcacactt ctgatattaa tgttgacagg gcccgtctca tatatggctt    8400
ggtgatgaag atggacctgg acgtggacag ttttatttcc cagcaaatca gtcagatcgc    8460
ccaatccaac acatccaggc tcgggttccc agcgttgatc acggcactgt gtgacattca    8520
gggggttgtt tctaacaccc tgattttga gttactcaat cctatgatta accttgcgta    8580
cattacacta ctaaaaaaaa gctatttac gacgcgcgtt ccacatcgtt tctgccaaaa     8640
```

| | |
|---|---|
| atgtcgtaat aggagtagcg gtggcaattc cgtaaataag tgagcatttt atgtgccatg | 8700 |
| tgcatggcgc gtgacacatt caacgacgtt ggccatgggt gcccgtcttt gtaggtggcg | 8760 |
| cgctggtaac ttaagacggt gcacttaaaa acatcgtcgt tgaaattttg aatttcgaag | 8820 |
| acgttgctct taagccaccg tcgttaaggt tgatgtatat aatgttgtaa tttgcgctat | 8880 |
| ttcgtgaaca ctcgctcgag ctcccgcttc cctgtgtgtc tgaaatttct gtgtactgtg | 8940 |
| acctcgccat gacttgtggc gtttgcccac accccgtca cctcgtccgg catctcgtct | 9000 |
| tgtggtggca ccgccgaagc cagtgagtac ccctttttgg aggggtcgta acacggctgt | 9060 |
| gttttgaagg taaggttgtg cgaagatttg atgctccata gttgttactt gctctgagtt | 9120 |
| tttcttttag tgatgtatct tttacccctc tttcagtgct tcttccctca gaatttgatt | 9180 |
| gccggtatta gaaccccact attcatcagg tccaaacaag cttaaatcat ggtaaatgta | 9240 |
| cttcttgaca aatccaacat ttgcaaggtg gtttgacata tgagaaatag ctttaaccta | 9300 |
| atgttcttaa atttattatg aagctctcta gcgattacga aaatctctca atatcttctc | 9360 |
| tctctgtctc acatgcatca ctgtaagata ggtgtcaaaa agaaaggatt gaagttaaat | 9420 |
| ttaaacctaa tgttttgaaa tgaaggaaaa aagaaagag attaatgacg ctagggaact | 9480 |
| tgaatgaaga aagagaaagg aacataatta gtccctttgaa ctgattgggg tggggagtgt | 9540 |
| ggcacgaaac ataatttcta gttctatgga tttattcgtg acactgtggt aggaccaagc | 9600 |
| aaactctgcc cccagagtgc gcagtgtctt gcagtctgag aggttctttt gttgggctag | 9660 |
| tttgaggaat tcttcattgc agggttgagc acggtggcca atggccaagg agagaaaaga | 9720 |
| cagtactgtc aaaatggtta atggtaagat gagtgaagat gacatgtttt tttgttgtct | 9780 |
| ctttgtgtgt ttccttttgg tgggaaaatg tgatgcatag agagatcga | 9829 |

<210> SEQ ID NO 20
<211> LENGTH: 12571
<212> TYPE: DNA
<213> ORGANISM: Glycine max

<400> SEQUENCE: 20

| | |
|---|---|
| gatcttaaat tcttaaactt tgataacagt gcatacggag agaagagaaa gttgcagtta | 60 |
| ctggaactcg aagaaatgag gttgaacgct tacgaatcat ctaggattta caagcagaag | 120 |
| gtaaaggcgt atcatgataa gaaattacaa aagaaagaat tccagccagg gcagcaagta | 180 |
| ctactcttca actccaggtt gagattattc acaggaaagc tgaagtcaaa gtggtcagga | 240 |
| tcgttcatta ttaaggaaat cagacctcac ggagcggtag aattggtgga ccctcgagaa | 300 |
| gaaaattatg agaagaaatg gatcgtcaac ggacaacgct taaaaattta caatggagga | 360 |
| caactagaga agttgacgac catcatgcat ttaaaagatt cttgaaagaa gccctatgtc | 420 |
| tagctaaaga cattaaacta agcgctggtt gggaggcaac ccaacatact tatgtaaggt | 480 |
| atttataagt atttatattc tgtctttatt atattttgca gttgttattt caggttaaaa | 540 |
| gaaaaaacag gggccctccg gactcgcacc agagtatcaa cgtccatatc tgaggcaccc | 600 |
| cctacttctc agccttccgc tccatcacct actgatcttc atgctcagat gttgcggtct | 660 |
| attcacacag gacaggagac ccttatggag aacatgcaca agctgtcctt tcatctacat | 720 |
| atggatccac cactgatcac tccataggtc tatcgtcagc gggtcgtctg gccatgagac | 780 |
| cagctctcca ctgacagggg ggaagagccc tctggagatg ctgcagttga tgaagacctc | 840 |
| atagcagact tggctagtgc tgattgggt ccatgggcag atttgggagg cggcacagga | 900 |

-continued

```
cactggtttt attttcttg atgttttgt ttatgtttaa tgtttatgtt ttatgtctttt      960 atgttttatt tggtttctag ttattatggt cttaattgta gttttatgtt caaaatgaaa    1020
agcagtggta ataatattag atttgagcat atgcgtgaat aaataaattg catgataact    1080
tgagaaatga caattttgag tttgttctaa aaggtccaac actggaaagg ctactagtca    1140
ttggaaagca ctggtcttgg aagcaaaagt caaatcaagg aatgaaacat gattcacgga    1200 aaggaaagg ttagcttgat ggaatgaaga cacatctggt acgccaatac tgaattaatc     1260
ccggtgagag tgtgacctta attgtgagag aaaacgcctg tttttaagct cttagttttg    1320
catcattctt ggactgttaa aattagttac ttaaggtgga tatgatcaag gccatgtttg    1380
ttttatttta cccactcagc caaaaagcca acccaacata attttatccc ttgcacccat    1440
attgagccaa aaagaattat aatgatttat ttgagtaaac ccctgagcca agaaattgat    1500
attcctaacc ttgtgtagga ttctaagaga gcagtagggt tccaaatgct tataaggcct    1560
tattttgggg gattttgaac aaatgggtaa agtagccaag gtaataacac acattagaac    1620
acctctaaat aattgtgagc ccattactat tattattatt attattatta ttattattat    1680
tattattatt attattatta ttattattat tattggttat aaaaaaaga agaaaaaaag     1740 agaaagaata agaagagaaa gggcaaagaa aaaaatgaa aaagagaggt ttcagtggaa     1800
agtgctgaag gcaaaaaagg ctaagtggga aataggtctt ggcaagacct taaatttttg    1860
gaatgtatgc tctcttataa ccttatattt tgaatttcca agaaaaacca tgattctttg    1920
ttagccaggc cccattacaa ggcatgaaag tccttagtga cccaccgaag gtaattaagg    1980
ctaaccttaa ccaagatgaa gtacaaaact cttgagtttt atttacaggt tgttaaaatt    2040
gcaaacactt gaccaggcac ttgtgagtag agagaaacac cagttttgta aggaagtaag    2100
gcaagccgga cctgttggaa ttccatataa ttgacttgtt tctgctcttg tgtttatgct    2160
tttatttcaa gatcatgaca gatgcaaaga gaccagccaa aggatcaagg aattgaagtc    2220
atggagagtg ttggaatgat tggaacttgc ttgagaaaat ttttgcttaa gaatggaata    2280 atttttattct ttttatttgc ttggggacaa gcaaagttta atttggggga ttttgataac   2340
tgctaaataa tagtgaatta atagtggaaa attggtctga aattaactta gaattaatta    2400
tttagtagtt atttatgctt taatttggaa agatttaatt aattttgaat tctgattgca    2460
gatgtgaaaa agggaggtac aacaagcaaa aaggagcaaa aataaagaaa aagaagaaga    2520
aaatcagacg aagacccaag cccaaatttt cacctataaa taagaaggtc agcctagcaa    2580
aacacacaca ctttcagaga gctcagtttt cagacttctg gcactcagtt ctctccttct    2640
ccttcccttt tcttatatt cttattacct ttctttcacc cccttctcat tgtaaagccc     2700
tcttgactat gagtggctaa accctagct agggcctggc aggcctaaaa agccaatgat     2760
gtatggagca tttcaagagt tatcaataaa gagaggattt ccttccaggt tctttattta    2820 ccgttcttc ttatttatcc tgtatttcgg accttatttt ctgttagggt ttagtccact     2880
cgggagaggg taaagcctaa ttaggggtaa ggaatgaata cttgaatcta ttttaagggt    2940
tagtccattc gggagagggt aaagcttaat agaacaataa aaggaagaaa ttatcgggtt    3000
atcattagag ggttttcctt ccaggttctt ttatctgctt ttctttctta ttctgcatct    3060
cagtctttat tttctgttag tctttagtcc actcgggaga gggtaaagcc taattaaggg    3120
taaggaatga ttgcgtgaat ctgtttaag ggttagttca ctcaggagag ggtaacgctt     3180
aatagaacaa taaagaaaa aaatcacagg gttagcattg acccgatgcc catactttag     3240
caaacatata gaatttaatc ttaatgcatc ttagttattg agtctttgca aagggcattt    3300
```

```
ggaagatagg taattaaggt aggcttgtca tcatgaggca tcaggggcaa gtagatggat      3360
agatgtgggg cagaatcagt tcactggtat tgataacaga caaatcttga atccatatat      3420
ctaggctgat tagactttt aggttttagc aattttatta tatagatttt attccctatt       3480
ttattgtttg aagtttctta ttctattgtt gggttttctt agaagtagct attccttatt      3540
ttactgttgg gttttcttag aaatagttat tccttattgt tgggtttctt agaagtagtt      3600
attccttatt ttactgttgg gttttattag gagtacttat cccctgttta ggagtaggta      3660
tttaggctta ttagatttag taatatttta tagacttat tctttattta ttgcttgagt       3720
ttcctttaat ttagaagtag ctgcttagat ttaaattact ttatcttat cctttaatct       3780 tatcttaaa tcttttatct ttccttatc ttatctttta tctttcttta tcttttattt        3840
caaatttctt atcccttgct agatttaaat tgcatttaat tttatacact aaatttacaa      3900
tttgcaaact aaaagtact tcacataagt gcaacaaaat ccctatggta cgatactcga       3960
cttaccgaga gattattact acgagcgatt tggtacactt gccaaagagc taacaaagat      4020
attgcctgat catctaaagt atgtgttctt ggaggaagat aaacctatag taatcagtaa      4080
cgcactcaca acaaaggagg aaaataggtt ggttgatgtc ctcaagaaat acaggaagc       4140 aattggatgg catatatcgg atctcaagga aattagccct gcttactaca tgcacagaat      4200
aatgatggaa gagaactaca agccagtccg acaaccccag aggcggctga atccaacaat      4260
gaaggaagag gtaagaaagg aggtactcaa gctcttggag gctgggctca tatacccctt      4320
ctctaacagt gcttgggtaa gcccagtaca ggtggttccc aagaaaggtg aaatgacagt      4380
ggtacgaaat gagaagaatg acttgatacc cagacgaact atcactggtt ggcgaatgtg      4440
tatcaactat cgcaagctga atgaagccac acgaaaggac catttcccct acttttcat       4500 ggatcagatg ctagagagac ttgtagggca ggcatactac tatttcttgg atggatactc      4560
gggatataat cagatcgcgg tggaccccag agatcaagag aaggcggcct ttacatgccc      4620
ttttggcgtt tttgcttata gaaggatgcc attcgggtta tgtaatgcac cagccacatt      4680
tcagaggttc atgctggcca tttttcaga catggtgtag aaaagcattg aggtatttat       4740
ggacgacttc tgggtttttg gaccctcatt taacagtttg aggaacctag atggtact        4800 ttagagttga gtagagacta acttggtact gaactgggag aagtgtcact tcatggttca      4860
agagggcatc gtcctaggcc acaagatctc agcaagaggg attgaggtcg atcgggcaaa      4920
gatagacgtc atcgagaagc tgccaccacc actgaatgtt aaaggggtta gaagtttctt     4980
agggcatgca ggtttctaca agaggtttat caaggacttc tcaaagattg ccaggcccct      5040
aagtaacctg ttgaataaag acatggtttt caagtttgat gaagaatgtt caacagcatt      5100
ccaatcattg aagaataagc ttaccactgc acctgtaatg attgcacccg actggaataa      5160
agattttgaa ctaatgtgtg atgccaatga ttatgcagta ggagcagttc tgggatagag      5220
gcacgacaag gtatttcacg ccatctatta tgctagcaag gtcctgaatg aagcatagtt      5280
gaattatgca accatagaaa aggagatgct agccattgtc tttgccttgg agaaattcaa      5340
gtcatacttg atagggttga gggtcaccat tttcacagat catgctgcca tcaagcacct      5400
gcttgccata acagactcaa aaccgaggtt gattagatgg gtcctactgt tacaagaatt      5460
tgacatcatc atcaaggaca agaaaggatc cgagaatgtg gtagccaatc atctatctcg      5520
attgaagaat gaagaagtca ccaaggaaga accagaggta aaaggtgaat tcctgatga      5580 gtttcttttg caggttaccg ctagatcttg gtttgcagac atggccaatt acaaagccac      5640
```

```
gggagtcatt ccagaggagc ttaattggag tcaaaggaag aaattcttgc acaatgcacg    5700
cttctatgtg tgggatgatc ctcatctgtt caaggcagga gcagataatt tactaaggag    5760
atgcgtcaca aaggaggaag cacggagcat tctttggcac tgccacagtt caccctatgg    5820
cggtcaccac agtggggaca gaacagcagc aaaagtgcta caatcaggtt ttttctggcc    5880
ctctattttt aaagatgctc acgagtttgt gcgttgttgt gataaatgcc aaagaacagg    5940
ggggatatct cgaagaaatg agatgccttt gcaaaatatc atggaagtag agatctttga    6000
ctgttggggc atagacttca tcgggcccct gccttcgtta tatggaaatg tctacatctt    6060
ggtagttgtg gattacgtct ccaaatgggt ggaagtcata gctacgccaa aggatgatgc    6120
caaggtagta atcaaatttc tgaagaagaa cattttttcc cgttttggag tcccacgagc    6180
cttgattagt gataggggaa cgcacttctg caacaatcag ttgaagaaag tcttggagca    6240
ctataatgtc cgacataagg tggccacacc ttatcatcct cagacaaatg gccaagcaga    6300
aatctctaac agggagctca aggcgaatct tggaaaagac aattgcatca tcaagaaagg    6360
attgggcctt gaagctcgat gatactctct tggcctatag ggcagcgttc aagactctca    6420
tcggcttatc gccatttcag ctagtgtatg ggaaggcatg ccatttacca gtggagctag    6480
agcacaaagc atattgggct ctcaagttgc tcaacttcga caacaacgca tgcggggaaa    6540
agaggaagct acagatgttg gaattagaag agatgagact gaatgcctac gagtcatcca    6600
gaatttacaa gcaaaagatg aaggcatatc atgataaaaa gctacagagg aaagaattcc    6660
atccagggaa gcaggtatta ctctttaact cgaggctaag gctattccca ggtaagctga    6720
agtccaagtg gtcaaggcca tttatcataa aagaagtcag acctcatgga gcagtagaat    6780
tggtggaccc ttgagaagag aactttaaga agaaatggat cgtcaatcga cagcgcttga    6840
agccctacaa cggaggacaa ctcgagcgat tgacgaccat catctactta aatgatcctt    6900
gagaaggcct actgtctagc taaagacaat aaactaagca ctggttggga ggcaacccaa    6960 catattttg taaaaatgta gttatttta ttttatgtaa aaaaaaacaa gagggcccaa    7020
taggtgcaaa tagcaaacag gaggtgcaaa aagcaaaggc ccaacaggtg aagacaacaa    7080
taggaagggt gccaatagca aaactgaagt gggctgcatg aagccgcgcg ctaagcgccc    7140
aggtatgttt ttaaaatctg atgggcaacc aagggacgct ttccttggtg cgcttagcgg    7200
ccacatgcgc gctaagcgcg taagtcataa attactggac agttttcgaa actgcccaac    7260
ccctcagctg cctcctccgc gttattaaat tacaaccatt tcatttcatt atccttcttt    7320
tctttcgcaa atctacccct ttttgcacct ctgctactgt aaccctgaa ttcttggtct    7380 tttcacacaa aacaatcact aacgaaggta aagaattgct ttgtatggat gttgttatga    7440
atgcacaggt aacagcacgc taagccctgc tcgacgctta gccaatgaag acggattgaa    7500
ggccataacg acgagctcgt taagcgtgac gaagcacgct aagcaggcgc ctgacaggac    7560
gagaaagcaa agcgcgcgct tagccggcac ttccgcgcta agcgcgctca tgaacatcac    7620
tgaacgcgct aaacgtgtgc cagaggcgct aaacgcgtgc cagaggcgct aaacgcgtgc    7680
attagtcaca gcaggatggt gctaagcgcg gggttgggcc tcagggccca tcaaccctcg    7740
caccttactt gttgcacccc tatttctact attcccactc ccttctaatt tcttttttgca    7800 cccccttct ttactgactg cacctctatt ttgattactt tttgcacccc cctgattgc    7860 taacttcaga ctatctttct tgtttttttgt tttttggtt ttttggtcag atggcctcct    7920
gtaaacaccg agctgtgccc acaccgggg aagcgtccaa ctgggactct tcacgtttca    7980
ctttcgagat tgcttggcac agataccagg atagcattca gctccggaac atccttccag    8040
```

```
agaggaatgt agagcttgga ccagggatgt ttgatgagtt cctgcaggaa ctccagaggc    8100
tcagatggga ccaggttctg acccgacttc cagagaagtg gattgatgtt gctctggtga    8160
aggagtttta ctccaaccta tatgatccag aggaccacag tccgaagttt tggagtgttc    8220
gaggacaggt tgtgagattt gatgctgaga cgattaatga tttcctcgac accccggtca    8280
tcttggcaga gggagaggat tatccagcct actctcagta cctcagcact cctccagacc    8340
atgatgccat cctttccgct ctgtgtactc caggggacg atttgttctg aatgttgata    8400 gtgcccctg gaagctgctg cggaaggatc tgatgacgct cgcgcagaca tggagtgtgc    8460
tctcttattt taaccttgca ctgacttttc acacttctga tattaatgtt gacagggccc    8520
gactcaatta tggcttggtg atgaagatgg acctggacgg gggcagcctc atttctcttt    8580
agatcagtca gatcgcccag tccatcactt ccaggcttgg gttcccagcg ttgatcacaa    8640
cactgtgtga gattcagggg gttgtctctg atacctgat ttttgagtca ctcagtcctg    8700
tgatcaacct tgcctacatt aagaagaact gctggaaccc tgccgatcca tctatcacat    8760
ttcaggggac ccgccgcacg cgcaccagag cttcggcgtc ggcatctgag gctcctcttc    8820
catcccagca tccttctcag ccttttttccc agtgaccacg gcctccactt ctatccacct    8880
cagcacctcc atacatgcat ggacagatgc tcaggtcctt gtaccagggt cagcagatca    8940
tcattcagaa cctgtatcga ttgtccctac atttgcagat ggatctgcca ctcatgactc    9000
cggaggccta tcgtcagcag gtcgcctagc taggagacca gccctccact gacagggggg    9060
aagagccttc tggagccgct gctactgagg atcctgccgt tgatgaagac ctcatagctg    9120
acttggctgg cgctgattgg agcccatggg cagacttggg cagaggcagc tgatcttatg    9180
ctttaatgtt ttcttttata ttatgtttgt gttctctttt atgttttatg ttatgttttt    9240
atgtagtctg tttggtaatt aaaaagaggt agtagtaaaa atattagtat ttcagtatgt    9300
gttttctgag taataagtgc atgataactc aagcaatcat aattctttag cttgttcaga    9360
aaggttcaac acttgagatg ccactgatcc ttggagaaac actggttctg gaagcaaaag    9420
tcaggtcaag aaatggaaca tgaatagcac agagtggaaa ggttagcttg atggaacaag    9480
gtcataactg gtacgccgaa tacttgttta agtccctgtg agcatggttg tcaaactcta    9540
gagtcaactc atagactctc atgagtttaa gagtttactt cagtcccgcg agttgactcg    9600
gaagcaaact cgcttttgag caaactcgtg gactcggagt gaactcatgt aaactcgtaa    9660
gagtctacga gttgactcta gagtttgaca accatgcata agtgttcaaa attaaagcat    9720
ttaaataatt aaaaaaagca caaatgtctt caaagaagca tgttcaatcc tctaatagga    9780
tcatcttcat gaatatcatc actttcatca tcatctccat ctccatcatc atcatcaagg    9840
tcttcctcag attgtgcatc atcattaggt tccacaaaga ttaaattatc tagatcaaaa    9900
gcttaaaata gatatcaaat atgctatatt agaaatagtt aaaacttaaa ataatacaca    9960
agcaaatttt aaatatgaga aagttcagaa attatacctt tcttggtgt tattaaagtt    10020 tcattttatc ttctcttttg catttttccat ctcctcacat atgaaaagca taattctatt    10080
gaatttcagt aacaagtttg atccaactcc aacattgtaa ggtcagttgt tgtgtttttgt    10140 aatagactaa tatgaagtat gaagtatgaa ctatgaactt attgtcatct gtttgcaaat    10200
tggtgcattt tgaatatatt tacttattat ccattttttt tttttttacga agtagactct    10260 cacgagtctg cgtagactct cgatatcgat aaccttgccg atgagagtgt gaacttaatt    10320
gtgagagaaa atgcctattt ttaagttcct ggttttgcat cattcttaga cggttagaat    10380
```

-continued

```
agttacttaa ggtggatatg atcaaggcca tgtttgtttg tttacctact tagccaaaaa    10440
gccaacctaa catagtttta ccccttgcac ccatgattga gccaactgat tattttgaat    10500
taaccttgag ccaattaaac aaaatcctga ccttttagga ttttaagaga gtaaaaatgg    10560
gttataaagg tcttaatttg ggggattttg ggaaataggt agccaagaca ataagtacag    10620
cacacaaagt aggacacctt ttacaaacag taggcccaat ttcgaaaaaa aaatgaaaag    10680
aatttaataa agggcagaaa caaagagca  agagaggtgt caaagaaaaa gtgttgtggg    10740
gaaataaaag ggctaagtaa aaaggcctag gcagaattgg aaatttttgt tctcttttaa    10800
tcctaacttt gaatttccaa gaaaaaccat gattttttgt aagccaggcc ccgatacaag    10860
ccaataaagt ccttagtgat ccaccaaagg taactagaga taactgtaac tgagatgaaa    10920
tgcaaaattt tgaagtgtta cttgcaggtt gttatcaaat tgcaaacact aaactaggca    10980
cttgtgagca gagggaaaca ccagccttgt gaggaaagta aggcaagcca aatttgattg    11040
agttccagat gactaactga ttcaattctt ctgttgtaat gctttcattt taagatgttg    11100
acagatgcag aaaggaccag tgaaagaagg aggaactgag ccattgatag tgttggaata    11160
tttaagaact tgcttgagaa tttacttgtt tttggttttc ttggggacaa gcaaagtttc    11220
atttggggaa ttttgataac tgctaaataa ttgtgaatta atagtaaaga attattcaaa    11280
ttttggcctg aaattaatta tttagcagtt atttgtgatt aaaagttaga aaattaatta    11340
aattgaattt ttggttgcag ataagaaaat tggagttaca ttaagcaaaa aaggcaacaa    11400
aaaatgaagg aaaagaagaa gtctgaagca ggcccagccc aacacgcacg ctaagcgcgt    11460
gtcacgcgct aagcgtgcaa ggcagtacag gcgctaagcg aggcgttaag ctcgaagatg    11520
cagaatccgt tacgcgcgct aagcaagggc cacgcgctaa gcgtgcgatc aacagaaac    11580 acacgctaag cctgcatctc gcgctaagcg cgcgatctga acgcgctaag cgcgaggtgt    11640
cgcgctaagc gcgcttacga aggcccaaaa cccactttag cagctataaa tagagagtca    11700
gtccaaggga acaacacat  ctcgcctcag agcacttccc tcagcattct aagcctaagc    11760 tctcccttt  ctcttttgttt ttattatcct cattcttcct ttcacccca  gttgtaaagc    11820 cctcaatggc catgagtggc taatctagta gctagggcct ggcaggccta aaaagccaac    11880
gatatatggt gtacttcaag agttatcaat gcaaagaaga ttcattccag gttttttgt    11940 tctaattatt ttcttttat  cttgcattca tttcttgaat ttcttttggg ttttatttgc    12000
tcgggagagg gtatttccta ataagggttt aaggattaat gcatgcatca gttttagggg    12060
ttatacgctt gggaaagggt aacacctaat agaacatctt aagaaaagaa tcatcgggtt    12120
agcattgcta ggcatagaat gataactcaa tgcccacgca tttagcaaca tctagaattt    12180
taccttaatg cattttaatt attgagtctt cgcaaaggca tttgggagat aggtagttaa    12240
aataggcttg tcatcgtgag gcatcagggg caagtaaaat taatagatgt gggtagaact    12300
gttacaaatg cattggtaat gaatatcata tttacatgca tcgtaggcca attgggtttg    12360
tccggtcttg gcatttatat taattgtctt tctaaaacta tttgatctag taatagcaat    12420
ctattcttgc acttactcct gttttactta ttttactctt acaaattgaa aagtattcga    12480
taaagtgcaa taaatccct  gtggaaacga tactcggact tccgaggttt actacttaga    12540
gcgatttggt acacttgcca aagtctcaac a                                   12571
```

```
<210> SEQ ID NO 21
<211> LENGTH: 4609
<212> TYPE: DNA
<213> ORGANISM: Glycine max
```

<400> SEQUENCE: 21

```
gatctcccat atcctatggt acccaccaag aagaacaagg aacattactt ctgacgtttc         60
ttggaaatat tcaaaggact ggaaatcacc atgccattcg gggaagcctt acagcagatg        120
cccctctact ccaaatttat gaaggacatc ctcaccaaga aggggaagta tattgacaat        180
gagaatattg tggtaggggg caactgtagt gcaataatac agaggaagct acccaagaag        240
tttaaggacc ccggaagtgt taccatcccg tgcaccatag gaaggaaga ggtaaacaag         300
gccctcattg atctaggagc aagtatcaat ctaatgccct tgtcaatgtg cagaagaatc        360
aggaatttga agatagatcc caccaagatg acacttcaac tggcagaccg ctcgatcaca        420
agaccataca gggtggtaga agatgtcctg gtcaaggtac accacttcac ttttccggtg       480
gactttgtta tcatggatat cgaagaagac acagagattc cccttatctt aggcagaccc        540
ttcatgctga ttgccaactg tgtggtggat atggggaatg ggacttgga ggtgagtatt         600
gacaatcaga agatcacctt tgaccttttc aaggcaataa agtacccata ggagggttgg        660
aagtgcttta aatgaggga gattgataag gaagatgtca gtattctcga cacaccacag         720
tcttcgctgg ggaaagcaat ggtaaatgct ttagactgtc taaccagtga agaggaagaa        780
gatctaaagg cttgcttgga agacttggat tgacaagaca gtattcctaa gggagaagcc        840
agatttgaga ctctagaaaa ggaagttccg tccgagaaga agaagataga gttgaagata        900
ttgcccgatc atctgaagta tgtgttcttg gaggaagata aacctgtagt gatcagtaac        960
gtactcacaa cagaggagga aaacaggtta gtagatgtcc tcaagaaaca cagggaatca       1020
attggatggc acacatcgga tctcaaggga attagccctg cttactgcat gcacaggata       1080
atgatggaag aggactacaa gccagtctga caaccccaga ggcggctgaa tccaacaatg       1140
aaggaagagg taagaaaaga ggtactcaag ctccttgagg ttgggctcat atacccatc        1200
tctgacaacg cttgggtaag cccagtacag gtggttccca agaaaggtgg aatgacagtg       1260
gtacaaaatg agaggaatga cttgatacca acacgaacag tcactggctg gcgaatgtgt       1320
attgactatc acaagctgaa tgaagctaca cggaaggacc atttcccctt acctttcatg       1380
gatcagatgc tggagagact tgcagggcag gcatactact gtttcttgga tggatactcg       1440
ggatacaacc agatcgcggt agaccccata gatcaggaga agacggtctt acatgccccc       1500
tttggcgtct ttgcttacag aaggatgtca ttcgggttat gtaatgtacc agccacattt       1560
cagaggtgca tgctgaccat tttttcagac atggtggaga aaagcatcga ggtatttatg       1620
gacgacttct cggttttttgg accctcattt gacagctgtt tgaggaacct agaaatggta       1680
cttcagaggt gcgtagagac taacttggta ctgaattggg aaaagtgtca ttttatggtt       1740
cgagagggca tagtcctagg ccacaagatc tcagctagag ggattgaggt tgatcgggcg       1800
aagatagacg tcatcgagaa gctgccacca ccactgaatt taaaggggt tagaagtttc        1860
ttagggcatg caggtttcta taggagggttt atcaaggatt tctcgaagat tgccaggccc       1920
ttaagcaatc tgctgaataa agacatgatt tttaagtttg atgaagaatg ttcagcagca       1980
tttcagacac tgaaaaataa gctcaccact gcaccggtaa tgattgcacc cgactggaat       2040
aaagattttg aactaatgtg tgatgctagt gattatgcag taggagcagt tttgggacag       2100
aggcacgaca aggtatttca ccatcctat tatgctagca aggtcctgaa tgaagcacag       2160
ttgaattatg caaccacaga aaaggagatg ctagccattg tctttgcctt ggagaagttt       2220
aggtcatact agatagggtc gagggtcacc attttcacag atcatgctgc catcaagcac       2280
```

-continued

```
ctgctcgcca aaacagactc aaagctgagg ttgattagat gggtcatgct attacaagag    2340
tttgacatca ttattaagga caagaaagga tccgagaatg tggtagctga tcatctatct    2400
cgattaaaga atgaagaagt caccaaggaa gaaccagagt taaaaggtga atttcctgat    2460
gagtttcttt tgcaggttac cgctagacct tggtttgcag acatggctaa ctacaaagcc    2520
atgggaatca tcccagagga gtttaattgg agtcagagga agaattttt gcacgatgca    2580 cgcttatatg tgtgggatga tcctcatttg ttcaaggcgg gagcaaataa tttattaagg    2640
agatgcgtca caaggagga agcacgaagc attctttggc actgccacag ttcaccctat    2700
ggcatacatc acagcgagga tagaacaaca gcaaaagtgc tacaatcaag ttttttctag    2760
cccttatttt ttaaagatgc tcacgagttt gtgcattgtt gtgataaatg tcagagaaca    2820
agggggatat ctcgaagaaa tgagatgcct ttgcagaata tcatggaggt agagatcttt    2880
gatagttggg gcatagactt catgggccct cttccttcat catacaggaa tgtctacatc    2940
ttggtagctg tggattacgt ctccaaatgg gtggaagcca tagccacgct gaaggacgat    3000 gccaggtag tgatcaaatt tctgaagaag aacattttt cccatttcgg agtcccacga    3060
gccttgatta gtgatggggg aacgcacttc tgcaacaatc agttgaagaa agtcctggag    3120
cactataatg tccgacacaa ggtggccaca ccttatcaca ctcagacgaa tggccaagca    3180
gaaatttcta acagggagct caagcgaatc ctggaaaaga cagttgcatc atcaagaaag    3240
gattgggcct tgaagctcga tgatactctc tgggcctata ggacagcgtt caagactccc    3300
atcggcttat caccatttca gctagtatat gggaaggcat gtcatttacc agtagagctg    3360
gagcacaagg catattgggc tctcaagttg ctcaactttg acaacaacgc atgcggggaa    3420
aagaggaagc tacaactgct ggaattagaa gagatgagc tgaatgccta cgagtcatcc    3480
aaaatttaca agcaaaagac aaaggcatat catgacaaga agctacaaag gaaagaattc    3540
cagccagggc agcaggtatt actcgttaac tcaaggctaa ggctattccc aagtaagctg    3600
aagtccaatt ggtcagggcc attcataatc aaagaagtca gacctcacag agcagtagaa    3660
ttggtggacc ctagagaaga gaactttgat aagaaatgga tcatcaatgg acagcgcttg    3720
aagccttata acggaggaca actagagcga ttgacgacca tcatctactt aaatgaccct    3780
tgagaaggcc tactgtcgag ctaaagacaa taaactaagc gctggttggg aggcaaccca    3840
acatattttg taaaaatgta gttatcttca ttctatgtaa aaaaaaagcc caacaggtgc    3900
aaataggaaa cacgaggtgc aaaaagcaaa ggcccaacat gtgaagacaa caataggagg    3960
ggtgccaata gcaaaactga agtgggctac acgaagctac gtgcttagct cgcgtccgcg    4020
cgctaagcgc ccagattgca caaaaatagg tgagacttgg aatctggact attgctgtaa    4080
tatcttgcag gtaccattac gctaagccct acacagaggc ttagcgagaa caggcagcat    4140
ggaaaaaggg aaggaggagc gcgctaagcc acaacaagta atagaagaaa cgaagcacg    4200 cgcttagcgg gcactgccgc gctaagcgca ctcttcaaca tcagtgaacg cgctaagcgc    4260
gtgccagaag cgctaagcgc gtgtcaccgt caccagcagg aaggcgctaa gcgcgaggtt    4320
gggccttagg gcccatcagc cttcgcgcct tacttttgc acaccccttc tttactaact    4380
gcacccctat tttgatttct ttttgcaccc cctctgttta ctaactgcag tttgtttctg    4440
ctgtttcttg ttttttgtttc agatggcctc ctgcaaacgc cgagccgtgc ccacacccag    4500
ggaagcgtct aattgggact cttcccgttt cacttcagag attgcatggc acagatatca    4560
ggacaacatt cagctctgga acatcctttc ggagaggaat gtcgagctc              4609
```

-continued

<210> SEQ ID NO 22
<211> LENGTH: 9139
<212> TYPE: DNA
<213> ORGANISM: Glycine max

<400> SEQUENCE: 22

| | | | | | |
|---|---|---|---|---|---|
| acctggttgt | ttgtatgctt | gtcttaatgc | ggataggttg | tcaagtagct | ttagtgctaa | 60 |
| cactgagaag | aatccgaagg | aagaatgtaa | agttttaatg | acaaagagca | gaatggaaat | 120 |
| tcaagttgat | gaagttagag | ctgaagagaa | ggtggaggga | tataaacaac | agtcgatagc | 180 |
| tgagcctgca | ctggaactag | tttccgatct | tattgaactt | gaggaagttt | tggaagagga | 240 |
| agatgaccaa | caggagagag | agacaccaat | aaaagatagt | caagaaggaa | taagatgaaa | 300 |
| ggaagagcat | gaaaaagaaa | aacaaaaaga | aaaagaagaa | atagaaaaag | aaaataataa | 360 |
| aaaaaatgaa | aaataaaaaa | agatggttga | tgaggagaaa | aaaagagca | agagtgaggt | 420 |
| ttcaagagaa | aaaagagag | agattacttc | agctgaaggc | aaggaagtac | catatctatt | 480 |
| ggtaccttcc | aagaaggata | aagagcaaca | cttagccaga | tttcttgaca | tcttcaagaa | 540 |
| actggaaatt | actttgcctt | ttggagaagc | tctccaacag | atgccactct | atgccaaatt | 600 |
| tttaaaagac | atgctgacaa | agaagaacta | gtatatccac | agtgacacaa | tagttgtgga | 660 |
| aggaaattgt | agtgctgtca | ttcaacacat | ccttccccca | aatcataagg | atcccggaag | 720 |
| tgtcactata | ttatgttcca | ttagcgaggt | tgttgtgggt | aaagctctca | tagacttggg | 780 |
| agctagtatc | aatttaatgc | ctctctcaat | gtgtcgacga | cttggagaga | tagagataat | 840 |
| gcccacacgc | atgacccttc | agttggttga | tcactccatc | acaagaccat | atggagtgat | 900 |
| tgaggatatg | ttgattcagg | tcaagcaact | tgtattccct | gtagatttcg | tggttatgga | 960 |
| tatagaggag | gatcctgaca | ttcccataat | cttgggacgt | cctttcatgt | ccgcgaccaa | 1020 |
| ctatatagta | gatataggga | aaggcaagtt | agaattgggt | gtggaggatc | agaaagtctc | 1080 |
| attcgactta | tttgaagcaa | ataagcatcc | aaatgataag | aaagcttgct | tgatctaga | 1140 |
| caaggtagaa | caataaatag | aattagctac | tatagccatg | gtactgaact | ctcctttgga | 1200 |
| aaaagcattg | attaatcatg | tagaatgtct | tactaaagag | gaggaacatg | aagtgcaaac | 1260 |
| ttgtattaaa | gagttggatg | gtgcaggaga | aaattctgag | ggacaggatg | catttcaaga | 1320 |
| attgaagaat | ggtgggcaaa | tagaaaaacc | aaaagtagaa | ttgaagacct | tgcctgcaca | 1380 |
| tttgaagtat | gtatttctcg | aagacaatga | ctccaaaacca | gtgattatta | gcagctcgtt | 1440 |
| gaagaaaata | gaagatcaac | tggtgaagat | tttgaagaga | cacaaagctg | caattggatg | 1500 |
| gcacatatct | gacttgcaag | gaattagtcc | atcttattgc | atgcacaaaa | tcaatatgga | 1560 |
| agctgattac | aaaccagtga | gagagcctca | agaagactg | aacccaatca | tgaaagaaga | 1620 |
| gatgcataag | gaggtgctta | aattgtagga | agcaggcctt | atttaccccct | cctcggatag | 1680 |
| tgcatgggtt | agccttgtgc | aggttgtccc | caagaaagga | ggtatgacag | tcattaaaaa | 1740 |
| tgataaagat | gagttaatat | ccataaggac | tgtcaccggg | tggagaatgt | gcattgacta | 1800 |
| tcggaagctg | aatgatgcca | ctcggaagga | ccattatcca | cttcctttca | tggaccaaat | 1860 |
| gcttgaaaga | cttgtagggt | aatcctatta | ttgttttctc | gatgagtact | ctggctataa | 1920 |
| ttagattgtt | gttgatccta | agatcaagaa | gaagactgct | tcacctacc | cttttggtgt | 1980 |
| attcgcatat | cggcacatgc | cttttggtct | gtgcaatgcc | ccagctacat | ttcagaggtg | 2040 |
| tattatggca | atttttttctg | atatggtgga | aaaatgcatc | gaagttttca | tggatgattt | 2100 |
| ctctattttt | gggccatcct | ttaaggggtg | cctattaaat | cttgaaagag | tattacagag | 2160 |

```
atgtgaagag tccaatctag ttctcaattg ggagaaattc catttcatgg ttcaagaagg      2220
aatagtgctg gggcataaaa tttcagtaag gggaatagag gtggacaagg caaagattga      2280
tgtaattgag aaacttcctc ctccaatgaa tgccaaagaa gtgagaagtt tcttatgaca      2340
tgcaggattc tacagatgat tcataaaaga tttctcaaaa gtcgcccagc cacttagcaa      2400
tctgttgaat aaagatgttg cttttgtgtt caatcaagag tgcatggaag catttaatga      2460
tctgaaaacc agattagtgt ctgctccagt aagtatagca ccagattggg gacaagaatt      2520
tgagttgatg tgtgatgcaa gtgactatgt cgtaggtgta gtgcttcgac aacgaagggg      2580 aaaactttt catgctatat actacgccaa caaggttcta aatgatgcac aggtgaacta      2640
tgctaccata gaaaaagaaa tgctggcaat tgtctatgca cttgaaaagt ttagatctta      2700
tttggtaggt tcaagagtta tcatctacat cgatcacgca gctattaaat atttgctcaa      2760
caaggctgat tccaaaccta gattgataag atggatcttg ttgttgcaag aatttgattt      2820
ggtgattcgg gataaaaagg gatcggaaaa tgttgtagct gaccatttgt ctagattggt      2880
gaatgaggaa gtcacattga aagaagcaga agtgagagat gaattccctg atgaatcatt      2940
attcttagtg agtgagagac cttggttttgc cgatatggcc aacttcaaag ctacaagaat      3000
catcccaaag gacttaactt ggtagcagag gaagaaattc ctacatgatg ctcgattcta      3060
tatctgggtt gatcctcatt tgttcaagat aggagctgac aatctcctat gaagatgtgt      3120
gacacaagaa gaggccaaga acatattatg aaattgccac aattctccat gtggcagcca      3180
ttatggtgga gataagacga tgaccaaggt tttgcaatct ggattctttt ggcccatgct      3240
tttcaaagat gctcatcagc atgtgcaaca ctgtgatcaa tgtaagagga tgagggtat      3300 atcaagaaga aatgaaatgc ctctacagaa tattatggag gttgaggtat tcaattgcta      3360
ggggattgat tttgtaggtc ccttcccttc gtcttttggc aatgaatata tactagtggc      3420
gattgactat gtctctaaat tggttgaagc agtggctacc ccgcataatg atgctaagac      3480
tgtggtaaag tttctaaaga aaaacatttt ctcaagatt ggggtgccta gaattctgat      3540
taacgatgga ggcacacact tctgcaataa tcatcctatag aaggtgttga agcaatataa      3600
tgtgacacaa agtagcatca ccttatcacc cccagaccaa tgggcaagca gaagtatcaa      3660
acagggaatt gaaaaagatt ttggagaaga ctatagcttc tactagaaaa gactagtcta      3720
tcaaattaga tgatgctta tgggcataca gaacaacatt caagactccg ataggattat      3780
ctccatttca gatggtgtac ggcaaggctt gtcacttacc agtggagatg gaatataaag      3840
catactaggc cttgaagttt ttgaactttg atgaagccgc atccagagaa caaggaggc      3900 tgcaactttt ggagttggga gatatgagat taactactta tgaatcttca aggctataca      3960
aagaaagggt caaaaagtat catgacaaga agctgctcaa gaaggacttt cagccaggac      4020
gacaagagtt gcttttcaac tcaagactta aattgttccc tggaaagctt acatcgaaat      4080
ggtctggacc atttaccatc aagaaagtcc gcccatatag agcagtggag ctttgtgatc      4140
ctcaatctaa agatcctgac aggacatggg tagtgaacgg acaaaggttg aatcaatatc      4200
atggttcatg caatcctacc cctcaagggt attggataga agactccaag aggattgggc      4260
tagagctgct aaagaaggcc ttggggttct catgaacccc aggtaaaatt tctgagccca      4320
tggaccaagg ttgggtcctc tcttctttgt aaatattaga ataggttttt ccttcttctc      4380
aggctaagca ccaatatgct tctgtttttc agtcctttga ataaggctaa gcgcagctgc      4440
tgcactaagc ccttgttgtg tgtcaaggag gttgagctaa gcgtgcccta ctgcgctaag      4500
ctcaactatc tcactatttt tgtgttttta tggtcaggct aagcgcgccc tatgtgctaa      4560
```

```
gcctaagggt cattctggtg agcgtgagct aagcgcgcca tgctgcacta agcttagacc    4620
cttttttgtt ttgaaaattt tagacttagg ctaagcccaa catgctacgc taagcctatc    4680
tacagaaaaa tattttgtgt ctttaggcta agctcgagtc tactgcgctt agctcatgag    4740
taatatttta taaggcgcgc taagcccagc ctgctgcgct aagtgcccag ttcagttttc    4800
agctttaatt ttttgttttt gatagaaata atcttattta accttgtggt ttgattttat    4860
tctttcagat agcatcaaag aagagaaagg cacctgccac accttcccag gtctgatatg    4920
gccgatcgag gttcacttct cttgtggcct aggaaaggta cactgatatt gtggtaccca    4980
ggaagatact ccctgagtgg aatgtggtaa tctaccacac tgagtttgat gagtttaagg    5040
aagaactaga gagaagaaaa tgggatgagg aattgaccag ttttgatgaa ggcaacattg    5100
atgttgccat tctgaaagag ttttatgata acctctatga ttccgacgat aaatcaccta    5160
agcaggtgag ggtgagaggc catttggtga agtttgatgc agacactctg aacactttct    5220
tgaagacccc tgtgataatt gagaggggg aaaagctgcc tgcctactct agatttgcac    5280
tcttgagtcc tgatcctcaa gagttggctg ctaagctctg catcccaggg agggaatttg    5340
agcttaatgt tgacgacttg ccactaaaga tcctcaggaa gaaaatgacc acactcgctc    5400
agactaggag tgttcttcct tactccaact tggtccctac ctcccacact tctcacatca    5460
cactggatcg ggccaagttg atttatggca ttatcatgaa gatggacatg aatttgggct    5520
acctcatctc ccaccagatt tctatcattg cccagcatga ctcctctagg cttggattta    5580
caaccttaat catagctttg tgtaaagcta aggagtcac attagattcc aaatctttgg    5640
agagtcttag ccctgccatt aacatggcat atataaagaa gaactgttgg aatctagatg    5700
atccaacagt gacattcaga gagccaagga aggccagggg taaaagaatc gaggctcccc    5760
ctacttcagc agcaccaggt gcttctgctc cttcttcatc ttctttacca gatccttcag    5820
caccatccac ttcgactcca catcttccat ggttactagc ttcagctccc actcccttac    5880
cagcttcaat tcagctcctt ctacaggacc ctcctcattc acctctaaga cattatttgc    5940
tatgctgcaa agcctgcaca aaggccagat catcatcata cagaggttgt agagctctgg    6000 ccagaaaacca accatgagta tagaggagtt ccttgcacaa gtggcttgcc caggagtcga    6060
gccttctcct tctggagggg gtgaggcctt tgcagcccaa gagccttgcc agcagagaag    6120
cctgtgccag aagcagagga tgagcttgtt cttcctgagc catttgttta tgagattgat    6180
ccagtcgctc aggaggaagc agcagctcag gagcttcctg cacctatttc tgaggatacc    6240
ctgccatctg caccagcatt ggagtaagag cagcctagtt cacaggatcc accagctgct    6300
ccaatgctgg atctgaacga gcatgcagaa gatcagcagt aggatgatca tgagttttaa    6360
attctacata gttttttaaaa ttttgcaaat tatgaatagt ttcttttatc aattatttag    6420
ttcatgtcaa ttatttgttt atgctttatt agtctttaaa ttttagtctt ttaaattttt    6480
gttgtttgag tgttgatagc ttgtacaaaa gcatgtttga acagtgaact tattgattat    6540
gatattcagt ggtgtgattt cttatgaatg aagtgtttgt gaatgacttg aatgagaaaa    6600
tgtatgaatt gagtggactg gaatgattag atgtttgttt tgatcaagct tgtagtcatt    6660
agaagaaaaa gaacatgtga ttagaagtat gactgaaaat gttagtcagt ttgtcaaatt    6720
gattgtgaag gaatgcattg accgtatccc agtgagagtg tgatccttaa attttgagag    6780
aaatgacttt aatttagcac taatttttgc acgaatcttt gaagtatgga ttgaatgcat    6840
gaattgagga taatgaaggc catgttttga ttgtgatagc tatttagcca aaaagctgac    6900
```

```
cttgtgcttg aatgatttat cccttgcacc cagtttgagc tgaatgaatt attgattgat   6960
tgaaccttga gcctatatag tgttttctcc tgcttccttg tcttaggtta taggagagca   7020
taatccacag aaaagcttgg ttcaaggcaa atttgttcca aatttggggg agacactggg   7080
taaagaaata aaatggtcaa aacagagcaa catatacaca ttgttttctg tatgtaaaaa   7140
aaactgtaag tataaataaa aatgtataaa agtgtgtgtg ctgcaaatca aatcaatgaa   7200
agctaagtgc ttaataaaag gcaagtatgg ggtaggaatg aataaaaaaa aaagtaaagg   7260
tttatctatg gatgaatgct ctcgtagaat ctaagctttt gaatcctaga aaaaccatga   7320
tttgttggca gcctaacctc attacaagcc tagaaagtcc tttggattca ttttgtgtgt   7380
ttatttctgt atggtatgag atgaaatgca aagttagga cttgtgttag ttgttcatga   7440
tggaatgagc ctaaacactt aagcttgagt gaaacaatga ctgtgaggct ttggttgatg   7500
attttttcct tgatatctgt cattctcact agcttatttt agttgtgact ctaatgcata   7560
tgttcctatc tttgaaaaac tgcatgtttg tgaaagaaa ttggttgaag cattccatga   7620
tattcatttc atatgattga atttctctgt gaggagaaca ccatttggat tgaccactgt   7680
attttgtcac ttgaggacaa gtgaactgtt cttctttgc ttgaggacaa gcaaaacttt   7740
aaatttgggg gagtatgtta gtcatcttat acgactaact tttgtataga aaaattttc   7800
caaaacttgt atagtttctc caattatag ttattttgta gggatttgta aataaatctt   7860
gttttattgt tatagttgtc tctagaatat tttccatttg atttaatgat gaaatctgtt   7920
caatttcagg ttaaaagagg ctaagtcttg aagtgctaaa agtgggattt acgctcagct   7980
caccatttgg cctcaacgcg catccaccgc taagcacagc ttcagcgcac ttagtgtgac   8040
agaagaatct ggcagagcat aaatatcaag gccgcttgct aagcaagatg gttgtctttta   8100
gccagactca gcgcatgact ggcgctaagc tcaaatccac taactcgcgc taagcacagg   8160
ggtggcacta agtgcaacgt cgcggattta agcctatttt aaagcctgtc ttgtgcagaa   8220
ttaggtaata tacacacata gaattttagc aagcaataca aaattccaaa gcaaggacac   8280
cacagtgcta atttcgatat agaagctctg gaggcagcaa gaggagaagc tttgcagaga   8340
agcctaggat tcttcaatta gagagagatt agtgagctgt agagtgattg tgaggtgttg   8400
agaagaggag gagggatccc ccttcttgtg taaggaacaa ttatttggta ctctcaaact   8460
catttgtgtt agggttttc tgtaatggct agctaaacac ccttgttggg gatttctaag   8520
gaacaactga tgtaattact ttaatatcta attaattatg ttttatgtgt tcaatgcttc   8580
tttcaatgct taattactgc atgctcttgg tctgatcacc catttgtgtg tattgttagg   8640
tgactttagc attgggaaat gtaccgttgc cttagaactt gatagaagca ggactaaata   8700
actacattac cagggatgga ttatgggtt ttggttttct aaatatgttg tgatgataat   8760
gctatttaag ttaagcctag tcatacaaga gggatctgcg gacgaagctt aggttaaatt   8820
agtataaact acaagggat cgagatttag tactttaggc tacaacatag aacacaagaa   8880
catgattaat tagagaaata tcctcatatg catcaacttg tttgttagaa agacccaacg   8940
cttttttacct attgttgtca acttttactt acttgcattt ttttttttacc atagaagtag   9000
tttatttctg ttttaaccat caattatcaa tgttgttcca acaatgcctt acttctgaat   9060
aaaactctgt ctaataagca agttccctaa attcgatact tggatcactc tgttttaatt   9120
ttaaatactt gacaactca                                                9139
```

<210> SEQ ID NO 23
<211> LENGTH: 10482

<212> TYPE: DNA
<213> ORGANISM: Glycine max

<400> SEQUENCE: 23

| | | | | | |
|---|---|---|---|---|---|
| tgttagtcgt | cttatatgac | taacttttgt | atagaaaaac | cttttcaaa | acatgtatag | 60 |
| tttccccaat | ttataattct | tttgtaggaa | tttgtaaata | aatcttgata | tgttttgata | 120 |
| cctgccatta | gagtatcttt | agttggagtt | aatgagaaaa | tttgtacaat | ttcaggtcaa | 180 |
| aagaggctaa | aatcttgaag | tgctaaaagg | agcagtcgtg | ctaaatagag | cctgtgggct | 240 |
| cagtgcacat | ccaccgctaa | gtgcagcttc | agcatgctta | gcgtgacaag | ggaacctgaa | 300 |
| agagcacaag | aatcaaggtc | gcgcgctaag | cgagacgttt | gtcttttgcc | aggctcagcg | 360 |
| cacgactggc | gccaagccca | aatccactta | ctcgcgctaa | gcgcgatgtc | gcgatttcag | 420 |
| agcctattta | agcctgaatt | gtcagaatta | gggtatgatt | taagagacc | agagctgtat | 480 |
| attttgcac | aaacttcgag | aatagtgctc | tggaggcagc | agagaggcag | cagctaagca | 540 |
| gggaagctag | ggttcatcac | tttgagagat | tagagagtgt | tttagtgatt | gtgaggtgcc | 600 |
| aagaagacga | ggagggatcc | cccttcctgt | gtaagcaaca | attgctctgt | actttctgtc | 660 |
| tcatttgtat | tagggttcct | tgtatggctt | ggtaaaaacc | ctagttgggg | atttctaatg | 720 |
| aacagttgat | gtaattactt | ttcatatcta | attaattgtg | ttttgtgtgt | tcagtgcttc | 780 |
| tttcaatact | taattactgc | atgctcttgg | cctgatcacc | ctcttgtgtg | tactattagg | 840 |
| tgactttagc | attgggaaat | gtagtgctgc | catagaacat | gatagaagca | aggctaaata | 900 |
| actgcattac | ctaggatgga | ttgtggggtt | ttagtttct | tattatgctg | tgatgataat | 960 |
| gttgtttaag | ttaagcctag | tccaacaaga | gggatctgag | gatgaagctt | gggttaaatt | 1020 |
| agtctaaact | tatgagggat | cgaggtttag | tactttaggc | ttcagcatag | aacacaagaa | 1080 |
| catgattaat | tagagaaata | tcttcatatg | cattaactcg | tttgttagaa | agacccaaca | 1140 |
| ctttatacct | attgctgtca | acttttaat | tacttgcatt | tactgctttt | taacatagca | 1200 |
| tctagtttac | ttttgtttat | attctcaatt | atcaatgttt | gttcacacaa | tgccatattt | 1260 |
| ctaaataaa | ctttgtctaa | taaacaagtt | ccctgagttt | gatactcgga | ttattccgtt | 1320 |
| ttaatttaa | atgcttgata | acctggtgcg | ttttccgata | tttcatttcc | cttgaatata | 1380 |
| ctgcttgtaa | atttgataga | aaggaactgt | gttgaagggt | aaacaaaaat | ttgacacaaa | 1440 |
| gcatttatgg | cgccgttgtc | ggggaactgg | attcattaga | agagttcagt | tcagttttaa | 1500 |
| ggcattgctt | tattttgttt | tctttaattc | attgattctt | tttgctaaca | ttttagttac | 1560 |
| tgcacatttt | attgttcttt | ggaattggat | aattttgtt | ttgtttcttt | tgtatgcaaa | 1620 |
| ggagatctgt | tgtaggtgat | ttaattccca | tagatttgga | gattaatgct | acttgcagga | 1680 |
| gacaaaatgc | agagagaatt | agaaattttt | tgcaggactt | agaagtagca | gcaactctag | 1740 |
| gagagtgacc | ctagaagatt | actcaagtta | aggccacagt | ccaagcagct | attagatgct | 1800 |
| tctgctgggg | gaaaaataaa | gttaaagacc | cccgaagaag | ccatggaact | cattgaaaat | 1860 |
| atgactgcaa | gtgacattac | tattttgaga | gatagagccc | acattccaac | aaaaagaagc | 1920 |
| ctactagagc | tttcatcaca | agatgcattg | ttggcacaaa | acaagttgat | gtccaagcaa | 1980 |
| ttggaagcat | tgaccaaaac | actaagtaag | tttccagctc | aattacattc | tgcacaatct | 2040 |
| ttaccatcta | ctattttgca | ggtcacagtg | tgtgccatct | gtggtggagc | tcacgattct | 2100 |
| ggttgttgta | tccccaatga | agaaccaaca | actcatgaag | tcaattacat | gggtaaccaa | 2160 |
| cctagaaata | attttaatgc | aggtggattt | cccgaattcc | agcatggaca | gtaatacaac | 2220 |

```
caacaacagg gacaatggag gaccaccctg ggaattaatt caatagagac cagggtggac      2280
cgtccacaag gccgtaacaa caagggccta gtctctatga gcgtacaacg aagttggaag      2340
agactctagc tcaatttatg caggtttcta tgtctaacca aaagagcacg gagtttgcca      2400
taaagaattt ggaagtccaa gtgggacagc ttgcaaaaca gttggtggat aggccgtcaa      2460
agagctttag tgctaacact gagaaaaatt cgaaggggga atgtaaagct gtcatgacaa      2520
gaagcagaat ggcaacccat gttgatgaag gaaaagctta agaaggtg gaggagcata       2580 aacaacagtt ggcagctgag ccggcacttg aacccatttc tgattttgtt gaacttgagg      2640
aagttatgga agatgaagat gaccaaaagg aaaagagaaa gaagaagtag aaaaagaaaa      2700
atattagaaa aatgaaaaag aaaatgagaa ggttgaggaa agaaagagga gcaagagtga      2760
ggtttcaaga gagaaaaaga gagagattac ttcagctgaa ggcaaggatg taccatatcc      2820
attggtacct tccaagaagg ataaagagcg acacttagcc agatttcttg acatcttcaa      2880
gaagtcggag atcacattgc cttttggaga aactctccaa cagatgccac tctatgccaa      2940
atttttaaaa gacatgctga caaagaaaaa ctggtatatc cacagtgaca cgatagctgt      3000
ggaaggaaat tgtagtgctg tcactcaacg catccttcca ccaaagcata aggatccagg      3060
aagtgtcaca ataccatgtt ctattggtga agttgcagta ggcaaggctc tcattgactt      3120
gggagccagt atcaatttaa tgactctctc catgtgccag caacttggag agttagagat      3180
aatgcccact cgcatgaccc tacagttggc agatcgctcc attgctagac catatggagt      3240
gatcgaggat gtgttgattc aggtcaagca gcttgtattc cctgcaattt tgtggttatg      3300
gatatagagg aggatcctaa cattcccata atcttgggac gtcctttcat gtccacgacc      3360
agctgtgtag tagatatggg gaaaggcaaa ttagaactgg ttgtggagga tcagaaagtc      3420
tcattcgact tatttgaagc aatgaagcat ccaaatgatc aaaaagcttg ctttgatctg      3480
gataaggtag aataggagat agaattagct gctatagcca tggtactgca ctctcatttg      3540
gaaaaagcac gattaatcat gtagaatgtt tgaccaagga ggaggaacat gaagtgtaga      3600
cttgtattaa agagttggat ggtgcaggag aaaattccga gggacatact gcatttgaag      3660
aattgaagaa cagtgggaaa atagaaaaac caaaagtaga attgaagact ttgcctgcac      3720
attcgaagta tgtatcttgg aagacaatga ctccaaacca gtgattatta gcagctcttt      3780
gaagaaaaca gaagaagatc agttggtgca gattttgaag aaacataaag ctacaattgg      3840
atggcacata tctgacttga aaggaattag tccatcttat tgcatgcaca aaattattat      3900
ggaagctgat tacaaaccaa tgagacagcc tcaaagaaga ctgaacccaa tcatgaaaga      3960
ggaggtgcgc aaggaggtgc ttaagttgct agaagcaggc ctcacccat ctcagatagt       4020 gcgtgggtta gcccggtgca ggttgttctc aagaagggag gtatgacagt cattaaaaat      4080
gataaagatg aattaatatc cacaaggact gtcaccgggt ggagaatgtg cattgattat      4140
cggaagttga ataatgccac ttggaaagac cattatccac tccctttcat ggaccatatg      4200
cttgagagac tcgcaaggca atcatattat tgttttctgg atggatattc tagttacaat      4260
tagattgcta tagatatcaa agatcaagat gtcgcaacct acccttcagt gggagggcga      4320
cgcgtgactt gcgcgtgcat gttccaagaa aggaatacgc gcggagtcgc caccaacgtt      4380
tatttgagga aaacgtcgga aaaccggaa aagacgtgat ctacgaactt taagtgaaag       4440
gttcgggagt tgtatttacg cacggggaag gtattagcac cccacacgtc cgtcacaaga      4500
gatgacaacc tctaatcaaa tgtgcaaata tgacttcaat ttatgttatc ttccccettt      4560 tttcacgttc ttatgttttt tttatgcctt tttatgtttt tatcttttg tggttgacaa       4620
```

```
gggcgtttcc ctttgctcct acgtattcct caattgtgat gagaaaatca aacctacgta   4680
gttcttttgt gaacaaagcg ttttggttaa gttatttttt atccttttt gcaagatatg    4740 ttttattgaa tgaaaggtca tttaaggtgt tggaccatta gacaatcttt cgattctttt   4800
gaaaagtgag aaaacattaa ggcattggac cattaatgat ttctttattt ttgaaagagt   4860
taacaaagtt acatattgat tttaggcttt ttagaaatct acacttaacc aataaaagcg   4920
gaaaagacca tttcaaggcg ttggacctt gaaaatggc gttttaggc gatgacaaaa       4980 gtttggttta tgaattgatt ttagccttag tttcactttg gttattagtc gattcgattt    5040
aagaaagaga atcccaaag aaaaacgtcc gattgatttt tgatttatt ttactaaaag      5100 atattttga ttattatatt attatttac ctattttgg ttttcaacgg gttacggcat       5160
gaccgaacag tcggatttca ttttaacaga aattaacgga tgttacaatt taaatgatcg    5220
gtggaaattt attttatttt ttgattaggc gagaaaatga cttaagtaaa tgactaaagc    5280
acgtcaaaag ggggtacgga aagtaaatga aatgaaaata aagcatgtg aaacaaatga     5340 ggaccactaa gggtacatag aatgaattgt ttgatttcgg gaacttaccg gttgaagatc    5400
gaagaacgac gaagaacgaa cgaagaacgt cgatgaacgg ttgaaaatct cgcaaaatc    5460 acccacggaa acgttacgga agcacctcgg cttggatttt cttcacgaa caattttc       5520 tcactaattt taagtgaatc tcagatacca ggagggtcga acattttgt tcttccctcc     5580 ttcccttatt tataggaaaa ggaaggagat gcttgccacc cagctcgccc aggcgagcta    5640
ggttgcttcc tccagaagca aatcctggaa ggcccaagtg ggcctggttg ctatttgaac    5700 ccccaattt actaaatata ccccctgcct ttttttggtg attctttttc cgtaaagtta     5760
tggaaactta cgaatttcgt aacgatactt gttttctttc cgtaatgttg tggaaccta     5820 cggattacgt aatcatccct ttttgcctt ccggaacgtt acagaacttt acggattgca     5880
cactaacact tccttttaat tttcggcatg tcacgaactt cacggattgt gctaccacgc    5940
ttttcttttg gcttccgaca tgtctcggaa cttcacaaat tgcctaacca tgggtgccaa    6000
atacctcgaa gtggtcaaac gacggtcgca tcccaacaac ggatggttct cggacgaaat    6060
tagggtatga cacaagagaa gacaactttc actttcccctt tcggtgtatt tgcatatcga   6120
tgcatgcctt tcggtctatg caatgcccta gctacatttc agaggtgtat gatggcaatt    6180
ttttctgata tggtgaaaaa atgcattgaa gttttcatgg acgatttctc tgtttttgga    6240
ccatctttga tggttgctta tcaaatctgg aaagagtatt ttagagatgt gaagagtcca    6300
acctggtact taattgggaa aatgtcattt catggttcaa gaaggaatag tgctggggca    6360
taaaatatca gtaaggggaa ttgaggtgga taaggtgaag attgatgtca ttgagaaact    6420
tcctcctcca atgaatgtca aacgaatgag aagtttctta ggacatgatg gattctatag    6480
gtgacttata aaagattttt caaaagtcgc caaaccactt agcaatttgt tgaacaaga     6540 tgttgctttt gtgttcaatg gaaagtgtat tgaagcattt aatgatttga aaaccagact    6600
agtgtctgct ccagtaatta ctacaccaga ttgggggtaa gaatttgagt tgatgtgtga    6660
cgcgagcgat tatgctatag gtgcagtgct tggacaaagg aagggcaaaa ttttcatgc     6720 tatctactac gccagcaaag ttttaaatga tgcacaggtt aactatgcta ccacagaaaa    6780
agaaatgttg gcaattgttt atgcacttga aaagttcaaa tcttatttgg taggctcaaa    6840
agtcatcatc tacattgatc atgcaactat taaatatttt ctcaacaagg ccaattccaa    6900
aaccctgctt aataagatgg attttgctgc tgcaagaatt tgatttggta attcgggata    6960
```

-continued

```
aaaagggatc ggaaaatgtt gtagctaacc aatttgtcta gattggggaa taaagaagtc   7020
atgtcgaaag aagctgaaat tagagatgaa ttccctaatg agtcattatt cttggtgaat   7080
gagagacctt gatttgctga tatggccaac ttcaaagccg caggaatcat tccaaaagac   7140
ctaacttggc agtagaggaa gcaattcctg catgatgctc gattttatat ctgggatgac   7200
ccgcacttgt tcaagattgg agttgacaat cttctccgaa gatgtgtgac acaagaagaa   7260
gccaagaaca tattatggca ctgtcacaat tctccatgtg gcggccatta tggtggagat   7320
aagacgacga ccaaggtttt gcaatctgga ttcttttggc ccacacttttt caaggatgct   7380
catcagaata tgctgcattg tgatcaatgt caaaggatgg ggggcatatc aaaaagaaat   7440
gaaatgcctt tacagaatat tatggaggtt gaggtatttg actgttgggg gattgatttt   7500
gtaggtccct tcccttttgtc ttttggcaat gaatacatac tagtggttgt tgactatgtc   7560
tctaaatggg ttgaagcagt ggctaccctg cataatgatg ctaagattgt ggtaaagttt   7620
ctaaagacga acattttctc cagatttggg gtgcccagag ttttgattag tgatggaagc   7680
acacatttct gcaataataa gatacagaag gtgttgaagc aatataatgt aacacacaag   7740
gtagcatcag cttatcaccc ccaaaccaat gggcaagcag aagtgtcgaa caaggaattg   7800
aaaaagattt tagagaagac tatggcttct actagaaagg actggtccat taaactagat   7860
gatgctttat gggcgtatag gactgcattc aagactccga taggtttatc tccatttcag   7920
atggtgtatg gcaagtcttg tcacttacca gtggagatga aatataaaac atattgggcc   7980
ttgaagttgt tgaactttga tgaagccgaa tccagagaac aaaggaggct acaacttttg   8040
gagttggaag agataaaaatt aactgcttat gaatcttcac agttgtacaa agaaaaaatt   8100
aaaaagtatc atgataaaaa actgctcaag agggattttc aacaaggaca acaagtgttg   8160
cttttcacct caagacttaa attgtttcct gggaagctta aatcgaaatg gtctagacca   8220
tttaccatca agaaagtccg aacatatgga gcagtggagc tttgtgatcc tcatatgggt   8280
ggtgaacgga caaaggctaa agcaatatca tggtggagct attgagagat tgaacactat   8340
tctacacttc aatccaggat aacaggacga tgcgtcaagc taatgacgtt aaccgagcgc   8400
ttacggggag gcaacccagg tctctttttta tttctatttt tcttgcattt aatttagtta   8460
gtttaattgc ttgtgattgt aaatgatttc taagcttggt tagtattgag aaaagggttt   8520
caaagtttta gtaaagagat ggatagaaaa gacttagaga aaaaattttc agttgtccat   8580
ccgctaagcg cagcccttgt gctaagtgcc atgtcttaat gcactaagca tgtgcttgct   8640
tgcgctaagc actttgacct ttcaccagtt ggctagatgg ttcagctaag cgcacatcac   8700
tgcgctaaac ctaagttctt ctctggattt gaacttcatg acttgggctt agaggagttg   8760
atgcgctaag cgcaactcct tctctgttga aaaattattg taatagcatt aagcttaatt   8820
tcctctctgg aattgaactt tcaggaattg ggcttagcag caggatacgc taagcgccaa   8880
tccttcacta ttttgaaata cttggaattg cgctaagcct ggaaccatca ctgtaagtag   8940
agcttgtttt agtgctaagc ctaacatctt aggctaagtg aaaattgcag gaccaatcag   9000
agttgcagac agtgctaagc gcgtgtcctc gcactaagct tgaatacctc tctggaattt   9060
gaaattattg aattaggctt aacgcgagag gtggcgctaa gcgcatgggc cttaaactca   9120
aatgtcatgt tggcatgcta agcgcaacta tgcgctaagt gcgccaaaca aaaatgctaa   9180
aataaaatag aactaccaat ggcagttacc atttacactt caaagctttt actcccttat   9240
gcttgtgccc acattcgtgc ttttgtgcat tttgctgcct ttgcttcaag ttattcctgc   9300
tttcttgctc tcatcttgca tttccatcac aatccaagta agttttcatg tttatttca   9360
```

-continued

```
ttttctttta taagcttaaa ccttagggta gatgatttag tgcttttag tttgcaattt      9420
tttttaggtt tagtgttttt aggttagttg ttagttaagg taggttttagg gtttacaatg    9480
taggttttag gttaggtttt tgagcccctt aggggcaatg cctgaaaaag gggtgaaaac    9540
ccgtgagtaa tttctagaaa tagcgatgaa cgtgctaagc gcacctgctg tgcttagcca    9600
gttcatcgca acttccttct aatgagtttc aatgatgagc tcgataagcg cgtttgtgcg    9660
ctaagtgaga caagtgtttt agacacttag tatttttttc aattttttgtt cagcactaaa   9720
gcctggcttc tcaggctaaa gcacaattct gtctttattt ttcaattgtt ggaataaggc    9780
taagtgcagc ttgttgtgct aagcccatgt tatgtcttag tgaggttgag ctaagcgtgc    9840
cctactgcgc taagctcaat tcctccactg ttttcaaaag tgtggattta ggataagccc    9900
agcttgttgc gctaagccta gtctatggaa aaacattttc tgagtactca cgctaagcgt    9960
gtggctatcg ggcttagccc atgagtaaat tttcataaag cgcgctaagc ccagccttct   10020
gtgctaagca cccagtccta ctttcagttt tattttttg tttttgttga ataatcctgt    10080
tttaactctg ttgtttgatc taattctttt cagatggcat ctaggaagag aaaggcccat   10140
gcctcaacat cccaggcccg ctatgataga tccagattca catctcagga ggcctgggat   10200
cgttattcta gtgttgtcat tggcaggaaa atattacctg aaagaaatgt catgctctat   10260
tacacagagt ttgatgaatt cactgaagag ttagagagaa gaaacaggca caggagtta   10320
acaaatttta tggatggcaa cattgatgtt gccattatga aggagttcta tgctaacctc   10380
tatgacccag aggataaatc acctaagcag gtgaggttca gaggtcattt agtgaaattt   10440
gatgcagatg ctctgaacac tttttttatg acccctgtga tc                       10482
```

<210> SEQ ID NO 24
<211> LENGTH: 1857
<212> TYPE: DNA
<213> ORGANISM: Arabidopsis thaliana

<400> SEQUENCE: 24

```
atgagcaatt acagtggcag ttcttctgtt gatcctgact acaacatgga tgagacagaa      60
tcgtcatctt caaggccaga gagagaacag agagaatacg aaagtttcag aaggaaagct    120
gagatagccc gaggaaagag agcgatgaga gagaggtatg agcttataga cgaagatctg    180
gaggacgagt acatgcctga acagactcgc agagctacca aacttctgca caagcccgac    240
atattgcctg ctgaggaata tgttaggctt ttcaagctga atgagttctg tagcacgagg    300
tatccttgct cgacctcact tgcacaactc ggattgttgg aagatgttca gcacctgtac    360
caaagttgtc atctggacac tttgatggct tatccgtatg tagcatatga agatgagaca    420
atacaattcc tctccacact acaagtagag ctctaccaag gtatgacctc tgatgagttg    480
gattgtgaag gattgggatt cttgcgattt tctgtgtatg gtcatgagta caggttatca    540
atcaagcgat tggaaggatt gtttgatttt cccagtggaa cgggatctaa gccaaagtat    600
gaaagagaag agttgaaaga cttgtggatc accatcggca gctctgtacc gttgaatgct    660
tccaggtcaa agagcaatca gatacgcagc cctgtcatca ggtacttcca gcgttctgta    720
gccaacgtac tctactcccg agagattaca gggactgtca ctaactctga tatggagatg    780
atcgcaatgg ccctcaaagg aactctccgc caaactaaaa atggcatgtc cctccagggt    840
gaagtcaatg acacacctct ctctatactt cttctgatcc atctgtgtgg atacaaaaac    900
tgggcggtca gcaataaccg caagagagca cgaggcgctc tgtgcatagg tggcgtggtg    960
```

-continued

```
acacctattc tgatagcttg tggagtccca ctcatttctg ctggactcga gccacgagca    1020
atggatatcg agcacctacg tcactgccaa ttcctggagt ttgcaatggt tgacgatttc    1080
cacaggttca ggtttgagca ctctacagac aggagagcta acatccttct ccctagccct    1140
gaggtcacac ggataatcga gggagataac attgatttta ggcctgagat tggacgcctc    1200
tactatgaga acgctccacc attagatgag gacgatcttc ttgaagaagc tgcttcggat    1260
gggatggatg aagatggagc agtaaagttc gacactagca tgtatcactt tgctgaacat    1320
gtacctccag cgaggcagag caagagcttg actgaagctc ataagaatta cagtaaattg    1380
cagaagtggt gcaagaagca ggacaggctg atcgccaagt gtttcaagct tctgacagac    1440
aagctgagtt gctcttcctc caccactgct attccacagg tacaacctcc tatggaaatg    1500
ccatcgagga gaattaatgc acctgcgcac aggcctgagc ttagcgagca gagagtccca    1560
catgtccagg ctaggcattc gtcattcgaa tcccgggaac acaagagaag aaggaaggct    1620
acactcactc gatctagcag cagatcacgc ctcattcact cgaggagatc actcgaccgt    1680
ggtgctggcc gcagcagaag gagagatgtc gagtttcctc agagcggtgc tggccgccac    1740
agagctgatg aggtcgagta cccatctgct ggagctgata cagaacaagg aggttcgtct    1800
atggcctggg agcaatcgca ggcagccatt gacgagcaac tacgttcatt cttcgac      1857
```

<210> SEQ ID NO 25
<211> LENGTH: 1254
<212> TYPE: DNA
<213> ORGANISM: Pisum sativum

<400> SEQUENCE: 25

```
atggaatcca ggtccggagc ttcgaaaaag agaaagggcg ggaatagttc ccgtcccgtg      60
cccatacaat tcgacaccga caaatttgtc gggccaaagc aagcagtaag atatgttgct     120
ttggaaaagc gaaagatttt gccggaaaag agatttataa tcaaccctga aggcacgaac     180
cgtacattcg ccgggctgat aacagcaaa aagtgggacc ggttaatatc ccccttgaag     240
cattacgaca tcgcaacagt gcgtgagttc tacgcgaacg cactgccgaa cgacgacgag     300
ccattcacat ggacgtctag agtgtccggc cgtcctgttg cgttcgatcg ggatgcaatt     360
aaccgtgtcc tgggtgaacc gctccatctg ggagccaatg agagagacac ttaccaccaa     420
gatttaaggc ttcaccggga taccgattcg atttctactg ccctgctttt ggaagggaaa     480
tcagttgagc tgaacccatc tggggttccg atgagatacc ataggagga catgattccc      540 ttggctcaac tgatccttttt gttggttctt acaaacatca aacccaagtc tcacacttct     600
accgtgccga tcccagtggc acacttggta cacatcatcc tcacgaatat ccagattgat     660
gtggcaagga ttattgcttt ggagttgaag tccgtgattg aaagcgggct aaagtcgggg     720
gaacgagtga attgtcccct tgctttccct tgtctaatca tggctttgtg ccaacaagcg     780
agggtgaggc taccctccaa gggtcaagta aggatcccgc cggccattga tgaccgatac     840
gtggccaagt actgcaaacc gaagaatgta agaagtagtt cagctgctga ggttaccggg     900
gcttctgatg gtcctggtac ttttactcta ggatccgatc ctttccagca ggctgtctgc     960
aactacaact gggattggat ggcggcaact cagcgcgtca tgctcgatat gcacgattct    1020
atgcagctgt tacagttgca gatgcgcgac ccctccggtg agcattctat gatgtcacgt    1080
gagcagtttc tgcagcacgc tagctggcct gtggacaggc tgtgtttgg agaggggcg     1140 ggtgctggtg caactggtgc tggtgctttt tctggtgctg ctgatgatga tgatgatgat    1200
gaggctaccg gttctgaagc cggtagtgat gagggttatg agtccttgga gggc            1254
```

<210> SEQ ID NO 26
<211> LENGTH: 564
<212> TYPE: DNA
<213> ORGANISM: Arabidopsis thaliana

<400> SEQUENCE: 26

```
tgtgattcat gccagagaaa aggcaacatc aatagaagaa atgagatgcc tcagaatcca      60
atcttggaag ttgagatctt tgatgtatgg gggattgatt ttatgggtcc attcccatct     120
tcatacggta ataatatat actggtcgcc gtagactacg tatcaaagtg ggtcgaagct     180
attgctagtc ctaccaacga tgcaaaagtt gtgctgaagt tgttcaaaac cataatcttc     240
ccaagatttg gagttcccag ggtagtaatc agtgatggcg aaagcatttt catcaacaag     300
gtttttgaga acctcttgaa gaagcatggg gtaaagcagg ttgagatctc caatagggag     360
ataaaaacaa ttctggaaaa gactgttggg attacaagga aagactggtc tgcaaagcta     420
gatgatgcat tatgggctta caggacagct ttcaagaccc ccataggtac aactcctttc     480
aatcttctct atggaaaatt atgtcatcta cccgttgagc tcgagtacaa agcaatgtgg     540
gcggtaaaac ttctgaactt tgac                                            564
```

<210> SEQ ID NO 27
<211> LENGTH: 180
<212> TYPE: DNA
<213> ORGANISM: Arabidopsis thaliana

<400> SEQUENCE: 27

```
atcgaggaga tggtggaggt tttcatggac gattttttcgg tctatggccc ctctttctcc     60
tcatgtttgt tgaatcttgg cagggtattg actaggtgcg aagagacgaa tcttgttctc    120
aattgggaaa agtgtcattt catggtgaag gaaggcatag tattggacca caagatatca    180
```

<210> SEQ ID NO 28
<211> LENGTH: 192
<212> TYPE: DNA
<213> ORGANISM: Arabidopsis thaliana

<400> SEQUENCE: 28

```
tttgaaatca tgtgtgatgc atcagattac gcagtaggag ctgttctagg ccagaaaata      60
gacaagaagc ttcatgtcat atattacgcc agccgaacgt tggatgacgc tcagggaaga    120
tatgcaacaa ctgagaagga gcttctagct gttgtattcg catttgagaa gttcagaagc    180
tatttggttg ga                                                        192
```

<210> SEQ ID NO 29
<211> LENGTH: 597
<212> TYPE: DNA
<213> ORGANISM: Pisum sativum

<400> SEQUENCE: 29

```
ttggatgcga gaatgattta cccgatctcg gatagtccat gggtcagtcc cgtgcatgtg      60
gttccgaaga aggtggaaa taccgtcatc cggaatgaca aggatgaatt gatccctacc    120
aaagttgcaa cggggtggag aatgtgtatt gaatataggc ggttgaatac cgcaactcga    180
aaggaccatt ttccactccc gttcatggat caaatgctgg aaagactctc cgggcaacaa    240
tactattgtt tcttggatgg ctattccggg tataaccaaa ttgccgttga cccggccgat    300
cattaaaaga cggctttcac atgtccgttt ggagtgttcg cataccgaaa aatgtccttt    360
```

```
gggttgtgca atgcaccgac gactttccaa cgatgtgtgc aagccatttt tgccgacctt      420
aatgagaaaa caatggaagt cttcatggat gacttctcgg tatttggtgt atcctttagt      480
ttatgcttgg caaacttgaa aacggtgctt gaaagatgtg tgaagaccaa tcttgtgctt      540
aattggtaga agtgccactt catggtgacc gaggggatag tgcttggcca taaagtc        597
```

```
<210> SEQ ID NO 30
<211> LENGTH: 192
<212> TYPE: DNA
<213> ORGANISM: Pisum sativum

<400> SEQUENCE: 30
tttgagctaa tgtgtgatgc gagcaactat gcaatcggag cggtattagg ccaaagaaaa       60
gagaaaaaat tcatgcgat acattacgca agtaaagttc ttaatgaggc tcaaattaac      120
tatgccacca ctgaaaaaga attacttgcg atagtgtatg cacttgaaaa gtttaggtct      180
tatcttatag gg                                                         192
```

```
<210> SEQ ID NO 31
<211> LENGTH: 581
<212> TYPE: DNA
<213> ORGANISM: Pisum sativum

<400> SEQUENCE: 31
tgtgatagtt gccagagaag cggtgggatt ggtaagagag cgagatgtc tctccaaaac       60 atccaagagg tcgaagtatt tgattgttgg ggcatcgatt tgtaggacc attccccct      120 cttatggtaa cgagtatatg cttgtcgcag ttgaggcgat tgcctcacct cgggcggatg      180
cgaaaacggt aataattttt ttgaagaaaa acatattttc ccgtttcgga acccccgag      240 tgttgataag tgacggaggg tcacactttt gtaatgcacc gttggaaagc attttaaaac      300
attacggtgt atcacacaga gtggcaactc cgtatcaccc acaggctaat ggacaagccg      360
aggtctctaa tcgtgagatt aagagaattc tcgaaaaaac tgtgtcaaat tcgaaaaaag      420
agtggtcaca aaaattggat gaagcgttat ggcataccg taccgccttt aaagctccaa      480
ttgggctcac tcctttttcaa ttggtgtttg gtaaaacttg ccatttgccg gtcgaattgg      540
agcacaaagc cttgtgggct ttgaaaatta ataattttga a                         581
```

```
<210> SEQ ID NO 32
<211> LENGTH: 1362
<212> TYPE: DNA
<213> ORGANISM: Glycine max

<400> SEQUENCE: 32
atggcctcct gtaaacaccg agctgtgccc acacccgggg aagcgtccaa ctgggactct       60
tcacgtttca ctttcgagat tgcttggcac agataccagg atagcattca gctccggaac      120
atccttccag agaggaatgt agagcttgga ccagggatgt tgatgagtt cctgcaggaa      180 ctccagaggc tcagatggga ccaggttctg acccgacttc cagagaagtg gattgatgtt      240
gctctggtga aggagtttta ctccaaccta tatgatccag aggaccacag tccgaagttt      300
tggagtgttc gaggacaggt tgtgagattt gatgctgaga cgattaatga tttcctcgac      360
accccggtca tcttggcaga gggagaggat tatccagcct actctcagta cctcagcact      420
cctccagacc atgatgccat ccttttccgct ctgtgtactc caggggacg atttgttctg      480 aatgttgata gtgcccctg gaagctgctg cggaaggatc tgatgacgct cgcgcagaca      540
tggagtgtgc tctcttattt taaccttgca ctgactttc acacttctga tattaatgtt      600
```

```
gacagggccc gactcaatta tggcttggtg atgaagatgg acctggacgt gggcagcctc      660
atttctcttt agatcagtca gatcgcccag tccatcactt ccaggcttgg gttcccagcg      720
ttgatcacaa cactgtgtga gattcagggg gttgtctctg ataccctgat ttttgagtca      780
ctcagtcctg tgatcaacct tgcctacatt aagaagaact gctggaaccc tgccgatcca      840
tctatcacat tcaggggac ccgccgcacg cgcaccagag cttcggcgtc ggcatctgag       900
gctcctcttc catcccagca tccttctcag ccttttccc agtgaccacg gcctccactt       960
ctatccacct cagcacctcc atacatgcat ggacagatgc tcaggtcctt gtaccagggt     1020
cagcagatca tcattcagaa cctgtatcga ttgtccctac atttgcagat ggatctgcca     1080
ctcatgactc cggaggccta tcgtcagcag gtcgcctagc taggagacca gccctccact     1140
gacagggggg aagagccttc tggagccgct gctactgagg atcctgccgt tgatgaagac     1200
ctcatagctc acttggctgg cgctgattgg agcccatggg cagacttggg cagaggcagc     1260
tgatcttatg ctttaatgtt ttcttttata ttatgtttgt gttctctttt atgttttatg     1320
ttatgttttt atgtagtctg tttggtaatt aaaaagaggt ag                        1362

<210> SEQ ID NO 33
<211> LENGTH: 192
<212> TYPE: DNA
<213> ORGANISM: Glycine max

<400> SEQUENCE: 33
tttgagttga tgtgtgacgc gagcgattat gctataggtg cagtgcttgg acaaaggaag       60
ggcaaaattt ttcatgctat ctactacgcc agcaaagttt taaatgatgc acaggttaac      120
tatgctacca cagaaaaaga aatgttggca attgtttatg cacttgaaaa gttcaaatct      180
tatttggtag gc                                                          192

<210> SEQ ID NO 34
<211> LENGTH: 597
<212> TYPE: DNA
<213> ORGANISM: Glycine max

<400> SEQUENCE: 34
ttggaggttg ggctcatata ccccatctct gacaacgctt gggtaagccc agtacaggtg       60
gttcccaaga aggtggaat gacagtggta caaaatgaga ggaatgactt gataccaaca      120
cgaacagtca ctggctggcg aatgtgtatt gactatcaca agctgaatga agctacacgg      180
aaggaccatt tcccttacc tttcatggat cagatgctgg agagacttgc agggcaggca      240
tactactgtt tcttggatgg atactcggga tacaaccaga tcgcggtaga ccccatagat      300
caggagaaga cggtctttac atgccccttt ggcgtctttg cttacagaag gatgtcattc      360
gggttatgta atgtaccagc cacatttcag aggtgcatgc tgaccatttt ttcagacatg      420
gtggagaaaa gcatcgaggt atttatggac gacttctcgg tttttggacc ctcatttgac      480
agctgtttga ggaacctaga aatggtactt cagaggtgcg tagagactaa cttggtactg      540
aattgggaaa agtgtcattt tatggttcga gagggcatag tcctaggcca caagatc        597

<210> SEQ ID NO 35
<211> LENGTH: 603
<212> TYPE: DNA
<213> ORGANISM: Glycine max

<400> SEQUENCE: 35
```

```
tgtgataaat gtcagagaac aaggggata tctcgaagaa atgagatgcc tttgcagaat      60
atcatggagg tagagatctt tgatagttgg ggcatagact tcatgggcc tcttccttca      120 tcatacagga atgtctacat cttggtagct gtggattacg tctccaaatg ggtgaagcc      180 atagccacgc tgaaggacga tgccagggta gtgatcaaat ttctgaagaa gaacattttt     240
tcccatttcg gagtcccacg agccttgatt agtgatgggg gaacgcactt ctgcaacaat     300
cagttgaaga aagtcctgga gcactataat gtccgacaca aggtggccac accttatcac     360
actcagacga atgccaagc agaaatttct aacaggagc tcaagcgaat cctgaaaaag       420
acagttgcat catcaagaaa ggattgggcc ttgaagctcg atgatactct ctgggcctat     480
aggacagcgt tcaagactcc catcggctta tcaccatttc agctagtata tgggaaggca    540
tgtcatttac cagtagagct ggagcacaag gcatattggg ctctcaagtt gctcaacttt    600
gac                                                                  603

<210> SEQ ID NO 36
<211> LENGTH: 150
<212> TYPE: DNA
<213> ORGANISM: Glycine max

<400> SEQUENCE: 36
cctaaaatac tacaacgaca tgattggtgt tttaggataa ttgactgaaa aacctattat     60
caatttggcg ccgttgccaa ttgggtgttt gtttgttaca tttgagattt cagacttgct    120
tagatcaagt tcttttttcaa ttttctttttt                                   150

<210> SEQ ID NO 37
<211> LENGTH: 11
<212> TYPE: DNA
<213> ORGANISM: Glycine max

<400> SEQUENCE: 37
tggcgccgtt g                                                         11

<210> SEQ ID NO 38
<211> LENGTH: 15
<212> TYPE: DNA
<213> ORGANISM: Glycine max

<400> SEQUENCE: 38
tggcgccgtt gccgg                                                     15

<210> SEQ ID NO 39
<211> LENGTH: 27
<212> TYPE: DNA
<213> ORGANISM: Glycine max

<400> SEQUENCE: 39
tttttggcgc cgttgtcggg gattttg                                        27

<210> SEQ ID NO 40
<211> LENGTH: 9
<212> TYPE: DNA
<213> ORGANISM: Glycine max

<400> SEQUENCE: 40 tttgggga                                                             9

<210> SEQ ID NO 41
<211> LENGTH: 16
```

-continued

```
<212> TYPE: DNA
<213> ORGANISM: Glycine max

<400> SEQUENCE: 41
tttaatttgg gggatt                                                            16

<210> SEQ ID NO 42
<211> LENGTH: 775
<212> TYPE: DNA
<213> ORGANISM: Nicotiana tabacum

<400> SEQUENCE: 42
gtgcgtaaag aggtttttaa actggagatt atcaagtgat tggatgccgg ggttatctac            60
cccatttacg atagttcatg aacttctccg gtgcaatgtg tcccaaagaa ggtggcatga           120
cggtggtcac caatgagaag aatgagttga ttcctacaag aatggtgacc ggttggagag           180
tgtgcatgga ctatcgcaag ctcaacaaac tcacaaggaa ggatcatttc ccatttccat           240
tccttgacca aatgcttgat aggttggcat gtcgtgcttt ctattgcttt ctagatgtat           300
agtcgggcta tagccaaatc tttattgctc cgtaggatca cgagaaaata cctttacatg           360
tccctatggt acttttgcct acaagcggat gccatttggt ttgtgtaatg cactagcgaa           420
cttttatagg tgtatgatgg ctatcttcac ggacatggtg aaggactacc ttaaagtttt           480
catggatgac ttctcgatgg ttggggattc ctttgatgat tgcttggaaa atttggataa           540
agtattggca agatatgaag aaacgaattt ggtactaaat tggagaagt gtcatttcat            600 gatcgaggaa ggcattgttc ttggccacaa gatctcaaat aatggcattg aagtcgacaa           660
ggcaaagatt aaggtgattt ctaaacttac acctccaact ttggtgaaag gcgtgcggag           720
tttcttaggc cacgcggggt tttaccaatt cttcataaaa gatttcacaa aggtt              775

<210> SEQ ID NO 43
<211> LENGTH: 259
<212> TYPE: PRT
<213> ORGANISM: Nicotiana tabacum

<400> SEQUENCE: 43

Val Arg Lys Glu Val Phe Lys Leu Glu Ile Ile Lys Glx Leu Asp Ala
 1               5                  10                  15

Gly Val Ile Tyr Pro Ile Tyr Asp Ser Ser Glx Thr Ser Pro Val Gln
                20                  25                  30

Cys Val Pro Lys Lys Gly Gly Met Thr Val Val Thr Asn Glu Lys Asn
            35                  40                  45

Glu Leu Ile Pro Thr Arg Met Val Thr Gly Trp Arg Val Cys Met Asp
        50                  55                  60

Tyr Arg Lys Leu Asn Lys Leu Thr Arg Lys Asp His Phe Pro Phe Pro
65                  70                  75                  80

Phe Leu Asp Gln Met Leu Asp Arg Leu Ala Cys Arg Ala Phe Tyr Cys
                85                  90                  95

Phe Leu Asp Val Glx Ser Gly Tyr Ser Gln Ile Phe Ile Ala Pro Glx
                100                 105                 110

Asp His Glu Lys Thr Thr Phe Thr Cys Pro Tyr Gly Thr Phe Ala Tyr
            115                 120                 125

Lys Arg Met Pro Phe Gly Leu Cys Asn Ala Leu Ala Asn Phe Tyr Arg
        130                 135                 140

Cys Met Met Ala Ile Phe Thr Asp Met Val Lys Asp Tyr Leu Lys Val
145                 150                 155                 160
```

```
Phe Met Asp Asp Phe Ser Met Val Gly Asp Ser Phe Asp Asp Cys Leu
            165                 170                 175

Glu Asn Leu Asp Lys Val Leu Ala Arg Tyr Glu Glu Thr Asn Leu Val
            180                 185                 190

Leu Asn Trp Glu Lys Cys His Phe Met Ile Glu Glu Gly Ile Val Leu
            195                 200                 205

Gly His Lys Ile Ser Asn Asn Gly Ile Glu Val Asp Lys Ala Lys Ile
            210                 215                 220

Lys Val Ile Ser Lys Leu Thr Pro Pro Thr Leu Val Lys Gly Val Arg
225                 230                 235                 240

Ser Phe Leu Gly His Ala Gly Phe Tyr Gln Phe Phe Ile Lys Asp Phe
            245                 250                 255

Thr Lys Val
```

<210> SEQ ID NO 44
<211> LENGTH: 761
<212> TYPE: DNA
<213> ORGANISM: Nicotiana tabacum

<400> SEQUENCE: 44

```
gtgcgtaaag aggtggtcaa gctgttggat gtcggggttg tgtacccat  ctctgatagc     60
tcttggactt cgccggtgca atgtgtacca agaaggttg  gcatgactgt ggtgaaaaat    120
tccaaaaatg agttgattcc gacaagaacc atcaccggtt ggagggtatg catggactac    180
cgcaagttga ataaagtgac ctgcaaggat cactttcctt tgccatttct ggatcagatg    240
ctagatcgac ttgctgggcg tgccttctat tgcttcttgg atgaatattc tgggtataac    300
caaatcttga ttgctccgga agatccggaa aagaccacat tcacttgtcc gtatggcaca    360
tttgttttct ctaggatgcc ttttaggttg tgtaatgcac cagctacatt tcagcggtgt    420
atgatggcca ttttctccta tatggtgaaa gacatttttg aggtgttcat ggacgatttt    480
agtgttgtgg ggcactcatt tgatgaatgc ttgaagaatc ttgatagggt gttggcccat    540
tgtgaagaaa ccaatcttgt cctcaattgg gagaaatgcc actttatggt agaagaagga    600
atcaatctct ggcataaaat ttcaaaacat ggcattgagg tggataaaca agatagatg     660
tgatttcaag gctccctccc cctacatccg tcaagggagt ccgatgtttt cttgggcatg    720
cggggttcta ttggagattc ataaaagact ctccaaggt t                         761
```

<210> SEQ ID NO 45
<211> LENGTH: 254
<212> TYPE: PRT
<213> ORGANISM: Nicotiana tabacum

<400> SEQUENCE: 45

```
Val Arg Lys Glu Val Val Lys Leu Leu Asp Val Gly Val Val Tyr Pro
1               5                   10                  15

Ile Ser Asp Ser Ser Trp Thr Ser Pro Val Gln Cys Val Pro Lys Lys
            20                  25                  30

Val Gly Met Thr Val Val Lys Asn Ser Lys Asn Glu Leu Ile Pro Thr
            35                  40                  45

Arg Thr Ile Thr Gly Trp Arg Val Cys Met Asp Tyr Arg Lys Leu Asn
            50                  55                  60

Lys Val Thr Cys Lys Asp His Phe Pro Leu Pro Phe Leu Asp Gln Met
65                  70                  75                  80

Leu Asp Arg Leu Ala Gly Arg Ala Phe Tyr Cys Phe Leu Asp Glu Tyr
            85                  90                  95
```

```
Ser Gly Tyr Asn Gln Ile Leu Ile Ala Pro Glu Asp Pro Glu Lys Thr
            100                 105                 110

Thr Phe Thr Cys Pro Tyr Gly Thr Phe Val Phe Ser Arg Met Pro Phe
        115                 120                 125

Arg Leu Cys Asn Ala Pro Ala Thr Phe Gln Arg Cys Met Met Ala Ile
        130                 135                 140

Phe Ser Tyr Met Val Lys Asp Ile Phe Glu Val Phe Met Asp Asp Phe
145                 150                 155                 160

Ser Val Val Gly His Ser Phe Asp Glu Cys Leu Lys Asn Leu Asp Arg
                165                 170                 175

Val Leu Ala His Cys Glu Glu Thr Asn Leu Val Leu Asn Trp Glu Lys
            180                 185                 190

Cys His Phe Met Val Glu Glu Gly Ile Asn Leu Trp His Lys Ile Ser
            195                 200                 205

Lys His Gly Ile Glu Val Asp Lys Ala Lys Ile Asp Val Ile Ser Arg
        210                 215                 220

Leu Pro Pro Pro Thr Ser Val Lys Gly Val Arg Cys Phe Leu Gly His
225                 230                 235                 240

Ala Gly Phe Tyr Trp Arg Phe Ile Lys Asp Phe Ser Lys Val
                245                 250
```

<210> SEQ ID NO 46
<211> LENGTH: 762
<212> TYPE: DNA
<213> ORGANISM: Nicotiana tabacum

<400> SEQUENCE: 46

```
gtgcgtaagg aggtgtttaa gttgttggat gttggggttg tgtaccccat ctctgatagc      60
tcttgcattt cgccggtgca atgtgtaccg aagaagggtg gcatgaccgt ggttgcaaat     120
tcgcaaaatg ggttgattcc taccaggatc gtcaccgggt ggaaggtatg catggattac     180
cgaaagttga ataaagtgac ccgcaaggat cactttccat gccttttct tgatcagatg      240
ttagatcgac ttgctgggcg tgccttctac tgtttcttgg atgggtattc tggatacaac     300
caaatcttca ttactccgga agatcaggag aagacaacat tcacttgtcc atatggcacc     360
tttgcttttt ctaggatgcc ttttggttg tgtaatgcac cgactacatt ctagcggtat      420
atgatggcca ttttcactga tatggtggaa gatattttgg aggtgttcat ggacgacttt     480
agtgttgtgg gtgattcatt tgatgaatgt ttgaataatc ttgatagagt gttggcccat     540
tgtaaagaaa ccaatcttgt tcttaattgg gagaaatgcc acttcatggt tgaggagggc     600
atagttcttg gcataaaat tttaaagcat ggtatagagg tggacaaagc aaaaattgat     660
gtgatttcaa ggctccctcc ccctacttct gtcaagggag tgagaagttt cttaggcat     720
gcggggttct accggagatt catcaaagat ttcaccaaag tt                      762
```

<210> SEQ ID NO 47
<211> LENGTH: 254
<212> TYPE: PRT
<213> ORGANISM: Nicotiana tabacum

<400> SEQUENCE: 47

```
Val Arg Lys Glu Val Phe Lys Leu Leu Asp Val Gly Val Val Tyr Pro
  1               5                  10                  15

Ile Ser Asp Ser Ser Cys Ile Ser Pro Val Gln Cys Val Pro Lys Lys
                20                  25                  30
```

Gly Gly Met Thr Val Val Ala Asn Ser Gln Asn Gly Leu Ile Pro Thr
         35                  40                  45
Arg Ile Val Thr Gly Trp Lys Val Cys Met Asp Tyr Arg Lys Leu Asn
     50                  55                  60
Lys Val Thr Arg Lys Asp His Phe Pro Leu Pro Phe Leu Asp Gln Met
65                  70                  75                  80
Leu Asp Arg Leu Ala Gly Arg Ala Phe Tyr Cys Phe Leu Asp Gly Tyr
             85                  90                  95
Ser Gly Tyr Asn Gln Ile Phe Ile Thr Pro Glu Asp Gln Glu Lys Thr
                100                 105                 110
Thr Phe Thr Cys Pro Tyr Gly Thr Phe Ala Phe Ser Arg Met Pro Phe
        115                 120                 125
Gly Leu Cys Asn Ala Pro Thr Thr Phe Glx Arg Tyr Met Met Ala Ile
        130                 135                 140
Phe Thr Asp Met Val Glu Asp Ile Leu Glu Val Phe Met Asp Asp Phe
145                 150                 155                 160
Ser Val Val Gly Asp Ser Phe Asp Glu Cys Leu Asn Asn Leu Asp Arg
            165                 170                 175
Val Leu Ala His Cys Lys Glu Thr Asn Leu Val Leu Asn Trp Glu Lys
            180                 185                 190
Cys His Phe Met Val Glu Glu Gly Ile Val Leu Gly His Lys Ile Leu
        195                 200                 205
Lys His Gly Ile Glu Val Asp Lys Ala Lys Ile Asp Val Ile Ser Arg
        210                 215                 220
Leu Pro Pro Pro Thr Ser Val Lys Gly Val Arg Ser Phe Leu Arg His
225                 230                 235                 240
Ala Gly Phe Tyr Arg Arg Phe Ile Lys Asp Phe Thr Lys Val
            245                 250

<210> SEQ ID NO 48
<211> LENGTH: 760
<212> TYPE: DNA
<213> ORGANISM: Nicotiana tabacum

<400> SEQUENCE: 48

```
gcggaaggag gtcgtcaagc tgttggatgt cggtgttgtg tacccatat ttgatagctc      60
ttggactttg ccggtgcaat atgtgccgaa gaagggtggt atgaccgtgg ttaccaatgt    120
aaaaaatgag ttgattccta ccaggactgt caccgggtgg agggtgtgca tggattacca    180
caaattgaat aaagtgaccc gcaaggatca ctttccatta cctttcttg atcagatgtt     240
agacagactg ctgggtgtg ccttctactg tttcttggat gggtattctg ggtgcaacaa    300
aattttgatt gcaccaaaag atcaggagaa gaccacctttt acttgtacgt atggtacctt    360
tgtctttct aggatgtcat ttgggttgtg taatgcaccg actacattct agaggtgtat    420
gatggccata tttacctaca tggtggagga cattttggag gtgtttatgg atgacttcag    480
tgttgttggt gactagtttg atgaatgttt gaaaatcttt gatagagtgt ggcccgttg    540
tgaagaagcc aaccttgtgc ttaattggga gaatgccac ttcatggttg aggagggcat    600
agtccttagc cataaaattt caaagcatgg tatagaggtg gacaaagcaa aaattgaagt    660
gatttcaagg ctccttcccc ctacttctgt caagggagtt agaagttttc ttgggcatgc    720
ggggttctac tggagattca tcaaagactt cacgaaggtt                          760
```

<210> SEQ ID NO 49
<211> LENGTH: 253

<212> TYPE: PRT
<213> ORGANISM: Nicotiana tabacum

<400> SEQUENCE: 49

```
Arg Lys Glu Val Val Lys Leu Leu Asp Val Gly Val Val Tyr Pro Ile
  1               5                  10                  15

Phe Asp Ser Ser Trp Thr Leu Pro Val Gln Tyr Val Pro Lys Lys Gly
             20                  25                  30

Gly Met Thr Val Val Thr Asn Val Lys Asn Glu Leu Ile Pro Thr Arg
         35                  40                  45

Thr Val Thr Gly Trp Arg Val Cys Met Asp Tyr His Lys Leu Asn Lys
     50                  55                  60

Val Thr Arg Lys Asp His Phe Pro Leu Pro Phe Leu Asp Gln Met Leu
 65                  70                  75                  80

Asp Arg Leu Ala Gly Cys Ala Phe Tyr Cys Phe Leu Asp Gly Tyr Ser
                 85                  90                  95

Gly Cys Asn Lys Ile Leu Ile Ala Pro Lys Asp Gln Glu Lys Thr Thr
            100                 105                 110

Phe Thr Cys Thr Tyr Gly Thr Phe Val Phe Ser Arg Met Ser Phe Gly
        115                 120                 125

Leu Cys Asn Ala Pro Thr Thr Phe Glx Arg Cys Met Met Ala Ile Phe
130                 135                 140

Thr Tyr Met Val Glu Asp Ile Leu Glu Val Phe Met Asp Asp Phe Ser
145                 150                 155                 160

Val Val Gly Asp Glx Phe Asp Glu Cys Leu Lys Asn Leu Asp Arg Val
                165                 170                 175

Leu Ala Arg Cys Glu Glu Ala Asn Leu Val Leu Asn Trp Glu Lys Cys
            180                 185                 190

His Phe Met Val Glu Glu Gly Ile Val Leu Ser His Lys Ile Ser Lys
        195                 200                 205

His Gly Ile Glu Val Asp Lys Ala Lys Ile Glu Val Ile Ser Arg Leu
    210                 215                 220

Leu Pro Pro Thr Ser Val Lys Gly Val Arg Ser Phe Leu Gly His Ala
225                 230                 235                 240

Gly Phe Tyr Trp Arg Phe Ile Lys Asp Phe Thr Lys Val
                245                 250
```

<210> SEQ ID NO 50
<211> LENGTH: 762
<212> TYPE: DNA
<213> ORGANISM: Oryza sativa

<400> SEQUENCE: 50

```
gtgcgtaagg aggtgtttaa gttcctgtat gccaggatta tttatctcgt accatacagc      60
gagtgggtta gcccagttca ggtcgtgcca agaagggag gaatgacggc cgttgcaaat     120
gctcaaaatg aactaatccc gcaacgaacc gtaaccggat ggagaatgtg catcgattac    180
aggaaactta acaggctac aaaaaaggat catttcccgc tacccttcat tgatgaaatg     240
ttggaacggc tggcaaatca ttccttcttc tgtttccttg atgggtattc aggatatcat    300
caaattccca tccatccgga ggaccagagt aagactacgt tcacatgtcc atatggcacc    360
tatgcgtatc gtaggatgcc ctttggactg tgcaacactc ctgcatcttt ccaaaggtgt    420
atgatgtcta ttttctcgga catgatcgag gatatcatgg aagtcttcat ggatgacttc    480
tcggtctatg gaaagacttt gggtcattgt ctgcagaatc tagacaaagt cttacaacga    540
```

-continued

```
tgccaagaaa aggacctagt gcttaactgg gaaaagtgcc atttcatggt ctgtgaaggg      600
atagttcttg ggcatcgagt gtccgaacga ggagtcgaag ttgatcgtgc taaaattgat      660
gtgatagatc agcttcctcc acccgtgaac atcaaaggaa tccgcagctt ctttggtcac      720
gctggctttt atagaaggtt catcaaggac ttcacaaaag tt                         762
```

<210> SEQ ID NO 51
<211> LENGTH: 254
<212> TYPE: PRT
<213> ORGANISM: Oryza sativa

<400> SEQUENCE: 51

```
Val Arg Lys Glu Val Phe Lys Phe Leu Tyr Ala Arg Ile Ile Tyr Leu
 1               5                  10                  15

Val Pro Tyr Ser Glu Trp Val Ser Pro Val Gln Val Val Pro Lys Lys
            20                  25                  30

Gly Gly Met Thr Ala Val Ala Asn Ala Gln Asn Glu Leu Ile Pro Gln
        35                  40                  45

Arg Thr Val Thr Gly Trp Arg Met Cys Ile Asp Tyr Arg Lys Leu Asn
    50                  55                  60

Lys Ala Thr Lys Lys Asp His Phe Pro Leu Pro Phe Ile Asp Glu Met
65                  70                  75                  80

Leu Glu Arg Leu Ala Asn His Ser Phe Phe Cys Phe Leu Asp Gly Tyr
                85                  90                  95

Ser Gly Tyr His Gln Ile Pro Ile His Pro Glu Asp Gln Ser Lys Thr
            100                 105                 110

Thr Phe Thr Cys Pro Tyr Gly Thr Tyr Ala Tyr Arg Arg Met Pro Phe
        115                 120                 125

Gly Leu Cys Asn Thr Pro Ala Ser Phe Gln Arg Cys Met Met Ser Ile
    130                 135                 140

Phe Ser Asp Met Ile Glu Asp Ile Met Glu Val Phe Met Asp Asp Phe
145                 150                 155                 160

Ser Val Tyr Gly Lys Thr Leu Gly His Cys Leu Gln Asn Leu Asp Lys
                165                 170                 175

Val Leu Gln Arg Cys Gln Glu Lys Asp Leu Val Leu Asn Trp Glu Lys
            180                 185                 190

Cys His Phe Met Val Cys Glu Gly Ile Val Leu Gly His Arg Val Ser
        195                 200                 205

Glu Arg Gly Val Glu Val Asp Arg Ala Lys Ile Asp Val Ile Asp Gln
    210                 215                 220

Leu Pro Pro Pro Val Asn Ile Lys Gly Ile Arg Ser Phe Phe Gly His
225                 230                 235                 240

Ala Gly Phe Tyr Arg Arg Phe Ile Lys Asp Phe Thr Lys Val
                245                 250
```

<210> SEQ ID NO 52
<211> LENGTH: 761
<212> TYPE: DNA
<213> ORGANISM: Oryza sativa

<400> SEQUENCE: 52

```
gtgcgcaagg aggttttgaa attgctgcat gccaggatta tctatcccgt accatacagt      60
gagagggtta gcccagtcca ggttgtgcca agaagggag gaatggcggt cgttgcaaat      120
gctcagaatg aactaattac gcaacaaacc gtaaccggat ggaggatgtg tatcgattac      180
aggaaactca acaaggctac aaaaaaggat catttcccgc taccttcat tgttgaaatg      240
```

```
ttggaacggc tgcaaatca ttccttcttt tgtttccttg atggatattt cggatatcat    300
caaattccca tccatccgga ggactagagt aagactacgt tcacatgtcc atatggcacc    360
tatgcgtatc ataggatgtc ctttggactg tgcaacgctc ctgcatcttt ccaaggtgta    420
tgatgtctat tttctcggac atgatcgagg atatcatgga agtcttcatg gatgacttct    480
cggtctatgg aaagactttc ggtcattgtc tgcaaaatct agacaaagtc ttacaacgat    540
gccaagaaaa ggacctggtg cttaactggg aaaagtgaca tttcatggtc cgtgaaggga    600
tagttcttgg gcatcgagtg ttcgaacaag gaatcgaagt tgatcatgct aaaattgatg    660
tgatagatca gcttcctcct cccgtgaaca tcaaggtat ccgcagcttc ttgggtcatg    720
tcggctttta tagaaggttc atcaaggact tcactaaagt t    761
```

<210> SEQ ID NO 53
<211> LENGTH: 254
<212> TYPE: PRT
<213> ORGANISM: Oryza sativa

<400> SEQUENCE: 53

```
Val Arg Lys Glu Val Leu Lys Leu Leu His Ala Arg Ile Ile Tyr Pro
  1               5                  10                  15

Val Pro Tyr Ser Glu Arg Val Ser Pro Val Gln Val Val Pro Lys Lys
             20                  25                  30

Gly Gly Met Ala Val Val Ala Asn Ala Gln Asn Glu Leu Ile Thr Gln
         35                  40                  45

Gln Thr Val Thr Gly Trp Arg Met Cys Ile Asp Tyr Arg Lys Leu Asn
     50                  55                  60

Lys Ala Thr Lys Lys Asp His Phe Pro Leu Pro Phe Ile Val Glu Met
 65                  70                  75                  80

Leu Glu Arg Leu Ala Asn His Ser Phe Phe Cys Phe Leu Asp Gly Tyr
                 85                  90                  95

Phe Gly Tyr His Gln Ile Pro Ile His Pro Glu Asp Glx Ser Lys Thr
            100                 105                 110

Thr Phe Thr Cys Pro Tyr Gly Thr Tyr Ala Tyr His Arg Met Ser Phe
        115                 120                 125

Gly Leu Cys Asn Ala Pro Ala Ser Phe Gln Arg Cys Met Met Ser Ile
    130                 135                 140

Phe Ser Asp Met Ile Glu Asp Ile Met Glu Val Phe Met Asp Asp Phe
145                 150                 155                 160

Ser Val Tyr Gly Lys Thr Phe Gly His Cys Leu Gln Asn Leu Asp Lys
                165                 170                 175

Val Leu Gln Arg Cys Gln Glu Lys Asp Leu Val Leu Asn Trp Glu Lys
            180                 185                 190

Glx His Phe Met Val Arg Glu Gly Ile Val Leu Gly His Arg Val Phe
        195                 200                 205

Glu Gln Gly Ile Glu Val Asp His Ala Lys Ile Asp Val Ile Asp Gln
    210                 215                 220

Leu Pro Pro Pro Val Asn Ile Lys Gly Ile Arg Ser Phe Leu Gly His
225                 230                 235                 240

Val Gly Phe Tyr Arg Arg Phe Ile Lys Asp Phe Thr Lys Val
                245                 250
```

<210> SEQ ID NO 54
<211> LENGTH: 762
<212> TYPE: DNA

```
<213> ORGANISM: Oryza sativa

<400> SEQUENCE: 54
gtgcggaaag aggtttttaa gctcctgcat gccgggatta tttataccgt tccatgcagt      60
gagtgggtca gcacagtcca ggttgggccg aagatgggat gaatgacggt cgttgcaaat     120
gctcaaaata aacttatccc gcaaccaacc ataaccggat ggaggatgtg catagactac     180
aggaaactca acaaggctac aaaagaggat catttccgc tacccttcat tgatgaaatg      240
ttggaacgga tgacaaatca ttccttcttc tgtttccttg atgggtattc cggatatcat     300
caaattccca tccgtccaga ggaccagagt aagactacgt tcacatgtcc atatggcacc     360
tatgcgtatc gtaggatgtc cttcggactg tgcaacgctc ctgcatcttt ccaaaggtgt     420
atgttgtcta ttttctcgga catgatcgaa gatatcatga aagtcttcat ggatgacttc     480
tcagtttatg gaaagacttt cggtcattgt ctgtagaatc tagacaaagt cttacaacga     540
tgccaagaaa atgacctagt gtttaattgg gaaaagtgcc attttatggt ccgtgaaggg     600
atagttcttg ggcatcgagt atccgaatga ggaatcgaag ttgatcgtgc taaaatcgat     660
gttatagatc aaattcgtcc tcctgcgaat atcaaggaa tccgcagctt cttgggacat      720
gccggctttt atagaaggtt cctcaaggac ttcacaaaag tt                        762

<210> SEQ ID NO 55
<211> LENGTH: 254
<212> TYPE: PRT
<213> ORGANISM: Oryza sativa

<400> SEQUENCE: 55

Val Arg Lys Glu Val Phe Lys Leu Leu His Ala Gly Ile Ile Tyr Thr
  1               5                  10                  15

Val Pro Cys Ser Glu Trp Val Ser Thr Val Gln Val Gly Pro Lys Met
             20                  25                  30

Gly Glx Met Thr Val Val Ala Asn Ala Gln Asn Lys Leu Ile Pro Gln
         35                  40                  45

Pro Thr Ile Thr Gly Trp Arg Met Cys Ile Asp Tyr Arg Lys Leu Asn
     50                  55                  60

Lys Ala Thr Lys Glu Asp His Phe Pro Leu Pro Phe Ile Asp Glu Met
 65                  70                  75                  80

Leu Glu Arg Met Thr Asn His Ser Phe Phe Cys Phe Leu Asp Gly Tyr
                 85                  90                  95

Ser Gly Tyr His Gln Ile Pro Ile Arg Pro Glu Asp Gln Ser Lys Thr
            100                 105                 110

Thr Phe Thr Cys Pro Tyr Gly Thr Tyr Ala Tyr Arg Arg Met Ser Phe
        115                 120                 125

Gly Leu Cys Asn Ala Pro Ala Ser Phe Gln Arg Cys Met Leu Ser Ile
    130                 135                 140

Phe Ser Asp Met Ile Glu Asp Ile Met Lys Val Phe Met Asp Asp Phe
145                 150                 155                 160

Ser Val Tyr Gly Lys Thr Phe Gly His Cys Leu Glx Asn Leu Asp Lys
                165                 170                 175

Val Leu Gln Arg Cys Gln Glu Asn Asp Leu Val Phe Asn Trp Glu Lys
            180                 185                 190

Cys His Phe Met Val Arg Glu Gly Ile Val Leu Gly His Arg Val Ser
        195                 200                 205

Glu Glx Gly Ile Glu Val Asp Arg Ala Lys Ile Asp Val Ile Asp Gln
    210                 215                 220
```

```
Ile Arg Pro Pro Ala Asn Ile Lys Gly Ile Arg Ser Phe Leu Gly His
225                 230                 235                 240

Ala Gly Phe Tyr Arg Arg Phe Leu Lys Asp Phe Thr Lys Val
            245                 250
```

<210> SEQ ID NO 56
<211> LENGTH: 762
<212> TYPE: DNA
<213> ORGANISM: Oryza sativa

<400> SEQUENCE: 56

```
gtgcgtaagg aggtcttgaa gctcttgcat gccgagatta tttatcccgt accatataga    60
gagtgggtta gcccggtcta ggttatgccg aagaagggac gaatgacggt cattgcaaat   120
gctcaaaatg aacttattcc gcaacgaaca gtaaccggat ggaggatgtg catagattac   180
atgaaactta acaaggctac gaaaaaggat catttcccac tacccttcat tgatgaaatg   240
ttggaacggc tggcaaatca ttctttcttc cgtttccttg atgggtattc taggtatgat   300
caaattccca tccatccgga ggaccaaagt aagactacgt tcacatgttc gtatgatacc   360
tatgcttatc gtaggatgtc cttcggactg tgcaacgctc ctgcatcttt ccaaaggtgt   420
atgatgtcta ttttctccga catgattaag gacattatgg aagtcttcat gcatgacttc   480
tctatttatg gaaagacctc cggtcattgt ctacaaaatt tagacaaaat tttgcaacga   540
tgccaagaga aggacctggt acttaattgg gaaaagtgtc atttcatggt ccgtgaaggg   600
atagttctta gtcatcgagt gtccgaataa ggaatcgaag ttgatcgtgc taaaaactat   660
gtaatagatt agcttccttc tcctgtgaac attaagggga tccgcaattt tttgggacat   720
gctggctttt atagaaggtt catcaaagac ttcacaaagg tt                     762
```

<210> SEQ ID NO 57
<211> LENGTH: 254
<212> TYPE: PRT
<213> ORGANISM: Oryza sativa

<400> SEQUENCE: 57

```
Val Arg Lys Glu Val Leu Lys Leu Leu His Ala Glu Ile Ile Tyr Pro
1               5                   10                  15

Val Pro Tyr Arg Glu Trp Val Ser Pro Val Glx Val Met Pro Lys Lys
            20                  25                  30

Gly Arg Met Thr Val Ile Ala Asn Ala Gln Asn Glu Leu Ile Pro Gln
        35                  40                  45

Arg Thr Val Thr Gly Trp Arg Met Cys Ile Asp Tyr Met Lys Leu Asn
    50                  55                  60

Lys Ala Thr Lys Lys Asp His Phe Pro Leu Pro Phe Ile Asp Glu Met
65                  70                  75                  80

Leu Glu Arg Leu Ala Asn His Ser Phe Phe Arg Phe Leu Asp Gly Tyr
                85                  90                  95

Ser Arg Tyr Asp Gln Ile Pro Ile His Pro Glu Asp Gln Ser Lys Thr
            100                 105                 110

Thr Phe Thr Cys Ser Tyr Asp Thr Tyr Ala Tyr Arg Arg Met Ser Phe
        115                 120                 125

Gly Leu Cys Asn Ala Pro Ala Ser Phe Gln Arg Cys Met Met Ser Ile
    130                 135                 140

Phe Ser Asp Met Ile Lys Asp Ile Met Glu Val Phe Met His Asp Phe
145                 150                 155                 160
```

```
Ser Ile Tyr Gly Lys Thr Ser Gly His Cys Leu Gln Asn Leu Asp Lys
                165                 170                 175

Ile Leu Gln Arg Cys Gln Glu Lys Asp Leu Val Leu Asn Trp Glu Lys
            180                 185                 190

Cys His Phe Met Val Arg Glu Gly Ile Val Leu Ser His Arg Val Ser
        195                 200                 205

Glu Glx Gly Ile Glu Val Asp Arg Ala Lys Asn Tyr Val Ile Asp Glx
    210                 215                 220

Leu Pro Ser Pro Val Asn Ile Lys Gly Ile Arg Asn Phe Leu Gly His
225                 230                 235                 240

Ala Gly Phe Tyr Arg Arg Phe Ile Lys Asp Phe Thr Lys Val
                245                 250

<210> SEQ ID NO 58
<211> LENGTH: 762
<212> TYPE: DNA
<213> ORGANISM: Hordeum vulgare

<400> SEQUENCE: 58
gtgcgcaagg aggtttagaa gttcctggaa gcaggtatca tctatcgtgt tgctcatagt     60
gattggttga gtcgggtgca ttgtgtccct aagaagggag gcattaccgt tgtccctaat    120
gataaggatg aattgatccc acagaggact attactggct ataggatggt gattgatttt    180
aggaaattga ataaagccac taggaaagat cattacccct tgccttttat cgaccaaatg    240
cgagaaaggc tgtctaaaca cacacacttc tgcttctaa acggttattt tggtttctcc     300
caaataccag ttgcacaatc tgatcaggag aaaaccactt tcacctgccc ttttggtaca    360
tttgcttata gacgtatgac ttttggctta tgtaatgcac ctgcctcctt tcaaagatgt    420
atgatggcta tattccctga cttttgtgaa aagattgttg aggttttcat ggatgacttc    480
tccatttacg gatcttcctt tgatgattgc ctcagcaacc ttgatcgagt cttgcagaga    540
tgtaaagaca ccaatctttt cttgaattgg aagaagtgcc actttatggt taatgacggc    600
atcgtcttag gacataaatt ttctgaaaga ggtattgaag tcgataaggc taaggttgat    660
ggaatcgaga aaatgccata ccccacagat atcaagggga taagaagttt ccttggtcat    720
gctggtttct atagaaggtt cataaaagac ttcactaagg tt                       762

<210> SEQ ID NO 59
<211> LENGTH: 254
<212> TYPE: PRT
<213> ORGANISM: Hordeum vulgare

<400> SEQUENCE: 59

Val Arg Lys Glu Val Glx Lys Phe Leu Glu Ala Gly Ile Ile Tyr Arg
1               5                   10                  15

Val Ala His Ser Asp Trp Leu Ser Arg Val His Cys Val Pro Lys Lys
                20                  25                  30

Gly Gly Ile Thr Val Val Pro Asn Asp Lys Asp Glu Leu Ile Pro Gln
            35                  40                  45

Arg Thr Ile Thr Gly Tyr Arg Met Val Ile Asp Phe Arg Lys Leu Asn
        50                  55                  60

Lys Ala Thr Arg Lys Asp His Tyr Pro Leu Pro Phe Ile Asp Gln Met
65                  70                  75                  80

Arg Glu Arg Leu Ser Lys His Thr His Phe Cys Phe Leu Asn Gly Tyr
                85                  90                  95

Phe Gly Phe Ser Gln Ile Pro Val Ala Gln Ser Asp Gln Glu Lys Thr
```

```
            100                 105                 110
Thr Phe Thr Cys Pro Phe Gly Thr Phe Ala Tyr Arg Arg Met Thr Phe
            115                 120                 125

Gly Leu Cys Asn Ala Pro Ala Ser Phe Gln Arg Cys Met Met Ala Ile
    130                 135                 140

Phe Pro Asp Phe Cys Glu Lys Ile Val Glu Val Phe Met Asp Asp Phe
145                 150                 155                 160

Ser Ile Tyr Gly Ser Ser Phe Asp Asp Cys Leu Ser Asn Leu Asp Arg
                165                 170                 175

Val Leu Gln Arg Cys Lys Asp Thr Asn Leu Phe Leu Asn Trp Lys Lys
            180                 185                 190

Cys His Phe Met Val Asn Asp Gly Ile Val Leu Gly His Lys Phe Ser
            195                 200                 205

Glu Arg Gly Ile Glu Val Asp Lys Ala Lys Val Asp Gly Ile Glu Lys
            210                 215                 220

Met Pro Tyr Pro Thr Asp Ile Lys Gly Ile Arg Ser Phe Leu Gly His
225                 230                 235                 240

Ala Gly Phe Tyr Arg Arg Phe Ile Lys Asp Phe Thr Lys Val
                245                 250

<210> SEQ ID NO 60
<211> LENGTH: 762
<212> TYPE: DNA
<213> ORGANISM: Hordeum vulgare

<400> SEQUENCE: 60
gtgcgtaaag aggtcctaaa gttcctggaa gcgggtatta tctatcctgt tgctcacaac      60
gattgggtga gtccggtgca ttgcgtccct aagaagggat gcattaccgt tgtccctaat     120
gataaggatg aattgatccc acataggatt attactggct ataggatggt gatcgatttt     180
aggaaaatga ataaagccac taggaaagaa cattacccct tgccttttag cgaccaaatg     240
ctagaaaggt tgtctaaaca cacacacttc tgctttctag acggttattc tagtttctcc     300
caaatactag ttgcacaatc tgatcaggag aaaaccactt tcacctaccc gttcggtacc     360
tttgcttata gacgtatgcc ttttggctta tgtaatgcac ctgccacctt tcaaagatgt     420
atgatggcta tattctctga cttttgtgaa agtttgtcg aggttttcat ggatgacttt      480
tccgtttacg gatcttcctt tgatgattgc ctcaacaacc ttgatcgggt cttgcagaga     540
tgtaaagata ctaatcttgt cttgaattgg gagaagtgcc actttatggt taatgaaggc     600
atcgtcttag acataaaat tccgaaaga ggtattgaat tcgataaggc taaggttggt       660
gcaatcaaga aaatgccata ccccacagat atcaaaggta taagaagttt cttggtccat    720
gctggtttct atagaaggtt catcaaggac tttacaaagg tt                        762

<210> SEQ ID NO 61
<211> LENGTH: 254
<212> TYPE: PRT
<213> ORGANISM: Hordeum vulgare

<400> SEQUENCE: 61

Val Arg Lys Glu Val Leu Lys Phe Leu Glu Ala Gly Ile Ile Tyr Pro
1               5                   10                  15

Val Ala His Asn Asp Trp Val Ser Pro Val His Cys Val Pro Lys Lys
            20                  25                  30

Gly Cys Ile Thr Val Val Pro Asn Asp Lys Asp Glu Leu Ile Pro His
        35                  40                  45
```

```
Arg Ile Ile Thr Gly Tyr Arg Met Val Ile Asp Phe Arg Lys Met Asn
     50                  55                  60
Lys Ala Thr Arg Lys Glu His Tyr Pro Leu Pro Phe Ser Asp Gln Met
 65                  70                  75                  80
Leu Glu Arg Leu Ser Lys His Thr His Phe Cys Phe Leu Asp Gly Tyr
                 85                  90                  95
Ser Ser Phe Ser Gln Ile Leu Val Ala Gln Ser Asp Gln Glu Lys Thr
                100                 105                 110
Thr Phe Thr Tyr Pro Phe Gly Thr Phe Ala Tyr Arg Arg Met Pro Phe
            115                 120                 125
Gly Leu Cys Asn Ala Pro Ala Thr Phe Gln Arg Cys Met Met Ala Ile
        130                 135                 140
Phe Ser Asp Phe Cys Glu Lys Phe Val Glu Val Phe Met Asp Asp Phe
145                 150                 155                 160
Ser Val Tyr Gly Ser Ser Phe Asp Asp Cys Leu Asn Asn Leu Asp Arg
                165                 170                 175
Val Leu Gln Arg Cys Lys Asp Thr Asn Leu Val Leu Asn Trp Glu Lys
            180                 185                 190
Cys His Phe Met Val Asn Glu Gly Ile Val Leu Gly His Lys Ile Ser
        195                 200                 205
Glu Arg Gly Ile Glu Phe Asp Lys Ala Lys Val Gly Ala Ile Lys Lys
    210                 215                 220
Met Pro Tyr Pro Thr Asp Ile Lys Gly Ile Arg Ser Phe Leu Val His
225                 230                 235                 240
Ala Gly Phe Tyr Arg Arg Phe Ile Lys Asp Phe Thr Lys Val
                245                 250
```

<210> SEQ ID NO 62
<211> LENGTH: 757
<212> TYPE: DNA
<213> ORGANISM: Hordeum vulgare

<400> SEQUENCE: 62

```
gaaagaggt tgtgaagctc ctggatgaag gtattatcta tcatgttgct catagcgatt      60
gggtgagtcc ggtgcatagc gttcctaaga agggaggcat taccgttgtc cctaatgata    120
aggatgaatt gatcccgcag aggattatca ctggctatag gatggtgatc gatttcagga    180
aactgaataa agccactagg aaagatcatt acccttttgcc ttttatcgac catatgctag   240
aaaggttgtc caaactcaca cacttctgct ttctagacgg ttattctagt ttctcccaaa    300
taccagttgc acaatctgat caggagaaaa ccactttcac ctgcccttc ggtacctttg     360
cttatagacg tatgcctttt ggcttatgta atgcacctgc caccttcaa agatgtatga     420
tggctatatt ctctaacttt tgtgaaaata ttgtcgaggt tttcatggat gactttccg     480
tttacgggtc ttcttttgat gattgcctca gcaaccttga tcgagtctta cagagatgta    540
aagacaccaa tcttgtcttg aatggggaga gtgccactt tatggttaat gaaggcatcg     600
tcttaggaca taaatttct gaaagaggta ttgaagtcga taaggctaag gttgatgcaa     660
tcgacaaaat gccatacccc acagatatca aaggtataag aagttccctt ggtcatggtg    720
gtttctatag aaggtttatc aaagatttca caaaggt                              757
```

<210> SEQ ID NO 63
<211> LENGTH: 251
<212> TYPE: PRT
<213> ORGANISM: Hordeum vulgare

<400> SEQUENCE: 63

```
Lys Glu Val Val Lys Leu Leu Asp Glu Gly Ile Ile Tyr His Val Ala
  1               5                  10                  15
His Ser Asp Trp Val Ser Pro Val His Ser Val Pro Lys Lys Gly Gly
             20                  25                  30
Ile Thr Val Val Pro Asn Asp Lys Asp Glu Leu Ile Pro Gln Arg Ile
         35                  40                  45
Ile Thr Gly Tyr Arg Met Val Ile Asp Phe Arg Lys Leu Asn Lys Ala
     50                  55                  60
Thr Arg Lys Asp His Tyr Pro Leu Pro Phe Ile Asp His Met Leu Glu
 65                  70                  75                  80
Arg Leu Ser Lys Leu Thr His Phe Cys Phe Leu Asp Gly Tyr Ser Ser
                 85                  90                  95
Phe Ser Gln Ile Pro Val Ala Gln Ser Asp Gln Glu Lys Thr Thr Phe
            100                 105                 110
Thr Cys Pro Phe Gly Thr Phe Ala Tyr Arg Arg Met Pro Phe Gly Leu
        115                 120                 125
Cys Asn Ala Pro Ala Thr Phe Gln Arg Cys Met Met Ala Ile Phe Ser
    130                 135                 140
Asn Phe Cys Glu Asn Ile Val Glu Val Phe Met Asp Asp Phe Ser Val
145                 150                 155                 160
Tyr Gly Ser Ser Phe Asp Asp Cys Leu Ser Asn Leu Asp Arg Val Leu
                165                 170                 175
Gln Arg Cys Lys Asp Thr Asn Leu Val Leu Asn Gly Glu Lys Cys His
            180                 185                 190
Phe Met Val Asn Glu Gly Ile Val Leu Gly His Lys Ile Ser Glu Arg
        195                 200                 205
Gly Ile Glu Val Asp Lys Ala Lys Val Asp Ala Ile Asp Lys Met Pro
    210                 215                 220
Tyr Pro Thr Asp Ile Lys Gly Ile Arg Ser Phe Leu Gly His Gly Gly
225                 230                 235                 240
Phe Tyr Arg Arg Phe Ile Lys Asp Phe Thr Lys
                245                 250
```

<210> SEQ ID NO 64
<211> LENGTH: 740
<212> TYPE: DNA
<213> ORGANISM: Hordeum vulgare

<400> SEQUENCE: 64

```
gtgcgtaaag aggtgattaa attcctagaa gaaggtatta tctatcctgt tgctcacagc    60
gattgggtga gtccggtgca ttgcattcct aagaaggag gcattaccgt tgtccctaat    120
gataaggatg aattgatccc atagaggatt attactggct ataggatggt gattgatttt    180
aggaagttga ataaagccac taggaaagat cattacccct tgccttttat cgaccaaatg    240
ctagaaaggc tgtctaaaca cacacacttc ttgtttctgg acggttatac tggtttctcc    300
caaataccag ttgcacaatt tgatcaggag aaaaccactt taacctgaca tttcggtacc    360
tttgcttata tacgtatgcc ttttggcttg tgtaatgcac ctgccacctt tcaaagatgt    420
atgatggcta tattctccga cttctgtgaa aagattgtca atgttttcat ggataacttc    480
tccgtttacg ggtgttcctt tgatgattgc ctcaacaacg ttgatcgagt cttacagaga    540
tgtaaggaca ccaatgttgt cttgaattgg gagaagtgtc actttatggt taatgaaggc    600
```

```
atcgtcttag gacataagat ttctgaaaga ggtattaaag ttgataaggc taaggttgat    660
gcaatcgaga aaatgccata tccacagata tcaaaggtat aagaagtttc cttggtcatg    720
ctggtttcta tagaaggttc                                                740
```

<210> SEQ ID NO 65
<211> LENGTH: 247
<212> TYPE: PRT
<213> ORGANISM: Hordeum vulgare

<400> SEQUENCE: 65

```
Val Arg Lys Glu Val Ile Lys Phe Leu Glu Glu Gly Ile Ile Tyr Pro
 1               5                  10                  15
Val Ala His Ser Asp Trp Val Ser Pro Val His Cys Ile Pro Lys Lys
             20                  25                  30
Gly Gly Ile Thr Val Val Pro Asn Asp Lys Asp Glu Leu Ile Pro Glx
         35                  40                  45
Arg Ile Ile Thr Gly Tyr Arg Met Val Ile Asp Phe Arg Lys Leu Asn
     50                  55                  60
Lys Ala Thr Arg Lys Asp His Tyr Pro Leu Pro Phe Ile Asp Gln Met
 65                  70                  75                  80
Leu Glu Arg Leu Ser Lys His Thr His Phe Leu Phe Leu Asp Gly Tyr
                 85                  90                  95
Thr Gly Phe Ser Gln Ile Pro Val Ala Gln Phe Asp Gln Glu Lys Thr
            100                 105                 110
Thr Leu Thr Glx His Phe Gly Thr Phe Ala Tyr Ile Arg Met Pro Phe
        115                 120                 125
Gly Leu Cys Asn Ala Pro Ala Thr Phe Gln Arg Cys Met Met Ala Ile
    130                 135                 140
Phe Ser Asp Phe Cys Glu Lys Ile Val Asn Val Phe Met Asp Asn Phe
145                 150                 155                 160
Ser Val Tyr Gly Cys Ser Phe Asp Asp Cys Leu Asn Asn Val Asp Arg
                165                 170                 175
Val Leu Gln Arg Cys Lys Asp Thr Asn Val Val Leu Asn Trp Glu Lys
            180                 185                 190
Cys His Phe Met Val Asn Glu Gly Ile Val Leu Gly His Lys Ile Ser
        195                 200                 205
Glu Arg Gly Ile Lys Val Asp Lys Ala Lys Val Asp Ala Ile Glu Lys
    210                 215                 220
Met Pro Tyr Pro Thr Asp Ile Lys Gly Ile Arg Ser Phe Leu Gly His
225                 230                 235                 240
Ala Gly Phe Tyr Arg Arg Phe
                245
```

<210> SEQ ID NO 66
<211> LENGTH: 762
<212> TYPE: DNA
<213> ORGANISM: Avena sativa

<400> SEQUENCE: 66

```
gtgcgaaagg aggttttcaa gctcatggat gctggtatta tttaccctat tgctgatagt    60
gaatgggtta gtcatgttca ttgtgttcct aaaaagggag gtattaccgt tgtccctaat   120
gataatgatg agcttattcc tcaaagaata gtggtaggct ataggatgtg catcgatttt   180
aggaaagtca ataagttcac taagaaagat cactacccgc ttcctttat tgatcaaatg    240 ttggaaagat ttctaaaaa gacccatttt tgttttcttg atggttattc tggtttctct    300
```

```
caaattgttg ttaaacaaca agatcaagaa aaaactactt ttacttgccc ttatggaact    360
tatgcttata gatgtatgcc ttttggttta tgtaatgctc cttctacttt cctaaggtgc    420
atgtctgcta tctttcatgg ttttttgtgag gaaattgtag aagtgttcat ggacgacttt    480
tctgtctacg gaacttcttt tgataattgt ctgcacaacc ttgataaagt tttacagaga    540
tgtgaaggaa ctaatcttgt tcttaattgg gagaaatgcc acttcatggt taatgaaggg    600
attgttcttg ggcataaagt ttctaaaaga ggcatagaag ttgatagagc taaggttgag    660
gcaattgaga agatgccatg tccaagagac atcaaggta ttcgtagtat ccttggtcat    720
gctggtttct ataggaggtt catcaaagac ttcacaaagg tt                      762
```

```
<210> SEQ ID NO 67
<211> LENGTH: 254
<212> TYPE: PRT
<213> ORGANISM: Avena sativa

<400> SEQUENCE: 67
```

```
Val Arg Lys Glu Val Phe Lys Leu Met Asp Ala Gly Ile Ile Tyr Pro
 1               5                   10                  15

Ile Ala Asp Ser Glu Trp Val Ser His Val His Cys Val Pro Lys Lys
            20                  25                  30

Gly Gly Ile Thr Val Val Pro Asn Asp Asn Asp Glu Leu Ile Pro Gln
        35                  40                  45

Arg Ile Val Val Gly Tyr Arg Met Cys Ile Asp Phe Arg Lys Val Asn
    50                  55                  60

Lys Val Thr Lys Lys Asp His Tyr Pro Leu Pro Phe Ile Asp Gln Met
65                  70                  75                  80

Leu Glu Arg Phe Ser Lys Lys Thr His Phe Cys Phe Leu Asp Gly Tyr
                85                  90                  95

Ser Gly Phe Ser Gln Ile Val Val Lys Gln Gln Asp Gln Glu Lys Thr
            100                 105                 110

Thr Phe Thr Cys Pro Tyr Gly Thr Tyr Ala Tyr Arg Cys Met Pro Phe
        115                 120                 125

Gly Leu Cys Asn Ala Pro Ser Thr Phe Leu Arg Cys Met Ser Ala Ile
    130                 135                 140

Phe His Gly Phe Cys Glu Glu Ile Val Glu Val Phe Met Asp Asp Phe
145                 150                 155                 160

Ser Val Tyr Gly Thr Ser Phe Asp Asn Cys Leu His Asn Leu Asp Lys
                165                 170                 175

Val Leu Gln Arg Cys Glu Gly Thr Asn Leu Val Leu Asn Trp Glu Lys
            180                 185                 190

Cys His Phe Met Val Asn Glu Gly Ile Val Leu Gly His Lys Val Ser
        195                 200                 205

Lys Arg Gly Ile Glu Val Asp Arg Ala Lys Val Glu Ala Ile Glu Lys
    210                 215                 220

Met Pro Cys Pro Arg Asp Ile Lys Gly Ile Arg Ser Ile Leu Gly His
225                 230                 235                 240

Ala Gly Phe Tyr Arg Arg Phe Ile Lys Asp Phe Thr Lys Val
                245                 250
```

```
<210> SEQ ID NO 68
<211> LENGTH: 762
<212> TYPE: DNA
<213> ORGANISM: Avena sativa
```

```
<400> SEQUENCE: 68
gtgcgcaaag aggtctttaa gttccttgat gctggtatta tttaccctat tgctgatagt      60
caatgggtta gccttgttca ttgtgtcccc aagaaagggg gaataactgt tgtgcctaat     120
gaagataatg agcttatacc ccaaagagta gtggttgtgt atagaatgtg cattgatttt     180
agaaggatta taaagttac taggaaagat cattatcctt tgcccttat tgatcaaatg      240
cttgagaggt tgtccaaaaa gactcacttt tgttttcttg atggtcattc tgggttttct     300
caaattgttg tgaaagcaca agaccaagag aaaactactt tcacttgtcc ttatggtact     360
tatgattata ggcgtatgcc ttttggttta tgtaatgctc ctgctacctt tcagagatgt     420
atgtctgcta tatttcatgg ttttttgtgaa gaaattgtgg aggttttcat ggacgatttt     480
tctgtctatg gaacttcttt tgataactgt ttgcacaacc ttgataaatt tttgcagaga     540
tttgaagaaa ccaaccttgt tcttaattgg gagaaatgcc atttcatggt taatgaaggg     600
attgttcttg gacacaagat ctcagaaaga ggcattgaag ttgacagagc caaaattgaa     660
gcaattgaga acatgccttg ccctagagat attaaaggta ttcgtagtat ccttggtcat     720
gctggtttct atagtaggtt catcaaagac tttacaaaag tt                        762

<210> SEQ ID NO 69
<211> LENGTH: 254
<212> TYPE: PRT
<213> ORGANISM: Avena sativa

<400> SEQUENCE: 69
```

Val Arg Lys Glu Val Phe Lys Phe Leu Asp Ala Gly Ile Ile Tyr Pro
 1               5                  10                  15

Ile Ala Asp Ser Gln Trp Val Ser Leu Val His Cys Val Pro Lys Lys
             20                  25                  30

Gly Gly Ile Thr Val Val Pro Asn Glu Asp Asn Glu Leu Ile Pro Gln
         35                  40                  45

Arg Val Val Val Tyr Arg Met Cys Ile Asp Phe Arg Arg Ile Asn
     50                  55                  60

Lys Val Thr Arg Lys Asp His Tyr Pro Leu Pro Phe Ile Asp Gln Met
 65                  70                  75                  80

Leu Glu Arg Leu Ser Lys Lys Thr His Phe Cys Phe Leu Asp Gly His
                 85                  90                  95

Ser Gly Phe Ser Gln Ile Val Val Lys Ala Gln Asp Gln Glu Lys Thr
            100                 105                 110

Thr Phe Thr Cys Pro Tyr Gly Thr Tyr Asp Tyr Arg Arg Met Pro Phe
        115                 120                 125

Gly Leu Cys Asn Ala Pro Ala Thr Phe Gln Arg Cys Met Ser Ala Ile
    130                 135                 140

Phe His Gly Phe Cys Glu Glu Ile Val Glu Val Phe Met Asp Asp Phe
145                 150                 155                 160

Ser Val Tyr Gly Thr Ser Phe Asp Asn Cys Leu His Asn Leu Asp Lys
                165                 170                 175

Phe Leu Gln Arg Phe Glu Glu Thr Asn Leu Val Leu Asn Trp Glu Lys
            180                 185                 190

Cys His Phe Met Val Asn Glu Gly Ile Val Leu Gly His Lys Ile Ser
        195                 200                 205

Glu Arg Gly Ile Glu Val Asp Arg Ala Lys Ile Glu Ala Ile Glu Asn
    210                 215                 220

Met Pro Cys Pro Arg Asp Ile Lys Gly Ile Arg Ser Ile Leu Gly His

```
                    225                 230                 235                 240
Ala Gly Phe Tyr Ser Arg Phe Ile Lys Asp Phe Thr Lys Val
                245                 250
```

<210> SEQ ID NO 70
<211> LENGTH: 756
<212> TYPE: DNA
<213> ORGANISM: Avena sativa

<400> SEQUENCE: 70

```
aaggaggttt ttaaactcct tgatgttggt attatttacc ctattgctga tagtgaatgg      60
gttagtcttg ttcattgtgt tcctaaaaag ggaggtatta ccgttgttcc taatgataat     120
gatgagctta ttcctcaaag aatagtggta ggctatagga tgtgcataga ttttaggaaa     180
gttaataaag ttactaagaa agatcactac ccgcttcctt ttattgatca aatgttggaa     240
aggttgtcta aaaagaccca tttttgtttt cttgatggtt actctagctt ctctcaaatt     300
gctgttaaac aacaagatca agaaaaaact acttttactt gcccttatgg aacttttgct     360
tatagacgta tgcctattgg tttatgtaat gctcctgcta cttttcaaag gtgtatgtct     420
gctatatttc atggttttg tgaggaaatt gtagaagtgt tcatggatga cttttctgtc      480
tatggaactt cttttgataa ttgcctgcac aaccttgata agttttgca gagatgtgaa      540
gaaactaata ttgttcttaa ttgggagaaa ttccacttca tggttaatga agggattgtc     600
cttgggcata agtttctaa agaggcata gaagttgata gagctaaggt tgaggcaatt      660
gagaagatgc catgcccaag agacatcaaa ggtatacgta gtatccttgg tcatgctggt     720
ttctatagaa ggtttatcaa agacttcaca aaggtt                              756
```

<210> SEQ ID NO 71
<211> LENGTH: 252
<212> TYPE: PRT
<213> ORGANISM: Avena sativa

<400> SEQUENCE: 71

```
Lys Glu Val Phe Lys Leu Leu Asp Val Gly Ile Ile Tyr Pro Ile Ala
  1               5                  10                  15

Asp Ser Glu Trp Val Ser Leu Val His Cys Val Pro Lys Lys Gly Gly
             20                  25                  30

Ile Thr Val Val Pro Asn Asp Asn Asp Glu Leu Ile Pro Gln Arg Ile
         35                  40                  45

Val Val Gly Tyr Arg Met Cys Ile Asp Phe Arg Lys Val Asn Lys Val
     50                  55                  60

Thr Lys Lys Asp His Tyr Pro Leu Pro Phe Ile Asp Gln Met Leu Glu
 65                  70                  75                  80

Arg Leu Ser Lys Lys Thr His Phe Cys Phe Leu Asp Gly Tyr Ser Ser
                 85                  90                  95

Phe Ser Gln Ile Ala Val Lys Gln Gln Asp Gln Glu Lys Thr Thr Phe
            100                 105                 110

Thr Cys Pro Tyr Gly Thr Phe Ala Tyr Arg Arg Met Pro Ile Gly Leu
        115                 120                 125

Cys Asn Ala Pro Ala Thr Phe Gln Arg Cys Met Ser Ala Ile Phe His
    130                 135                 140

Gly Phe Cys Glu Glu Ile Val Glu Val Phe Met Asp Asp Phe Ser Val
145                 150                 155                 160

Tyr Gly Thr Ser Phe Asp Asn Cys Leu His Asn Leu Asp Lys Val Leu
                165                 170                 175
```

-continued

```
Gln Arg Cys Glu Glu Thr Asn Ile Val Leu Asn Trp Glu Lys Phe His
            180                 185                 190

Phe Met Val Asn Glu Gly Ile Val Leu Gly His Lys Val Ser Lys Arg
        195                 200                 205

Gly Ile Glu Val Asp Arg Ala Lys Val Glu Ala Ile Glu Lys Met Pro
    210                 215                 220

Cys Pro Arg Asp Ile Lys Gly Ile Arg Ser Ile Leu Gly His Ala Gly
225                 230                 235                 240

Phe Tyr Arg Arg Phe Ile Lys Asp Phe Thr Lys Val
                245                 250
```

<210> SEQ ID NO 72
<211> LENGTH: 748
<212> TYPE: DNA
<213> ORGANISM: Secale cereale

<400> SEQUENCE: 72

```
gtgcggaaag aggtctttaa actcctagag gcaggtatta actatcccat tgctgatagc      60
cagcgggtaa gtcatgtcca ttgtgttcct aagaaaggag gtatgactgt cgtccctaag     120
gataaagatg aatttatccc gcaaagaata gttacaggtt ataggatggt aattgatttt     180
cgtaagttaa ataaagctac tatgaaagat cattacccct tgccatttat tgatcaaatg     240
ccagacaggt tatccaaaca tactcatttc tgctttctag atggttattc tggtttctct     300
caaatacctt tgtcaaaggg ggatcaagaa agaccaccct ttacttgtcc tttcggtacc     360
tttgcttata gaggtatgcc ttttggttta tgtaatgcac ctgctacctt tcaaagatgt     420
atgatcgtta tattctctgt cttttttgaa aagattgttg aggtattcat ggatgatttc     480
tccgtttatg gaacttcttt tgatgattgc ttaagcaacc ttgatcgagt tttgcagaga     540
tgtgaagata ctaaccttgt cttgaattgg gagaagtgcc actttatggt taatgaaggc     600
attttcttgg gacataaaat ttctgaaaga ggtactgaag ttgagaaagc taaagtggat     660
gctattgaaa agatgccatg ccctaaggat atgaaaggta tacgaagttt ccttggtcac     720
gctgggtttt ataggaggtt cataaaag                                        748
```

<210> SEQ ID NO 73
<211> LENGTH: 249
<212> TYPE: PRT
<213> ORGANISM: Secale cereale

<400> SEQUENCE: 73

```
Val Arg Lys Glu Val Phe Lys Leu Leu Glu Ala Gly Ile Asn Tyr Pro
  1               5                  10                  15

Ile Ala Asp Ser Gln Arg Val Ser His Val His Cys Val Pro Lys Lys
            20                  25                  30

Gly Gly Met Thr Val Val Pro Lys Asp Lys Asp Glu Phe Ile Pro Gln
        35                  40                  45

Arg Ile Val Thr Gly Tyr Arg Met Val Ile Asp Phe Arg Lys Leu Asn
    50                  55                  60

Lys Ala Thr Met Lys Asp His Tyr Pro Leu Pro Phe Ile Asp Gln Met
65                  70                  75                  80

Pro Asp Arg Leu Ser Lys His Thr His Phe Cys Phe Leu Asp Gly Tyr
                85                  90                  95

Ser Gly Phe Ser Gln Ile Pro Leu Ser Lys Gly Asp Gln Glu Lys Thr
            100                 105                 110
```

```
Thr Phe Thr Cys Pro Phe Gly Thr Phe Ala Tyr Arg Gly Met Pro Phe
            115                 120                 125

Gly Leu Cys Asn Ala Pro Ala Thr Phe Gln Arg Cys Met Ile Val Ile
        130                 135                 140

Phe Ser Val Phe Phe Glu Lys Ile Val Glu Val Phe Met Asp Asp Phe
145                 150                 155                 160

Ser Val Tyr Gly Thr Ser Phe Asp Asp Cys Leu Ser Asn Leu Asp Arg
                165                 170                 175

Val Leu Gln Arg Cys Glu Asp Thr Asn Leu Val Leu Asn Trp Glu Lys
            180                 185                 190

Cys His Phe Met Val Asn Glu Gly Ile Phe Leu Gly His Lys Ile Ser
            195                 200                 205

Glu Arg Gly Thr Glu Val Glu Lys Ala Lys Val Asp Ala Ile Glu Lys
        210                 215                 220

Met Pro Cys Pro Lys Asp Met Lys Gly Ile Arg Ser Phe Leu Gly His
225                 230                 235                 240

Ala Gly Phe Tyr Arg Arg Phe Ile Lys
                245
```

<210> SEQ ID NO 74
<211> LENGTH: 762
<212> TYPE: DNA
<213> ORGANISM: Secale cereale

<400> SEQUENCE: 74

```
gtgcggaagg aggtcgttaa gcttccagag gcaggtatta tctatcccgt tgctgatagc    60
cagtgggtaa gtcatgtcca ttgtgtccct aagaagggag gtatgactgt cgttcctaat   120
gacaaacatg aattgatccc gcaaagaata gttacaggtt ataggatggt aattgatttc   180
cgtaagttaa ataaagctac taagaaagat cattacccct tgccattat tgatcaaatg   240
ctagacaggt tatccaaaca tactcatttt tgctttctag atggttatta tggtttctct   300
caaatacctg tgtcaaaagg ggatcaagaa agaccactt tcacttgtcc tttcggtacc   360
tttgcttata gacgtatgcc ttttggttta tgtaatgcac ctgctacctt tcaaagatgt   420
atgatggcta tattatctga tttttgagaa aagattgttg aggttttcat ggatgatttc   480
tccgtttacg gaacttcttt tgatgactac ttaagcaaca atgatcgagt tttgcagaga   540
tgtgaagaca ctaatcttgt tttgaattgg gagaagtgcc actttatggt taatgaaggc   600
attgtcttgg gacaaaaaat ttctgaaaga ggtattgaag ttgacaaagc taaagtcgat   660
gctgttgaaa agatgccatg ccccaaggac atcaaggta tacgaagttt ccttggtcat   720
gttgggtttt ataggaggtt catcaaagac ttcacgaaag tt                       762
```

<210> SEQ ID NO 75
<211> LENGTH: 254
<212> TYPE: PRT
<213> ORGANISM: Secale cereale

<400> SEQUENCE: 75

```
Val Arg Lys Glu Val Val Lys Leu Pro Glu Ala Gly Ile Ile Tyr Pro
1               5                   10                  15

Val Ala Asp Ser Gln Trp Val Ser His Val His Cys Val Pro Lys Lys
                20                  25                  30

Gly Gly Met Thr Val Val Pro Asn Asp Lys His Glu Leu Ile Pro Gln
            35                  40                  45

Arg Ile Val Thr Gly Tyr Arg Met Val Ile Asp Phe Arg Lys Leu Asn
```

```
                50                   55                   60
Lys Ala Thr Lys Lys Asp His Tyr Pro Leu Pro Phe Ile Asp Gln Met
 65                  70                   75                  80

Leu Asp Arg Leu Ser Lys His Thr His Phe Cys Phe Leu Asp Gly Tyr
                 85                   90                   95

Tyr Gly Phe Ser Gln Ile Pro Val Ser Lys Gly Asp Gln Glu Lys Thr
                100                  105                  110

Thr Phe Thr Cys Pro Phe Gly Thr Phe Ala Tyr Arg Arg Met Pro Phe
            115                  120                  125

Gly Leu Cys Asn Ala Pro Ala Thr Phe Gln Arg Cys Met Met Ala Ile
            130                  135                  140

Leu Ser Asp Phe Glx Glu Lys Ile Val Glu Val Phe Met Asp Asp Phe
145                 150                  155                 160

Ser Val Tyr Gly Thr Ser Phe Asp Asp Tyr Leu Ser Asn Asn Asp Arg
                165                  170                  175

Val Leu Gln Arg Cys Glu Asp Thr Asn Leu Val Leu Asn Trp Glu Lys
            180                  185                  190

Cys His Phe Met Val Asn Glu Gly Ile Val Leu Gly Gln Lys Ile Ser
            195                  200                  205

Glu Arg Gly Ile Glu Val Asp Lys Ala Lys Val Asp Ala Val Glu Lys
            210                  215                  220

Met Pro Cys Pro Lys Asp Ile Lys Gly Ile Arg Ser Phe Leu Gly His
225                 230                  235                 240

Val Gly Phe Tyr Arg Arg Phe Ile Lys Asp Phe Thr Lys Val
                245                  250
```

<210> SEQ ID NO 76
<211> LENGTH: 762
<212> TYPE: DNA
<213> ORGANISM: Secale cereale

<400> SEQUENCE: 76

```
gtgcgtaagg aggtggttaa gctcctagaa gcaggtatta tctatccagt tgctgatagt      60
cagtgggtaa gtcatgtcca ttatgttcct aagaaggag gtatgactgt tgtccctaat      120
gataaagatg aattgatccc gcaaagaata gttacaggtt ataggatggt aagtgatttc     180
cgtaagttga ataaagccac taagaaagat cattacccct gccatttat tgatcaaatg      240
ctagaaaggt tatccaaaca tactcatttc ttctttctag atggttattc tggtttctct     300
caaatacctg tgtcaaaagg ggatcaagaa aagaccacct ttacttgtac tttcggtacc     360
tttgcttata gacgtatgcc ttttggttta tgtaatgcac ctgctacctt tcaaagatgc     420
atgatggcta tattctctga cttttgtgaa agattgttg aggtattcat ggatgatttc      480
tccgtttacg gaacttcttt tgatgattgc ttaagcaacc ttgatcgagt tttgcagaga     540
tgtgaagaca ctaaccttgt cttgaattgc gagaagtgcc actttatggt taatgaaggc    600
attgtcttgg gacataaaat ttctgaaata ggtattgaag ttgacaaagc taaagttgat    660
gctattgaaa agatgccatg cgcaaaggac atcaaggta tacggagttt ccttggtcat     720
gccgggtttt ataggaggtt catcaaagat ttctcaaagg tt                        762
```

<210> SEQ ID NO 77
<211> LENGTH: 254
<212> TYPE: PRT
<213> ORGANISM: Secale cereale

<400> SEQUENCE: 77

-continued

```
Val Arg Lys Glu Val Val Lys Leu Leu Glu Ala Gly Ile Ile Tyr Pro
  1               5                  10                  15
Val Ala Asp Ser Gln Trp Val Ser His Val His Tyr Val Pro Lys Lys
             20                  25                  30
Gly Gly Met Thr Val Val Pro Asn Asp Lys Asp Glu Leu Ile Pro Gln
             35                  40                  45
Arg Ile Val Thr Gly Tyr Arg Met Val Ser Asp Phe Arg Lys Leu Asn
         50                  55                  60
Lys Ala Thr Lys Lys Asp His Tyr Pro Leu Pro Phe Ile Asp Gln Met
 65                  70                  75                  80
Leu Glu Arg Leu Ser Lys His Thr His Phe Phe Leu Asp Gly Tyr
                 85                  90                  95
Ser Gly Phe Ser Gln Ile Pro Val Ser Lys Gly Asp Gln Glu Lys Thr
                100                 105                 110
Thr Phe Thr Cys Thr Phe Gly Thr Phe Ala Tyr Arg Arg Met Pro Phe
                115                 120                 125
Gly Leu Cys Asn Ala Pro Ala Thr Phe Gln Arg Cys Met Met Ala Ile
            130                 135                 140
Phe Ser Asp Phe Cys Glu Lys Ile Val Glu Val Phe Met Asp Phe
145                 150                 155                 160
Ser Val Tyr Gly Thr Ser Phe Asp Asp Cys Leu Ser Asn Leu Asp Arg
                165                 170                 175
Val Leu Gln Arg Cys Glu Asp Thr Asn Leu Val Leu Asn Cys Glu Lys
            180                 185                 190
Cys His Phe Met Val Asn Glu Gly Ile Val Leu Gly His Lys Ile Ser
            195                 200                 205
Glu Ile Gly Ile Glu Val Asp Lys Ala Lys Val Asp Ala Ile Glu Lys
        210                 215                 220
Met Pro Cys Ala Lys Asp Ile Lys Gly Ile Arg Ser Phe Leu Gly His
225                 230                 235                 240
Ala Gly Phe Tyr Arg Arg Phe Ile Lys Asp Phe Ser Lys Val
                245                 250
```

<210> SEQ ID NO 78
<211> LENGTH: 759
<212> TYPE: DNA
<213> ORGANISM: Secale cereale

<400> SEQUENCE: 78

```
gtgcgcaagg aagttttaa gtttctagag gcaggtataa tctatccagt tgctgatagc    60
cagtgggtaa gtcctgtcca ttgtgtccct aagaagggag gtatgactgt agttcctaat   120
gataaagatg aattgatctc gcaaagaatt gttacaggtt ataggatggt aattgatttt   180
cgcaaattaa ataagccac taagaaagat caatacccctt tgcctttat tgatcaaatg    240
ctagaaaggt tatccaaaca cacccatttt tgctttctag atggttattc tagtttctct   300
caaatacct  tgtcaaaagg ggataaagaa agaccactt ttacttgtcc ctttggtact    360
ttgcttatag acgtatgcct tttggtttat gtaatgcatc tgctaccttt caaacatgca   420
tgatggctat actctatgat ttttgtgaaa gaatgttgat gttttcatgg atgattttg    480
tatttacgaa acttctttg atgattgctt gagcaacctt gatcgagttt tgcagagatg    540
tgaagaaact aatcttgtct tgaactggga aaagtcccac tttatggtta atgaaggcat   600
tgcttgggac ataaaatttc tgaaagaggt accgaagttg acaaagctaa agttgatgct   660
```

```
gttgaaaaga tgccatgtcc caaggacatc aaaggtataa gaagtttcct tggtcatgcc    720
gggttttata ggaggtttat caaggacttc accaaggtt                            759
```

<210> SEQ ID NO 79
<211> LENGTH: 254
<212> TYPE: PRT
<213> ORGANISM: Secale cereale

<400> SEQUENCE: 79

```
Val Arg Lys Glu Val Phe Lys Phe Leu Glu Ala Gly Ile Ile Tyr Pro
  1               5                  10                  15

Val Ala Asp Ser Gln Trp Val Ser Pro Val His Cys Val Pro Lys Lys
                 20                  25                  30

Gly Gly Met Thr Val Val Pro Asn Asp Lys Asp Glu Leu Ile Ser Gln
             35                  40                  45

Arg Ile Val Thr Gly Tyr Arg Met Val Ile Asp Phe Arg Lys Leu Asn
         50                  55                  60

Lys Ala Thr Lys Lys Asp Gln Tyr Pro Leu Pro Phe Ile Asp Gln Met
 65                  70                  75                  80

Leu Glu Arg Leu Ser Lys His Thr His Phe Cys Phe Leu Asp Gly Tyr
                 85                  90                  95

Ser Ser Phe Ser Gln Ile Pro Met Ser Lys Gly Asp Lys Glu Lys Thr
            100                 105                 110

Thr Phe Thr Cys Pro Phe Gly Thr Phe Ala Tyr Arg Arg Met Pro Phe
        115                 120                 125

Gly Leu Cys Asn Ala Ser Ala Thr Phe Gln Thr Cys Met Met Ala Ile
    130                 135                 140

Leu Tyr Asp Phe Cys Glu Arg Ile Val Asp Val Phe Met Asp Asp Phe
145                 150                 155                 160

Cys Ile Tyr Glu Thr Ser Phe Asp Asp Cys Leu Ser Asn Leu Asp Arg
                165                 170                 175

Val Leu Gln Arg Cys Glu Glu Thr Asn Leu Val Leu Asn Trp Glu Lys
            180                 185                 190

Ser His Phe Met Val Asn Glu Gly Ile Val Leu Gly His Lys Ile Ser
        195                 200                 205

Glu Arg Gly Thr Glu Val Asp Lys Ala Lys Val Asp Ala Val Glu Lys
    210                 215                 220

Met Pro Cys Pro Lys Asp Ile Lys Gly Ile Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 80
<211> LENGTH: 761
<212> TYPE: DNA
<213> ORGANISM: Triticum aestivum

<400> SEQUENCE: 80

```
gtgcgtaagg aggttctcaa gtttctggag gtaggtataa tttatcccgt tgctgatagt     60
cagtgggtaa gtcctgtcca ttgtgtccct aagaagggag gtattactgt tgtccctaat    120
gataaagatg aattgattcc tcaaagaatt attacggtta taggatggta attgatttcc    180
gcaaattaaa taaagccact aagagagatc attacccctt acctttatt gatcaaattc     240 tagaaagatt atgcaaacat acacattatt gcttccaaga tggttatcct ggttttctc     300 aaatacctgt gtcggctaaa gatcaatcaa agactacttt tacatgccct tttggtactt    360
```

```
ttgcttatag atgtatgcct tttggttat gtaatgcacc tgctacctt  caaagatgca    420 tgatggctat attctctgat ttttgtgaaa agatttgtga ggttttcatg gatgactttt    480
ccgtctatgg ttcctctttt gatgattgct tgagcaatct tgatcgagtt ttgcagagat    540
gtgaagaaac taatcttgtc ttgaattggg aaaagtgtca ctttatggtt aatgaaggta    600
ttgtcttggg gcacaaagtt tctgaaagag gtattgaagt tgataaagcc aaggttgaca    660
ctattgaaaa gataccatgt cccaaggaca tcaaaggtac aagaagtttc cttggtcacg    720
ccggatttta taggaggttc ataaaagatt tcacaaaggt t                        761
```

<210> SEQ ID NO 81
<211> LENGTH: 254
<212> TYPE: PRT
<213> ORGANISM: Triticum aestivum

<400> SEQUENCE: 81

```
Val Arg Lys Glu Val Leu Lys Phe Leu Glu Val Gly Ile Ile Tyr Pro
  1               5                  10                  15
Val Ala Asp Ser Gln Trp Val Ser Pro Val His Cys Val Pro Lys Lys
                 20                  25                  30
Gly Gly Ile Thr Val Val Pro Asn Asp Lys Asp Glu Leu Ile Pro Gln
             35                  40                  45
Arg Ile Ile Thr Gly Tyr Arg Met Val Ile Asp Phe Arg Lys Leu Asn
         50                  55                  60
Lys Ala Thr Lys Arg Asp His Tyr Pro Leu Pro Phe Ile Asp Gln Ile
 65                  70                  75                  80
Leu Glu Arg Leu Cys Lys His Thr His Tyr Cys Phe Gln Asp Gly Tyr
                 85                  90                  95
Pro Gly Phe Ser Gln Ile Pro Val Ser Ala Lys Asp Gln Ser Lys Thr
            100                 105                 110
Thr Phe Thr Cys Pro Phe Gly Thr Phe Ala Tyr Arg Cys Met Pro Phe
        115                 120                 125
Gly Leu Cys Asn Ala Pro Ala Thr Phe Gln Arg Cys Met Met Ala Ile
    130                 135                 140
Phe Ser Asp Phe Cys Glu Lys Ile Cys Glu Val Phe Met Asp Asp Phe
145                 150                 155                 160
Ser Val Tyr Gly Ser Ser Phe Asp Asp Cys Leu Ser Asn Leu Asp Arg
                165                 170                 175
Val Leu Gln Arg Cys Glu Glu Thr Asn Leu Val Leu Asn Trp Glu Lys
            180                 185                 190
Cys His Phe Met Val Asn Glu Gly Ile Val Leu Gly His Lys Val Ser
        195                 200                 205
Glu Arg Gly Ile Glu Val Asp Lys Ala Lys Val Asp Thr Ile Glu Lys
    210                 215                 220
Ile Pro Cys Pro Lys Asp Ile Lys Gly Thr Arg Ser Phe Leu Gly His
225                 230                 235                 240
Ala Gly Phe Tyr Arg Arg Phe Ile Lys Asp Phe Thr Lys Val
                245                 250
```

<210> SEQ ID NO 82
<211> LENGTH: 780
<212> TYPE: DNA
<213> ORGANISM: Triticum aestivum

<400> SEQUENCE: 82

-continued

```
gtgcggaagg aggtgtttaa gctccttgag gcaggtataa tttatcccgt tgctgatagt      60
aagtgggtaa ttcctgtcca ttaagtgatc gtgattactg ttgttcctaa gaagggaggt     120
attaccgttg ttcctaatga taaagatgaa ttgattcctc aaagaaccat tactggttat     180
aggatggtaa ttgatttccg caaattaaat aaggctacta aaaatatca ttacccctta     240
cctttatcg atcaaatgct agaaagatta tccaaacata cacattttg ctttctagat      300
ggttactctg gtttctctca aatacctgtg tcagccaaag atcaatcaaa gactactttt     360
acatgccctt ttggtacttt tgcttataga cgtatgcctt ttggtttatg taatgcacct     420
gctacctttc aaagatacat gatggctata ttatctgact tttgtgaaaa gatttgtgag     480
gttttcatgg acgactcttc catctatgga tcttcttttg atgattgctt gagcaacctt     540
gatcgagttt tgcagagatg tgaagaaact tatcttgtct tgaattggga aaagtgccaa     600
tttatggtta atgaaggtat tgtcctgggg cataaagttt ctgaaagagg tattcgagtt     660
gataaagcca aggttgatgc tattgaaaag atgccatgtc ccatggacat caaaggtata     720
agaagtttcc ttggtcatgc cggttttat aggaggttca taaaagactt cacgaaggtt     780
```

<210> SEQ ID NO 83
<211> LENGTH: 260
<212> TYPE: PRT
<213> ORGANISM: Triticum aestivum

<400> SEQUENCE: 83

```
Val Arg Lys Glu Val Phe Lys Leu Leu Glu Ala Gly Ile Ile Tyr Pro
  1               5                  10                  15

Val Ala Asp Ser Lys Trp Val Ile Pro Val His Glx Val Ile Val
                 20                  25                  30

Thr Val Pro Lys Lys Gly Gly Ile Thr Val Val Pro Asn Asp Lys
             35                  40                  45

Asp Glu Leu Ile Pro Gln Arg Thr Ile Thr Gly Tyr Arg Met Val Ile
 50                  55                  60

Asp Phe Arg Lys Leu Asn Lys Ala Thr Lys Lys Tyr His Tyr Pro Leu
 65                  70                  75                  80

Pro Phe Ile Asp Gln Met Leu Glu Arg Leu Ser Lys His Thr His Phe
                 85                  90                  95

Cys Phe Leu Asp Gly Tyr Ser Gly Phe Ser Gln Ile Pro Val Ser Ala
                100                 105                 110

Lys Asp Gln Ser Lys Thr Thr Phe Thr Cys Pro Phe Gly Thr Phe Ala
            115                 120                 125

Tyr Arg Arg Met Pro Phe Gly Leu Cys Asn Ala Pro Ala Thr Phe Gln
130                 135                 140

Arg Tyr Met Met Ala Ile Leu Ser Asp Phe Cys Glu Lys Ile Cys Glu
145                 150                 155                 160

Val Phe Met Asp Asp Ser Ser Ile Tyr Gly Ser Ser Phe Asp Asp Cys
                165                 170                 175

Leu Ser Asn Leu Asp Arg Val Leu Gln Arg Cys Glu Glu Thr Tyr Leu
            180                 185                 190

Val Leu Asn Trp Glu Lys Cys Gln Phe Met Val Asn Glu Gly Ile Val
        195                 200                 205

Leu Gly His Lys Val Ser Glu Arg Gly Ile Arg Val Asp Lys Ala Lys
    210                 215                 220

Val Asp Ala Ile Glu Lys Met Pro Cys Pro Met Asp Ile Lys Gly Ile
225                 230                 235                 240
```

-continued

Arg Ser Phe Leu Gly His Ala Gly Phe Tyr Arg Arg Phe Ile Lys Asp
                245                 250                 255
Phe Thr Lys Val
            260

<210> SEQ ID NO 84
<211> LENGTH: 762
<212> TYPE: DNA
<213> ORGANISM: Triticum aestivum

<400> SEQUENCE: 84

```
gtgcgtaagg aggtattcaa gcttctggag gcaggtataa tttatcccgt tgttgatagt      60
caatgggtaa gtcctgtcca ttgtgtcctt aagaagggag gtattactgt tgtccctaat     120
gataaagatg aattgattcc gcaaagaatt atcacaggtt ataggatggt aattgatttc     180
cgtaagttaa ataaagctac taagaaagat cattacccct tacctttat tgatcaaatg      240
ttagaaagat tatgcaaaca tacacattat tgctttctag atggttattc tggtttctct     300
caaatacctg tgtcagctaa ggatcaatca aagactactt ttacatgccc ttttggtact     360
tttggttata gacgtatgcc tttcgattta tgtaatgcac ctgctacctt tcaaatatgc     420
atgatggcta tattctctga cttttgcgaa aagatttgtg aggttttcat ggacgacttt     480
tccgtctatg gttcctctta tgatgattgc ttgagcaatc ttaatcgagt tttgcagaga     540
tgtgaagaaa ctaatcttgt cttgaattgg gaaaagtgcc actttatggt taatgaaggt     600
attgtcttgg ggcacaaagt ttctgaacga ggtattgaag ttgataaggc caaggttgat     660
gctattgaaa agatgacatg tcccaaggac atcaaggta taagaagttt ccttggtcac      720
gccagatttt ataggaggtt cataaaagac ttcacaaagg tt                        762
```

<210> SEQ ID NO 85
<211> LENGTH: 254
<212> TYPE: PRT
<213> ORGANISM: Triticum aestivum

<400> SEQUENCE: 85

Val Arg Lys Glu Val Phe Lys Leu Leu Glu Ala Gly Ile Ile Tyr Pro
 1               5                  10                  15
Val Val Asp Ser Gln Trp Val Ser Pro Val His Cys Val Leu Lys Lys
                20                  25                  30
Gly Gly Ile Thr Val Val Pro Asn Asp Lys Asp Glu Leu Ile Pro Gln
            35                  40                  45
Arg Ile Ile Thr Gly Tyr Arg Met Val Ile Asp Phe Arg Lys Leu Asn
        50                  55                  60
Lys Ala Thr Lys Lys Asp His Tyr Pro Leu Pro Phe Ile Asp Gln Met
65                  70                  75                  80
Leu Glu Arg Leu Cys Lys His Thr His Tyr Cys Phe Leu Asp Gly Tyr
                85                  90                  95
Ser Gly Phe Ser Gln Ile Pro Val Ser Ala Lys Asp Gln Ser Lys Thr
            100                 105                 110
Thr Phe Thr Cys Pro Phe Gly Thr Phe Gly Tyr Arg Arg Met Pro Phe
        115                 120                 125
Asp Leu Cys Asn Ala Pro Ala Thr Phe Gln Ile Cys Met Met Ala Ile
    130                 135                 140
Phe Ser Asp Phe Cys Glu Lys Ile Cys Glu Val Phe Met Asp Asp Phe
145                 150                 155                 160
Ser Val Tyr Gly Ser Ser Tyr Asp Asp Cys Leu Ser Asn Leu Asn Arg

```
                165                 170                 175
Val Leu Gln Arg Cys Glu Glu Thr Asn Leu Val Leu Asn Trp Glu Lys
                180                 185                 190

Cys His Phe Met Val Asn Glu Gly Ile Val Leu Gly His Lys Val Ser
            195                 200                 205

Glu Arg Gly Ile Glu Val Asp Lys Ala Lys Val Asp Ala Ile Glu Lys
        210                 215                 220

Met Thr Cys Pro Lys Asp Ile Lys Gly Ile Arg Ser Phe Leu Gly His
225                 230                 235                 240

Ala Arg Phe Tyr Arg Arg Phe Ile Lys Asp Phe Thr Lys Val
                245                 250

<210> SEQ ID NO 86
<211> LENGTH: 762
<212> TYPE: DNA
<213> ORGANISM: Triticum aestivum

<400> SEQUENCE: 86
gtgcggaaag aggtgctcaa gcttctggag gcaggtataa tttatcccgt tgctgagagt    60
cagtgggtaa gtcctgtcca ttgtgtccct aagaagggag gtattactgt tgtccctaat   120
gataaagatg aattgattcc tcaaagaatt attacaggtt ataggatggt aattgatttc   180
cgcaaattaa ataaagccac caagaaagat cattacccct taccttttat tgatcaaatg   240
ctagaaagat tatgcaaaca tacacattat tgcttcctag atggttattc tggtttctct   300
caaatacctg tgtcggctaa agatcaatca aagactactt ttacatgccc ttttggtact   360
tttgcttata gacgtatgcc ttttggttta tgtaatgcac cttctacctt tcaaagatgc   420
atgatggcta tattctctga tttttgtgaa aagatttgtg aggttttcat ggacgaattt   480
tccgtctatg gttcctcttt tgatgattgc ttgagcaatc ctgatcgagt tttgcagaga   540
tgtgaagaaa ctaatcttgt cttgaattgg gaaaagtgcc actttatggt taatgaaggt   600
attgtcttgg ggcacaaagt ttctgaaaga ggtattgaag ttgataaagc caaggttgac   660
gctattgaaa agatgccatg tcccaaggac atcaaaggta taagaagttt ccttggtcac   720
gccggatttt ataggaggtt cataaaagac ttcacaaagg tt                      762

<210> SEQ ID NO 87
<211> LENGTH: 254
<212> TYPE: PRT
<213> ORGANISM: Triticum aestivum

<400> SEQUENCE: 87

Val Arg Lys Glu Val Leu Lys Leu Leu Glu Ala Gly Ile Ile Tyr Pro
1               5                   10                  15

Val Ala Glu Ser Gln Trp Val Ser Pro Val His Cys Val Pro Lys Lys
            20                  25                  30

Gly Gly Ile Thr Val Val Pro Asn Asp Lys Asp Glu Leu Ile Pro Gln
        35                  40                  45

Arg Ile Ile Thr Gly Tyr Arg Met Val Ile Asp Phe Arg Lys Leu Asn
    50                  55                  60

Lys Ala Thr Lys Lys Asp His Tyr Pro Leu Pro Phe Ile Asp Gln Met
65                  70                  75                  80

Leu Glu Arg Leu Cys Lys His Thr His Tyr Cys Phe Leu Asp Gly Tyr
                85                  90                  95

Ser Gly Phe Ser Gln Ile Pro Val Ser Ala Lys Asp Gln Ser Lys Thr
            100                 105                 110
```

```
Thr Phe Thr Cys Pro Phe Gly Thr Phe Ala Tyr Arg Arg Met Pro Phe
            115                 120                 125

Gly Leu Cys Asn Ala Pro Ser Thr Phe Gln Arg Cys Met Met Ala Ile
    130                 135                 140

Phe Ser Asp Phe Cys Glu Lys Ile Cys Glu Val Phe Met Asp Glu Phe
145                 150                 155                 160

Ser Val Tyr Gly Ser Ser Phe Asp Asp Cys Leu Ser Asn Pro Asp Arg
                165                 170                 175

Val Leu Gln Arg Cys Glu Glu Thr Asn Leu Val Leu Asn Trp Glu Lys
                180                 185                 190

Cys His Phe Met Val Asn Glu Gly Ile Val Leu Gly His Lys Val Ser
            195                 200                 205

Glu Arg Gly Ile Glu Val Asp Lys Ala Lys Val Asp Ala Ile Glu Lys
    210                 215                 220

Met Pro Cys Pro Lys Asp Ile Lys Gly Ile Arg Ser Phe Leu Gly His
225                 230                 235                 240

Ala Gly Phe Tyr Arg Arg Phe Ile Lys Asp Phe Thr Lys Val
                245                 250

<210> SEQ ID NO 88
<211> LENGTH: 762
<212> TYPE: DNA
<213> ORGANISM: Triticum aestivum

<400> SEQUENCE: 88
gtgcgtaagg aggttttcaa gttccttgag gcaggtatta cttatcccgt tgctgatagt    60
gaatgggtaa gccctctcca ttgtgttcct aaaaagggag gtattaccgt tgttcttaat   120
gataaagatg aattgatccc gcaaataatt attacaggtt ataggatggt aattgatttc   180
cataagttaa ataaagctac taagaaagat cattacccctt tacctcttat tgatcaaatt   240
ctagaaagac tatccaaaca cacacatttc tgctttctag atggttatac tggtttctct   300
caaatacctg tgtcagtgaa ggatcaatct aaaactactt ttacttgccc ttttggtact   360
tttgcttata gacttatgcc ttttggttta tgtaatgcac ctacttcctt tcaaagatgc   420
atgatggcta tattctctgt tttttgtgaa aatatttgtg aggtattcat ggatgatttc   480
tccgtttatg gatcctcttt tgatgattgt ttgagcaacc ttgatcgagt tttgcagaga   540
tgcgaagaca ctagtctcat cctgaattgg gaaaagtgtc actttatggt taatgaaggc   600
attgtcttgg ggcataagat ttccgagaga ggtattgaag ttgacaaagc caaagttgat   660
gctattgaaa agattccatg tcccaaggac ataaaaggta taagaagttt ccttggtcat   720
gctggttttt ataggaggtt catcaaagac ttctcaaagg tt                     762

<210> SEQ ID NO 89
<211> LENGTH: 254
<212> TYPE: PRT
<213> ORGANISM: Triticum aestivum

<400> SEQUENCE: 89

Val Arg Lys Glu Val Phe Lys Phe Leu Glu Ala Gly Ile Thr Tyr Pro
  1                 5                  10                  15

Val Ala Asp Ser Glu Trp Val Ser Pro Leu His Cys Val Pro Lys Lys
                 20                  25                  30

Gly Gly Ile Thr Val Val Leu Asn Asp Lys Asp Glu Leu Ile Pro Gln
             35                  40                  45
```

```
Ile Ile Ile Thr Gly Tyr Arg Met Val Ile Asp Phe His Lys Leu Asn
 50                  55                  60
Lys Ala Thr Lys Asp His Tyr Pro Leu Pro Leu Ile Asp Gln Ile
 65                  70                  75                  80
Leu Glu Arg Leu Ser Lys His Thr His Phe Cys Phe Leu Asp Gly Tyr
                 85                  90                  95
Thr Gly Phe Ser Gln Ile Pro Val Ser Val Lys Asp Gln Ser Lys Thr
                100                 105                 110
Thr Phe Thr Cys Pro Phe Gly Thr Phe Ala Tyr Arg Leu Met Pro Phe
            115                 120                 125
Gly Leu Cys Asn Ala Pro Thr Ser Phe Gln Arg Cys Met Met Ala Ile
130                 135                 140
Phe Ser Val Phe Cys Glu Asn Ile Cys Glu Val Phe Met Asp Asp Phe
145                 150                 155                 160
Ser Val Tyr Gly Ser Ser Phe Asp Asp Cys Leu Ser Asn Leu Asp Arg
                165                 170                 175
Val Leu Gln Arg Cys Glu Asp Thr Ser Leu Ile Leu Asn Trp Glu Lys
            180                 185                 190
Cys His Phe Met Val Asn Glu Gly Ile Val Leu Gly His Lys Ile Ser
        195                 200                 205
Glu Arg Gly Ile Glu Val Asp Lys Ala Val Asp Ala Ile Glu Lys
    210                 215                 220
Ile Pro Cys Pro Lys Asp Ile Lys Gly Ile Arg Ser Phe Leu Gly His
225                 230                 235                 240
Ala Gly Phe Tyr Arg Arg Phe Ile Lys Asp Phe Ser Lys Val
                245                 250

<210> SEQ ID NO 90
<211> LENGTH: 791
<212> TYPE: DNA
<213> ORGANISM: Gossypium hirsutum

<400> SEQUENCE: 90
gtgcgcaagg aggttttaaa gctacttgat gacgggatga tctatcccat atctaacagt      60
aattgggtta gcccagtaca catagtacca aaaaagacca gtgcaaccgt aatcgagaat     120
tcggcaggtg agatagttcc cactcgggtc caaaacgggt ggagagtatg catcgattac     180
aggaagttga attccttaac tcggaaggat cactttccac ttccttttat tgaccagatg     240
ttagaacgtt tagctggaaa gtctcattat ttagaacgtt tagctggaaa gtctcattat     300
tgttgtttgg atggttacta aggttttttc cagatcccag tggcaccgga ggatcaagaa     360
agacaatgtt tacgtgccca tttggcacgt tttcttacag acggatgccg ttcggactct     420
gtaatgcacc agccagtttt cataggtgca tggtaagtat attttcagac tacgtcgata     480
aaattatcga ggtgttcatg gacgacttta ctgtatatgt gagtccttc gaggtaagtc      540
tgacgaacct tgcaaaaatt ttggaaagat gcttagaatt taatcttgtt ctaaattatg     600
agaaatgcca tttatggta gacaagggat tagttctagg tcatattatt tctgctgatg     660
gaatttctgt tgataaagca aaaatcaaca tcattaactc actaccatac cccacaactg     720
tgagggagat ttggtctttc cttggtcatg caggtttcta caagtggttc atcaaagact     780
tttcaaaagt t                                                          791

<210> SEQ ID NO 91
<211> LENGTH: 264
<212> TYPE: PRT
```

```
<213> ORGANISM: Gossypium hirsutum

<400> SEQUENCE: 91

Val Arg Lys Glu Val Leu Lys Leu Leu Asp Asp Gly Met Ile Tyr Pro
 1               5                  10                  15

Ile Ser Asn Ser Asn Trp Val Ser Pro Val His Ile Val Pro Lys Lys
                20                  25                  30

Thr Ser Ala Thr Val Ile Glu Asn Ser Ala Gly Glu Ile Val Pro Thr
            35                  40                  45

Arg Val Gln Asn Gly Trp Arg Val Cys Ile Asp Tyr Arg Lys Leu Asn
        50                  55                  60

Ser Leu Thr Arg Lys Asp His Phe Pro Leu Pro Phe Ile Asp Gln Met
65                  70                  75                  80

Leu Glu Arg Leu Ala Gly Lys Ser His Tyr Leu Glu Arg Leu Ala Gly
                85                  90                  95

Lys Ser His Tyr Cys Cys Leu Asp Gly Tyr Glx Gly Phe Phe Gln Ile
                100                 105                 110

Pro Val Ala Pro Glu Asp Gln Glu Lys Thr Met Phe Thr Cys Pro Phe
            115                 120                 125

Gly Thr Phe Ser Tyr Arg Arg Met Pro Phe Gly Leu Cys Asn Ala Pro
    130                 135                 140

Ala Ser Phe His Arg Cys Met Val Ser Ile Phe Ser Asp Tyr Val Asp
145                 150                 155                 160

Lys Ile Ile Glu Val Phe Met Asp Asp Phe Thr Val Tyr Gly Glu Ser
                165                 170                 175

Phe Glu Val Ser Leu Thr Asn Leu Ala Lys Ile Leu Glu Arg Cys Leu
                180                 185                 190

Glu Phe Asn Leu Val Leu Asn Tyr Glu Lys Cys His Phe Met Val Asp
                195                 200                 205

Lys Gly Leu Val Leu Gly His Ile Ile Ser Ala Asp Gly Ile Ser Val
                210                 215                 220

Asp Lys Ala Lys Ile Asn Ile Ile Asn Ser Leu Pro Tyr Pro Thr Thr
225                 230                 235                 240

Val Arg Glu Ile Trp Ser Phe Leu Gly His Ala Gly Phe Tyr Lys Trp
                245                 250                 255

Phe Ile Lys Asp Phe Ser Lys Val
                260

<210> SEQ ID NO 92
<211> LENGTH: 763
<212> TYPE: DNA
<213> ORGANISM: Gossypium hirsutum

<400> SEQUENCE: 92
gtgcgtaaag aggtcgtaaa gctacttgat tccgggatga tctatcccat atctgacaat    60
aattgggtta gtccagtcca catagtaccc aaaaagaccg gtgtaaccgt aattgagaat   120
tcagcaggtg agatggttcc cacttaagtc cgaaacggtc ggagagtatg catcgattac   180
aggaagttga attccttaac tcggaaagat cactttccac ttctttttat tgatcagatg   240
ttagaacatt tagccagaaa gtctcattat tgttgtctgg atggttactc aggttttttc   300
cagatcccaa tggcactaaa ggatcaagaa aagatgacat ttacgtgccc atttggcatg   360
ttcgcttata gaaggatgtc gtttcagact ttgcaatgca ccaaccatgt ttcagaggtg   420
catgataagt atatttttg actatgttaa gaaataatt gaggtgttca tggacgaatt    480
```

```
tactgtatat agtgagtcct tcgaggtata tttgtcaaat ctagaaaaat ttttggaaag    540
atgcttagaa tttaatcttg ttctaaatta tgagaattgc tatttaatgg tagacaaggg    600
attagttcta ggtcatatca tttctgctaa gggaatttct gtcgataaag taaaaattaa    660
catcataagc tcaataccat accccacaac tgtgagggag attcgttctt tccttagtca    720
tataggtttc tataggcgat tcatcaagga cttttcaaaa gtt                      763
```

```
<210> SEQ ID NO 93
<211> LENGTH: 254
<212> TYPE: PRT
<213> ORGANISM: Gossypium hirsutum

<400> SEQUENCE: 93

Val Arg Lys Glu Val Val Lys Leu Leu Asp Ser Gly Met Ile Tyr Pro
  1               5                  10                  15

Ile Ser Asp Asn Asn Trp Val Ser Pro Val His Ile Val Pro Lys Lys
             20                  25                  30

Thr Gly Val Thr Val Ile Glu Asn Ser Ala Gly Glu Met Val Pro Thr
         35                  40                  45

Glx Val Arg Asn Gly Arg Arg Val Cys Ile Asp Tyr Arg Lys Leu Asn
     50                  55                  60

Ser Leu Thr Arg Lys Asp His Phe Pro Leu Leu Phe Ile Asp Gln Met
 65                  70                  75                  80

Leu Glu His Leu Ala Arg Lys Ser His Tyr Cys Cys Leu Asp Gly Tyr
                 85                  90                  95

Ser Gly Phe Phe Gln Ile Pro Met Ala Leu Lys Asp Gln Glu Lys Met
            100                 105                 110

Thr Phe Thr Cys Pro Phe Gly Met Phe Ala Tyr Arg Arg Met Ser Phe
        115                 120                 125

Arg Leu Cys Asn Ala Pro Thr Met Phe Gln Arg Cys Met Ile Ser Ile
    130                 135                 140

Phe Phe Asp Tyr Val Lys Lys Ile Ile Glu Val Phe Met Asp Glu Phe
145                 150                 155                 160

Thr Val Tyr Ser Glu Ser Phe Glu Val Tyr Leu Ser Asn Leu Glu Lys
                165                 170                 175

Phe Leu Glu Arg Cys Leu Glu Phe Asn Leu Val Leu Asn Tyr Glu Asn
            180                 185                 190

Cys Tyr Leu Met Val Asp Lys Gly Leu Val Leu Gly His Ile Ile Ser
        195                 200                 205

Ala Lys Gly Ile Ser Val Asp Lys Val Lys Ile Asn Ile Ile Ser Ser
    210                 215                 220

Ile Pro Tyr Pro Thr Thr Val Arg Glu Ile Arg Ser Phe Leu Ser His
225                 230                 235                 240

Ile Gly Phe Tyr Arg Arg Phe Ile Lys Asp Phe Ser Lys Val
                245                 250
```

```
<210> SEQ ID NO 94
<211> LENGTH: 723
<212> TYPE: DNA
<213> ORGANISM: Gossypium hirsutum

<400> SEQUENCE: 94
gtgcgtaagg aggttttgaa attgttggat gctggaatga tatactcgat ctttgacagt     60
gattgggtta gctgggttca gtcgtgcca aagaaaactg gcgtgacagt ggtgaaaaac     120
tcatcaggag agctagtccc tacccgagtc cagaatcgat ggagggtttg catcgattac    180
```

```
aggaagttga acgcagctac ccgaaatgac cattttccac ttcccttcat tgatcaaatg    240
ctcgagcgat tagctaataa gacccattat tgttgtctcg atgggtactc aggacttttc    300
caaattccgg tggcacctga ggatcaagac aaaacaactt tcacgtgccc ctttggaacg    360
tttgcgtata gaagaatgtc gtttggactc tgtaatgctc cggccacttt ccagagatgt    420
atggtgagca tattctctga ttatgtcgag aaaatcattg aattcttcat ggatgacttc    480
acggtgtacg gtaactcttt taacgaatgt ctcgataatc ttgctaagat attacagaga    540
tgcctagaat ttaatcttgt tttaaattat gaaaatgcc acttcatggt tgacaaagga     600
ttaattttgg gtcatatagt ttcttcagaa ggtattgagg tcaataaagc aaaaacgaat    660
attattgact cattacctta ccccagattt tacagacgat tcataaagga cttcacaaaa    720
gtt                                                                  723
```

<210> SEQ ID NO 95
<211> LENGTH: 241
<212> TYPE: PRT
<213> ORGANISM: Gossypium hirsutum

<400> SEQUENCE: 95

```
Val Arg Lys Glu Val Leu Lys Leu Leu Asp Ala Gly Met Ile Tyr Ser
 1               5                  10                  15

Ile Phe Asp Ser Asp Trp Val Ser Trp Val His Val Pro Lys Lys
                20                  25                  30

Thr Gly Val Thr Val Lys Asn Ser Ser Gly Glu Leu Val Pro Thr
            35                  40                  45

Arg Val Gln Asn Arg Trp Arg Val Cys Ile Asp Tyr Arg Lys Leu Asn
50                  55                  60

Ala Ala Thr Arg Asn Asp His Phe Pro Leu Pro Phe Ile Asp Gln Met
65                  70                  75                  80

Leu Glu Arg Leu Ala Asn Lys Thr His Tyr Cys Cys Leu Asp Gly Tyr
                85                  90                  95

Ser Gly Leu Phe Gln Ile Pro Val Ala Pro Glu Asp Gln Asp Lys Thr
            100                 105                 110

Thr Phe Thr Cys Pro Phe Gly Thr Phe Ala Tyr Arg Arg Met Ser Phe
        115                 120                 125

Gly Leu Cys Asn Ala Pro Ala Thr Phe Gln Arg Cys Met Val Ser Ile
130                 135                 140

Phe Ser Asp Tyr Val Glu Lys Ile Ile Glu Phe Met Asp Asp Phe
145                 150                 155                 160

Thr Val Tyr Gly Asn Ser Phe Asn Glu Cys Leu Asp Asn Leu Ala Lys
                165                 170                 175

Ile Leu Gln Arg Cys Leu Glu Phe Asn Leu Val Leu Asn Tyr Glu Lys
            180                 185                 190

Cys His Phe Met Val Asp Lys Gly Leu Ile Leu Gly His Ile Val Ser
        195                 200                 205

Ser Glu Gly Ile Glu Val Asn Lys Ala Lys Thr Asn Ile Ile Asp Ser
    210                 215                 220

Leu Pro Tyr Pro Arg Phe Tyr Arg Arg Phe Ile Lys Asp Phe Thr Lys
225                 230                 235                 240

Val
```

<210> SEQ ID NO 96
<211> LENGTH: 762

```
<212> TYPE: DNA
<213> ORGANISM: Lycopersicon esculentum

<400> SEQUENCE: 96
gtgcggaaag aggttgtgaa gctgttagat acgggtattg tctagccaat ttcggacaac      60
aagtaggtta gtccagtaca atgtgaacct aaaaagggag acataacggt gatcactaat     120
gaaaaaaatg agttgatccc aaccatgata gtcacataat ggagaatatg catggattac     180
aggaaattga atgaagccac caggaaggac cattacccgg tcccttttat tgatcagatg     240
ttggaccggt tggctgggga ataatattat tgttttctta atggctattt acggtacaac     300
caaattgtga tttcaccaaa ggattaagag aaaaccactt tcacttgccc gtatggtaca     360
tatgctttca aaagatacc ttttgggtta tgaaatgcct cggctacttt ccaatgatgc      420
atgatggcta tttttcatga tatggttgaa gattttgttg agatattcat gaatgatttc     480
tcagtgtttg gggattcttt tgatatgtgc ttggagaatt tggacagtgt gttgctagt      540 tgtgaagaaa ctaatctttt cctaaactgg gaataatagc aatttctagt aaaggaaggg     600
attatgctag gacataaggt gtcaaagaga ggtatggaag ttgatagtgc caaagtggag     660
gttattgaaa gcttccccc tcctatatct gttaaaggga tgcaaagttt tctgggtcat      720
gttgggttct ataggagatt cataaaagac ttcacaaagg tt                        762

<210> SEQ ID NO 97
<211> LENGTH: 254
<212> TYPE: PRT
<213> ORGANISM: Lycopersicon esculentum

<400> SEQUENCE: 97

Val Arg Lys Glu Val Val Lys Leu Leu Asp Thr Gly Ile Val Glx Pro
 1               5                  10                  15

Ile Ser Asp Asn Lys Glx Val Ser Pro Val Gln Cys Glu Pro Lys Lys
            20                  25                  30

Gly Asp Ile Thr Val Ile Thr Asn Glu Lys Asn Glu Leu Ile Pro Thr
        35                  40                  45

Met Ile Val Thr Glx Trp Arg Ile Cys Met Asp Tyr Arg Lys Leu Asn
    50                  55                  60

Glu Ala Thr Arg Lys Asp His Tyr Pro Val Pro Phe Ile Asp Gln Met
65                  70                  75                  80

Leu Asp Arg Leu Ala Gly Glu Glx Tyr Tyr Cys Phe Leu Asn Gly Tyr
                85                  90                  95

Leu Arg Tyr Asn Gln Ile Val Ile Ser Pro Lys Asp Glx Glu Lys Thr
            100                 105                 110

Thr Phe Thr Cys Pro Tyr Gly Thr Tyr Ala Phe Lys Lys Ile Pro Phe
        115                 120                 125

Gly Leu Glx Asn Ala Ser Ala Thr Phe Gln Glx Cys Met Met Ala Ile
    130                 135                 140

Phe His Asp Met Val Glu Asp Phe Val Glu Ile Phe Met Asn Asp Phe
145                 150                 155                 160

Ser Val Phe Gly Asp Ser Phe Asp Met Cys Leu Glu Asn Leu Asp Ser
                165                 170                 175

Val Leu Ala Ser Cys Glu Glu Thr Asn Leu Phe Leu Asn Trp Glu Glx
            180                 185                 190

Glx Gln Phe Leu Val Lys Glu Gly Ile Met Leu Gly His Lys Val Ser
        195                 200                 205

Lys Arg Gly Met Glu Val Asp Ser Ala Lys Val Glu Val Ile Glu Lys
```

```
              210                 215                 220
Leu Pro Pro Ile Ser Val Lys Gly Met Gln Ser Phe Leu Gly His
225                 230                 235                 240

Val Gly Phe Tyr Arg Arg Phe Ile Lys Asp Phe Thr Lys Val
                245                 250

<210> SEQ ID NO 98
<211> LENGTH: 689
<212> TYPE: DNA
<213> ORGANISM: Lycopersicon esculentum

<400> SEQUENCE: 98
cgaaaggagg tggtgaaact ggaaattatc aagtagttgg atgctagagt aatctatcca     60
atcgccgata gtagttgggt atgcctagtt cagtgtgtac caaagaaagg gggaatgact    120
gtggtcccca acgaaaagaa tgaacttgtt cgaatgagac cggttactgg atggagggtg    180
tgcatggatt accgtaaact gaactcatag actgaaaaag actattttca tatgcccttc    240
atggatcaga tgttggatag acttgccgga aaagggtggt attgttttct tgatgggtat    300
tcggggtata atcagatttc tattgcacca gaagatcaag agaaaaccac tttcacttgt    360
ccatacggga cttttgcatt cagaagaatg tcgtttgggt tgtgcaatgc acccgcaacc    420
tttcagagat ggatgatgtc aatatttct gacatgatgg aggatactat agaggttttt    480
atggatgatt tttctgtggt tggtgattca ttcgagcggt gcttgtccaa tttatctgag    540
gttcttaaga gatgtgaaga ctgcaatttg gtactaaact gggaaaagtg tcatttcatg    600
gtgaaagagg gtattgtgtt gggtcatcgc atttcagaaa agggcatgca tgttttact    660 ggtgattcat caaagacttc acaaaggtt                                      689

<210> SEQ ID NO 99
<211> LENGTH: 229
<212> TYPE: PRT
<213> ORGANISM: Lycopersicon esculentum

<400> SEQUENCE: 99

Arg Lys Glu Val Val Lys Leu Glu Ile Ile Lys Glx Leu Asp Ala Arg
  1               5                  10                  15

Val Ile Tyr Pro Ile Ala Asp Ser Ser Trp Val Cys Leu Val Gln Cys
                 20                  25                  30

Val Pro Lys Lys Gly Gly Met Thr Val Val Pro Asn Glu Lys Asn Glu
             35                  40                  45

Leu Val Arg Met Arg Pro Val Thr Gly Trp Arg Val Cys Met Asp Tyr
 50                  55                  60

Arg Lys Leu Asn Ser Glx Thr Glu Lys Asp Tyr Phe His Met Pro Phe
 65                  70                  75                  80

Met Asp Gln Met Leu Asp Arg Leu Ala Gly Lys Gly Trp Tyr Cys Phe
                 85                  90                  95

Leu Asp Gly Tyr Ser Gly Tyr Asn Gln Ile Ser Ile Ala Pro Glu Asp
                100                 105                 110

Gln Glu Lys Thr Thr Phe Thr Cys Pro Tyr Gly Thr Phe Ala Phe Arg
            115                 120                 125

Arg Met Ser Phe Gly Leu Cys Asn Ala Pro Ala Thr Phe Gln Arg Trp
        130                 135                 140

Met Met Ser Ile Phe Ser Asp Met Met Glu Asp Thr Ile Glu Val Phe
145                 150                 155                 160

Met Asp Asp Phe Ser Val Val Gly Asp Ser Phe Glu Arg Cys Leu Ser
```

```
                165                 170                 175
Asn Leu Ser Glu Val Leu Lys Arg Cys Glu Asp Cys Asn Leu Val Leu
                180                 185                 190

Asn Trp Glu Lys Cys His Phe Met Val Lys Glu Gly Ile Val Leu Gly
            195                 200                 205

His Arg Ile Ser Glu Lys Gly Met His Val Phe Thr Gly Asp Ser Ser
        210                 215                 220

Lys Thr Ser Gln Arg
225

<210> SEQ ID NO 100
<211> LENGTH: 760
<212> TYPE: DNA
<213> ORGANISM: Lycopersicon esculentum

<400> SEQUENCE: 100
gtgcgtaagg aggtgtttaa gcttctagat gcgggtattg tctacccaat taggacaaca      60
agtgggttag tctagtacaa tgtgtaccta aaagggagg catggcaatg attactaatg     120
aaaacaatga gtttatccca accagcacag tcacaagatg gcgaatatgc atgaattaca    180
cgaagttaat gaagccacta ggaagaatca ttacccaatt cttttttattg attatatgtt   240
ggaccggtta gctgggcaag aatattattg tttttttggat tactaatcag ggtacaacta   300
aattttgatt gcaccagagg atcaagagaa acaactttc acttgcccgt atggtacata    360
tgctttcaag aggatacctt ttgggttatg caatgctctg tctaatttcc aaagatgcat   420
gatgactatt tttcatgata tggttgaata ttttgaggat atattcatgg atgatttctt   480
agtgttttgg gagtcttttg atagatgctt ggagaatttg aacaggttgt tagctaggtg   540
cgaacaaact aatcttgtcc tgaactggga aaaatgtcat tttttagtaa aggaagggaa   600
tttttcgggg cataaggtgt aaaagatagg gctggaagtt gatcatgaca aagtggaagt   660
aattgaaaag atctcctctc ccattttttgt gaaacgggtg agaagtttac taggtcatgc   720
tgagttttac aggatattca tcaaggactt ctcaaaggtt                          760

<210> SEQ ID NO 101
<211> LENGTH: 254
<212> TYPE: PRT
<213> ORGANISM: Lycopersicon esculentum

<400> SEQUENCE: 101

Val Arg Lys Glu Val Phe Lys Leu Leu Asp Ala Gly Ile Val Tyr Pro
1               5                   10                  15

Ile Ser Asp Asn Lys Trp Val Ser Leu Val Gln Cys Val Pro Lys Lys
            20                  25                  30

Gly Gly Met Ala Met Ile Thr Asn Glu Asn Asn Glu Phe Ile Pro Thr
        35                  40                  45

Ser Thr Val Thr Arg Trp Arg Ile Cys Met Asn Tyr Thr Lys Leu Asn
    50                  55                  60

Glu Ala Thr Arg Lys Asn His Tyr Pro Ile Leu Phe Ile Asp Tyr Met
65                  70                  75                  80

Leu Asp Arg Leu Ala Gly Gln Glu Tyr Tyr Cys Phe Leu Asp Tyr Glx
                85                  90                  95

Ser Gly Tyr Asn Glx Ile Leu Ile Ala Pro Glu Asp Gln Glu Lys Thr
            100                 105                 110

Thr Phe Thr Cys Pro Tyr Gly Thr Tyr Ala Phe Lys Arg Ile Pro Phe
        115                 120                 125
```

```
Gly Leu Cys Asn Ala Leu Ser Asn Phe Gln Arg Cys Met Met Thr Ile
    130                 135                 140

Phe His Asp Met Val Glu Tyr Phe Glu Asp Ile Phe Met Asp Asp Phe
145                 150                 155                 160

Leu Val Phe Trp Glu Ser Phe Asp Arg Cys Leu Glu Asn Leu Asn Arg
                165                 170                 175

Leu Leu Ala Arg Cys Glu Gln Thr Asn Leu Val Leu Asn Trp Glu Lys
            180                 185                 190

Cys His Phe Leu Lys Glu Gly Asn Phe Ser Gly His Lys Val Glx
        195                 200                 205

Lys Ile Gly Leu Glu Val Asp His Asp Lys Val Glu Val Ile Glu Lys
    210                 215                 220

Ile Ser Ser Pro Ile Phe Val Lys Arg Val Arg Ser Leu Leu Gly His
225                 230                 235                 240

Ala Glu Phe Tyr Arg Ile Phe Ile Lys Asp Phe Ser Lys Val
                245                 250

<210> SEQ ID NO 102
<211> LENGTH: 776
<212> TYPE: DNA
<213> ORGANISM: Lycopersicon esculentum

<400> SEQUENCE: 102
gtgcggaaag aagtgtttaa actggaatca ttaaatggtt ggatgctgga gtaatatatc      60
cgatctccga tagtagttgg gtatgcccta ttcagtgtgt acctaagaaa gggggaatga     120
ctgtggtccc caataagaaa aatgaacttg ttctaatgag accggttact ggagggtggg     180
tgtgtatgga ttaccgtaaa ttaaatgcat ggactgaaaa agaccatttt cctatgccct     240
tcatggatca gatgttggat agacttgccg aaaaagggtg gtactgtttt cttgatggat     300
agtcagggta taattagatt tctattgcac cagaagatca agagaaaacc acatttactt     360
gtccatatgg gacctttgca ttgaagagaa tgtcgtttgg gttgtgcaat gcacccgcca     420
catttcacag atgtaaaaat gttgatattc ttcgacatgg tggatgatac tattgatgct     480
tttatggatg atttttctct tgttggtgaa tcattcgaga ggtgtttgaa ccatttatct     540
gatgtcctta agagatgtga agactgcaat ttagtactaa attgggaaaa atgccacttc     600
atggtgaaaa aagtattgt tttgggtcat cgcattccag aaaagggcat agaggttgat     660
cgagctaaag tagaggtaat agagagactt ccccactat ctctgtaaaa ggtgtgagaa     720
gctttcttgg gcatgcaagt ttttaccgga gattcatcaa agacttcaca aaagtt        776

<210> SEQ ID NO 103
<211> LENGTH: 258
<212> TYPE: PRT
<213> ORGANISM: Lycopersicon esculentum

<400> SEQUENCE: 103

Ala Glu Arg Ser Val Glx Thr Gly Ile Ile Lys Trp Leu Asp Ala Gly
  1               5                  10                  15

Val Ile Tyr Pro Ile Ser Asp Ser Ser Trp Val Cys Pro Ile Gln Cys
                 20                  25                  30

Val Pro Lys Lys Gly Gly Met Thr Val Val Pro Asn Lys Lys Asn Glu
            35                  40                  45

Leu Val Leu Met Arg Pro Val Thr Gly Gly Trp Val Cys Met Asp Tyr
        50                  55                  60
```

Arg Lys Leu Asn Ala Trp Thr Glu Lys Asp His Phe Pro Met Pro Phe
65                  70                  75                  80

Met Asp Gln Met Leu Asp Arg Leu Ala Glu Lys Gly Trp Tyr Cys Phe
            85                  90                  95

Leu Asp Gly Glx Ser Gly Tyr Asn Glx Ile Ser Ile Ala Pro Glu Asp
            100                 105                 110

Gln Glu Lys Thr Thr Phe Thr Cys Pro Tyr Gly Thr Phe Ala Leu Lys
        115                 120                 125

Arg Met Ser Phe Gly Leu Cys Asn Ala Pro Ala Thr Phe His Arg Cys
130                 135                 140

Lys Met Leu Ile Phe Phe Asp Met Val Asp Thr Ile Asp Ala Phe
145                 150                 155                 160

Met Asp Asp Phe Ser Leu Val Gly Glu Ser Phe Glu Arg Cys Leu Asn
                165                 170                 175

His Leu Ser Asp Val Leu Lys Arg Cys Glu Asp Cys Asn Leu Val Leu
            180                 185                 190

Asn Trp Glu Lys Cys His Phe Met Val Lys Lys Gly Ile Val Leu Gly
            195                 200                 205

His Arg Ile Pro Glu Lys Gly Ile Glu Val Asp Arg Ala Lys Val Glu
210                 215                 220

Val Ile Glu Arg Leu Pro Pro Ile Ser Val Lys Gly Val Arg Ser
225                 230                 235                 240

Phe Leu Gly His Ala Ser Phe Tyr Arg Arg Phe Ile Lys Asp Phe Thr
                245                 250                 255

Lys Val

<210> SEQ ID NO 104
<211> LENGTH: 761
<212> TYPE: DNA
<213> ORGANISM: Solanum tuberosum

<400> SEQUENCE: 104

```
gtgcggaagg aggtacttaa attgttggat gcacggattg tgtacccaat atcagacagt      60
aaatgggtaa gtccagtaaa gtgtgtgccc aagaagggca gaatgacggt gttgactaat     120
gagaagaatg aggtaatccc cacaagaaca gtgactgggt gacggatttg catggactac     180
atgaagttga acgacgccac cagaaaggac cattatccgg tacctttcat tgataaaata     240
ttggataggt tggcaggaca tgagtactat tgttttcttg gtgtctactc aggtacaat     300 cagattgtta ttgcaataga ggactaggtg aaaaccacct tcacctgttc gtatggcaca     360
tatgcgttca agcacatgcc attcggcttg tgcaatgccc tggccacatt tcagagatgc     420
atgttggcaa tcttccatga tatggtggag gattttgttg aagttttcat ggatgacttc     480
ttggtgtttg gtgagtcttt tgaactttgt ttgactaatt ttgacagatt tcttgctagg     540
tgtgaagaga cgaatctggt gataaactga tagaagtgtc actttctggt tcgagaggga     600
attgtgttgg gacacaagat ctccaaaaat gggctgaaag ttgacaaagc caacgtagag     660
gttattgaga aattgccacc cccatcacag tgaaggtaat taaagcttta ctaggacatg     720
cttggtttta tacgaggttc atcaaagact tcacaaaggt t                         761
```

<210> SEQ ID NO 105
<211> LENGTH: 254
<212> TYPE: PRT
<213> ORGANISM: Solanum tuberosum

<400> SEQUENCE: 105

```
Val Arg Lys Glu Val Leu Lys Leu Leu Asp Ala Arg Ile Val Tyr Pro
 1               5                  10                  15
Ile Ser Asp Ser Lys Trp Val Ser Pro Val Lys Cys Val Pro Lys Lys
                20                  25                  30
Gly Arg Met Thr Val Leu Thr Asn Glu Lys Asn Glu Val Ile Pro Thr
                35                  40                  45
Arg Thr Val Thr Gly Glx Arg Ile Cys Met Asp Tyr Met Lys Leu Asn
         50                  55                  60
Asp Ala Thr Arg Lys Asp His Tyr Pro Val Pro Phe Ile Asp Lys Ile
 65                  70                  75                  80
Leu Asp Arg Leu Ala Gly His Glu Tyr Tyr Cys Phe Leu Gly Val Tyr
                 85                  90                  95
Ser Gly Tyr Asn Gln Ile Val Ile Ala Ile Glu Asp Glx Val Lys Thr
                100                 105                 110
Thr Phe Thr Cys Ser Tyr Gly Thr Tyr Ala Phe Lys His Met Pro Phe
                115                 120                 125
Gly Leu Cys Asn Ala Leu Ala Thr Phe Gln Arg Cys Met Leu Ala Ile
                130                 135                 140
Phe His Asp Met Val Glu Asp Phe Val Glu Val Phe Met Asp Asp Phe
145                 150                 155                 160
Leu Val Phe Gly Glu Ser Phe Glu Leu Cys Leu Thr Asn Phe Asp Arg
                165                 170                 175
Phe Leu Ala Arg Cys Glu Glu Thr Asn Leu Val Ile Asn Glx Glx Lys
                180                 185                 190
Cys His Phe Leu Val Arg Glu Gly Ile Val Leu Gly His Lys Ile Ser
                195                 200                 205
Lys Asn Gly Leu Lys Val Asp Lys Ala Asn Val Glu Val Ile Glu Lys
                210                 215                 220
Leu Pro Pro Pro Ile Thr Val Lys Val Ile Lys Ser Leu Leu Gly His
225                 230                 235                 240
Ala Trp Phe Tyr Thr Arg Phe Ile Lys Asp Phe Thr Lys Val
                245                 250

<210> SEQ ID NO 106
<211> LENGTH: 760
<212> TYPE: DNA
<213> ORGANISM: Solanum tuberosum

<400> SEQUENCE: 106
gtgcgtaaag aggttttcaa actgctagat gtcggtattg tatatccgat ttcagaaagc      60
aaatgggtca gcccagttta gtgtgtgcct aaaaaaagag gcatgccggt gatcaccaat     120
gaaaaaaatg agttgattcc aaccaggaca gtgacagggt ggcgaatatg catggattat     180
aggaaattga atgaggccac agaaaggat cactgcccgg ttcctttat tgatcagatg       240
ctggacaggt tagttgggca agaatattat tgtttcctgg aaggctattc aggatacaac     300
caaattgtga ttgcaccaga ggaccaggag aaaactacat tcacttgtct gtatgggaca     360
tatgctttca agtgactgcc gtttgggcta tgcaatgctc cagccacctt ccaaagatga     420
atgatggcta tctttcatga tatggttgaa gattttgtgg agatattcat ggatgacttc     480
tcagtcttta gggagtcttt tgataggtgt ttggagaatt gggacagggt gctggctaga     540
tgcgaggaaa ctaatctcat cctaaactgg aaaaaatgtc atttcctagt aaatgaaggg     600
attgtattgg gccataaggt gtcaaagaga gggctggaag ttgatcgtgc caaagtggaa     660
```

```
gttattgaaa aactacctcc tccaatctgt taaaggggtg agaagctttc tgggtcatgc    720
tggtttttac aggagattta taaaggactt cacaaaggtt                          760
```

<210> SEQ ID NO 107
<211> LENGTH: 254
<212> TYPE: PRT
<213> ORGANISM: Solanum tuberosum

<400> SEQUENCE: 107

```
Val Arg Lys Glu Val Phe Lys Leu Leu Asp Val Gly Ile Val Tyr Pro
 1               5                  10                  15

Ile Ser Glu Ser Lys Trp Val Ser Pro Val Glx Cys Val Pro Lys Lys
            20                  25                  30

Arg Gly Met Pro Val Ile Thr Asn Glu Lys Asn Glu Leu Ile Pro Thr
        35                  40                  45

Arg Thr Val Thr Gly Trp Arg Ile Cys Met Asp Tyr Arg Lys Leu Asn
    50                  55                  60

Glu Ala Thr Arg Lys Asp His Cys Pro Val Pro Phe Ile Asp Gln Met
65                  70                  75                  80

Leu Asp Arg Leu Val Gly Gln Glu Tyr Tyr Cys Phe Leu Glu Gly Tyr
                85                  90                  95

Ser Gly Tyr Asn Gln Ile Val Ile Ala Pro Glu Asp Gln Glu Lys Thr
            100                 105                 110

Thr Phe Thr Cys Leu Tyr Gly Thr Tyr Ala Phe Lys Glx Leu Pro Phe
        115                 120                 125

Gly Leu Cys Asn Ala Pro Ala Thr Phe Gln Arg Glx Met Met Ala Ile
    130                 135                 140

Phe His Asp Met Val Glu Asp Phe Val Glu Ile Phe Met Asp Asp Phe
145                 150                 155                 160

Ser Val Phe Arg Glu Ser Phe Asp Arg Cys Leu Glu Asn Trp Asp Arg
                165                 170                 175

Val Leu Ala Arg Cys Glu Glu Thr Asn Leu Ile Leu Asn Trp Lys Lys
            180                 185                 190

Cys His Phe Leu Val Asn Glu Gly Ile Val Leu Gly His Lys Val Ser
        195                 200                 205

Lys Arg Gly Leu Glu Val Asp Arg Ala Lys Val Glu Val Ile Glu Lys
    210                 215                 220

Leu Pro Pro Pro Ile Ser Val Lys Gly Val Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 108
<211> LENGTH: 761
<212> TYPE: DNA
<213> ORGANISM: Solanum tuberosum

<400> SEQUENCE: 108

```
gtgcgtaaag aggttttcaa gctctggatg caggtattgt ctatccaatt tcagacagca    60
agtgggtcag tccagttcag tgtgtgccta aaaagggagg catgacggtg atcactaatg   120
aaaaaaatga gttgattcca accaggacag tgacaggatg gcgaatatgc atggattaca   180
gaaaattaaa tgaagctacc agaaaggatc actacccggt tccttttatt gatcagatgc   240
tggacaggtt ggctggacaa gaatattatt gtttcttgga tggttattca ggatacaacc   300
aaatagtgat tgcaccagag gaccagggga aaactacatt cacttgcttg tatgggacat   360
```

```
atgtttccaa gagaatgtcg tttgggctat gcaatgctcc atccattttc caaagatgca    420
tgatggccat cttccatgat aaggttgaag attttatgga atattcatg gatgacttct    480 cagtatttgg ggagtctttt gacaggtgct tggagaattt agacagagtg ttggctagat    540
gcgaggaaac taattttgtc ctaaactggg aaaaatgtca tttcctagtg aaggaaggga    600
ttgtgttggg tcataaggtg tcaaagagag ggctggaagt tgatcgtgcc agagtggaaa    660
taatcaaaaa gctacctccc ccaatttctg ttaaaggggt gcgaagtttt ttgggtcatg    720
ttagtttcta cgaaagattc ataaaggact tcaccaaggt t                      761
```

<210> SEQ ID NO 109
<211> LENGTH: 254
<212> TYPE: PRT
<213> ORGANISM: Solanum tuberosum

<400> SEQUENCE: 109

```
Val Arg Lys Glu Val Phe Lys Leu Leu Asp Ala Gly Ile Val Tyr Pro
  1               5                  10                  15

Ile Ser Asp Ser Lys Trp Val Ser Pro Val Gln Cys Val Pro Lys Lys
             20                  25                  30

Gly Gly Met Thr Val Ile Thr Asn Glu Lys Asn Glu Leu Ile Pro Thr
         35                  40                  45

Arg Thr Val Thr Gly Trp Arg Ile Cys Met Asp Tyr Arg Lys Leu Asn
     50                  55                  60

Glu Ala Thr Arg Lys Asp His Tyr Pro Val Pro Phe Ile Asp Gln Met
 65                  70                  75                  80

Leu Asp Arg Leu Ala Gly Gln Glu Tyr Tyr Cys Phe Leu Asp Gly Tyr
                 85                  90                  95

Ser Gly Tyr Asn Gln Ile Val Ile Ala Pro Glu Asp Gln Gly Lys Thr
            100                 105                 110

Thr Phe Thr Cys Leu Tyr Gly Thr Tyr Val Ser Lys Arg Met Ser Phe
        115                 120                 125

Gly Leu Cys Asn Ala Pro Ser Ile Phe Gln Arg Cys Met Met Ala Ile
    130                 135                 140

Phe His Asp Lys Val Glu Asp Phe Met Glu Ile Phe Met Asp Asp Phe
145                 150                 155                 160

Ser Val Phe Gly Glu Ser Phe Asp Arg Cys Leu Glu Asn Leu Asp Arg
                165                 170                 175

Val Leu Ala Arg Cys Glu Glu Thr Asn Phe Val Leu Asn Trp Glu Lys
            180                 185                 190

Cys His Phe Leu Val Lys Glu Gly Ile Val Leu Gly His Lys Val Ser
        195                 200                 205

Lys Arg Gly Leu Glu Val Asp Arg Ala Arg Val Glu Ile Ile Lys Lys
    210                 215                 220

Leu Pro Pro Pro Ile Ser Val Lys Gly Val Arg Ser Phe Leu Gly His
225                 230                 235                 240

Val Ser Phe Tyr Glu Arg Phe Ile Lys Asp Phe Thr Lys Val
                245                 250
```

<210> SEQ ID NO 110
<211> LENGTH: 762
<212> TYPE: DNA
<213> ORGANISM: Solanum tuberosum

<400> SEQUENCE: 110

-continued

```
gtgcgtaagg aggtcctcaa gctgtctgat gcaggaattg tgtacccat ttatgatata      60 aagtggatca gcccagttca ctgtgtgccg aaaaagggag gcatgacgat tattactaat    120
gaaaagaagg agttgatttc agctagaacg gtgatagagt ggcacatatg aatggactat    180
aggagactaa atgaggcaac tagaaaggaa cactacccag ttcctttcat tgatcaaatg    240
ttggacaggt ttattgggca agagtattat tgtttcctag atggctattc aggatataat    300
caaattgtga ttgcgccata agataaagag aaaactacat ttacttctct atatgggaca    360
tatgccttca agagaatgtc gtttgggccg tgcaatgctc caaccacatt ccaaagatgc    420
atgacagcca tttttcatga tatggtcaaa tattttgtgg agatattcat ggatgaattc    480
ttagtctttg gggagtcttt tgacacgtgt ctagaatatt tggacaatgt gcttgccaga    540
tgtgaggaaa ctaatcccgt cctcaactgg gaaaaatgtc attttctagt gaagaagggg    600
attgtactag gccacaaggt ttcagaggaa ggactggaag ttgatcgtgg aaaagtagag    660
gtaatttaaa agctaccccc tcaagtcttc gttaaagggg tgagaaggtt ccttggtcat    720
tctaggttcg aaatgagatt cataaaagac ttcacaaaag tt                      762
```

<210> SEQ ID NO 111
<211> LENGTH: 254
<212> TYPE: PRT
<213> ORGANISM: Solanum tuberosum

<400> SEQUENCE: 111

```
Val Arg Lys Glu Val Leu Lys Leu Ser Asp Ala Gly Ile Val Tyr Pro
 1               5                  10                  15

Ile Tyr Asp Ile Lys Trp Ile Ser Pro Val His Cys Val Pro Lys Lys
                20                  25                  30

Gly Gly Met Thr Ile Ile Thr Asn Glu Lys Lys Glu Leu Ile Ser Ala
            35                  40                  45

Arg Thr Val Ile Glu Trp His Ile Glx Met Asp Tyr Arg Arg Leu Asn
        50                  55                  60

Glu Ala Thr Arg Lys Glu His Tyr Pro Val Pro Phe Ile Asp Gln Met
 65                  70                  75                  80

Leu Asp Arg Phe Ile Gly Gln Glu Tyr Tyr Cys Phe Leu Asp Gly Tyr
                 85                  90                  95

Ser Gly Tyr Asn Gln Ile Val Ile Ala Pro Glx Asp Lys Glu Lys Thr
            100                 105                 110

Thr Phe Thr Ser Leu Tyr Gly Thr Tyr Ala Phe Lys Arg Met Ser Phe
        115                 120                 125

Gly Pro Cys Asn Ala Pro Thr Thr Phe Gln Arg Cys Met Thr Ala Ile
    130                 135                 140

Phe His Asp Met Val Lys Tyr Phe Val Glu Ile Phe Met Asp Glu Phe
145                 150                 155                 160

Leu Val Phe Gly Glu Ser Phe Asp Thr Cys Leu Glu Tyr Leu Asp Asn
                165                 170                 175

Val Leu Ala Arg Cys Glu Glu Thr Asn Pro Val Leu Asn Trp Glu Lys
            180                 185                 190

Cys His Phe Leu Val Lys Lys Gly Ile Val Leu Gly His Lys Val Ser
        195                 200                 205

Glu Glu Gly Leu Glu Val Asp Arg Gly Lys Val Glu Val Ile Glx Lys
    210                 215                 220

Leu Pro Pro Gln Val Phe Val Lys Gly Val Arg Arg Phe Leu Gly His
225                 230                 235                 240
```

Ser Arg Phe Glu Met Arg Phe Ile Lys Asp Phe Thr Lys Val
                245                 250

<210> SEQ ID NO 112
<211> LENGTH: 762
<212> TYPE: DNA
<213> ORGANISM: Solanum tuberosum

<400> SEQUENCE: 112
gtgcggaagg aggtttttaa gctgctggat gcgggtattg tataccagat ttcagatagc      60
aaagggtct  acccgattta gtttgtgcct aaaaaatgca gcatgacagt gatcaccaat     120
gaaaagaatg agctgattcc aaccaggaca gtgacagggt ggcgaatatg catggattat     180
atgaagttga atgaggccac cagaaaggat cactacccga ttcatttat  tgatcagatg     240
ttggacaagt tagctgagta aaaatattat tgtttcttgg cttgttattc aagatacaac     300
caatttctca ttgcaccaca ggaccaggag gaaactacat tcacttgtcc ttatgggaca     360
tatgctttca agcgaatgtc gtttgggcta tgcaatgctc caaccacctt ccaaagatgc     420
ataagggcta tctttcatga tatggttgaa gattttgtgg agatattcat ggatgacttc     480
tcagtctttg ggtagtcttt tgagaggtgt ctggaaaatt ttgacagggt gctggctgta     540
tgcgaggaaa ctaattttt  cctaaactgg aaaaatgtc  attttctagt gaaggaaggg     600
attgtattgg gacataaggt gtcaaagtga aggcttgaag ttgatcgtgc caaagtggaa     660
gtcgttgaaa acctaccttc cccattctct gttaaagggg tgagaagttt tttgggtcat     720
gctggtttct ataggagatt tatcaaagac ttcactaagg tt                         762

<210> SEQ ID NO 113
<211> LENGTH: 254
<212> TYPE: PRT
<213> ORGANISM: Solanum tuberosum

<400> SEQUENCE: 113

Val Arg Lys Glu Val Phe Lys Leu Leu Asp Ala Gly Ile Val Tyr Gln
 1               5                  10                  15

Ile Ser Asp Ser Lys Gly Val Tyr Pro Ile Glx Phe Val Pro Lys Lys
            20                  25                  30

Cys Ser Met Thr Val Ile Thr Asn Glu Lys Asn Glu Leu Ile Pro Thr
        35                  40                  45

Arg Thr Val Thr Gly Trp Arg Ile Cys Met Asp Tyr Met Lys Leu Asn
    50                  55                  60

Glu Ala Thr Arg Lys Asp His Tyr Pro Ile His Phe Ile Asp Gln Met
65                  70                  75                  80

Leu Asp Lys Leu Ala Glu Glx Lys Tyr Tyr Cys Phe Leu Ala Cys Tyr
                85                  90                  95

Ser Arg Tyr Asn Gln Phe Leu Ile Ala Pro Gln Asp Gln Glu Glu Thr
            100                 105                 110

Thr Phe Thr Cys Pro Tyr Gly Thr Tyr Ala Phe Lys Arg Met Ser Phe
        115                 120                 125

Gly Leu Cys Asn Ala Pro Thr Thr Phe Gln Arg Cys Ile Arg Ala Ile
    130                 135                 140

Phe His Asp Met Val Glu Asp Phe Val Glu Ile Phe Met Asp Asp Phe
145                 150                 155                 160

Ser Val Phe Gly Glx Ser Phe Glu Arg Cys Leu Glu Asn Phe Asp Arg
                165                 170                 175

Val Leu Ala Val Cys Glu Glu Thr Asn Phe Phe Leu Asn Trp Glu Lys

```
                180                 185                 190
Cys His Phe Leu Val Lys Glu Gly Ile Val Leu Gly His Lys Val Ser
            195                 200                 205

Lys Glx Arg Leu Glu Val Asp Arg Ala Lys Val Glu Val Glu Asn
        210                 215                 220

Leu Pro Ser Pro Phe Ser Val Lys Gly Val Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 114
<211> LENGTH: 793
<212> TYPE: DNA
<213> ORGANISM: Solanum tuberosum

<400> SEQUENCE: 114

```
aacttttgtg aagtctttaa tgaaggatgt tgtcagagaa gaagtcatca agtggctgga    60
tacagggatt gtgtacccaa tatctgacaa taaatgggca agtccagtgc agtgtgtgcc   120
taaaaaggga ggaatgacag ttgtgaccaa tgagaaaaat gagttgatcc ccacaagaac   180
agtaactggg tggaggctat gcatggacta cagaaaactc aatgaagcca ccaggaagga   240
ccactattcg gtaccgttca ttgatcaaat gttagacagg ttggctggcc aagagtatta   300
ctgtttcctt gatggttatt caaggtataa ttagatcgtc attgcacctg aggatcaaga   360
gaatacgaca ttcacttgcc catatggcac gtatgcattc aaacgcttgc cattcggctt   420
gtgcaatgcc ccaaccctat ttcagagatg tatgatggca atcttccatg atatggtgga   480
agattttgtt aaagtataca tggacgattt ctcggtgttt ggtgagtcgt tcgaactttg   540
tttatctaat cgtgatagag ttcttactag gtgtgaggag accaatttgg tgctgaactg   600
ggagaagtgt cactttctgg tcagagaagg aattatgttg gggcagaaga tctccaaaag   660
tgggctagaa gtagacaagg cgaaggtgga agtgattgag aagttgccac caccaatata   720
agtaaaggga gtgcgaagct tccttggaca tgctggtttt acaagaggt tcataaagga   780
cttttcaaag gtt                                                       793
```

<210> SEQ ID NO 115
<211> LENGTH: 264
<212> TYPE: PRT
<213> ORGANISM: Solanum tuberosum

<400> SEQUENCE: 115

```
Thr Phe Val Lys Ser Leu Met Lys Asp Val Val Arg Glu Glu Val Ile
1               5                   10                  15

Lys Trp Leu Asp Thr Gly Ile Val Tyr Pro Ile Ser Asp Asn Lys Trp
            20                  25                  30

Ala Ser Pro Val Gln Cys Val Pro Lys Lys Gly Gly Met Thr Val Val
        35                  40                  45

Thr Asn Glu Lys Asn Glu Leu Ile Pro Thr Arg Thr Val Thr Gly Trp
    50                  55                  60

Arg Leu Cys Met Asp Tyr Arg Lys Leu Asn Glu Ala Thr Arg Lys Asp
65                  70                  75                  80

His Tyr Ser Val Pro Phe Ile Asp Gln Met Leu Asp Arg Leu Ala Gly
                85                  90                  95

Gln Glu Tyr Tyr Cys Phe Leu Asp Gly Tyr Ser Arg Tyr Asn Glx Ile
            100                 105                 110
```

-continued

```
Val Ile Ala Pro Glu Asp Gln Glu Asn Thr Thr Phe Thr Cys Pro Tyr
        115                 120                 125

Gly Thr Tyr Ala Phe Lys Arg Leu Pro Phe Gly Leu Cys Asn Ala Pro
    130                 135                 140

Thr Leu Phe Gln Arg Cys Met Met Ala Ile Phe His Asp Met Val Glu
145                 150                 155                 160

Asp Phe Val Lys Val Tyr Met Asp Asp Phe Ser Val Phe Gly Glu Ser
                165                 170                 175

Phe Glu Leu Cys Leu Ser Asn Arg Asp Arg Val Leu Thr Arg Cys Glu
            180                 185                 190

Glu Thr Asn Leu Val Leu Asn Trp Glu Lys Cys His Phe Leu Val Arg
        195                 200                 205

Glu Gly Ile Met Leu Gly Gln Lys Ile Ser Lys Ser Gly Leu Glu Val
    210                 215                 220

Asp Lys Ala Lys Val Glu Val Ile Glu Lys Leu Pro Pro Ile Glx
225                 230                 235                 240

Val Lys Gly Val Arg Ser Phe Leu Gly His Ala Gly Phe Tyr Lys Arg
                245                 250                 255

Phe Ile Lys Asp Phe Ser Lys Val
            260
```

<210> SEQ ID NO 116
<211> LENGTH: 761
<212> TYPE: DNA
<213> ORGANISM: Platanus occidentalis

<400> SEQUENCE: 116

| | | | | | |
|---|---|---|---|---|---|
| gtgcgtaagg | aggttttcaa | acttcttaaa | gtttgagtga | tttatcctat | ttaggatagg | 60 |
| aattgggtca | gcccggttca | agtggttcct | aaaaagattg | gaataaccgt | tgtgaaaaat | 120 |
| tagaatgatg | agttggttcc | taccagtgtt | cagaatgggg | ggagggttgt | atagattata | 180 |
| gaaaattgaa | tgttgtaacc | cgcaaggatc | acttcccttt | accttttatt | gatcaaatgc | 240 |
| ttgaaaggtt | agttggtcat | tcttactatt | gtttcctaga | tggttattca | agttattttcc | 300 |
| agattgtaat | tactccagag | gattaagaaa | agacaacttt | tacatgtcca | tttgggactt | 360 |
| ttgcatatcg | ttgcatgccc | tttggccttt | gcaatgcccc | aaccactttc | caaaggtgta | 420 |
| tggttagcat | attttcatat | tacattgaga | atatcataga | agtttttatg | gatgatttca | 480 |
| tagtttatgg | agactccttt | aataattttc | tgcataacct | tacacttgtt | cttcaaagat | 540 |
| gcatagaaac | taaccttgtg | ttaaattatg | aaaaatgtca | ttttatggtt | gaacaaggta | 600 |
| tagttttggg | tcatgttatt | tcatctaaag | gaattgaggt | agataaagct | aaagttgata | 660 |
| ttattcaatc | tttaccttat | ctcattagta | tgcggaaagt | tcattctttt | cttggacatg | 720 |
| caggtttcta | ccgaagattc | attaaagact | ttacaaaggt | t | | 761 |

<210> SEQ ID NO 117
<211> LENGTH: 254
<212> TYPE: PRT
<213> ORGANISM: Platanus occidentalis

<400> SEQUENCE: 117

```
Val Arg Lys Glu Val Phe Lys Leu Leu Lys Val Glx Val Ile Tyr Pro
 1               5                  10                  15

Ile Glx Asp Arg Asn Trp Val Ser Pro Val Gln Val Val Pro Lys Lys
            20                  25                  30

Ile Gly Ile Thr Val Val Lys Asn Glx Asn Asp Glu Leu Val Pro Thr
```

```
            35                  40                  45
Ser Val Gln Asn Gly Trp Arg Val Cys Ile Asp Tyr Arg Lys Leu Asn
 50                  55                  60
Val Val Thr Arg Lys Asp His Phe Pro Leu Pro Phe Ile Asp Gln Met
 65                  70                  75                  80
Leu Glu Arg Leu Val Gly His Ser Tyr Tyr Cys Phe Leu Asp Gly Tyr
                 85                  90                  95
Ser Ser Tyr Phe Gln Ile Val Ile Thr Pro Glu Asp Glx Glu Lys Thr
                100                 105                 110
Thr Phe Thr Cys Pro Phe Gly Thr Phe Ala Tyr Arg Cys Met Pro Phe
                115                 120                 125
Gly Leu Cys Asn Ala Pro Thr Thr Phe Gln Arg Cys Met Val Ser Ile
130                 135                 140
Phe Ser Tyr Tyr Ile Glu Asn Ile Ile Glu Val Phe Met Asp Asp Phe
145                 150                 155                 160
Ile Val Tyr Gly Asp Ser Phe Asn Asn Phe Leu His Asn Leu Thr Leu
                165                 170                 175
Val Leu Gln Arg Cys Ile Glu Thr Asn Leu Val Leu Asn Tyr Glu Lys
                180                 185                 190
Cys His Phe Met Val Glu Gln Gly Ile Val Leu Gly His Val Ile Ser
                195                 200                 205
Ser Lys Gly Ile Glu Val Asp Lys Ala Lys Val Asp Ile Ile Gln Ser
210                 215                 220
Leu Pro Tyr Leu Ile Ser Met Arg Lys Val His Ser Phe Leu Gly His
225                 230                 235                 240
Ala Gly Phe Tyr Arg Arg Phe Ile Lys Asp Phe Thr Lys Val
                245                 250
```

<210> SEQ ID NO 118
<211> LENGTH: 762
<212> TYPE: DNA
<213> ORGANISM: Platanus occidentalis

<400> SEQUENCE: 118

```
gtgcgtaagg aagttttcaa gcttcttgaa gttggagtga tttatcttat ttcgaatagc    60
aattgggtta gcccagttca gtggctcct  aaaaagactg gaataaccgt tgtgaaaaat   120
cagaatgatg agttagttcc tacccatgtt cagaatgggt ggtgggtttg tataaattat   180
agaaaattaa atgttataac ctgcaaggat cacttcccct tacctttat  tgataaaatg   240
cttgaaaggt tagctggtca ttcttactat tgtttccttg atggttattt aggttatttt   300
caaattgcaa ttacttcgga ggatcaagaa agatgatttt  taagtgccc  attcgggact   360
tttgcatatc gtcacatgcc ctttggcctt tgcaatgccc caaccacttt ctaaaggtgt   420
atggttagca tattttcaga ttacattgag aatatcatag aagtctttat ggatgatttc   480
acagtttatg gagactcctt tgataattgt ctgcataacc ttacacttgt tattcaaaga   540
tgcatagaaa ctaacctagt gttaaattct taaaatgtc  attttatggt tgaacaaggt   600
atagttttgg gtcatgttgt ttcatctagg ggaattgagg tagataaacc taagttgat    660
attattcaaa ctttacctta ttccactagt gtgcgagaag ttcgttcttt tcttggacat   720
gtaggttttt actgaagatt cataaaagac ttcacaaagg tt                      762
```

<210> SEQ ID NO 119
<211> LENGTH: 254
<212> TYPE: PRT

<213> ORGANISM: Platanus occidentalis

<400> SEQUENCE: 119

| | | | | | | | | | | | | | | |
|---|---|---|---|---|---|---|---|---|---|---|---|---|---|---|
| Val | Arg | Lys | Glu | Val | Phe | Lys | Leu | Leu | Glu | Val | Gly | Val | Ile | Tyr | Leu |
| 1 | | | | 5 | | | | | 10 | | | | | 15 | |

| Ile | Ser | Asn | Ser | Asn | Trp | Val | Ser | Pro | Val | Gln | Val | Ala | Pro | Lys | Lys |
|---|---|---|---|---|---|---|---|---|---|---|---|---|---|---|---|
| | | | 20 | | | | | 25 | | | | | 30 | | |

| Thr | Gly | Ile | Thr | Val | Val | Lys | Asn | Gln | Asn | Asp | Glu | Leu | Val | Pro | Thr |
|---|---|---|---|---|---|---|---|---|---|---|---|---|---|---|---|
| | | | 35 | | | | | 40 | | | | | 45 | | |

| His | Val | Gln | Asn | Gly | Trp | Trp | Val | Cys | Ile | Asn | Tyr | Arg | Lys | Leu | Asn |
|---|---|---|---|---|---|---|---|---|---|---|---|---|---|---|---|
| | 50 | | | | | 55 | | | | | 60 | | | | |

| Val | Ile | Thr | Cys | Lys | Asp | His | Phe | Pro | Leu | Pro | Phe | Ile | Asp | Lys | Met |
|---|---|---|---|---|---|---|---|---|---|---|---|---|---|---|---|
| 65 | | | | | 70 | | | | | 75 | | | | | 80 |

| Leu | Glu | Arg | Leu | Ala | Gly | His | Ser | Tyr | Tyr | Cys | Phe | Leu | Asp | Gly | Tyr |
|---|---|---|---|---|---|---|---|---|---|---|---|---|---|---|---|
| | | | | 85 | | | | | 90 | | | | | 95 | |

| Leu | Gly | Tyr | Phe | Gln | Ile | Ala | Ile | Thr | Ser | Glu | Asp | Gln | Glu | Lys | Met |
|---|---|---|---|---|---|---|---|---|---|---|---|---|---|---|---|
| | | | | 100 | | | | | 105 | | | | | 110 | |

| Ile | Phe | Lys | Cys | Pro | Phe | Gly | Thr | Phe | Ala | Tyr | Arg | His | Met | Pro | Phe |
|---|---|---|---|---|---|---|---|---|---|---|---|---|---|---|---|
| | | 115 | | | | | 120 | | | | | 125 | | | |

| Gly | Leu | Cys | Asn | Ala | Pro | Thr | Thr | Phe | Glx | Arg | Cys | Met | Val | Ser | Ile |
|---|---|---|---|---|---|---|---|---|---|---|---|---|---|---|---|
| | 130 | | | | | 135 | | | | | 140 | | | | |

| Phe | Ser | Asp | Tyr | Ile | Glu | Asn | Ile | Ile | Glu | Val | Phe | Met | Asp | Asp | Phe |
|---|---|---|---|---|---|---|---|---|---|---|---|---|---|---|---|
| 145 | | | | | 150 | | | | | 155 | | | | | 160 |

| Thr | Val | Tyr | Gly | Asp | Ser | Phe | Asp | Asn | Cys | Leu | His | Asn | Leu | Thr | Leu |
|---|---|---|---|---|---|---|---|---|---|---|---|---|---|---|---|
| | | | | 165 | | | | | 170 | | | | | 175 | |

| Val | Ile | Gln | Arg | Cys | Ile | Glu | Thr | Asn | Leu | Val | Leu | Asn | Ser | Glx | Lys |
|---|---|---|---|---|---|---|---|---|---|---|---|---|---|---|---|
| | | | | 180 | | | | | 185 | | | | | 190 | |

| Cys | His | Phe | Met | Val | Glu | Gln | Gly | Ile | Val | Leu | Gly | His | Val | Val | Ser |
|---|---|---|---|---|---|---|---|---|---|---|---|---|---|---|---|
| | | | 195 | | | | | 200 | | | | | 205 | | |

| Ser | Arg | Gly | Ile | Glu | Val | Asp | Lys | Pro | Lys | Val | Asp | Ile | Ile | Gln | Thr |
|---|---|---|---|---|---|---|---|---|---|---|---|---|---|---|---|
| | | 210 | | | | | 215 | | | | | 220 | | | |

| Leu | Pro | Tyr | Ser | Thr | Ser | Val | Arg | Glu | Val | Arg | Ser | Phe | Leu | Gly | His |
|---|---|---|---|---|---|---|---|---|---|---|---|---|---|---|---|
| 225 | | | | | 230 | | | | | 235 | | | | | 240 |

| Val | Gly | Phe | Tyr | Glx | Arg | Phe | Ile | Lys | Asp | Phe | Thr | Lys | Val |
|---|---|---|---|---|---|---|---|---|---|---|---|---|---|
| | | | | 245 | | | | | 250 | | | | |

<210> SEQ ID NO 120
<211> LENGTH: 759
<212> TYPE: DNA
<213> ORGANISM: Platanus occidentalis

<400> SEQUENCE: 120

```
gtgcggaaag aggtttttaa gcttttggat gtagggatta tatacccaat ttttatagt      60
aattaggtaa gtcccactca agtggaccca agaattctgg tgtgactgta gttaaaatg     120
caaatgatga attgattcca aatagactca ctattggttg gcgtgtatgc attaactata    180
agaagttgaa ctcagtgact aggaaggacc atttcccttt accattcatg actaaatcct    240
agaaagggta gctggtcaca aatttttatta tttcctatat ggttattcta gatataacta   300
aatagagatt gcacctgagg actaagaaaa taccactttt acatgtccat ttggcacttt    360
tgcttatcga aggatgtcat ttggattatg taatgctctt gccacgttct aaagatgcat    420
gttgagtata tttagtgata tggtagaaca ttttcttgag gtgtttatgg attttttttg    480
tttttggtaa ttcatttgat gattgtttgc ataatttgaa aaaagtgtta aatagatgtg    540
aaggaaaaaa acatcatttt gaattgagag aagtgtcatt tcatggtctc taaaagaatt    600
```

```
gtacttggtc acattgtctc ctcccaagga attaaagtgg tcaaagccaa aattgaattg      660
atagtcaatt tgcctagccc aaagactctt aaagacattc gatcttttct aggtcatgca      720
ggatttaaca aaaggttcat caaagacttc acgaaagtt                             759
```

<210> SEQ ID NO 121
<211> LENGTH: 254
<212> TYPE: PRT
<213> ORGANISM: Platanus occidentalis

<400> SEQUENCE: 121

```
Val Arg Lys Glu Val Phe Lys Leu Leu Asp Val Gly Ile Ile Tyr Pro
  1               5                  10                  15

Ile Phe Tyr Ser Asn Glx Val Ser Pro Thr Gln Val Val Pro Lys Asn
                 20                  25                  30

Ser Gly Val Thr Val Val Lys Asn Ala Asn Asp Glu Leu Ile Pro Asn
             35                  40                  45

Arg Leu Thr Ile Gly Trp Arg Val Cys Ile Asn Tyr Lys Lys Leu Asn
         50                  55                  60

Ser Val Thr Arg Lys Asp His Phe Pro Leu Pro Phe Met Asp Glx Ile
 65                  70                  75                  80

Leu Glu Arg Val Ala Gly His Lys Phe Tyr Tyr Phe Leu Tyr Gly Tyr
                 85                  90                  95

Ser Arg Tyr Asn Glx Ile Glu Ile Ala Pro Glu Asp Glx Glu Asn Thr
                100                 105                 110

Thr Phe Thr Cys Pro Phe Gly Thr Phe Ala Tyr Arg Arg Met Ser Phe
            115                 120                 125

Gly Leu Cys Asn Ala Leu Ala Thr Phe Glx Arg Cys Met Leu Ser Ile
        130                 135                 140

Phe Ser Asp Met Val Glu His Phe Leu Glu Val Phe Met Asp Asp Phe
145                 150                 155                 160

Phe Val Phe Gly Asn Ser Phe Asp Asp Cys Leu His Asn Leu Lys Lys
                165                 170                 175

Val Leu Asn Arg Cys Glu Glu Lys Asn Ile Ile Leu Asn Glx Glu Lys
                180                 185                 190

Cys His Phe Met Val Ser Lys Arg Ile Val Leu Gly His Ile Val Ser
            195                 200                 205

Ser Gln Gly Ile Lys Val Val Lys Ala Lys Ile Glu Leu Ile Val Asn
        210                 215                 220

Leu Pro Ser Pro Lys Thr Leu Lys Asp Ile Arg Ser Phe Leu Gly His
225                 230                 235                 240

Ala Gly Phe Asn Lys Arg Phe Ile Lys Asp Phe Thr Lys Val
                245                 250
```

<210> SEQ ID NO 122
<211> LENGTH: 761
<212> TYPE: DNA
<213> ORGANISM: Platanus occidentalis

<400> SEQUENCE: 122

```
tgcgtaaaga ggtggtcaag cttcttgaag ttggagtgat ttatcctatt tcggatagca       60
attgggttag cccggttcaa gtggttccta aaaagactgg aataaccgtt gtgaaaaatc      120
aaaatgatga gttagttcct acccgtgttc agaatgggtg gcaggtttgt atagattata      180
taaaattaaa tgttgtaacc cgcaaggatc acttcccttt acctttatt gatcaaatgt       240
```

| | | |
|---|---|---|
| ttgaaaggtt agctggtcat tcttactatt gtttccttga tggatattca tgttattttt | | 300 |
| agattgcaat tactccagag gatcaagaaa agacgacttt tacgtgccca ttcgggactt | | 360 |
| tttcatatcg ttgcatgccc tttggccttt gcaacgcccc agccactttc caaaggtgta | | 420 |
| tggttagcat attttcagat tacattgaga atatcataga agtctttatg gatgatttca | | 480 |
| tagtttatga agactccttt gataattgtc tgcataacct tacacttgtt ttttaaagat | | 540 |
| gcatagaaac taaccttgtg ttaaattttg aaaaatgtca tgttatggtt gaataaggta | | 600 |
| tagttttggg tcatgttgtt tcatctatgg gaattgaggt agataaagtt aaagttgata | | 660 |
| ttattcaatc tttaccttat cccattagtg tgcaggaagt tcgttctttt cttggacatg | | 720 |
| cgggtttta ccaaagattc attaaagact tcacgaaagt t | | 761 |

<210> SEQ ID NO 123
<211> LENGTH: 253
<212> TYPE: PRT
<213> ORGANISM: Platanus occidentalis

<400> SEQUENCE: 123

Arg Lys Glu Val Val Lys Leu Leu Glu Val Gly Val Ile Tyr Pro Ile
1               5                   10                  15

Ser Asp Ser Asn Trp Val Ser Pro Val Gln Val Pro Lys Lys Thr
            20                  25                  30

Gly Ile Thr Val Val Lys Asn Gln Asn Asp Glu Leu Val Pro Thr Arg
        35                  40                  45

Val Gln Asn Gly Trp Gln Val Cys Ile Asp Tyr Ile Lys Leu Asn Val
    50                  55                  60

Val Thr Arg Lys Asp His Phe Pro Leu Pro Phe Ile Asp Gln Met Phe
65                  70                  75                  80

Glu Arg Leu Ala Gly His Ser Tyr Tyr Cys Phe Leu Asp Gly Tyr Ser
                85                  90                  95

Cys Tyr Phe Glx Ile Ala Ile Thr Pro Glu Asp Gln Glu Lys Thr Thr
            100                 105                 110

Phe Thr Cys Pro Phe Gly Thr Phe Ser Tyr Arg Cys Met Pro Phe Gly
        115                 120                 125

Leu Cys Asn Ala Pro Ala Thr Phe Gln Arg Cys Met Val Ser Ile Phe
    130                 135                 140

Ser Asp Tyr Ile Glu Asn Ile Ile Glu Val Phe Met Asp Asp Phe Ile
145                 150                 155                 160

Val Tyr Glu Asp Ser Phe Asp Asn Cys Leu His Asn Leu Thr Leu Val
                165                 170                 175

Phe Glx Arg Cys Ile Glu Thr Asn Leu Val Leu Asn Phe Glu Lys Cys
            180                 185                 190

His Val Met Val Glu Glx Gly Ile Val Leu Gly His Val Val Ser Ser
        195                 200                 205

Met Gly Ile Glu Val Asp Lys Val Lys Val Asp Ile Ile Gln Ser Leu
    210                 215                 220

Pro Tyr Pro Ile Ser Val Gln Glu Val Arg Ser Phe Leu Gly His Ala
225                 230                 235                 240

Gly Phe Tyr Gln Arg Phe Ile Lys Asp Phe Thr Lys Val
                245                 250

<210> SEQ ID NO 124
<211> LENGTH: 761
<212> TYPE: DNA
<213> ORGANISM: Sorghum bicolor -continued

<400> SEQUENCE: 124

```
gtgcgtaaag aggtcttcaa gctctatcat gctgggatta tttatcctgt gccgcatagt      60
gagtgggtta gccctgttca agtagtgcca aagaaaggag gaatgacggt cgttaggaat     120
gagaagaatg aactcatccc tcaacgaatt gtcactgggt ggcgtatgtg tattgactat     180
caaaaactca acacggctac aaagaaagat aactttccgt tacccttcat tgatgaaatg     240
ttggaacggc ttgcaaacca ctctttcttc tgtttccttg atggttattc tggatatcac     300
caaatcccaa tccacccaga tgaccaagaa aagactacct ttacatgccc gtatggaact     360
tatgcataac gacgaatgtc gttcggactg tgcaatgctc cagcttcttt ccaacggtgc     420
atgatgtcta ttttctcgga catgattgag aagatcatgg aggttttcat ggatgatttt     480
accgtctatg gtaaaacctt cgatcattgt ttggagaatt tagatagagt cttgcagcga     540
tgtgaagaaa agcacttaat cctgaactgg gagaaatgcc attttatggt tcaggaagga     600
atagtgctag gacataaagt gtccgaacgt ggtatagagg tggacaaagc aaagattgaa     660
gttattgaaa aacttccacc tcccacgaat gtgaaaggat ccgtagcttc ttgggacatg     720
cagggttcta tagatgcttc ataaaagact tcacaaaggt t                         761
```

<210> SEQ ID NO 125
<211> LENGTH: 254
<212> TYPE: PRT
<213> ORGANISM: Sorghum bicolor

<400> SEQUENCE: 125

```
Val Arg Lys Glu Val Phe Lys Leu Tyr His Ala Gly Ile Ile Tyr Pro
 1               5                  10                  15
Val Pro His Ser Glu Trp Val Ser Pro Val Gln Val Val Pro Lys Lys
                20                  25                  30
Gly Gly Met Thr Val Val Arg Asn Glu Lys Asn Glu Leu Ile Pro Gln
            35                  40                  45
Arg Ile Val Thr Gly Trp Arg Met Cys Ile Asp Tyr Gln Lys Leu Asn
        50                  55                  60
Thr Ala Thr Lys Lys Asp Asn Phe Pro Leu Pro Phe Ile Asp Glu Met
 65                 70                  75                  80
Leu Glu Arg Leu Ala Asn His Ser Phe Phe Cys Phe Leu Asp Gly Tyr
                85                  90                  95
Ser Gly Tyr His Gln Ile Pro Ile His Pro Asp Asp Gln Glu Lys Thr
            100                 105                 110
Thr Phe Thr Cys Pro Tyr Gly Thr Tyr Ala Glx Arg Arg Met Ser Phe
        115                 120                 125
Gly Leu Cys Asn Ala Pro Ala Ser Phe Gln Arg Cys Met Met Ser Ile
    130                 135                 140
Phe Ser Asp Met Ile Glu Lys Ile Met Glu Val Phe Met Asp Asp Phe
145                 150                 155                 160
Thr Val Tyr Gly Lys Thr Phe Asp His Cys Leu Glu Asn Leu Asp Arg
                165                 170                 175
Val Leu Gln Arg Cys Glu Glu Lys His Leu Ile Leu Asn Trp Glu Lys
            180                 185                 190
Cys His Phe Met Val Gln Glu Gly Ile Val Leu Gly His Lys Val Ser
        195                 200                 205
Glu Arg Gly Ile Glu Val Asp Lys Ala Lys Ile Glu Val Ile Glu Lys
    210                 215                 220
```

Leu Pro Pro Pro Thr Asn Val Lys Gly Ile Arg Ser Phe Leu Gly His
225                 230                 235                 240

Ala Gly Phe Tyr Arg Cys Phe Ile Lys Asp Phe Thr Lys Val
            245                 250

<210> SEQ ID NO 126
<211> LENGTH: 762
<212> TYPE: DNA
<213> ORGANISM: Sorghum bicolor

<400> SEQUENCE: 126

```
gtgcggaagg aggtccttaa attgctgcat gcagggatta tatatcctgt gccgcacagt      60
gagtgggtga gcccagtaca agttgtgcct aaaaaaggag gcatgactgt tattataaat     120
gaaaagaacg agctaattcc gcaacgcacc gtcacaggat ggcagatgtg catagactat     180
agaaaactaa acaaagccac gagaaaggat cactttcctt tacctttat agatgagatg     240
ctagagcggt tagcaaacca ttcgttcttc tgtttcttag atggatattc agggtatcat     300
cagatcccga tccatcccga tgatcaaagc aaaaccactt ttacatgccc ttatggaact     360
tatgcttacc gtagaatgtc ttttgggtta tgtaatgcac cagcttcttt tcaaagatgc     420
atgatgtcta tattctga tatgattgaa gagattatgg aagttttcat ggatgatttc     480
tctgtttatg gaaaagcttt tgatagttgt cttgaaaact tagacaaggt tttgcaaagt     540
tgtgaagaaa agcacttaat ccttaattgg gaaaatgtc atttatggt tagggaagga     600
atagtgctag acacttagt gtctgaaagg ggtattgagg tagacaaagc tgaaattgaa     660
gtaattgaac aactacctcc acctgtgaat ataaaggaa ttcgaagctt tcttggccat     720
gctggttttt atcgtagatt catcaaagat ttcacgaaag tt                       762
```

<210> SEQ ID NO 127
<211> LENGTH: 254
<212> TYPE: PRT
<213> ORGANISM: Sorghum bicolor

<400> SEQUENCE: 127

Val Arg Lys Glu Val Leu Lys Leu Leu His Ala Gly Ile Ile Tyr Pro
1               5                  10                  15

Val Pro His Ser Glu Trp Val Ser Pro Val Gln Val Val Pro Lys Lys
            20                  25                  30

Gly Gly Met Thr Val Ile Ile Asn Glu Lys Asn Glu Leu Ile Pro Gln
        35                  40                  45

Arg Thr Val Thr Gly Trp Gln Met Cys Ile Asp Tyr Arg Lys Leu Asn
    50                  55                  60

Lys Ala Thr Arg Lys Asp His Phe Pro Leu Pro Phe Ile Asp Glu Met
65                  70                  75                  80

Leu Glu Arg Leu Ala Asn His Ser Phe Phe Cys Phe Leu Asp Gly Tyr
                85                  90                  95

Ser Gly Tyr His Gln Ile Pro Ile His Pro Asp Asp Gln Ser Lys Thr
            100                 105                 110

Thr Phe Thr Cys Pro Tyr Gly Thr Tyr Ala Tyr Arg Arg Met Ser Phe
        115                 120                 125

Gly Leu Cys Asn Ala Pro Ala Ser Phe Gln Arg Cys Met Met Ser Ile
    130                 135                 140

Phe Ser Asp Met Ile Glu Glu Ile Met Glu Val Phe Met Asp Asp Phe
145                 150                 155                 160

Ser Val Tyr Gly Lys Ala Phe Asp Ser Cys Leu Glu Asn Leu Asp Lys

```
                    165                 170                 175
Val Leu Gln Ser Cys Glu Glu Lys His Leu Ile Leu Asn Trp Glu Lys
                180                 185                 190

Cys His Phe Met Val Arg Glu Gly Ile Val Leu Gly His Leu Val Ser
            195                 200                 205

Glu Arg Gly Ile Glu Val Asp Lys Ala Glu Ile Glu Val Ile Glu Gln
        210                 215                 220

Leu Pro Pro Pro Val Asn Ile Lys Gly Ile Arg Ser Phe Leu Gly His
225                 230                 235                 240

Ala Gly Phe Tyr Arg Arg Phe Ile Lys Asp Phe Thr Lys Val
                245                 250

<210> SEQ ID NO 128
<211> LENGTH: 762
<212> TYPE: DNA
<213> ORGANISM: Sorghum bicolor

<400> SEQUENCE: 128
gtgcggaagg aagtcttaaa gcttttacac actaggatta tttatctcgt tcctcatagt     60
gagtgggtta gcacggtaca agttgtgcca agaaaggag gaatgtcggt tgttaggaat    120
gagaagaacg aattcatccc tcaacaaact gtcactgggt ggcgtatgtg cattgactac    180
caaaaactca acaaggccac aaggaaagat cacttcccgt taccttctat tgatgaaatg    240
ttgtaatggc ttacaaatca ctcgttcttt tgtttccttg aagggtattc cagatatcat    300
caaatcccga tccaccacga tgaccaaagt aagactactt tcacatgacc ctatggaact    360
tacgcatacc gacgaatgtc gttcaggtta tgtaatgctc cagcttcttt tcaacggtgc    420
atgatgtcta ttttttccaa tatgattgag aaaatcatgg aggtattcac ggatgatttt    480
accgtatatg gcaaaacctt tgatgattgt ttagagaatt tggacaaagt cttacaattg    540
tgtgaaggaa agcacttaat cgtaaactag gagaaatgcc attttatggt ccgagaagga    600
atagtgctag ggcacaaggt gtccgaacgt gggatagagg tggatagagc caagattgaa    660
gttattgaaa aacttccacc tcccacaaat gtgaaagaca tccgcagttt tcttggacat    720
gcagggttct ataggcgctt catcaaagat ttcaccaagg tt                       762

<210> SEQ ID NO 129
<211> LENGTH: 254
<212> TYPE: PRT
<213> ORGANISM: Sorghum bicolor

<400> SEQUENCE: 129

Val Arg Lys Glu Val Leu Lys Leu Leu His Thr Arg Ile Ile Tyr Leu
1               5                   10                  15

Val Pro His Ser Glu Trp Val Ser Thr Val Gln Val Val Pro Lys Lys
            20                  25                  30

Gly Gly Met Ser Val Val Arg Asn Glu Lys Asn Glu Phe Ile Pro Gln
        35                  40                  45

Gln Thr Val Thr Gly Trp Arg Met Cys Ile Asp Tyr Gln Lys Leu Asn
    50                  55                  60

Lys Ala Thr Arg Lys Asp His Phe Pro Leu Pro Phe Ile Asp Glu Met
65                  70                  75                  80

Leu Glx Trp Leu Thr Asn His Ser Phe Phe Cys Phe Leu Glu Gly Tyr
                85                  90                  95

Ser Arg Tyr His Gln Ile Pro Ile His His Asp Asp Gln Ser Lys Thr
            100                 105                 110
```

-continued

```
Thr Phe Thr Glx Pro Tyr Gly Thr Tyr Ala Tyr Arg Arg Met Ser Phe
            115                 120                 125

Arg Leu Cys Asn Ala Pro Ala Ser Phe Gln Arg Cys Met Met Ser Ile
        130                 135                 140

Phe Ser Asn Met Ile Glu Lys Ile Met Glu Val Phe Thr Asp Asp Phe
145                 150                 155                 160

Thr Val Tyr Gly Lys Thr Phe Asp Asp Cys Leu Glu Asn Leu Asp Lys
                165                 170                 175

Val Leu Gln Leu Cys Glu Gly Lys His Leu Ile Val Asn Glx Glu Lys
            180                 185                 190

Cys His Phe Met Val Arg Glu Gly Ile Val Leu Gly His Lys Val Ser
        195                 200                 205

Glu Arg Gly Ile Glu Val Asp Arg Ala Lys Ile Glu Val Ile Glu Lys
    210                 215                 220

Leu Pro Pro Pro Thr Asn Val Lys Asp Ile Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 130
<211> LENGTH: 761
<212> TYPE: DNA
<213> ORGANISM: Sorghum bicolor

<400> SEQUENCE: 130

```
gtgcgtaagg aggtttttaa gctgctgcat gcagagatta tatatcatgt gccgcacagt      60
gagtgggtaa gcccagttca agttgtgcct aaaaagggag gcatgattgt tgttacgaat     120
gaaaagaacg agctaattcc gcaacgcacc gtcacagggt ggcggatgtg catagactat     180
agaaaactaa acaaagccac gagaaaggat catttccctt tacctttcat agatgagatg     240
ctagagcgat tagcaaacca ttcgttcttc tgtttcttag atggataatt agggtatcac     300
cagatcccaa tcaatcttga tgatcaaagc aaaaccactt ttccatgccc acatggaact     360
tatgcttacc gtagaatgtc ttttgggtta tgtaatgcac cagcttcttt tcaaagatgc     420
atgatgtctg tattttctaa tatgattgaa gagattatgg aatttcatg gatgatttct     480
ctgtttatgg aaaaacttttt gatagttgtc ttgaaaactt agacagggtt ttgcaaagat     540
gtgaagaaaa gtactagtc cttaattgga aaaaatgtca ttttatggtt agggaaggaa     600
tagtgctggg acacctagtg tctgaaagag gtattgaggt cgacaaagct aaaattgaag     660
taattgaaca actacctcca cctttgaata taaaaggaat tcgaagcttt cttggccatg     720
ctggttttta tcgtagattc attaaggact ttacaaaggt t                         761
```

<210> SEQ ID NO 131
<211> LENGTH: 254
<212> TYPE: PRT
<213> ORGANISM: Sorghum bicolor

<400> SEQUENCE: 131

```
Val Arg Lys Glu Val Phe Lys Leu Leu His Ala Glu Ile Ile Tyr His
 1               5                  10                  15

Val Pro His Ser Glu Trp Val Ser Pro Val Gln Val Pro Lys Lys
            20                  25                  30

Gly Gly Met Ile Val Val Thr Asn Glu Lys Asn Glu Leu Ile Pro Gln
        35                  40                  45
```

| | | | | | | | | | | |
|---|---|---|---|---|---|---|---|---|---|---|
|Arg|Thr|Val|Thr|Gly|Trp|Arg|Met|Cys|Ile|Asp|Tyr|Arg|Lys|Leu|Asn|
| |50| | | | |55| | | |60| | | | | |

Arg Thr Val Thr Gly Trp Arg Met Cys Ile Asp Tyr Arg Lys Leu Asn
    50              55                  60

Lys Ala Thr Arg Lys Asp His Phe Pro Leu Pro Phe Ile Asp Glu Met
65              70                  75                  80

Leu Glu Arg Leu Ala Asn His Ser Phe Phe Cys Phe Leu Asp Gly Glx
                85                  90                  95

Leu Gly Tyr His Gln Ile Pro Ile Asn Leu Asp Asp Gln Ser Lys Thr
                100                 105                 110

Thr Phe Pro Cys Pro His Gly Thr Tyr Ala Tyr Arg Arg Met Ser Phe
            115                 120                 125

Gly Leu Cys Asn Ala Pro Ala Ser Phe Gln Arg Cys Met Met Ser Val
        130                 135                 140

Phe Ser Asn Met Ile Glu Ile Met Glu Ile Phe Met Asp Asp Phe
145                 150                 155                 160

Ser Val Tyr Gly Lys Thr Phe Asp Ser Cys Leu Glu Asn Leu Asp Arg
                165                 170                 175

Val Leu Gln Arg Cys Glu Glu Lys Tyr Leu Val Leu Asn Trp Lys Lys
                180                 185                 190

Cys His Phe Met Val Arg Glu Gly Ile Val Leu Gly His Leu Val Ser
            195                 200                 205

Glu Arg Gly Ile Glu Val Asp Lys Ala Lys Ile Glu Val Ile Glu Gln
        210                 215                 220

Leu Pro Pro Pro Leu Asn Ile Lys Gly Ile Arg Ser Phe Leu Gly His
225                 230                 235                 240

Ala Gly Phe Tyr Arg Arg Phe Ile Lys Asp Phe Thr Lys Val
                245                 250

<210> SEQ ID NO 132
<211> LENGTH: 763
<212> TYPE: DNA
<213> ORGANISM: Sorghum bicolor

<400> SEQUENCE: 132

```
gtgcggaaag aggtcgtcaa gctctatcat gctgggatta tttatcctgt gccacatagt      60
gagtgggtta gccctgttca agtagtgcca agaaagaag gaatgacggt cgttaggaat      120
gagaagaatg aactcatccc tcaacaaatt gtcactagat ggcgtatgtg tattgactat      180
cgaaaactca acaaagctac aaagaaagat cactttccgt tacccttcat tgatgaaatg      240
ttggaatggc ttgcaaacca ctctttcttc tgtttccttg atggttattc tggatatcac      300
caaatcccaa tccacccaga tgaccaagaa aagactacct ttacatgccc gtattgaact      360
tatgcatact gacgaatgtc gttcggattg tgcaatgctc tagcttcttt tccagcggtg      420
catgatgtct attttctcgg acatgattga gaagatcatg gaggttttca tggatgattt      480
taccgtctat ggcaaaacct tcgatcattg tttggagaat ttagatagag tcttgcagcg      540
atgtgaggaa atcacttaa tcttgaactg ggagaaatgt cattttatgg ttcaggaagg      600
aatagtgcta ggacataaag tgtccgaacg tggtatagat gtggacaaag caaagattaa      660
agttattgaa aaacttccac ctcacacgaa tgtgaaagga atccatagct ttttgggaca      720
tgcagggttc tatagacgct tcatcaagga tttcacaaag gtt                        763
```

<210> SEQ ID NO 133
<211> LENGTH: 254
<212> TYPE: PRT
<213> ORGANISM: Sorghum bicolor -continued

```
<400> SEQUENCE: 133

Val Arg Lys Glu Val Lys Leu Tyr His Ala Gly Ile Ile Tyr Pro
1               5                   10                  15

Val Pro His Ser Glu Trp Val Ser Pro Val Gln Val Pro Lys Lys
            20                  25                  30

Glu Gly Met Thr Val Val Arg Asn Glu Lys Asn Glu Leu Ile Pro Gln
        35                  40                  45

Gln Ile Val Thr Arg Trp Arg Met Cys Ile Asp Tyr Arg Lys Leu Asn
    50                  55                  60

Lys Ala Thr Lys Lys Asp His Phe Pro Leu Pro Phe Ile Asp Glu Met
65              70                  75                  80

Leu Glu Trp Leu Ala Asn His Ser Phe Phe Cys Phe Leu Asp Gly Tyr
                85                  90                  95

Ser Gly Tyr His Gln Ile Pro Ile His Pro Asp Asp Gln Glu Lys Thr
            100                 105                 110

Thr Phe Thr Cys Pro Tyr Glx Thr Tyr Ala Tyr Glx Arg Met Ser Phe
        115                 120                 125

Gly Leu Cys Asn Ala Leu Ala Ser Phe Gln Arg Cys Met Met Ser Ile
    130                 135                 140

Phe Ser Asp Met Ile Glu Lys Ile Met Glu Val Phe Met Asp Asp Phe
145                 150                 155                 160

Thr Val Tyr Gly Lys Thr Phe Asp His Cys Leu Glu Asn Leu Asp Arg
                165                 170                 175

Val Leu Gln Arg Cys Glu Glu Asn His Leu Ile Leu Asn Trp Glu Lys
            180                 185                 190

Cys His Phe Met Val Gln Glu Gly Ile Val Leu Gly His Lys Val Ser
        195                 200                 205

Glu Arg Gly Ile Asp Val Asp Lys Ala Lys Ile Lys Val Ile Glu Lys
    210                 215                 220

Leu Pro Pro His Thr Asn Val Lys Gly Ile His Ser Phe Leu Gly His
225                 230                 235                 240

Ala Gly Phe Tyr Arg Arg Phe Ile Lys Asp Phe Thr Lys Val
                245                 250

<210> SEQ ID NO 134
<211> LENGTH: 756
<212> TYPE: DNA
<213> ORGANISM: Sorghum bicolor

<400> SEQUENCE: 134
aaggaggttt tcaagttgct gcatgcaggg attatatatc ttgtgccgca tagtgagtgg      60
gtaagcccag ttcaagttgt gcctaaaaag ggaggcatga ctattattat gaatgaaaag     120
aacgagctaa ttccgcaacg caccgttaca gtatggcgga tgtgcataga ctatagaaaa     180
ctaaacaaag ccacgagaga ggatcacttt cctttaccct tcatagatga gatgctagag     240
tggttagcaa accattcgtt cttctgtttc ttagatggat attgagggta tcatcagatc     300
ccgatccatc ccgatgatca aagcaaaacc acttttacat gcccatatgg aacttatgct     360
taccgtagaa tgtctttttgg gttatgtaat gcactagctt cttttcaaag atgcatgatg     420
tctatatttt ctgatatgat tgaagagatt atggaagttt tcatggatga tttctctgtt     480
tatggaaaaa cttttgatag ttgtcttaaa aacttagaca aggttttgca aagatgtgaa     540
gaaaagcact tagtccttaa ttgggaaaaa tgtcatttca tggttaggga aggaatagtg     600
ctgggacact tagtgtctga aagagctatt gaggtagata aagctaaaat tgaagtaatt     660
```

```
gaacaactac gtccacctgt gaacataaaa ggaatttgaa gctttcttgg ccatgctggt      720
tttcatcgta gattcataaa agactttaca aaggtt                                756
```

<210> SEQ ID NO 135
<211> LENGTH: 252
<212> TYPE: PRT
<213> ORGANISM: Sorghum bicolor

<400> SEQUENCE: 135

```
Lys Glu Val Phe Lys Leu Leu His Ala Gly Ile Ile Tyr Leu Val Pro
 1               5                  10                  15

His Ser Glu Trp Val Ser Pro Val Gln Val Pro Lys Lys Gly Gly
            20                  25                  30

Met Thr Ile Ile Met Asn Glu Lys Asn Glu Leu Ile Pro Gln Arg Thr
        35                  40                  45

Val Thr Val Trp Arg Met Cys Ile Asp Tyr Arg Lys Leu Asn Lys Ala
    50                  55                  60

Thr Arg Glu Asp His Phe Pro Leu Pro Phe Ile Asp Glu Met Leu Glu
65                  70                  75                  80

Trp Leu Ala Asn His Ser Phe Phe Cys Phe Leu Asp Gly Tyr Glx Gly
                85                  90                  95

Tyr His Gln Ile Pro Ile His Pro Asp Asp Gln Ser Lys Thr Thr Phe
            100                 105                 110

Thr Cys Pro Tyr Gly Thr Tyr Ala Tyr Arg Arg Met Ser Phe Gly Leu
        115                 120                 125

Cys Asn Ala Leu Ala Ser Phe Gln Arg Cys Met Met Ser Ile Phe Ser
    130                 135                 140

Asp Met Ile Glu Glu Ile Met Glu Val Phe Met Asp Asp Phe Ser Val
145                 150                 155                 160

Tyr Gly Lys Thr Phe Asp Ser Cys Leu Lys Asn Leu Asp Lys Val Leu
                165                 170                 175

Gln Arg Cys Glu Glu Lys His Leu Val Leu Asn Trp Glu Lys Cys His
            180                 185                 190

Phe Met Val Arg Glu Gly Ile Val Leu Gly His Leu Val Ser Glu Arg
        195                 200                 205

Ala Ile Glu Val Asp Lys Ala Lys Ile Glu Val Ile Glu Gln Leu Arg
    210                 215                 220

Pro Pro Val Asn Ile Lys Gly Ile Glx Ser Phe Leu Gly His Ala Gly
225                 230                 235                 240

Phe His Arg Arg Phe Ile Lys Asp Phe Thr Lys Val
                245                 250
```

<210> SEQ ID NO 136
<211> LENGTH: 762
<212> TYPE: DNA
<213> ORGANISM: Glycine max

<400> SEQUENCE: 136

```
gtgcgtaagg aggttgtcaa gcttttggag gttgggctca tatacctcat ctctgacagc      60
gcttgggtaa gcctagtaca ggtggctccc aagaaatgcg gaatgacagt ggtacaaaat     120
gagaggaatg acttgatacc aacacgaact gtcactggct agcggatgtg tatcgactac     180
tgcaagttga atgaagccac acggaaggac catttcccct tacctttcat ggatcagatg     240
ctggagaggc ttgcagggca ggcatactac tgtttcttgg atagatattc aggatacaac     300
```

```
caaatcgcgg tagaccccag agatcaggag aagatggcct ttacatgccc ctttggcgtc    360
tttgcttaca gaaggatgtc attcaggtta tgtaacgcac cagccacatt tcagaggtgc    420
gtgctggcca ttttttcaga catggtggag aagagcatcg aggtatttat ggatgaattc    480 tcgattttg  gaccctatt  tgacagttgc ttaaggaact tagagatggt actacagagg    540
tgcgtataga ctaacttggt actaaattag gaaaaatgtc atttcatggt tcgagaggga    600
atagtgatgg accacaatat ctcagctaga gggattgagg ttgatcaggc aaagatagac    660
gtcattgaga agttgccacc accactgaat gttaaaggcg tcagaagttt cttagggcat    720
gcaggtttct acaggaggtt tatcaaggac ttcaccaagg tt                       762
```

<210> SEQ ID NO 137
<211> LENGTH: 254
<212> TYPE: PRT
<213> ORGANISM: Glycine max

<400> SEQUENCE: 137

```
Val Arg Lys Glu Val Val Lys Leu Leu Glu Val Gly Leu Ile Tyr Leu
 1               5                   10                  15

Ile Ser Asp Ser Ala Trp Val Ser Leu Val Gln Val Ala Pro Lys Lys
                20                  25                  30

Cys Gly Met Thr Val Val Gln Asn Glu Arg Asn Asp Leu Ile Pro Thr
            35                  40                  45

Arg Thr Val Thr Gly Glx Arg Met Cys Ile Asp Tyr Cys Lys Leu Asn
        50                  55                  60

Glu Ala Thr Arg Lys Asp His Phe Pro Leu Pro Phe Met Asp Gln Met
65                  70                  75                  80

Leu Glu Arg Leu Ala Gly Gln Ala Tyr Tyr Cys Phe Leu Asp Arg Tyr
                85                  90                  95

Ser Gly Tyr Asn Gln Ile Ala Val Asp Pro Arg Asp Gln Glu Lys Met
            100                 105                 110

Ala Phe Thr Cys Pro Phe Gly Val Phe Ala Tyr Arg Arg Met Ser Phe
        115                 120                 125

Arg Leu Cys Asn Ala Pro Ala Thr Phe Gln Arg Cys Val Leu Ala Ile
    130                 135                 140

Phe Ser Asp Met Val Glu Lys Ser Ile Glu Val Phe Met Asp Glu Phe
145                 150                 155                 160

Ser Ile Phe Gly Pro Leu Phe Asp Ser Cys Leu Arg Asn Leu Glu Met
                165                 170                 175

Val Leu Gln Arg Cys Val Glx Thr Asn Leu Val Leu Asn Glx Glu Lys
            180                 185                 190

Cys His Phe Met Val Arg Glu Gly Ile Val Met Asp His Asn Ile Ser
        195                 200                 205

Ala Arg Gly Ile Glu Val Asp Gln Ala Lys Ile Asp Val Ile Glu Lys
    210                 215                 220

Leu Pro Pro Pro Leu Asn Val Lys Gly Val Arg Ser Phe Leu Gly His
225                 230                 235                 240

Ala Gly Phe Tyr Arg Arg Phe Ile Lys Asp Phe Thr Lys Val
                245                 250
```

<210> SEQ ID NO 138
<211> LENGTH: 763
<212> TYPE: DNA
<213> ORGANISM: Glycine max

<400> SEQUENCE: 138

```
gtgcgtaagg aggtctttaa gttcttggag gctgggctca tatatcccat ctctaatagc      60
acttaggtaa gcccagtaca ggtggttccc aagaaaggtg gaatgacagt agtacagaat     120
gagaagaatg acttgatacc aacacgaact gtcactagct ggcgaatatg catcgattat     180
cgcaagctga atgaggccac ccggaaggac cacttccctc tacctttcat ggatcagatg     240
ttggagagac ttgcagggca ggcgtattat tgtttcttgg atggatactc gagatataat     300
cagattgcgg tggaccctag agaccaagag aagacgacct tcacatgccc tttttggcgt     360
ctttgcttac agaaggatgc cattcgggtt atgtaatgca ccagccacat ttcagaggtg     420
catgctggcc atttttcag acatggtgga gaaaaatatc gaggtattca tggatgactt     480
ttcagttttt gggccctcat ttgacagttg tttgaggaac ctagagatgg tactttagag     540
gtgcgtagag actaatttag tgctgaactg ggagaagtgt cattttatgg ttcgagaggg     600
catagtcctg agccacaaga tctcagctag agggattgag gttgaccggg caaagataga     660
cgtcatagag aagctgccac caccattgaa tattaaaggt gtcagaagtt cttagggca      720 tgcaggattc tacaggagat tcataaagga ctttacaaag gtt                       763
```

<210> SEQ ID NO 139
<211> LENGTH: 254
<212> TYPE: PRT
<213> ORGANISM: Glycine max

<400> SEQUENCE: 139

```
Val Arg Lys Glu Val Phe Lys Phe Leu Glu Ala Gly Leu Ile Tyr Pro
 1               5                  10                  15
Ile Ser Asn Ser Thr Glx Val Ser Pro Val Gln Val Val Pro Lys Lys
            20                  25                  30
Gly Gly Met Thr Val Val Gln Asn Glu Lys Asn Asp Leu Ile Pro Thr
        35                  40                  45
Arg Thr Val Thr Ser Trp Arg Ile Cys Ile Asp Tyr Arg Lys Leu Asn
    50                  55                  60
Glu Ala Thr Arg Lys Asp His Phe Pro Leu Pro Phe Met Asp Gln Met
65                  70                  75                  80
Leu Glu Arg Leu Ala Gly Gln Ala Tyr Tyr Cys Phe Leu Asp Gly Tyr
                85                  90                  95
Ser Arg Tyr Asn Gln Ile Ala Val Asp Pro Arg Asp Gln Glu Lys Thr
            100                 105                 110
Thr Phe Thr Cys Pro Phe Gly Val Phe Ala Tyr Arg Arg Met Pro Phe
        115                 120                 125
Gly Leu Cys Asn Ala Pro Ala Thr Phe Gln Arg Cys Met Leu Ala Ile
    130                 135                 140
Phe Ser Asp Met Val Glu Lys Asn Ile Glu Val Phe Met Asp Asp Phe
145                 150                 155                 160
Ser Val Phe Gly Pro Ser Phe Asp Ser Cys Leu Arg Asn Leu Glu Met
                165                 170                 175
Val Leu Glx Arg Cys Val Glu Thr Asn Leu Val Leu Asn Trp Glu Lys
            180                 185                 190
Cys His Phe Met Val Arg Glu Gly Ile Val Leu Ser His Lys Ile Ser
        195                 200                 205
Ala Arg Gly Ile Glu Val Asp Arg Ala Lys Ile Asp Val Ile Glu Lys
    210                 215                 220
Leu Pro Pro Pro Leu Asn Ile Lys Gly Val Arg Ser Phe Leu Gly His
225                 230                 235                 240
```

```
Ala Gly Phe Tyr Arg Arg Phe Ile Lys Asp Phe Thr Lys Val
                245                 250
```

<210> SEQ ID NO 140
<211> LENGTH: 762
<212> TYPE: DNA
<213> ORGANISM: Glycine max

<400> SEQUENCE: 140

```
gtgcgcaagg aggttttgaa gcttctagag gttgggctta tctacccat ctccgacagc    60
gcttgggtaa gcccagtctt ggtggtgtcg aagaaagagg gcatgacagt cattcgaaat   120
gaaaagaatg acctgatacc aacacgaact gtcactagtt ggaaattatg catcgattac   180
cgcaagctca acgaagccac aaggaaagac catttccctc tacccttcat ggatcagatg   240
ttggagagac ttgcaggaca cgcttattat tgcttcttgg atgcatactt tggatataat   300
cagattgttg tagaccccaa ggatcaggag aagatggcct tcacatgccc ttttggtgtc   360
tttgcctata gacggattcc atttggggttg tgcaatgcac ctaccacatt ccaaatgtgc   420
atgttggcca ttttgcaga tatagtggag aaaagcatcg aagtattcat ggatgacttt   480
tcagtatttg tgccctcatt agaaagttgt ttgaagaagt tggagatggt actacaaaga   540
tgcgtggaaa caaacttagt actaaattgg gagaagtgtc acttcatggt tcgagaaggc   600
atagtcttag gccataaaat ttcgacccga ggaattgagg tagaccaaac aaagattgat   660
gtcattgaaa agttgccacc accatcaaat gttaaaggca tcaggagctt cctaggacaa   720
gccaggttct acagaagatt catcaaggac ttcacaaaag tt                      762
```

<210> SEQ ID NO 141
<211> LENGTH: 254
<212> TYPE: PRT
<213> ORGANISM: Glycine max

<400> SEQUENCE: 141

```
Val Arg Lys Glu Val Leu Lys Leu Leu Glu Val Gly Leu Ile Tyr Pro
  1               5                  10                  15

Ile Ser Asp Ser Ala Trp Val Ser Pro Val Leu Val Val Ser Lys Lys
                 20                  25                  30

Glu Gly Met Thr Val Ile Arg Asn Glu Lys Asn Asp Leu Ile Pro Thr
             35                  40                  45

Arg Thr Val Thr Ser Trp Lys Leu Cys Ile Asp Tyr Arg Lys Leu Asn
         50                  55                  60

Glu Ala Thr Arg Lys Asp His Phe Pro Leu Pro Phe Met Asp Gln Met
 65                  70                  75                  80

Leu Glu Arg Leu Ala Gly His Ala Tyr Tyr Cys Phe Leu Asp Ala Tyr
                 85                  90                  95

Phe Gly Tyr Asn Gln Ile Val Val Asp Pro Lys Asp Gln Glu Lys Met
                100                 105                 110

Ala Phe Thr Cys Pro Phe Gly Val Phe Ala Tyr Arg Arg Ile Pro Phe
            115                 120                 125

Gly Leu Cys Asn Ala Pro Thr Thr Phe Gln Met Cys Met Leu Ala Ile
        130                 135                 140

Phe Ala Asp Ile Val Glu Lys Ser Ile Glu Val Phe Met Asp Asp Phe
145                 150                 155                 160

Ser Val Phe Val Pro Ser Leu Glu Ser Cys Leu Lys Lys Leu Glu Met
                165                 170                 175
```

```
Val Leu Gln Arg Cys Val Glu Thr Asn Leu Val Leu Asn Trp Glu Lys
            180                 185                 190

Cys His Phe Met Val Arg Glu Gly Ile Val Leu Gly His Lys Ile Ser
            195                 200                 205

Thr Arg Gly Ile Glu Val Asp Gln Thr Lys Ile Asp Val Ile Glu Lys
            210                 215                 220

Leu Pro Pro Ser Asn Val Lys Gly Ile Arg Ser Phe Leu Gly Gln
225                 230                 235                 240

Ala Arg Phe Tyr Arg Arg Phe Ile Lys Asp Phe Thr Lys Val
                245                 250
```

<210> SEQ ID NO 142
<211> LENGTH: 762
<212> TYPE: DNA
<213> ORGANISM: Glycine max

<400> SEQUENCE: 142

```
gtgcggaagg aggttattaa gttgctagag gcagggctca tttacctaat ctcagatagt    60
tcataggtta gtcctgttca tgttgctctg aaaaagggag gtatgacagt gataaagaat   120
gatagagatg agttaattcc tacaagaata gttactggat ggaggatggg tattgattac   180
aagaagctaa atgaagccac caggaaagac cattacccgc ttcccttcat ggatcaaatg   240
cttgagagac ttgcagggca atcttcctac tatttattag atggatactc gggctacaat   300
caaattgcag tggatcctca ggaccaagaa agacagcctt tcacatgtcc ttttggtgta   360
tttgcttatc gccgcatgtc gttcggttta tgtaatgccc caactacttt ccagagatgt   420
atgatggcaa ttttttgctga catggtaaag aaatgtattg aagtttttat ggacgatttc   480
tctgtctttg gtgcatcttt tgaaaattgc ctagcaaatt tagagaaagt gttacaacgc   540
tatgaagaat ctaatttggt gctcaactgg gaaaaatgtc actttatggt tcaagaaggt   600
atcatgctgg gacacaagat tctagaaga ggaattaagg tggataaggc aaagattgag   660
gttattgata aacttccacc tctagttaat gttagaggca tacgaagttt tttgggtcat   720
gctagattct atcgatgatt tatcaaggac ttcaccaaag tt                      762
```

<210> SEQ ID NO 143
<211> LENGTH: 254
<212> TYPE: PRT
<213> ORGANISM: Glycine max

<400> SEQUENCE: 143

```
Val Arg Lys Glu Val Ile Lys Leu Leu Glu Ala Gly Leu Ile Tyr Leu
 1               5                  10                  15

Ile Ser Asp Ser Ser Glx Val Ser Pro Val His Val Ala Leu Lys Lys
            20                  25                  30

Gly Gly Met Thr Val Ile Lys Asn Asp Arg Asp Glu Leu Ile Pro Thr
            35                  40                  45

Arg Ile Val Thr Gly Trp Arg Met Gly Ile Asp Tyr Lys Lys Leu Asn
            50                  55                  60

Glu Ala Thr Arg Lys Asp His Tyr Pro Leu Pro Phe Met Asp Gln Met
65                  70                  75                  80

Leu Glu Arg Leu Ala Gly Gln Ser Ser Tyr Tyr Leu Leu Asp Gly Tyr
                85                  90                  95

Ser Gly Tyr Asn Gln Ile Ala Val Asp Pro Gln Asp Gln Glu Lys Thr
            100                 105                 110

Ala Phe Thr Cys Pro Phe Gly Val Phe Ala Tyr Arg Arg Met Ser Phe
```

```
              115                 120                     125
Gly Leu Cys Asn Ala Pro Thr Thr Phe Gln Arg Cys Met Met Ala Ile
    130                 135                 140

Phe Ala Asp Met Val Lys Lys Cys Ile Glu Val Phe Met Asp Asp Phe
145                 150                 155                 160

Ser Val Phe Gly Ala Ser Phe Glu Asn Cys Leu Ala Asn Leu Glu Lys
                165                 170                 175

Val Leu Gln Arg Tyr Glu Glu Ser Asn Leu Val Leu Asn Trp Glu Lys
            180                 185                 190

Cys His Phe Met Val Gln Glu Gly Ile Met Leu Gly His Lys Ile Ser
        195                 200                 205

Arg Arg Gly Ile Lys Val Asp Lys Ala Lys Ile Glu Val Ile Asp Lys
    210                 215                 220

Leu Pro Pro Leu Val Asn Val Arg Gly Ile Arg Ser Phe Leu Gly His
225                 230                 235                 240

Ala Arg Phe Tyr Arg Glx Phe Ile Lys Asp Phe Thr Lys Val
                245                 250
```

<210> SEQ ID NO 144
<211> LENGTH: 761
<212> TYPE: DNA
<213> ORGANISM: Glycine max

<400> SEQUENCE: 144

```
gtgcggaagg aggtctttaa gttgctggaa gcaggcctta tttatcccat ttcggatagt      60
gcatgggtta gccctatgca agttgtccct aagaaggag gtatgacagt cattaagaat     120
gataaagatg agttgatatc acaaggacc gtcaccgggt ggagaatgtg cattgactat     180
cgaaagctga atgatgcacc cggaaggacc attatccact ccctttcatg ggccatatgc     240
ttgaaagact tgttgggcaa tcctattatt gttttctaga tggatattat ggttataatc     300
agattgttgt agatcccaaa gatcaagaga agacagcttt cacctaccct tttggtgtat     360
tcgcatatca gtgcatgcct tttggtctat gcaatgcccc agctacattt cagaggtgta     420
tgatggctat tttttctgat atggtggaaa tatgcattga agttttcatg gacgatttct     480
ctattttttgg gccatccttt gaagggtgct tatcaaatct gaaaaagta ttaaagagat     540
gtgaagagtc caatctagtt ctcaattgga gaaatgcca tttcatggtt caagaaggaa     600
taatgttggg gcataaaatt tcagtaagag ggatagaggt ggacaaggca agattgatg     660
taattgagaa actacttgct cccatgaatg tcaagggaat aagaagcttc ttaggacatg     720
cagggttcta caggcgattc ataaaagact tcaccaaagt t                         761
```

<210> SEQ ID NO 145
<211> LENGTH: 254
<212> TYPE: PRT
<213> ORGANISM: Glycine max

<400> SEQUENCE: 145

```
Val Arg Lys Glu Val Phe Lys Leu Leu Glu Ala Gly Leu Ile Tyr Pro
  1               5                  10                  15

Ile Ser Asp Ser Ala Trp Val Ser Pro Met Gln Val Val Pro Lys Lys
                 20                  25                  30

Gly Gly Met Thr Val Ile Lys Asn Asp Lys Asp Glu Leu Ile Ser Thr
             35                  40                  45

Arg Thr Val Thr Gly Trp Arg Met Cys Ile Asp Tyr Arg Lys Leu Asn
         50                  55                  60
```

```
Asp Ala Thr Arg Lys Asp His Tyr Pro Leu Pro Phe Met Gly His Met
 65                  70                  75                  80

Leu Glu Arg Leu Val Gly Gln Ser Tyr Tyr Cys Phe Leu Asp Gly Tyr
                 85                  90                  95

Tyr Gly Tyr Asn Gln Ile Val Val Asp Pro Lys Asp Gln Glu Lys Thr
            100                 105                 110

Ala Phe Thr Tyr Pro Phe Gly Val Phe Ala Tyr Gln Cys Met Pro Phe
        115                 120                 125

Gly Leu Cys Asn Ala Pro Ala Thr Phe Gln Arg Cys Met Met Ala Ile
    130                 135                 140

Phe Ser Asp Met Val Glu Ile Cys Ile Glu Val Phe Met Asp Asp Phe
145                 150                 155                 160

Ser Ile Phe Gly Pro Ser Phe Glu Gly Cys Leu Ser Asn Leu Glu Lys
                165                 170                 175

Val Leu Lys Arg Cys Glu Glu Ser Asn Leu Val Leu Asn Trp Lys Lys
            180                 185                 190

Cys His Phe Met Val Gln Glu Gly Ile Met Leu Gly His Lys Ile Ser
        195                 200                 205

Val Arg Gly Ile Glu Val Asp Lys Ala Lys Ile Asp Val Ile Glu Lys
    210                 215                 220

Leu Leu Ala Pro Met Asn Val Lys Gly Ile Arg Ser Phe Leu Gly His
225                 230                 235                 240

Ala Gly Phe Tyr Arg Arg Phe Ile Lys Asp Phe Thr Lys Val
                245                 250
```

```
<210> SEQ ID NO 146
<211> LENGTH: 762
<212> TYPE: DNA
<213> ORGANISM: Glycine max

<400> SEQUENCE: 146
gtgcgtaagg aggtggtcaa gttgcttgaa gtaggactaa tttatccaat ctctgatagt      60
gcttgggtga gttcgaacta ggtggtgcct aagaaaggtg gtatgacggt gatccacaat     120
gataagaatg atcttattcc tacacagaca atcattaggt ggcaaatgtg tattgactat     180
cacaagttga atgatgtcac caagaaggac catttcctc tgccattcat ggaccaaatg      240
ttagagaggt tagctggcca agcttttat tgttttttgg atggttattc tgggtataac      300
caaatagcgg tgcatcttaa agatcaagag aagactacta tcatatgccc atttggtgtc     360
tttgcttaca gacaaatgtc atttgaactg tgtaatgccc ctaccacctt ctagagattc     420
atgatggcca ttttgctga ccttgtggag aaatgcatag aggtgttcat gaatgatttc      480
tctatttccg gctcttcctt ttatcattgt ttatccaacc tggaattagt gttacaacgg     540
tgtgcggaaa ccaatttgtt gatgaactgg gagaaatgtc atttcatggt ccaagagggg     600
attgtcttag gccacaagat ctcttccaga gggttggaag tggacaaggc aaaaattgat     660
gttattgaga agttgcctcc acctatgaat gtgaaaggca tccgaagttt tctcgaatat     720
gttggatttt ataggaggtt catcaaagac ttcacgaaag tt                        762

<210> SEQ ID NO 147
<211> LENGTH: 254
<212> TYPE: PRT
<213> ORGANISM: Glycine max

<400> SEQUENCE: 147
```

```
Val Arg Lys Glu Val Lys Leu Leu Glu Val Gly Leu Ile Tyr Pro
 1               5                  10                  15

Ile Ser Asp Ser Ala Trp Val Ser Ser Asn Glx Val Val Pro Lys Lys
            20                  25                  30

Gly Gly Met Thr Val Ile His Asn Asp Lys Asn Asp Leu Ile Pro Thr
            35                  40                  45

Gln Thr Ile Ile Arg Trp Gln Met Cys Ile Asp Tyr His Lys Leu Asn
 50                  55                  60

Asp Val Thr Lys Lys Asp His Phe Pro Leu Pro Phe Met Asp Gln Met
65                  70                  75                  80

Leu Glu Arg Leu Ala Gly Gln Ala Phe Tyr Cys Phe Leu Asp Gly Tyr
                85                  90                  95

Ser Gly Tyr Asn Gln Ile Ala Val His Leu Lys Asp Gln Glu Lys Thr
            100                 105                 110

Thr Ile Ile Cys Pro Phe Gly Val Phe Ala Tyr Arg Gln Met Ser Phe
            115                 120                 125

Glu Leu Cys Asn Ala Pro Thr Thr Phe Glx Arg Phe Met Met Ala Ile
130                 135                 140

Phe Ala Asp Leu Val Glu Lys Cys Ile Glu Val Phe Met Asn Asp Phe
145                 150                 155                 160

Ser Ile Phe Gly Ser Ser Phe Tyr His Cys Leu Ser Asn Leu Glu Leu
                165                 170                 175

Val Leu Gln Arg Cys Ala Glu Thr Asn Leu Leu Met Asn Trp Glu Lys
            180                 185                 190

Cys His Phe Met Val Gln Glu Gly Ile Val Leu Gly His Lys Ile Ser
            195                 200                 205

Ser Arg Gly Leu Glu Val Asp Lys Ala Lys Ile Asp Val Ile Glu Lys
            210                 215                 220

Leu Pro Pro Pro Met Asn Val Lys Gly Ile Arg Ser Phe Leu Glu Tyr
225                 230                 235                 240

Val Gly Phe Tyr Arg Arg Phe Ile Lys Asp Phe Thr Lys Val
                245                 250
```

<210> SEQ ID NO 148
<211> LENGTH: 762
<212> TYPE: DNA
<213> ORGANISM: Glycine max

<400> SEQUENCE: 148

```
gtgcgtaagg aggttctcaa gcttttggag gttgggctca tatacctcat ctctgacagc    60
gcttgggtaa gcctagtaca ggtggctccc aagaaatgcg gaatgacagt ggtacaaaat   120
gagaggaatg acttgatacc aacacgaact gtcactggct agcggatgtg tatcgactac   180
tgcaagttga atgaagccac acggaaggac catttcccct tacctttcat ggatcagatg   240
ctggagaggc ttgcagggca ggcatactac tgtttcttgg atagatattc aggatacaac   300
caaatcgcgg tagaccccag agatcaggag aagatggcct tcatgcccc tttggcgtc    360
tttgcttaca gaaggatgtc attcaggtta tgtaacgcac cagccacatt tcagaggtgc   420
atgctggcca ttttttcaga catggtggag aagagcatcg aggtatttat ggatgaattc   480
tcgattttg gaccttatt tgacagttgc ttaaggaact tagagatggt actacagagg    540
tgcgtataga ctaacttggt actaaattag gaaaaatgtc atttcatggt tcgagaggga   600
atagtgatgg gccacaatat ctcagctaga gggattgagg ttgatcagac aaagatagac   660
gtcattgaga agttgccacc accactgaat gttaaaggcg tcagaagttt cttagggcat   720
```

```
gcaggtttct acaggaggtt cataaaagac ttcacaaagg tt                    762
```

<210> SEQ ID NO 149
<211> LENGTH: 254
<212> TYPE: PRT
<213> ORGANISM: Glycine max

<400> SEQUENCE: 149

```
Val Arg Lys Glu Val Leu Lys Leu Leu Glu Val Gly Leu Ile Tyr Leu
1               5                   10                  15
Ile Ser Asp Ser Ala Trp Val Ser Leu Val Gln Val Ala Pro Lys Lys
            20                  25                  30
Cys Gly Met Thr Val Val Gln Asn Glu Arg Asn Asp Leu Ile Pro Thr
        35                  40                  45
Arg Thr Val Thr Gly Glx Arg Met Cys Ile Asp Tyr Cys Lys Leu Asn
    50                  55                  60
Glu Ala Thr Arg Lys Asp His Phe Pro Leu Pro Phe Met Asp Gln Met
65                  70                  75                  80
Leu Glu Arg Leu Ala Gly Gln Ala Tyr Tyr Cys Phe Leu Asp Arg Tyr
                85                  90                  95
Ser Gly Tyr Asn Gln Ile Ala Val Asp Pro Arg Asp Gln Glu Lys Met
            100                 105                 110
Ala Phe Thr Cys Pro Phe Gly Val Phe Ala Tyr Arg Arg Met Ser Phe
        115                 120                 125
Arg Leu Cys Asn Ala Pro Ala Thr Phe Gln Arg Cys Met Leu Ala Ile
    130                 135                 140
Phe Ser Asp Met Val Glu Lys Ser Ile Glu Val Phe Met Asp Glu Phe
145                 150                 155                 160
Ser Ile Phe Gly Pro Leu Phe Asp Ser Cys Leu Arg Asn Leu Glu Met
                165                 170                 175
Val Leu Gln Arg Cys Val Glx Thr Asn Leu Val Leu Asn Glx Glu Lys
            180                 185                 190
Cys His Phe Met Val Arg Glu Gly Ile Val Met Gly His Asn Ile Ser
        195                 200                 205
Ala Arg Gly Ile Glu Val Asp Gln Thr Lys Ile Asp Val Ile Glu Lys
    210                 215                 220
Leu Pro Pro Pro Leu Asn Val Lys Gly Val Arg Ser Phe Leu Gly His
225                 230                 235                 240
Ala Gly Phe Tyr Arg Arg Phe Ile Lys Asp Phe Thr Lys Val
                245                 250
```

<210> SEQ ID NO 150
<211> LENGTH: 761
<212> TYPE: DNA
<213> ORGANISM: Glycine max

<400> SEQUENCE: 150

```
gtgcgtaagg aggtttttaa gttgctggaa gcaggtctta tttatcccat ttcggatagt    60
gcatgggtta gccctgtgca ggttgtcccc aagaaagaag gtaagacagt cattaaggat   120
gaaaaggatg agttgatatc cacaaggact atcaccgggt ggagaatgtg cattgactat   180
cagaagctga atgatgccac ccggaaggac cattatccac tcccttttca tggaccaaatg   240
cttgaaagac ttgccgggca atcttattat tgttttctgg atggatattc tggttataat   300
cagattgatg tagatcccaa ggatcaagag aagactgctt tcacctaccc ttttggtgta   360
```

```
ttcgcctatc ggcgcatgcc ctttggtttg tgcaatgccc cagctacatt tcagaggtgt      420
atgatgacta ttttttctga tatggtggaa aaatgaattg aagttttcat ggacgatttc      480 tctattttg  ggccatcttt tgaagggtgc ttatcaaatc ttgaaagagt attaaagaga      540
cgtgaagagt ccaaactagt tctcaattgg gagaaatgcc atttcatggt tcaagaagga      600
atagtgtggg gcataaaatt tcagtaagag ggatagaggt ggacaaggca aagattgatg      660
taatagagaa actacctcct cccatgaatg tcaagggaat aagaagcttc ctaggacatg      720
cagggttcta caagcgattc atcaaagatt tcacaaaggt t                         761
```

<210> SEQ ID NO 151
<211> LENGTH: 254
<212> TYPE: PRT
<213> ORGANISM: Glycine max

<400> SEQUENCE: 151

```
Val Arg Lys Glu Val Phe Lys Leu Leu Glu Ala Gly Leu Ile Tyr Pro
  1               5                  10                  15

Ile Ser Asp Ser Ala Trp Val Ser Pro Val Gln Val Val Pro Lys Lys
                 20                  25                  30

Glu Gly Lys Thr Val Ile Lys Asp Glu Lys Asp Glu Leu Ile Ser Thr
             35                  40                  45

Arg Thr Ile Thr Gly Trp Arg Met Cys Ile Asp Tyr Gln Lys Leu Asn
         50                  55                  60

Asp Ala Thr Arg Lys Asp His Tyr Pro Leu Pro Phe Met Asp Gln Met
 65                  70                  75                  80

Leu Glu Arg Leu Ala Gly Gln Ser Tyr Tyr Cys Phe Leu Asp Gly Tyr
                 85                  90                  95

Ser Gly Tyr Asn Gln Ile Asp Val Asp Pro Lys Asp Gln Glu Lys Thr
                100                 105                 110

Ala Phe Thr Tyr Pro Phe Gly Val Phe Ala Tyr Arg Arg Met Pro Phe
            115                 120                 125

Gly Leu Cys Asn Ala Pro Ala Thr Phe Gln Arg Cys Met Met Thr Ile
        130                 135                 140

Phe Ser Asp Met Val Glu Lys Glx Ile Glu Val Phe Met Asp Asp Phe
145                 150                 155                 160

Ser Ile Phe Gly Pro Ser Phe Glu Gly Cys Leu Ser Asn Leu Glu Arg
                165                 170                 175

Val Leu Lys Arg Arg Glu Glu Ser Lys Leu Val Leu Asn Trp Glu Lys
                180                 185                 190

Cys His Phe Met Val Gln Glu Gly Ile Val Leu Gly His Lys Ile Ser
            195                 200                 205

Val Arg Gly Ile Glu Val Asp Lys Ala Lys Ile Asp Val Ile Glu Lys
        210                 215                 220

Leu Pro Pro Pro Met Asn Val Lys Gly Ile Arg Ser Phe Leu Gly His
225                 230                 235                 240

Ala Gly Phe Tyr Lys Arg Phe Ile Lys Asp Phe Thr Lys Val
                245                 250
```

<210> SEQ ID NO 152
<211> LENGTH: 762
<212> TYPE: DNA
<213> ORGANISM: Glycine max

<400> SEQUENCE: 152

```
gtgcggaaag aggtattcaa gttactagag gcagggctca tctacccaat ttcagatagc       60
```

-continued

```
tcctgggtta gtccggttca agttgttcca aaaaaaggag ggatgacagt ggtaaaaaat      120
gatagaaatg agctaattcc tacaagaaga gtcaccagat ggagaatgtg tattgattat      180
aggaagctca atgaagccac aagaaaagac cattacccac ttcccttcat ggatcaaatg      240
cttaagagac ttgcaaggca atccttctac cgtttcttgg acggatactc aggttacaat      300
cagattgcag tggatcctca ggatcaagaa aaaacagctt ttacatgtcc tttcagtgtt      360
tttgcttatc gccgcatgcc gttcggttta tgtaatgcct ctactacttt tcagagatgt      420
atgatggcaa ttttttgatga catggtagag aaatgtattg aagtctttat ggatgatttt     480
tcgttctttg gtgcatcttt tggaaattgc ttagcaaatt tagagaaagt gttacaacgt      540
tgtgaaaaat ctaatttggt gcttaactgg gaaaaatgtc actttatggt acaagaaggt      600
attgtgctag gacacaaaat ctctaaaaga ggaattgagg tggttaaaga aaaactagat      660
gttattgata aacttccacc cccagttaat gtaaaaggca tacacagttt tttgggtcat      720
gttggatttt atcggcgatt cataaaggac ttcaccaaag tt                         762
```

<210> SEQ ID NO 153
<211> LENGTH: 254
<212> TYPE: PRT
<213> ORGANISM: Glycine max

<400> SEQUENCE: 153

```
Val Arg Lys Glu Val Phe Lys Leu Leu Glu Ala Gly Leu Ile Tyr Pro
  1               5                  10                  15

Ile Ser Asp Ser Ser Trp Val Ser Pro Val Gln Val Val Pro Lys Lys
                 20                  25                  30

Gly Gly Met Thr Val Val Lys Asn Asp Arg Asn Glu Leu Ile Pro Thr
             35                  40                  45

Arg Arg Val Thr Arg Trp Arg Met Cys Ile Asp Tyr Arg Lys Leu Asn
         50                  55                  60

Glu Ala Thr Arg Lys Asp His Tyr Pro Leu Pro Phe Met Asp Gln Met
 65                  70                  75                  80

Leu Lys Arg Leu Ala Arg Gln Ser Phe Tyr Arg Phe Leu Asp Gly Tyr
                 85                  90                  95

Ser Gly Tyr Asn Gln Ile Ala Val Asp Pro Gln Asp Gln Glu Lys Thr
            100                 105                 110

Ala Phe Thr Cys Pro Phe Ser Val Phe Ala Tyr Arg Arg Met Pro Phe
        115                 120                 125

Gly Leu Cys Asn Ala Ser Thr Thr Phe Gln Arg Cys Met Met Ala Ile
    130                 135                 140

Phe Asp Asp Met Val Glu Lys Cys Ile Glu Val Phe Met Asp Asp Phe
145                 150                 155                 160

Ser Phe Phe Gly Ala Ser Phe Gly Asn Cys Leu Ala Asn Leu Glu Lys
                165                 170                 175

Val Leu Gln Arg Cys Glu Lys Ser Asn Leu Val Leu Asn Trp Glu Lys
            180                 185                 190

Cys His Phe Met Val Gln Glu Gly Ile Val Leu Gly His Lys Ile Ser
        195                 200                 205

Lys Arg Gly Ile Glu Val Val Lys Glu Leu Asp Val Ile Asp Lys
    210                 215                 220

Leu Pro Pro Pro Val Asn Val Lys Gly Ile His Ser Phe Leu Gly His
225                 230                 235                 240

Val Gly Phe Tyr Arg Arg Phe Ile Lys Asp Phe Thr Lys Val
                245                 250
```

<210> SEQ ID NO 154
<211> LENGTH: 761
<212> TYPE: DNA
<213> ORGANISM: Glycine max

<400> SEQUENCE: 154

```
gtgcgtaaag aagttttgaa gctgctagaa gcagacctta tttatcccat ttcggatagt      60
acatgggtta gccctgtgca agttgtcccc gagaaaggag gtatgacagt cattaagaat     120
gataaagatg agttgatatc cacaaggact gtcaccgggt gagaatgtgc attgactatc     180
ggaagctgaa tgatgccacc cagaaggacc attattcact cccctttcatg accagatgc     240
ttgaaagact tgccggacaa tcctattatt gttttctgaa tggatactct ggctataatc     300
agattgtggt agatcccaaa gatcaggaga aaactgcttt cacctgcctt tttggtgtat     360
ttgcatacaa gcgtatgcat tttggcttgt gtaatgctcc aactacgtgt cagaggtgta     420
tgatgactat ttttttctggt atcgtggaaa aatgcattga acttttcatg gacgatttct     480
ctatttttgg gccatctttt gaaggctact tatcaaacct gaaagagta ttacagagat      540
gtgaagagtc taatctagtt ctcaattggg agaaatgcca tttcatggtt caagaaggaa     600
tagtgctggg gcataaaatt tcagtaagag ggatagaggt ggacaaggca aagattgatg     660
taattgagaa actacctcct cccatgattg tcaagggaat aagaagcctc ctaggacatg     720
tagggttcta caggcgattc atcaaagact tcacaaaggt t                          761
```

<210> SEQ ID NO 155
<211> LENGTH: 254
<212> TYPE: PRT
<213> ORGANISM: Glycine max

<400> SEQUENCE: 155

```
Val Arg Lys Glu Val Leu Lys Leu Leu Glu Ala Asp Leu Ile Tyr Pro
  1               5                  10                  15

Ile Ser Asp Ser Thr Trp Val Ser Pro Val Gln Val Val Pro Glu Lys
             20                  25                  30

Gly Gly Met Thr Val Ile Lys Asn Asp Lys Asp Glu Leu Ile Ser Thr
         35                  40                  45

Arg Thr Val Thr Gly Trp Arg Met Cys Ile Asp Tyr Arg Lys Leu Asn
     50                  55                  60

Asp Ala Thr Gln Lys Asp His Tyr Ser Leu Pro Phe Met Asp Gln Met
 65                  70                  75                  80

Leu Glu Arg Leu Ala Gly Gln Ser Tyr Tyr Cys Phe Leu Asn Gly Tyr
                 85                  90                  95

Ser Gly Tyr Asn Gln Ile Val Val Asp Pro Lys Asp Gln Glu Lys Thr
            100                 105                 110

Ala Phe Thr Cys Leu Phe Gly Val Phe Ala Tyr Lys Arg Met His Phe
        115                 120                 125

Gly Leu Cys Asn Ala Pro Thr Thr Cys Gln Arg Cys Met Met Thr Ile
    130                 135                 140

Phe Ser Gly Ile Val Glu Lys Cys Ile Glu Leu Phe Met Asp Asp Phe
145                 150                 155                 160

Ser Ile Phe Gly Pro Ser Phe Glu Gly Tyr Leu Ser Asn Leu Glu Arg
                165                 170                 175

Val Leu Gln Arg Cys Glu Glu Ser Asn Leu Val Leu Asn Trp Glu Lys
            180                 185                 190
```

```
Cys His Phe Met Val Gln Glu Gly Ile Val Leu Gly His Lys Ile Ser
            195                 200                 205

Val Arg Gly Ile Glu Val Asp Lys Ala Lys Ile Asp Val Ile Glu Lys
        210                 215                 220

Leu Pro Pro Pro Met Ile Val Lys Gly Ile Arg Ser Leu Leu Gly His
225                 230                 235                 240

Val Gly Phe Tyr Arg Arg Phe Ile Lys Asp Phe Thr Lys Val
                245                 250
```

<210> SEQ ID NO 156
<211> LENGTH: 762
<212> TYPE: DNA
<213> ORGANISM: Glycine max

<400> SEQUENCE: 156

```
gtgcgtaagg aggtttttaa gttgctggaa gcaggtctta tttatcccat ttcggatagt      60
gcatgggtta gccctgtgca ggttgtcccc aagaagaag gtaagacagt cattaaggat     120
gaaaaagatg agttgatatc cacaaggact atcaccgggt ggagaatgtg cattgactat    180
cagaagctga atgatgccac ccggaaggac cattatccac tccctttcat ggaccaaatg    240
cttgaaagac ttgccgggca atcttattat tgttttctgg atggatattc tggttataat    300
cagattgatg tagatcccaa ggatcaagag aagactgctt tcacctaccc ttttggtgta    360
ttcgcctatc ggcgcatgcc ctttggtttg tgcaatgccc cagctacatt tcagaggtgt    420
atgatgacta tttttctga tatggtggaa aaatgaattg aagttttcat ggacgatgtc     480
tctattttg ggccatcttt tgaagggtgc ttatcaaatc ttgaaagagt attaaagaga     540
cgtgaagagt ccaaactagt tctcaattgg gagaaatgcc atttcatggt tcaagaagga    600
atagtgttgg ggcataaaat ttcagtaaga gggatagagg tggacaaggc aaagattgat    660
gtaatagaga aactacctcc tcccatgaat gtcaagggaa taagaagctt cctaggacat    720
gcagggttct acaagcgatt catcaaagac ttctcaaaag tt                        762
```

<210> SEQ ID NO 157
<211> LENGTH: 254
<212> TYPE: PRT
<213> ORGANISM: Glycine max

<400> SEQUENCE: 157

```
Val Arg Lys Glu Val Phe Lys Leu Leu Glu Ala Gly Leu Ile Tyr Pro
1               5                   10                  15

Ile Ser Asp Ser Ala Trp Val Ser Pro Val Gln Val Val Pro Lys Lys
            20                  25                  30

Glu Gly Lys Thr Val Ile Lys Asp Glu Lys Asp Glu Leu Ile Ser Thr
        35                  40                  45

Arg Thr Ile Thr Gly Trp Arg Met Cys Ile Asp Tyr Gln Lys Leu Asn
    50                  55                  60

Asp Ala Thr Arg Lys Asp His Tyr Pro Leu Pro Phe Met Asp Gln Met
65                  70                  75                  80

Leu Glu Arg Leu Ala Gly Gln Ser Tyr Tyr Cys Phe Leu Asp Gly Tyr
                85                  90                  95

Ser Gly Tyr Asn Gln Ile Asp Val Asp Pro Lys Asp Gln Glu Lys Thr
            100                 105                 110

Ala Phe Thr Tyr Pro Phe Gly Val Phe Ala Tyr Arg Arg Met Pro Phe
        115                 120                 125
```

```
Gly Leu Cys Asn Ala Pro Ala Thr Phe Gln Arg Cys Met Met Thr Ile
    130                 135                 140

Phe Ser Asp Met Val Glu Lys Glx Ile Glu Val Phe Met Asp Asp Val
145                 150                 155                 160

Ser Ile Phe Gly Pro Ser Phe Glu Gly Cys Leu Ser Asn Leu Glu Arg
                165                 170                 175

Val Leu Lys Arg Arg Glu Glu Ser Lys Leu Val Leu Asn Trp Glu Lys
            180                 185                 190

Cys His Phe Met Val Gln Glu Gly Ile Val Leu Gly His Lys Ile Ser
            195                 200                 205

Val Arg Gly Ile Glu Val Asp Lys Ala Lys Ile Asp Val Ile Glu Lys
        210                 215                 220

Leu Pro Pro Met Asn Val Lys Gly Ile Arg Ser Phe Leu Gly His
225                 230                 235                 240

Ala Gly Phe Tyr Lys Arg Phe Ile Lys Asp Phe Ser Lys Val
                245                 250
```

<210> SEQ ID NO 158
<211> LENGTH: 761
<212> TYPE: DNA
<213> ORGANISM: Glycine max

<400> SEQUENCE: 158

| | | | | | |
|---|---|---|---|---|---|
| gtgcggaagg | aggttcttaa | gctcctggaa | gcagggctca | tctatcttat | ctcagatagt | 60 |
| gttgggtgag | tccagtgcat | gtggttccca | agaagggtgg | gaagactgtg | gtgagaaatg | 120 |
| agaaaaatga | cctcattcta | acccgaactg | tcacaggatg | gagaatgtgc | atagattatc | 180 |
| ggaagttgaa | tgatgccatc | aagaaggatc | acttccctct | accattcata | gatcagatgc | 240 |
| ttgagaggtt | agcaagccag | tctttctatt | atttcttgga | tgaatattct | agatacaatc | 300 |
| agattgctat | acatcccaag | gaccaagaga | agattgcatt | acatgcccca | tttggtgtct | 360 |
| ttgcctatag | aaggatgcca | tttgaactat | gcaatgctcc | agctaccttt | tagaggcata | 420 |
| tgctagccat | attcgctaac | atggtggaga | atgcatcga | agtgttcata | gatgattttt | 480 |
| cggtgtttgg | tccatccttt | gtttgttgtt | tgaccaattt | agagctagtg | ttgaagtact | 540 |
| gtgaggagac | aaatttagta | ttgaattggg | agaaatgtca | tttcatggtc | caagaaggaa | 600 |
| ttatgttggg | gcataaaatt | tttgctagag | gtattgaggt | ggacaaggcc | aaaattgatg | 660 |
| ttattgaaaa | gctgcctcca | ccagtcaatg | taaaaggcat | caggagtttt | cttggacaca | 720 |
| ctggtttctt | caggcgtttc | atcaaggact | tcacaaaagt | t | | 761 |

<210> SEQ ID NO 159
<211> LENGTH: 254
<212> TYPE: PRT
<213> ORGANISM: Glycine max

<400> SEQUENCE: 159

```
Val Arg Lys Glu Val Leu Lys Leu Leu Glu Ala Gly Leu Ile Tyr Leu
1               5                   10                  15

Ile Ser Asp Ser Ala Trp Val Ser Pro Val His Val Pro Lys Lys
                20                  25                  30

Gly Gly Lys Thr Val Val Arg Asn Glu Lys Asn Asp Leu Ile Leu Thr
            35                  40                  45

Arg Thr Val Thr Gly Trp Arg Met Cys Ile Asp Tyr Arg Lys Leu Asn
        50                  55                  60

Asp Ala Ile Lys Lys Asp His Phe Pro Leu Pro Phe Ile Asp Gln Met
```

```
                65                  70                  75                  80
Leu Glu Arg Leu Ala Ser Gln Ser Phe Tyr Tyr Phe Leu Asp Glu Tyr
                        85                  90                  95

Ser Arg Tyr Asn Gln Ile Ala Ile His Pro Lys Asp Gln Glu Lys Ile
                100                 105                 110

Ala Phe Thr Cys Pro Phe Gly Val Phe Ala Tyr Arg Arg Met Pro Phe
                115                 120                 125

Glu Leu Cys Asn Ala Pro Ala Thr Phe Glx Arg His Met Leu Ala Ile
    130                 135                 140

Phe Ala Asn Met Val Glu Lys Cys Ile Glu Val Phe Ile Asp Asp Phe
145                 150                 155                 160

Ser Val Phe Gly Pro Ser Phe Val Cys Cys Leu Thr Asn Leu Glu Leu
                165                 170                 175

Val Leu Lys Tyr Cys Glu Glu Thr Asn Leu Val Leu Asn Trp Glu Lys
                180                 185                 190

Cys His Phe Met Val Gln Glu Gly Ile Met Leu Gly His Lys Ile Phe
            195                 200                 205

Ala Arg Gly Ile Glu Val Asp Lys Ala Lys Ile Asp Val Ile Glu Lys
        210                 215                 220

Leu Pro Pro Val Asn Val Lys Gly Ile Arg Ser Phe Leu Gly His
225                 230                 235                 240

Thr Gly Phe Phe Arg Arg Phe Ile Lys Asp Phe Thr Lys Val
                    245                 250
```

<210> SEQ ID NO 160
<211> LENGTH: 762
<212> TYPE: DNA
<213> ORGANISM: Pisum sativum

<400> SEQUENCE: 160

```
gtgcgcaagg aagtactcaa gttgttagat tcgggaatga tttacccccat ttctgacagc    60
tcgtgggtaa gtccagtgca cgtggtacca agaaaggag gaacctcagt aattttaaat    120
gaaaagaatg aactgatccc aactcgcaca gtgacaggt ggcgagtatg catcgatcac     180
agaagactga acacagcaac aagaaaggat cattttcctc tccctttat tgatcaaatg     240
ttagaaagac ttgcaggtca tgagtattat tgctttctgg atggatattc gggatacaat    300
caaattgttg tagccccgga agatcaggaa aaaactgcat ttacatgtcc ttatggtatt    360
ttcgcttaca gacggatgcc atttgggcta tgcaatgccc cagctacttt tcagaggtgt    420
atgcatccta tattctccga catgcttgaa agtatatgaa aggtgtttat ggatgatttc    480
tctgtgtttg gttcttcttt tgataattgt ttagctaact tgtctcttgt tttgcaaaga    540
tgtcaggaaa ctaaccttgt tctcaattgg gagaaatgtc atttcatggt gcaggaagga   600
attgtgctag gacacaaaat tcccacaaa ggaattgaag tggacaaagc caagtggag     660
gttatagcta acctcccacc tccggtgaat gaaaaaggga taaggagttt tttgggtcat    720
gcaggttttt atcgcaggtt catcaaagac ttcacaaagg tt                       762
```

<210> SEQ ID NO 161
<211> LENGTH: 254
<212> TYPE: PRT
<213> ORGANISM: Pisum sativum

<400> SEQUENCE: 161

```
Val Arg Lys Glu Val Leu Lys Leu Leu Asp Ser Gly Met Ile Tyr Pro
 1               5                  10                  15
```

Ile Ser Asp Ser Ser Trp Val Ser Pro Val His Val Pro Lys Lys
            20                  25                  30

Gly Gly Thr Ser Val Ile Leu Asn Glu Lys Asn Glu Leu Ile Pro Thr
        35                  40                  45

Arg Thr Val Thr Gly Trp Arg Val Cys Ile Asp His Arg Arg Leu Asn
50                  55                  60

Thr Ala Thr Arg Lys Asp His Phe Pro Leu Pro Phe Ile Asp Gln Met
65                  70                  75                  80

Leu Glu Arg Leu Ala Gly His Glu Tyr Tyr Cys Phe Leu Asp Gly Tyr
                85                  90                  95

Ser Gly Tyr Asn Gln Ile Val Val Ala Pro Glu Asp Gln Glu Lys Thr
            100                 105                 110

Ala Phe Thr Cys Pro Tyr Gly Ile Phe Ala Tyr Arg Arg Met Pro Phe
        115                 120                 125

Gly Leu Cys Asn Ala Pro Ala Thr Phe Gln Arg Cys Met Thr Ser Ile
    130                 135                 140

Phe Ser Asp Met Leu Glu Lys Tyr Met Lys Val Phe Met Asp Asp Phe
145                 150                 155                 160

Ser Val Phe Gly Ser Ser Phe Asp Asn Cys Leu Ala Asn Leu Ser Leu
                165                 170                 175

Val Leu Gln Arg Cys Gln Glu Thr Asn Leu Val Leu Asn Trp Glu Lys
            180                 185                 190

Cys His Phe Met Val Gln Glu Gly Ile Val Leu Gly His Lys Ile Ser
        195                 200                 205

His Lys Gly Ile Glu Val Asp Lys Ala Lys Val Glu Val Ile Ala Asn
    210                 215                 220

Leu Pro Pro Pro Val Asn Glu Lys Gly Ile Arg Ser Phe Leu Gly His
225                 230                 235                 240

Ala Gly Phe Tyr Arg Arg Phe Ile Lys Asp Phe Thr Lys Val
                245                 250

<210> SEQ ID NO 162
<211> LENGTH: 762
<212> TYPE: DNA
<213> ORGANISM: Pisum sativum

<400> SEQUENCE: 162
gtgcgtaagg aggtctttaa actattggat gcgggaatga tttacccgat ctcggatagt      60
ccgtgggtta gtcccgtgca cgtggttccg aagaagggtg gaatgaccgt aatccgtaat     120
gacaaagacg aattgatccc gactaaagtt gcaacggggt ggagaatatg tatagattat     180
agacagttga ataccgcgac tcgaaaggac cattttccac tcccatttat ggatcaaatg     240
cttgaaagac tatcgggcca acaatactat tgtttcttgg acggctactc cgggtacaac     300
caaattgcgg ttgacccggt tgatcatgag aagacggctt tcacgtgtcc gtttggagtg     360
ttcgcataca gaaaaatgcc ctttgggctg tgcaatgcac cggcgacttt ccaacgatgc     420
gtcctagcca ttttttgccga tctaatagag aaaacaatgg acgtcttcat ggatgacttc     480
tcggtatttg gtgggacgtt tagtctatgc ttggcaaatt tgaagacggt gttgaaagg     540 tgtgtgaaga ccaatttggt gctaaattgg gaaaagtgtc acttcatggt gaccgagggg     600
atcgtgctag gccacaaagt ctctaaaagg gggcttgaag tggatagagc taaggttgaa     660
gtaattgaaa aattaccccc tccggtgaat gtgaaggca ccgtagctt tttgggggcac     720 gcggggtttt accggcgctt cattaaagac ttctcaaaag tt                         762

```
<210> SEQ ID NO 163
<211> LENGTH: 254
<212> TYPE: PRT
<213> ORGANISM: Pisum sativum

<400> SEQUENCE: 163

Val Arg Lys Glu Val Phe Lys Leu Leu Asp Ala Gly Met Ile Tyr Pro
 1               5                  10                  15

Ile Ser Asp Ser Pro Trp Val Ser Pro Val His Val Pro Lys Lys
                20                  25                  30

Gly Gly Met Thr Val Ile Arg Asn Asp Lys Asp Glu Leu Ile Pro Thr
            35                  40                  45

Lys Val Ala Thr Gly Trp Arg Ile Cys Ile Asp Tyr Arg Gln Leu Asn
     50                  55                  60

Thr Ala Thr Arg Lys Asp His Phe Pro Leu Pro Phe Met Asp Gln Met
 65                  70                  75                  80

Leu Glu Arg Leu Ser Gly Gln Gln Tyr Tyr Cys Phe Leu Asp Gly Tyr
                 85                  90                  95

Ser Gly Tyr Asn Gln Ile Ala Val Asp Pro Val Asp His Glu Lys Thr
            100                 105                 110

Ala Phe Thr Cys Pro Phe Gly Val Phe Ala Tyr Arg Lys Met Pro Phe
        115                 120                 125

Gly Leu Cys Asn Ala Pro Ala Thr Phe Gln Arg Cys Val Leu Ala Ile
    130                 135                 140

Phe Ala Asp Leu Ile Glu Lys Thr Met Asp Val Phe Met Asp Asp Phe
145                 150                 155                 160

Ser Val Phe Gly Gly Thr Phe Ser Leu Cys Leu Ala Asn Leu Lys Thr
                165                 170                 175

Val Leu Glu Arg Cys Val Lys Thr Asn Leu Val Leu Asn Trp Glu Lys
            180                 185                 190

Cys His Phe Met Val Thr Glu Gly Ile Val Leu Gly His Lys Val Ser
        195                 200                 205

Lys Arg Gly Leu Glu Val Asp Arg Ala Lys Val Glu Val Ile Glu Lys
    210                 215                 220

Leu Pro Pro Pro Val Asn Val Lys Gly Ile Arg Ser Phe Leu Gly His
225                 230                 235                 240

Ala Gly Phe Tyr Arg Arg Phe Ile Lys Asp Phe Ser Lys Val
                245                 250

<210> SEQ ID NO 164
<211> LENGTH: 762
<212> TYPE: DNA
<213> ORGANISM: Pisum sativum

<400> SEQUENCE: 164
gtgcggaagg aggtctttaa attgttggat gcggggatga tttacccgat ctcggatagt      60
ccatgggtta gtcctgtgca cgttgttccg aagaaggggg ggattaccgt aatccggaat     120
gacaaggatg aattgatccc cactaaagtt gaaacggggt ggagaatgtg tattgattat     180
aggcggttga ataccgcgac tcgaaaagac cattttccac tcccatttat ggatcaaatg     240
ctcgaaagac tatcgggcca acaatattat tgttttttgg acggctactc cgggtacaac     300
caaattgcgg ttgacccggc cgatcatgag aagacggctt tcacatgtcc gtttggagtg     360
ttcgcatacc gaaaaatgcc ctttgggctg tgcaatgcac cggcgacctt ccaacgatgt     420
```

-continued

```
gtccaagcca tttttgtcga tctgatagag aaaacaatgg aagtcttcat ggatgacttc      480
tcggtatttg gtgggtcttt tagtctatgc ttggcgaact tgaaaacggt gttggagaga      540
tgtgtgaaga ccaatttggt gcttaattgg gagaagtgtc acttcatggt gaccgagggg      600
atcgtgctag gccacaaagt ctctagaagg gggcttgaag tggatagagc taaggttgaa      660
gtgatagaaa aattacctcc tccggtgaat gtgaagggca tccgaagctt tttggggcac      720
gccgggttct accggcgctt cattaaagat ttcacaaagg tt                         762
```

<210> SEQ ID NO 165
<211> LENGTH: 254
<212> TYPE: PRT
<213> ORGANISM: Pisum sativum

<400> SEQUENCE: 165

```
Val Arg Lys Glu Val Phe Lys Leu Leu Asp Ala Gly Met Ile Tyr Pro
 1               5                  10                  15
Ile Ser Asp Ser Pro Trp Val Ser Pro Val His Val Pro Lys Lys
                20                  25                  30
Gly Gly Ile Thr Val Ile Arg Asn Asp Lys Asp Glu Leu Ile Pro Thr
            35                  40                  45
Lys Val Glu Thr Gly Trp Arg Met Cys Ile Asp Tyr Arg Arg Leu Asn
 50                  55                  60
Thr Ala Thr Arg Lys Asp His Phe Pro Leu Pro Phe Met Asp Gln Met
 65                  70                  75                  80
Leu Glu Arg Leu Ser Gly Gln Gln Tyr Tyr Cys Phe Leu Asp Gly Tyr
                85                  90                  95
Ser Gly Tyr Asn Gln Ile Ala Val Asp Pro Ala Asp His Glu Lys Thr
            100                 105                 110
Ala Phe Thr Cys Pro Phe Gly Val Phe Ala Tyr Arg Lys Met Pro Phe
        115                 120                 125
Gly Leu Cys Asn Ala Pro Ala Thr Phe Gln Arg Cys Val Gln Ala Ile
    130                 135                 140
Phe Val Asp Leu Ile Glu Lys Thr Met Glu Val Phe Met Asp Asp Phe
145                 150                 155                 160
Ser Val Phe Gly Gly Ser Phe Ser Leu Cys Leu Ala Asn Leu Lys Thr
                165                 170                 175
Val Leu Glu Arg Cys Val Lys Thr Asn Leu Val Leu Asn Trp Glu Lys
            180                 185                 190
Cys His Phe Met Val Thr Glu Gly Ile Val Leu Gly His Lys Val Ser
        195                 200                 205
Arg Arg Gly Leu Glu Val Asp Arg Ala Lys Val Glu Val Ile Glu Lys
    210                 215                 220
Leu Pro Pro Pro Val Asn Val Lys Gly Ile Arg Ser Phe Leu Gly His
225                 230                 235                 240
Ala Gly Phe Tyr Arg Arg Phe Ile Lys Asp Phe Thr Lys Val
                245                 250
```

<210> SEQ ID NO 166
<211> LENGTH: 23
<212> TYPE: DNA
<213> ORGANISM: Artificial Sequence
<220> FEATURE:
<223> OTHER INFORMATION: synthetically generated oligonucleotide
<220> FEATURE:
<221> NAME/KEY: misc_feature
<222> LOCATION: 6, 15, 16, 18
<223> OTHER INFORMATION: n = A,T,C or G

<400> SEQUENCE: 166
gtgcgnaarg argtnntnaa ryt                                              23

<210> SEQ ID NO 167
<211> LENGTH: 8
<212> TYPE: PRT
<213> ORGANISM: Artificial Sequence
<220> FEATURE:
<223> OTHER INFORMATION: plant retroelement sequence

<400> SEQUENCE: 167

Val Arg Lys Glu Val Leu Lys Leu
 1               5

<210> SEQ ID NO 168
<211> LENGTH: 24
<212> TYPE: DNA
<213> ORGANISM: Artificial Sequence
<220> FEATURE:
<223> OTHER INFORMATION: synthetically generated oligonucleotide
<220> FEATURE:
<221> NAME/KEY: misc_feature
<222> LOCATION: 7
<223> OTHER INFORMATION: n = A,T,C or G

<400> SEQUENCE: 168
aacyttngwr aartcyttda traa                                             24

<210> SEQ ID NO 169
<211> LENGTH: 8
<212> TYPE: PRT
<213> ORGANISM: Artificial Sequence
<220> FEATURE:
<223> OTHER INFORMATION: plant retroelement sequence

<400> SEQUENCE: 169

Val Lys Ser Phe Asp Lys Ile Phe
 1               5

<210> SEQ ID NO 170
<211> LENGTH: 20
<212> TYPE: DNA
<213> ORGANISM: Artificial Sequence
<220> FEATURE:
<223> OTHER INFORMATION: primer

<400> SEQUENCE: 170
gggatccgca attagaatct                                                  20

<210> SEQ ID NO 171
<211> LENGTH: 20
<212> TYPE: DNA
<213> ORGANISM: Artificial Sequence
<220> FEATURE:
<223> OTHER INFORMATION: primer

<400> SEQUENCE: 171
cgaattcggt ccacttcgga                                                  20

<210> SEQ ID NO 172
<211> LENGTH: 24
<212> TYPE: DNA
<213> ORGANISM: Artificial Sequence
<220> FEATURE:
<223> OTHER INFORMATION: primer

```
<400> SEQUENCE: 172
ccacaagatt ctaattgcgg attc                                              24

<210> SEQ ID NO 173
<211> LENGTH: 24
<212> TYPE: DNA
<213> ORGANISM: Artificial Sequence
<220> FEATURE:
<223> OTHER INFORMATION: primer

<400> SEQUENCE: 173
ccgaaatgga ccgaacccga catc                                              24

<210> SEQ ID NO 174
<211> LENGTH: 24
<212> TYPE: DNA
<213> ORGANISM: Artificial Sequence
<220> FEATURE:
<223> OTHER INFORMATION: primer

<400> SEQUENCE: 174
tttccaggct cttgacgaga tttg                                              24

<210> SEQ ID NO 175
<211> LENGTH: 22
<212> TYPE: DNA
<213> ORGANISM: Artificial Sequence
<220> FEATURE:
<223> OTHER INFORMATION: primer

<400> SEQUENCE: 175
cgactcgagc tccatagcga tg                                                22

<210> SEQ ID NO 176
<211> LENGTH: 24
<212> TYPE: DNA
<213> ORGANISM: Artificial Sequence
<220> FEATURE:
<223> OTHER INFORMATION: primer

<400> SEQUENCE: 176
cggattgggc cgaaatggac cgaa                                              24

<210> SEQ ID NO 177
<211> LENGTH: 18
<212> TYPE: DNA
<213> ORGANISM: Arabidopsis thaliana

<400> SEQUENCE: 177
gaggacttgg ggggcaaa                                                     18

<210> SEQ ID NO 178
<211> LENGTH: 13
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 2-3, 5-7, 9-12
<223> OTHER INFORMATION: Xaa = Any Amino Acid

<400> SEQUENCE: 178

Cys Xaa Xaa Cys Xaa Xaa Xaa His Xaa Xaa Xaa Xaa Cys
 1               5                  10
```

```
<210> SEQ ID NO 179
<211> LENGTH: 6
<212> TYPE: PRT
<213> ORGANISM: Artificial Sequence
<220> FEATURE:
<223> OTHER INFORMATION: exemplary motif

<400> SEQUENCE: 179

Leu Ile Asp Leu Gly Ala
 1               5

<210> SEQ ID NO 180
<211> LENGTH: 4
<212> TYPE: PRT
<213> ORGANISM: Artificial Sequence
<220> FEATURE:
<223> OTHER INFORMATION: consensus sequence

<400> SEQUENCE: 180

Lys Thr Ala Phe
 1

<210> SEQ ID NO 181
<211> LENGTH: 8
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 2
<223> OTHER INFORMATION: Xaa = Pro or Ser

<400> SEQUENCE: 181

Met Xaa Phe Gly Leu Cys Asn Ala
 1               5

<210> SEQ ID NO 182
<211> LENGTH: 10
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 1
<223> OTHER INFORMATION: Xaa = Val, Ile, or Met
<220> FEATURE:
<221> NAME/KEY: VARIANT
<222> LOCATION: 9
<223> OTHER INFORMATION: Xaa = Ser or Trp
<220> FEATURE:
<221> NAME/KEY: VARIANT
<222> LOCATION: 10
<223> OTHER INFORMATION: Xaa = Val or Ile

<400> SEQUENCE: 182

Xaa Glu Val Phe Met Asp Asp Phe Xaa Xaa
 1               5                  10

<210> SEQ ID NO 183
<211> LENGTH: 19
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 12
<223> OTHER INFORMATION: Xaa = Ile or Val
```

```
<400> SEQUENCE: 183

Phe Glu Leu Met Cys Asp Ala Ser Asp Tyr Ala Xaa Gly Ala Val Leu
  1               5                  10                  15

Gly Gln Arg

<210> SEQ ID NO 184
<211> LENGTH: 27
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 4
<223> OTHER INFORMATION: Xaa = Thr or Ile
<220> FEATURE:
<221> NAME/KEY: VARIANT
<222> LOCATION: 8
<223> OTHER INFORMATION: Xaa = Leu or Met
<220> FEATURE:
<221> NAME/KEY: VARIANT
<222> LOCATION: 13
<223> OTHER INFORMATION: Xaa = Phe or Tyr
<220> FEATURE:
<221> NAME/KEY: VARIANT
<222> LOCATION: 15
<223> OTHER INFORMATION: Xaa = Leu or Phe
<220> FEATURE:
<221> NAME/KEY: VARIANT
<222> LOCATION: 19
<223> OTHER INFORMATION: Xaa = Arg or Lys
<220> FEATURE:
<221> NAME/KEY: VARIANT
<222> LOCATION: 23
<223> OTHER INFORMATION: Xaa = Ile or Val
<220> FEATURE:
<221> NAME/KEY: VARIANT
<222> LOCATION: 26
<223> OTHER INFORMATION: Xaa = Arg or Lys

<400> SEQUENCE: 184

Tyr Ala Thr Xaa Glu Lys Glu Xaa Leu Ala Ile Val Xaa Ala Xaa Glu
  1               5                  10                  15

Lys Phe Xaa Ser Tyr Leu Xaa Gly Ser Xaa Val
               20                  25

<210> SEQ ID NO 185
<211> LENGTH: 46
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 4, 6-7, 11-40, 43
<223> OTHER INFORMATION: Xaa = Any Amino Acid

<400> SEQUENCE: 185

His Cys His Xaa Ser Xaa Xaa Gly Gly His Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
               20                  25                  30

Xaa Xaa Xaa Xaa Xaa Xaa Xaa Xaa Cys Asp Xaa Cys Gln Arg
               35                  40                  45

<210> SEQ ID NO 186
<211> LENGTH: 8
<212> TYPE: PRT
```

```
<213> ORGANISM: Artificial Sequence
<220> FEATURE:
<223> OTHER INFORMATION: consensus sequence
<220> FEATURE:
<221> NAME/KEY: VARIANT
<222> LOCATION: 6
<223> OTHER INFORMATION: Xaa = Ile, Val, or Met

<400> SEQUENCE: 186

Trp Gly Ile Asp Phe Xaa Gly Pro
 1               5

<210> SEQ ID NO 187
<211> LENGTH: 11
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 10
<223> OTHER INFORMATION: Xaa = Ala or Val

<400> SEQUENCE: 187

Pro Tyr His Pro Gln Thr Xaa Gly Gln Xaa Glu
 1               5                  10

<210> SEQ ID NO 188
<211> LENGTH: 13
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: 11, 12
<223> OTHER INFORMATION: n = A,T,C or G

<400> SEQUENCE: 188
atttggggra nnt                                                        13

<210> SEQ ID NO 189
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 5, 8
<223> OTHER INFORMATION: Xaa = Arg or Lys

<400> SEQUENCE: 189

Gln Met Ala Ser Xaa Lys Arg Xaa Ala
 1               5

<210> SEQ ID NO 190
<211> LENGTH: 6
<212> TYPE: PRT
<213> ORGANISM: Pisum sativum

<400> SEQUENCE: 190

Ala Ser Lys Lys Arg Lys
 1               5
```